United States Patent
Hallam et al.

(10) Patent No.: US 8,012,979 B2
(45) Date of Patent: Sep. 6, 2011

(54) COMPOUNDS AND THEIR USES 707

(75) Inventors: Matthew Hallam, Leicestershire (GB);
Barrie Martin, Leicestershire (GB);
Piotr Raubo, Leicestershire (GB);
Bryan Roberts, Leicestershire (GB);
Stephen St-Gallay, Leicestershire (GB);
Paul Willis, Leicestershire (GB)

(73) Assignee: AstraZeneca AB, Södertälje (SE)

( * ) Notice: Subject to any disclaimer, the term of this patent is extended or adjusted under 35 U.S.C. 154(b) by 610 days.

(21) Appl. No.: 12/062,718

(22) Filed: Apr. 4, 2008

(65) Prior Publication Data
US 2009/0023746 A1    Jan. 22, 2009

Related U.S. Application Data

(60) Provisional application No. 60/910,235, filed on Apr. 5, 2007, provisional application No. 60/979,523, filed on Oct. 12, 2007.

(51) Int. Cl.
*C07D 401/10* (2006.01)
*C07D 217/24* (2006.01)
*A61K 31/4725* (2006.01)

(52) U.S. Cl. .................. 514/253.05; 514/309; 540/575; 544/363; 546/141

(58) Field of Classification Search .......... None
See application file for complete search history.

(56) References Cited

U.S. PATENT DOCUMENTS
2004/0044258 A1    3/2004    Shoda et al.

FOREIGN PATENT DOCUMENTS
| | | |
|---|---|---|
| CA | 2535665 | 2/2005 |
| EP | 1484320 | 12/2004 |
| WO | WO 00/55153 | 9/2000 |
| WO | WO 2005/016852 | 2/2005 |
| WO | WO 2005/035503 | 4/2005 |
| WO | WO 2006/039718 | 4/2006 |
| WO | WO 2006/067444 | 6/2006 |
| WO | WO 2007/012422 | 2/2007 |

*Primary Examiner* — Zinna Northington Davis
(74) *Attorney, Agent, or Firm* — Connolly Bove Lodge & Hutz LLP

(57) ABSTRACT

The present invention relates to isoquinolinone derivatives of formula (I):

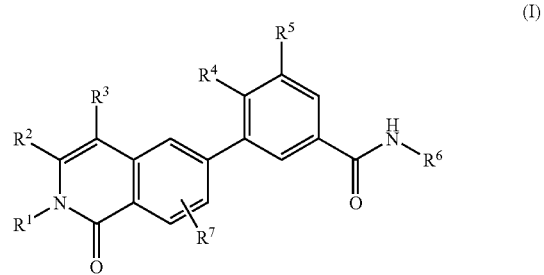

wherein $R^1$, $R^2$, $R^3$, $R^4$, $R^5$, $R^6$ and $R^7$ are as herein defined; processes for their preparation, pharmaceutical compositions containing them and their use in therapy.

13 Claims, 2 Drawing Sheets

Figure 1: XRPD for Example 47 polymorph A
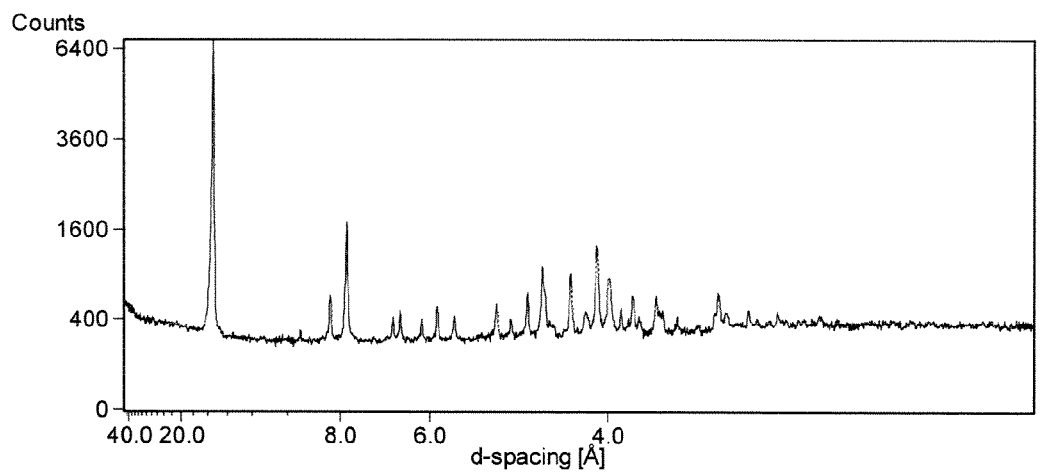
Figure 2: XRPD for Example 60 polymorph A
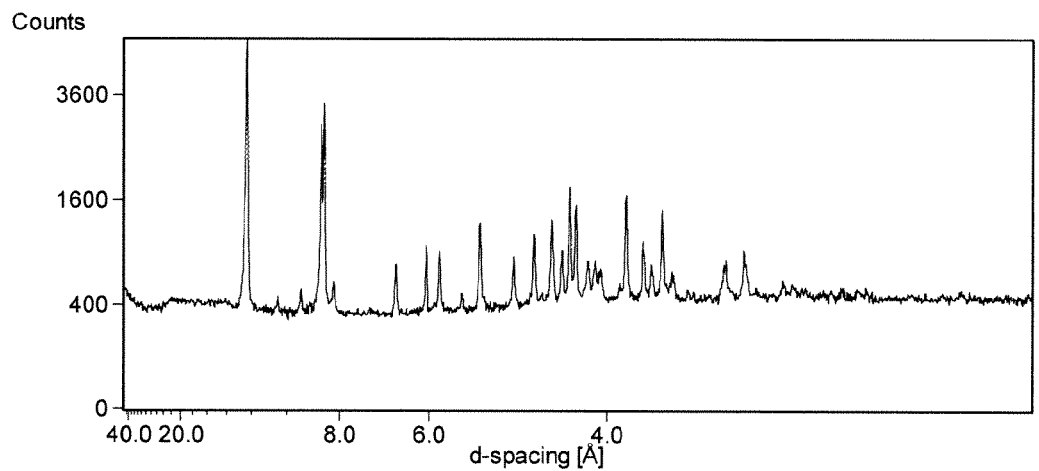

Figure 3: XRPD for Example 78 polymorph A
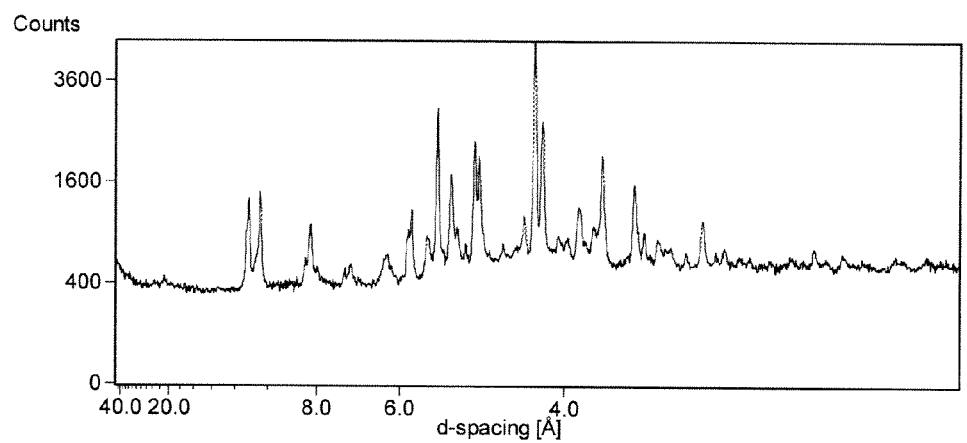
Figure 4: XRPD for Example 88 polymorph A
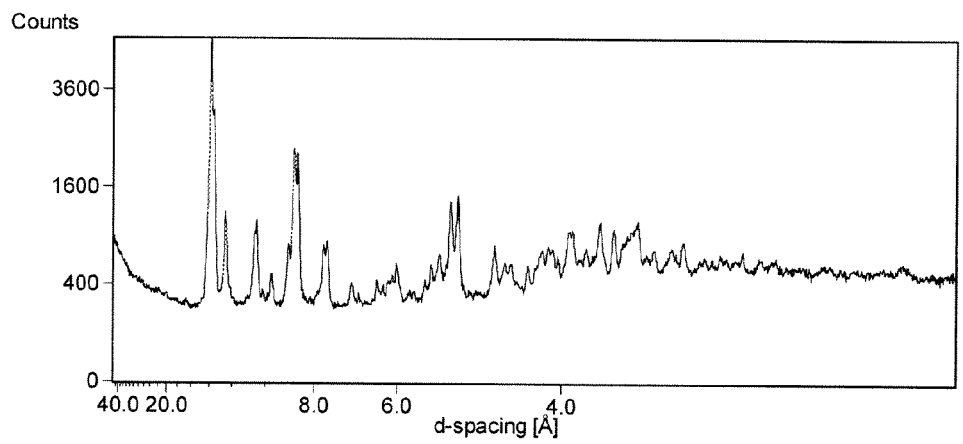

COMPOUNDS AND THEIR USES 707

RELATED APPLICATIONS

The present application claims the benefit of U.S. Provisional Application No. 60/910,235 (filed Apr. 5, 2007) and U.S. Provisional Application No. 60/979,523 (filed Oct. 12, 2007), both of which are hereby incorporated by reference in their entirety.

The present invention relates to isoquinolinone derivatives, processes for their preparation, pharmaceutical compositions containing them and their use in therapy.

BACKGROUND OF THE INVENTION

The essential function of the lungs requires a fragile structure with enormous exposure to the environment, including pollutants, microbes, allergens, and carcinogens. Host factors, resulting from interactions of lifestyle choices and genetic composition, influence the response to this exposure. Damage or infection to the lungs can give rise to a wide range of diseases of the respiratory system (or respiratory diseases). A number of these diseases are of great public health importance. Respiratory diseases include Acute Lung Injury, Acute Respiratory Distress Syndrome (ARDS), occupational lung disease, lung cancer, tuberculosis, fibrosis, pneumoconiosis, pneumonia, emphysema, Chronic Obstructive Pulmonary Disease (COPD) and asthma.

Among the most common of the respiratory diseases is asthma. Asthma is generally defined as an inflammatory disorder of the airways with clinical symptoms arising from intermittent airflow obstruction. It is characterised clinically by paroxysms of wheezing, dyspnea and cough. It is a chronic disabling disorder that appears to be increasing in prevalence and severity. It is estimated that 15% of children and 5% of adults in the population of developed countries suffer from asthma. Therapy should therefore be aimed at controlling symptoms so that normal life is possible and at the same time provide basis for treating the underlying inflammation.

COPD is a term which refers to a large group of lung diseases which can interfere with normal breathing. Current clinical guidelines define COPD as a disease state characterized by airflow limitation that is not fully reversible. The airflow limitation is usually both progressive and associated with an abnormal inflammatory response of the lungs to noxious particles and gases. The most important contributory source of such particles and gases, at least in the western world, is tobacco smoke. COPD patients have a variety of symptoms, including cough, shortness of breath, and excessive production of sputum; such symptoms arise from dysfunction of a number of cellular compartments, including neutrophils, macrophages, and epithelial cells. The two most important conditions covered by COPD are chronic bronchitis and emphysema.

Chronic bronchitis is a long-standing inflammation of the bronchi which causes increased production of mucous and other changes. The patients' symptoms are cough and expectoration of sputum. Chronic bronchitis can lead to more frequent and severe respiratory infections, narrowing and plugging of the bronchi, difficult breathing and disability.

Emphysema is a chronic lung disease which affects the alveoli and/or the ends of the smallest bronchi. The lung loses its elasticity and therefore these areas of the lungs become enlarged. These enlarged areas trap stale air and do not effectively exchange it with fresh air. This results in difficult breathing and may result in insufficient oxygen being delivered to the blood. The predominant symptom in patients with emphysema is shortness of breath.

Therapeutic agents used in the treatment of respiratory diseases include corticosteroids. Corticosteroids (also known as glucocorticosteroids or glucocorticoids) are potent anti-inflammatory agents. Whilst their exact mechanism of action is not clear, the end result of corticosteroid treatment is a decrease in the number, activity and movement of inflammatory cells into the bronchial submucosa, leading to decreased airway responsiveness. Corticosteroids may also cause reduced shedding of bronchial epithelial lining, vascular permeability, and mucus secretion. Whilst corticosteroid treatment can yield important benefits, the efficacy of these agents is often far from satisfactory, particularly in COPD. Moreover, whilst the use of steroids may lead to therapeutic effects, it is desirable to be able to use steroids in low doses to minimise the occurrence and severity of undesirable side effects that may be associated with regular administration. Recent studies have also highlighted the problem of the acquisition of steroid resistance amongst patients suffering from respiratory diseases. For example, cigarette smokers with asthma have been found to be insensitive to short term inhaled corticosteroid therapy, but the disparity of the response between smokers and non-smokers appears to be reduced with high dose inhaled corticosteroid (Tomlinson et al., Thorax 2005;60:282-287).

A further class of therapeutic agent used in the treatment of respiratory diseases are bronchodilators. Bronchodilators may be used to alleviate symptoms of respiratory diseases by relaxing the bronchial smooth muscles, reducing airway obstruction, reducing lung hyperinflation and decreasing shortness of breath. Types of bronchodilators in clinical use include $\beta_2$ adrenoceptor agonists, muscarinic receptor antagonists and methylxanthines. Bronchodilators are prescribed mainly for symptomatic relief and they are not considered to alter the natural history of respiratory diseases.

The serine/threonine kinase, p38, is a member of the stress and mitogen activated protein kinase family (SAPK/MAPK) and participates in intracellular signalling cascades involved in a number of responses associated with inflammatory processes. Four isoforms of p38 kinase are known to exist, identified as p38$\alpha$, p38$\beta$, p38$\gamma$ and p38$\delta$.

The p38 pathway is activated by stress (including tobacco smoke, infections or oxidative products) and pro-inflammatory cytokines (e.g. IL-1 or TNF-$\alpha$) and is involved in induction of cytokines such as TNF-$\alpha$, IL-1, IL-6 and matrix metalloprotease by bacterial lipopolysaccharide (LPS). Activation of p38 by dual phosphorylation of thr$^{180}$ and tyr$^{182}$ located in the activation loop is achieved by two dual specificity upstream MAP kinase kinases (MKK); MKK3 and MKK6. In turn p38 phosphorylates numerous targets including other kinases and transcription factors. In addition to effects on transcription, p38 is involved in the control of mRNA stability of several cytokines including TNF-$\alpha$, IL-3, IL-6 and IL-8. Thus through this cascade, p38 kinase is thought to play a significant role in the control of transcription and translation responsible for the induction of pro-inflammatory genes and the subsequent release of pro-inflammatory cytokines such as TNF-$\alpha$ from cells. This mechanism has been validated by investigation of the effects of inhibiting the p38 kinase enzyme on chronic inflammation and arthritis (Kumar et al, Nature Reviews Drug Discovery (2003) 2: 717-725). In particular, p38 kinase inhibitors have been described as potential agents for treating rheumatoid arthritis.

In addition to the links between p38 activation and chronic inflammation and arthritis, there is also data implicating a role for p38 in the pathogenesis of airway diseases in particular COPD and asthma. Stress stimuli (including tobacco smoke, infections or oxidative products) can cause inflammation within the lung environment. Inhibitors of p38 have been shown to inhibit LPS and ovalbumin induced airway TNF-α, IL-1-β, IL-6, IL-4, IL-5 and IL-13 (Haddad et al Br J Pharmacol, 2001, 132 (8), 1715; Underwood et al., Am J Physiol Lung cell Mol 200, 279, L895; Duan et al., 2005 Am J Respir Crit. Care Med, 171, 571; Escott et al Br J. Pharmacol., 2000, 131, 173; Underwood et al., J Pharmacol Exp Ther. 293, 281). Furthermore, they significantly inhibit neutrophilia and the release of MMP-9 in LPS, ozone or cigarette smoke models. There is also a significant body of preclinical data highlighting the potential benefits of inhibition of the p38 kinase that could be relevant in the lung (Lee et al. Immunopharmacology, 2000, 47, 185-200). Thus, therapeutic inhibition of p38 activation may be important in the regulation of airway inflammation. Efficacy is anticipated when p38 kinase inhibitors are administered either locally to the lung (for example by inhalation and intranasal delivery) or via systemic routes (for example, oral, intravenous and subcutaneous delivery).

BRIEF SUMMARY OF THE INVENTION

A particular aspect of the present invention relates to pharmaceutical compositions that are formulated to allow the compounds described herein to be administered locally to the lung. Advantages associated with such inhaled drug delivery include large lung surface area for dose absorption; rapid drug absorption, rapid onset of action; avoidance of the gastrointestinal tract and first-pass metabolism, lower dose and reduced side effects.

Known inhibitors of p38 kinase have been reviewed by G. J. Hanson in Expert Opinions on Therapeutic Patents, 1997, 7, 729-733, J Hynes et al Current Topics in Medicinal chemistry 2005, 5, 967-985, C Dominguez et al in Expert Opinions on Therapeutic Patents, 2005, 15, 801-816.

BRIEF DESCRIPTION OF THE DRAWINGS

FIG. 1 is an X-ray powder diffraction pattern of polymorph A Example 47
FIG. 2 is an X-ray powder diffraction pattern of polymorph A Example 60
FIG. 3 is an X-ray powder diffraction pattern of polymorph A Example 78
FIG. 4 is an X-ray powder diffraction pattern of polymorph A Example 88

DETAILED DESCRIPTION OF THE INVENTION

The present invention provides compounds of formula (I):

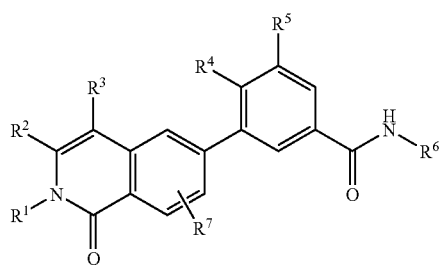

wherein:
$R^1$ is selected from H, $(C_1-C_6)$alkyl, $(C_2-C_6)$alkenyl, $(C_3-C_6)$alkynyl, $(CH_2)_a$—X—Ar and $(CR^{101}R^{102})_a$—X—Ar, wherein said $(C_1-C_6)$alkyl is optionally substituted with 1, 2 or 3 groups independently selected from —$(C_1-C_6)$alkoxy, -halo, —OH, -heterocycloalkyl, $(C_3-C_7)$cycloalkyl, and —$NR^8R^9$;

$R^2$ and $R^3$ are independently selected from H, halo, $(C_1-C_6)$alkyl, $(C_1-C_6)$alkoxy and $(CH_2)_d$—Y; wherein said $(C_1-C_6)$alkyl is optionally substituted with 1, 2 or 3 groups independently selected from —$(C_1-C_6)$alkoxy, -halo and —OH; and wherein said $(C_1-C_6)$alkoxy is optionally substituted with 1, 2 or 3 groups independently selected from -halo and —OH; and provided that when $R^2$ is $(CH_2)_d$—Y, $R^3$ is selected from H, halo, $(C_1-C_6)$alkyl and $(C_1-C_6)$alkoxy; and provided that when $R^3$ is $(CH_2)_d$—Y, $R^2$ is selected from H, halo, $(C_1-C_6)$alkyl and $(C_1-C_6)$alkoxy;

$R^4$ and $R^5$ are independently selected from H, $(C_1-C_6)$alkyl, $(C_1-C_6)$alkoxy, halo, $CF_3$, and CN;

$R^6$ is selected from $(C_1-C_6)$alkyl, $(C_1-C_6)$alkoxy, $(C_3-C_7)$cycloalkyl, aryl, heteroaryl and OH, wherein said $(C_1-C_6)$alkyl, $(C_1-C_6)$alkoxy, $(C_3-C_7)$cycloalkyl, aryl or heteroaryl group may be substituted by 1 or more halo atoms;

$R^7$ is selected from H, $(C_1-C_6)$alkyl, $(C_1-C_6)$alkoxy and halo;

Ar is an aryl or heteroaryl ring optionally substituted with 1, 2 or 3 groups independently selected from —$(C_1-C_6)$alkyl, —$(C_2-C_6)$alkenyl, —$(C_3-C_6)$alkynyl, —$(CH_2)_e$—O—$(C_1-C_6)$alkyl, —$(CH_2)_e$—S(O)$_f$$(C_1-C_6)$alkyl, —$(CH_2)_e$—N$(R^{10})$—$(C_1-C_6)$alkyl, —$(CH_2)_e$-Z-$(C_1-C_6)$alkyl, —O-heterocycloalkyl, —S—(O)$_b$-heterocycloalkyl, —N$(R^{11})$-heterocycloalkyl, —CN, —OH, -halo, -phenyl, -heterocycloalkyl, —$(C_3-C_7)$cycloalkyl, —C(O)NR$^8$R$^9$, —NR$^8$R$^9$, —C(O)OH and C(O)NR$^{10}$SO$_2$—$(C_1-C_6)$alkyl, wherein each occurrence of $(C_1-C_6)$alkyl is, independently, optionally substituted with 1, 2 or 3 groups independently selected from -halo, —OH, —$(C_1-C_6)$alkoxy, —NR$^{12}$R$^{13}$ and heterocycloalkyl;

X is selected from a single bond, O, NR$^{14}$ and S(O)$_g$;

Y is selected from heterocycloalkyl, O-heterocycloalkyl, O—$(CH_2)_h$—NR$^{16}$R$^{17}$, NR$^{18}$—$(CH_2)_h$—NR$^{16}$R$^{17}$, S—(O)$_j$-heterocycloalkyl, S—(O)$_j$—$(CH_2)_h$—NR$^{16}$R$^{17}$, NR$^{16}$R$^{17}$, NR$^{15}$C(O)R$^{16}$, NR$^{15}$SO$_2$R$^{16}$, C(O)NR$^{16}$R$^{17}$, OC(O)NR$^{16}$R$^{17}$, OC(O)R$^{16}$, C(O)OR$^{16}$ and NR$^{15}$C(O)OR$^{16}$;

Z is selected from C(O)N(R$^{18}$), N(R$^{18}$)C(O), C(O)O, OC(O), SO$_2$N(R$^{18}$), N(R$^{18}$)SO$_2$, OC(O)N(R$^{18}$), N(R$^{18}$)C(O)O, and OC(O)O;

R$^8$ and R$^9$ are independently selected from H and $(C_1-C_6)$alkyl, wherein said $(C_1-C_6)$alkyl is optionally substituted with 1, 2 or 3 groups independently selected from —$(C_1-C_6)$alkoxy, -halo, —OH and NR$^{19}$R$^{20}$; or R$^8$ and R$^9$ together with the nitrogen atom to which they are attached form a 3 to 7 membered ring, optionally containing a further heteroatom selected from NR$^{21}$, S and O; and optionally containing, where possible, 1 or 2 double bonds; wherein said ring is optionally substituted on carbon by 1 or 2 substituents independently selected from —$(C_1-C_6)$alkyl, $(C_1-C_6)$alkoxy, $(C_2-C_6)$alkenyl, —OH, —CN, halo and —NR$^{19}$R$^{20}$;

R$^{12}$ and R$^{13}$ are independently selected from H and $(C_1-C_6)$alkyl wherein said $(C_1-C_6)$alkyl is optionally substituted with —$(C_1-C_6)$alkoxy, —OH, -halo, —$(C_3-C_7)$cycloalkyl and —NR$^{22}$R$^{23}$; or R$^{12}$ and R$^{13}$ together with the nitrogen atom to which they are attached form a 3 to 7 membered ring, optionally containing a further heteroatom selected from NR$^{24}$, S and O; and optionally containing, where possible, 1 or 2 double bonds; wherein said ring is optionally substituted on carbon by 1 or 2 substituents independently selected from —($C_1$-$C_6$)alkyl, ($C_1$-$C_6$)alkoxy, ($C_2$-$C_6$)alkenyl, —OH, —CN, halo and —$NR^{22}R^{23}$;

$R^{16}$ is selected from H, ($C_1$-$C_6$)alkyl and heterocycloalkyl, wherein said ($C_1$-$C_6$)alkyl is optionally substituted with —($C_1$-$C_6$)alkoxy, —OH, -halo, —($C_3$-$C_7$)cycloalkyl and —$NR^{25}R^{26}$;

$R^{17}$ is selected from H and ($C_1$-$C_6$)alkyl;

or $R^{16}$ and $R^{17}$ together with the nitrogen atom to which they are attached form a 3 to 7 membered ring, optionally containing a further heteroatom selected from $NR^{27}$, S and O; and optionally containing, where possible, 1 or 2 double bonds; wherein said ring is optionally substituted on carbon by 1 or 2 substituents independently selected from —($C_1$-$C_6$)alkyl, ($C_1$-$C_6$)alkoxy, ($C_2$-$C_6$)alkenyl, —OH, —CN, halo and —$NR^{25}R^{26}$, wherein said —($C_1$-$C_6$)alkyl is optionally substituted by —OH.

$R^{25}$ and $R^{26}$ are independently selected from H and ($C_1$-$C_6$)alkyl wherein said ($C_1$-$C_6$)alkyl is optionally substituted with —($C_1$-$C_6$)alkoxy, —OH, -halo, —($C_3$-$C_7$)cycloalkyl and —$NR^{22}R^{23}$; or $R^{25}$ and $R^{26}$ together with the nitrogen atom to which they are attached form a 3 to 7 membered ring, optionally containing a further heteroatom selected from $NR^{24}$, S and O; and optionally containing, where possible, 1 or 2 double bonds; wherein said ring is optionally substituted on carbon by 1 or 2 substituents independently selected from —($C_1$-$C_6$)alkyl, ($C_1$-$C_6$)alkoxy, ($C_2$-$C_6$)alkenyl, —OH, —CN, halo and —$NR^{22}R^{23}$;

$R^{27}$ is selected from H, ($C_1$-$C_6$)alkyl and heterocycloalkyl, wherein said ($C_1$-$C_6$)alkyl is optionally substituted by a substituent selected from —OH, -halo and —$NR^{22}R^{23}$;

$R^{10}$, $R^{11}$, $R^{14}$, $R^{15}$, $R^{18}$, $R^{19}$, $R^{20}R^{21}$, $R^{22}$, $R^{23}$ and $R^{24}$ are independently selected from H and ($C_1$-$C_6$)alkyl;

a is selected from 0, 1, 2, 3, 4, 5 and 6;

d, e and h are independently selected from 0, 1, 2 and 3;

b, f, g and j are independently selected from 0, 1 and 2;

heterocycloalkyl is a C-linked 3 to 7 membered non-aromatic cyclic ring, containing from 1 to 2 $NR^{28}$ atoms, or one $NR^{28}$ atom and an S or an O atom, or one S atom, or one O atom; optionally containing, where possible, 1 or 2 double bonds; which unless otherwise stated, may be optionally substituted with 1 to 3 substituents independently selected from ($C_1$-$C_6$)alkyl, ($C_1$-$C_6$)alkoxy, ($C_2$-$C_6$)alkenyl, —OH, —CN, halo and —$NR^{29}R^{30}$, wherein said —($C_1$-$C_6$)alkyl is optionally substituted by —OH;

heteroaryl is a 5, 6, 9 or 10 membered aromatic ring, containing from 1 to 2 N atoms and, optionally, an $NR^{31}$ atom, or one $NR^{31}$ atom and an S or an O atom, or one S atom, or one O atom; which, unless otherwise stated, may be optionally substituted with 1-3 substituents independently selected from ($C_1$-$C_6$)alkyl, ($C_1$-$C_6$)alkoxy, ($C_2$-$C_6$)alkenyl, —OH, —CN, halo and —$NR^{38}R^{39}$;

cycloalkyl is a non-aromatic carbocyclic ring containing the requisite number of carbon atoms, optionally containing, where possible, up to 3 double bonds; which, unless otherwise stated, may be optionally substituted with 1 to 3 substituents independently selected from ($C_1$-$C_6$)alkyl, ($C_1$-$C_6$)alkoxy, ($C_2$-$C_6$)alkenyl, —OH, —CN, halo and —$NR^{34}R^{35}$;

aryl is an aromatic ring containing 6 or 10 carbon atoms; which unless otherwise stated, may be optionally substituted with 1 to 3 substituents independently selected from ($C_1$-$C_6$)alkyl, ($C_1$-$C_6$)alkoxy, ($C_2$-$C_6$)alkenyl, —OH, —CN, halo and —$NR^{36}R^{37}$;

$R^{28}$ and $R^{31}$ are each independently selected from H, ($C_1$-$C_6$)alkyl and —C(O)O—($C_1$-$C_6$)alkyl, wherein said ($C_1$-$C_6$)alkyl may be optionally substituted with ($C_1$-$C_6$)alkoxy, —OH, halo, ($C_3$-$C_7$)cycloalkyl and —$NR^{32}R^{33}$;

$R^{29}$, $R^{30}$, $R^{32}$ and $R^{33}$ are each independently selected from H and ($C_1$-$C_6$)alkyl;

$R^{34}$, $R^{35}$, $R^{36}$, $R^{37}$, $R^{38}$ and $R^{39}$ are each independently selected from H, and ($C_1$-$C_6$)alkyl;

$R^{101}$ is ($C_1$-$C_6$)alkyl;

$R^{102}$ is H or ($C_1$-$C_6$)alkyl;

or a pharmaceutically acceptable salt or N-oxide thereof.

In another aspect the present invention provides a prodrug of a compound of formula (I) as herein defined, or a pharmaceutically acceptable salt thereof.

In yet another aspect the present invention provides an N-oxide of a compound of formula (I) as herein defined, or a prodrug or pharmaceutically acceptable salt thereof.

It will be understood that certain compounds of the present invention may exist in solvated, for example hydrated, as well as unsolvated forms. It is to be understood that the present invention encompasses all such solvated forms.

A further embodiment of the present invention provides compounds of formula (I) wherein:

$R^1$ is selected from H, ($C_1$-$C_6$)alkyl, ($C_2$-$C_6$)alkenyl, ($C_3$-$C_6$)alkynyl and $(CH_2)_a$—Ar, wherein said ($C_1$-$C_6$)alkyl is optionally substituted with 1, 2 or 3 groups independently selected from —($C_1$-$C_6$)alkoxy, ($C_3$-$C_7$)cycloalkyl, -halo, —OH, and —$NR^8R^9$;

$R^2$ and $R^3$ are independently selected from H, halo, ($C_1$-$C_6$)alkyl and ($C_1$-$C_6$)alkoxy, wherein said ($C_1$-$C_6$)alkyl is optionally substituted with 1, 2 or 3 groups independently selected from —($C_1$-$C_6$)alkoxy, -halo and —OH; and wherein said ($C_1$-$C_6$)alkoxy is optionally substituted with 1, 2 or 3 groups independently selected from -halo and —OH;

Ar is an aryl ring optionally substituted with 1, 2 or 3 groups independently selected from —($C_1$-$C_6$)alkyl, —($C_2$-$C_6$)alkenyl, —O—($C_1$-$C_6$)alkyl, —S(O)$_j$($C_1$-$C_6$)alkyl, —N($R^{10}$)—($C_1$-$C_6$)alkyl, —CN, —OH, -halo, -phenyl, -heterocycloalkyl, —($C_3$-$C_7$)cycloalkyl and —$NR^8R^9$, wherein each occurrence of ($C_1$-$C_6$)alkyl is, independently, optionally substituted with 1, 2 or 3 groups independently selected from -halo, —OH, —($C_1$-$C_6$)alkoxy, —$NR^{12}R^{13}$;

and $R^4$, $R^5$, $R^6$, $R^7$, $R^8$, $R^9$, $R^{10}$, $R^{12}$, $R^{13}$, a, f and heterocycloalkyl are as previously defined above;

or a pharmaceutically acceptable salt thereof.

A further embodiment of the present invention provides compounds of formula (I) wherein:

$R^1$ is selected from H, ($C_1$-$C_6$)alkyl, ($C_2$-$C_6$)alkenyl, ($C_3$-$C_6$)alkynyl and $(CH_2)_a$—Ar, wherein said ($C_1$-$C_6$)alkyl is optionally substituted with 1, 2 or 3 groups independently selected from —($C_1$-$C_6$)alkoxy, ($C_3$-$C_7$)cycloalkyl, -halo, —OH, and —$NR^8R^9$;

$R^2$ is selected from selected from H, halo, ($C_1$-$C_6$)alkyl and ($C_1$-$C_6$)alkoxy;

$R^3$ is $(CH_2)_d$—Y; wherein d is 1 and Y is selected from heterocycloalkyl, O-heterocycloalkyl, O—$(CH_2)_h$—$NR^{16}R^{17}$, $NR^{18}$—$(CH_2)_h$—$NR^{16}R^{17}$, S—(O)$_j$-heterocycloalkyl, S—(O)$_j$—$(CH_2)_h$—$NR^{16}R^{17}$, $NR^{16}R^{17}$, $NR^{15}$C(O)$R^{16}$, $NR^{15}SO_2R^{16}$, C(O)$NR^{16}R^{17}$, OC(O)$NR^{16}R^{17}$, OC(O)$R^{16}$, C(O)O$R^{16}$ and $NR^{15}$C(O)O$R^{16}$;

$R^{16}$ is selected from H, ($C_1$-$C_6$)alkyl and heterocycloalkyl, wherein said ($C_1$-$C_6$)alkyl is optionally substituted with —($C_1$-$C_6$)alkoxy, —OH, -halo, —($C_3$-$C_7$)cycloalkyl and —$NR^{25}R^{26}$;

$R^{17}$ is selected from H and ($C_1$-$C_6$)alkyl;

or $R^{16}$ and $R^{17}$ together with the nitrogen atom to which they are attached form a 3 to 7 membered ring, optionally containing a further heteroatom selected from $NR^{27}$, S and O; and optionally containing, where possible, 1 or 2 double bonds; wherein said ring is optionally substituted on carbon by 1 or 2 substituents independently selected from —($C_1$-$C_6$)alkyl, ($C_1$-$C_6$)alkoxy, ($C_2$-$C_6$)alkenyl, —OH, —CN, halo and —$NR^{25}R^{26}$, wherein said —($C_1$-$C_6$)alkyl is optionally substituted by —OH;

$R^{27}$ is selected from H, ($C_1$-$C_6$)alkyl and heterocycloalkyl, wherein said ($C_1$-$C_6$)alkyl is optionally substituted by a substituent selected from —OH, -halo and —$NR^{22}R^{23}$;

$R^{18}$, $R^{22}$ and $R^{23}$ are independently selected from H and ($C_1$-$C_6$)alkyl;

or a pharmaceutically acceptable salt or N-oxide thereof.

The present invention also comprises the following embodiments and combinations thereof:

In one embodiment, the present invention provides a compound of formula (I) wherein $R^1$ is selected from ($C_1$-$C_6$)alkyl, ($C_2$-$C_6$)alkenyl, and $(CH_2)_a$—X—Ar, wherein said ($C_1$-$C_6$)alkyl is optionally substituted with 1 or 2 groups independently selected from ($C_1$-$C_6$)alkoxy, ($C_3$-$C_7$)cycloalkyl, halo, —OH, and —$NR^8R^9$.

In a further embodiment, the present invention provides a compound of formula (I) wherein $R^1$ is selected from ($C_1$-$C_6$)alkyl and $(CH_2)_a$—X—Ar, wherein said ($C_1$-$C_6$)alkyl is optionally substituted with 1 or 2 groups independently selected from halo, —OH, and —$NR^8R^9$.

In a yet further embodiment, the present invention provides a compound of formula (I) wherein $R^1$ is selected from ($C_1$-$C_6$)alkyl and $(CH_2)_a$—X—Ar, wherein said ($C_1$-$C_6$)alkyl is substituted with —$NR^8R^9$.

In a yet further embodiment, the present invention provides a compound of formula (I) wherein $R^1$ is selected from ($C_1$-$C_6$)alkyl and $(CH_2)_a$—X—Ar, wherein said ($C_1$-$C_6$)alkyl is substituted with a substituent selected from ($C_3$-$C_7$)cycloalkyl and —$NR^8R^9$.

In yet further still embodiment, the present invention provides a compound of formula (I) wherein $R^1$ is $(CH_2)_a$—X—Ar.

In a yet further embodiment, the present invention provides a compound of formula (I) wherein $R^1$ is selected from ($C_1$-$C_6$)alkyl and $(CH_2)_a$—X—Ar, wherein said ($C_1$-$C_6$)alkyl is substituted with a substituent selected from ($C_3$-$C_7$)cycloalkyl and —$NR^8R^9$.

In a yet further embodiment, the present invention provides a compound of formula (I) wherein Ar is a phenyl ring optionally substituted with 1 or 2 groups independently selected from —($C_1$-$C_6$)alkyl, —$(CH_2)_e$—O—($C_1$-$C_6$)alkyl, —$(CH_2)_e$—S(O)$_f$—($C_1$-$C_6$)alkyl, —OH, -halo, -heterocycloalkyl and —$NR^8R^9$, wherein each occurrence of ($C_1$-$C_6$)alkyl is, independently, optionally substituted with a group independently selected from -halo, —OH and —$NR^{12}R^{13}$.

In another yet further still embodiment, the present invention provides a compound of formula (I) wherein $R^1$ is selected from:

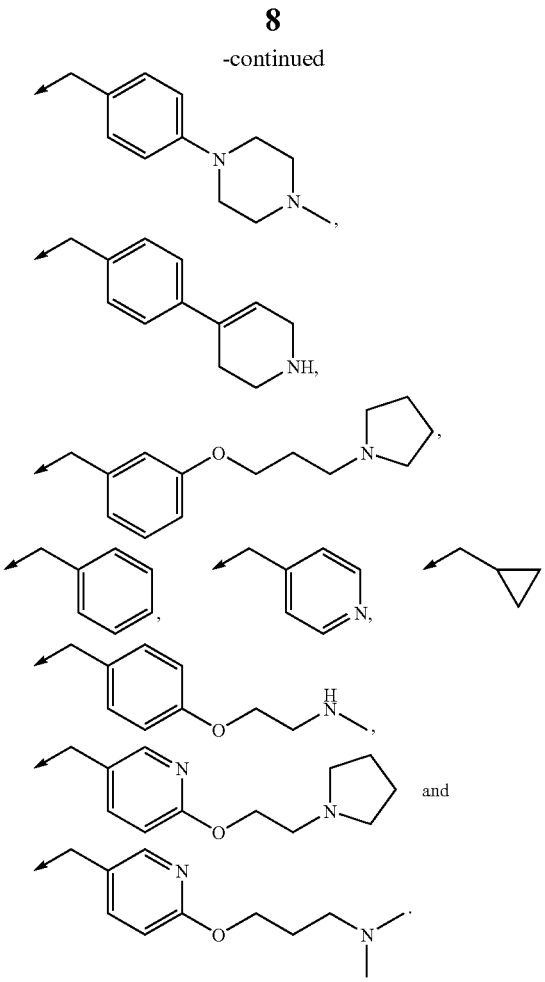

In another yet further still embodiment, the present invention provides a compound of formula (I) wherein $R^1$ is selected from:

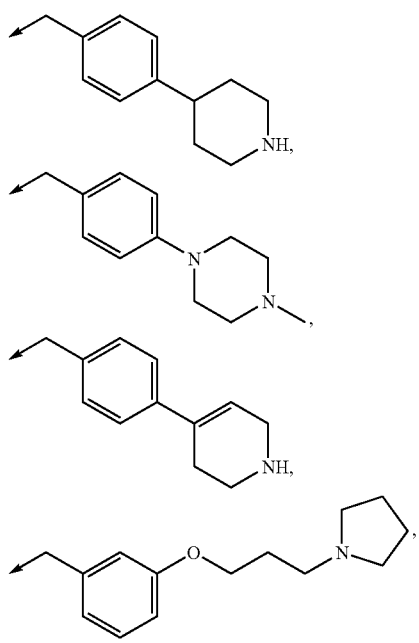

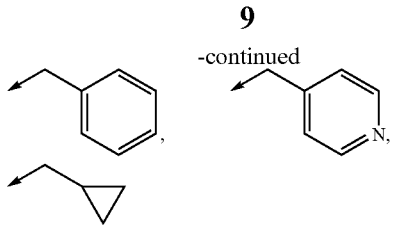

In another yet further still embodiment, the present invention provides a compound of formula (I) wherein $R^1$ is selected from:

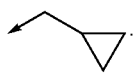

In one embodiment, the present invention provides a compound of formula (I) wherein $R^2$ and $R^3$ are independently selected from H, Cl, F, $(C_1$-$C_6)$alkyl, $(C_1$-$C_6)$alkoxy and $(CH_2)_d$—Y; provided that when $R^2$ is $(CH_2)_d$—Y, $R^3$ is selected only from H, Cl, F and $(C_1$-$C_6)$alkyl; and provided that when $R^3$ is $(CH_2)_d$—Y, $R^2$ is selected only from H, Cl, F and $(C_1$-$C_6)$alkyl.

In a further embodiment, the present invention provides a compound of formula (I) wherein $R^2$ is selected from H, F and $(C_1$-$C_6)$alkyl and $R^3$ is selected from H, F and $(C_1$-$C_6)$alkyl and $(CH_2)_d$—Y.

In a yet further embodiment, the present invention provides a compound of formula (I) wherein $R^3$ is selected from H, F and $(C_1$-$C_6)$alkyl and $R^2$ is selected from H, F, $(C_1$-$C_6)$alkyl and $(CH_2)_d$—Y.

In a yet further still embodiment, the present invention provides a compound of formula (I) wherein $R^2$ and $R^3$ are independently selected from H, F and $(C_1$-$C_6)$alkyl.

In a yet further still embodiment, the present invention provides a compound of formula (I) wherein $R^2$ is H and $R^3$ is $(CH_2)_d$—Y.

In a yet further still embodiment, the present invention provides a compound of formula (I) wherein $R^3$ represents $(CH_2)_d$—Y, d represents 0 and Y represents $C(O)NR^{16}R^{17}$.

In a yet further still embodiment, the present invention provides a compound of formula (I) wherein $R^3$ represents $(CH_2)_d$—Y, d represents 1 and Y represents $NR^{16}R^{17}$.

In a yet further still embodiment, the present invention provides a compound of formula (I) wherein $R^2$ represents H, $R^3$ represents $(CH_2)_d$—Y, d represents 1 and Y represents $NR^{16}R^{17}$.

In one embodiment, the present invention provides a compound of formula (I) wherein $R^4$ and $R^5$ are independently selected from H, $(C_1$-$C_4)$alkyl, halo and $CF_3$.

In another embodiment, the present invention provides a compound of formula (I) wherein $R^4$ and $R^5$ are independently selected from H, $(C_1$-$C_3)$alkyl and halo.

In yet another embodiment, the present invention provides a compound of formula (I) wherein $R^4$ is methyl and $R^5$ is selected from H and F.

In yet another embodiment, the present invention provides a compound of formula (I) wherein $R^4$ is methyl and $R^5$ is H.

In yet another embodiment, the present invention provides a compound of formula (I) wherein $R^4$ is methyl and $R^5$ is F.

In one embodiment, the present invention provides a compound of formula (I) wherein $R^6$ is selected from $(C_1$-$C_6)$alkyl, $(C_1$-$C_6)$alkoxy, $(C_3$-$C_7)$cycloalkyl and heteroaryl, each of which may be substituted by 1 or more halo atoms.

In another embodiment, the present invention provides a compound of formula (I) wherein $R^6$ is selected from $(C_1$-$C_3)$ alkyl, $(C_1$-$C_3)$alkoxy and $(C_3$-$C_7)$cycloalkyl.

In a further embodiment, the present invention provides a compound of formula (I) wherein $R^6$ is selected from ethyl, methoxy (—$OCH_3$) and $(C_3$-$C_7)$cycloalkyl.

In a further embodiment, the present invention provides a compound of formula (I) wherein $R^6$ is $(C_3$-$C_7)$cycloalkyl.

In a further embodiment, the present invention provides a compound of formula (I) wherein $R^6$ is cyclopropyl.

In one embodiment, the present invention provides a compound of formula (I) wherein $R^7$ is selected from H, $(C_1$-$C_4)$ alkyl and halo.

In another embodiment, the present invention provides a compound of formula (I) wherein $R^7$ is selected from H and $(C_1$-$C_4)$.

In a further embodiment, the present invention provides a compound of formula (I) wherein $R^7$ is H.

In one embodiment, the present invention provides a compound of formula (I) wherein Ar is an aryl or heteroaryl ring optionally substituted with 1, 2 or 3 groups independently selected from —$(C_1$-$C_6)$alkyl, —$(C_2$-$C_6)$alkenyl, —$(CH_2)_e$—O—$(C_1$-$C_6)$alkyl, —$(CH_2)_e$—$S(O)_f$—$(C_1$-$C_6)$ alkyl, —$(CH_2)_e$—$N(R^{10})$—$(C_1$-$C_6)$alkyl, —CN, —OH, -halo, -phenyl, -heterocycloalkyl, —$(C_3$-$C_7)$cycloalkyl and —$NR^8R^9$, wherein each occurrence of $(C_1$-$C_6)$alkyl is, independently, optionally substituted with 1, 2 or 3 groups independently selected from -halo, —OH, —$(C_1$-$C_6)$alkoxy, —$NR^{12}R^{13}$ and heterocycloalkyl;

In a further embodiment, the present invention provides a compound of formula (I) wherein Ar is an aryl ring optionally substituted with 1, 2 or 3 groups independently selected from —$(C_1$-$C_6)$alkyl, —$(CH_2)_e$—O—$(C_1$-$C_6)$alkyl, —$(CH_2)_e$—S $(O)_f$—$(C_1$-$C_6)$alkyl, —CN, —OH, -halo, -phenyl, -heterocycloalkyl, —$(C_3$-$C_7)$cycloalkyl and —$NR^8R^9$, wherein each occurrence of $(C_1$-$C_6)$alkyl is, independently, optionally substituted with 1, 2 or 3 groups independently selected from -halo, —OH and —$NR^{12}R^{13}$.

In a yet further embodiment, the present invention provides a compound of formula (I) wherein Ar is a phenyl ring optionally substituted with 1 or 2 groups independently selected from —$(C_1$-$C_6)$alkyl, —$(CH_2)_e$—O—$(C_1$-$C_6)$alkyl, —$(CH_2)_e$—$S(O)_f$—$(C_1$-$C_6)$alkyl, —OH, -halo, -heterocycloalkyl and —$NR^8R^9$, wherein each occurrence of $(C_1$-$C_6)$ alkyl is, independently, optionally substituted with a group independently selected from -halo, —OH and —$NR^{12}R^{13}$.

In one embodiment, the present invention provides a compound of formula (I) wherein X is a single bond.

In one embodiment, the present invention provides a compound of formula (I) wherein Y is selected from O—$(CH_2)_h$—$NR^{16}R^{17}$, $NR^{16}R^{17}$, $NR^{15}C(O)R^{16}$, $NR^{15}SO_2NR^{16}$, $C(O)NR^{16}R^{17}$, $OC(O)NR^{16}R^{17}$, $SO_2NR^{16}R^{17}$ and $NR^{15}C(O)OR^{16}$.

In one embodiment, the present invention provides a compound of formula (I) wherein $R^3$ is —$CH_2Y$ and Y is $NR^{16}R^{17}$.

In one embodiment, the present invention provides a compound of formula (I) wherein Y is $NR^{16}R^{17}$, wherein $R^{16}$ and $R^{17}$ together with the nitrogen atom to which they are attached form a 6 to 7 membered ring, optionally containing a further heteroatom $NR^{27}$, wherein said ring is optionally substituted on carbon by 1 or 2 substituents independently selected from —$(C_1$-$C_6)$alkyl wherein said —$(C_1$-$C_6)$alkyl is optionally substituted by —OH; and wherein $R^{27}$ is selected from H and $(C_1$-$C_6)$alkyl wherein said $(C_1$-$C_6)$alkyl is optionally substituted by —OH.

In one embodiment, the present invention provides a compound of formula (I) wherein Y is $NR^{16}R^{17}$, wherein $R^{16}$ and $R^{17}$ together with the nitrogen atom to which they are attached form a 6 to 7 membered ring containing a further heteroatom selected from $NR^{27}$, wherein said ring is optionally substituted on carbon by 1 or 2 substituents independently selected from —$(C_1-C_6)$alkyl wherein said —$(C_1-C_6)$alkyl is optionally substituted by —OH; and wherein $R^{27}$ is selected from H and $(C_1-C_6)$alkyl.

In one embodiment, the present invention provides a compound of formula (I) wherein Z is selected from $C(O)N(R^{18})$, $N(R^{18})C(O)$, $SO_2N(R^{18})$, $N(R^{18})SO_2$ and $OC(O)N(R^{18})$.

In one embodiment, the present invention provides a compound of formula (I) wherein $R^8$ and $R^9$ together with the nitrogen atom to which they are attached form a 5 or 6 membered ring, optionally containing a further heteroatom selected from $NR^{21}$ and O. In another embodiment, the present invention provides a compound of formula (I) wherein $R^8$ and $R^9$ together with the nitrogen atom to which they are attached form a 6 membered ring, containing a further heteroatom selected from $NR^{21}$ and O.

In yet another embodiment, the present invention provides a compound of formula (I) wherein $R^8$ and $R^9$ together with the nitrogen atom to which they are attached form a ring selected from azetidine, pyrrolidine, piperidine, homopiperidine, piperazine, homopiperazine, morpholine, homomorpholine and thiomorpholine.

In a yet further embodiment, the present invention provides a compound of formula (I) wherein $R^8$ and $R^9$ together with the nitrogen atom to which they are attached form N-methylpiperazinyl.

In one embodiment, the present invention provides a compound of formula (I) wherein $R^{12}$ and $R^{13}$ together with the nitrogen atom to which they are attached form a ring selected from azetidine, pyrrolidine, piperidine, homopiperidine, piperazine, homopiperazine, morpholine, homomorpholine and thiomorpholine.

In one embodiment, the present invention provides a compound of formula (I) wherein $R^{16}$ and $R^{17}$ together with the nitrogen atom to which they are attached form a ring selected from azetidine, pyrrolidine, piperidine, homopiperidine, piperazine, homopiperazine, morpholine, homomorpholine and thiomorpholine.

In one embodiment, the present invention provides a compound of formula (I) wherein $R^{25}$ and $R^{26}$ together with the nitrogen atom to which they are attached form a ring selected from azetidine, pyrrolidine, piperidine, homopiperidine, piperazine, homopiperazine, morpholine, homomorpholine and thiomorpholine.

In one embodiment, the present invention provides a compound of formula (I) wherein a is 1.

In one embodiment, the present invention provides a compound of formula (I) wherein d is 0 or 1.

In one embodiment, the present invention provides a compound of formula (I) wherein e is 0.

In one embodiment, the present invention provides a compound of formula (I) wherein h is 0 or 2.

In one embodiment, the present invention provides a compound of formula (I) wherein halo is selected from Cl and F.

In another embodiment, the present invention provides a compound of formula (I) wherein halo is F.

In one embodiment, the present invention provides a compound of formula (I) wherein heterocycloalkyl is selected from 1,2,3,6-tetrahydropyridin-4-yl, N-methyl piperidin-4-yl and piperindin-4-yl.

In one embodiment, the present invention provides a compound of formula (IC),

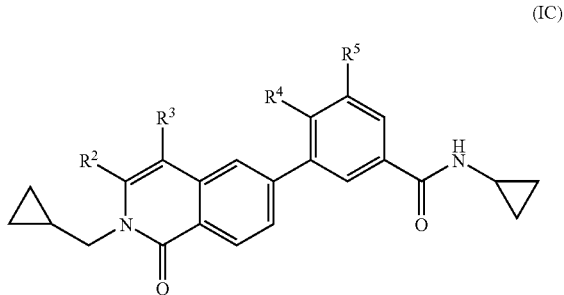

(IC)

wherein
$R^2$ is hydrogen;
$R^3$ is $(CH_2)_d$—Y;
$R^4$ is methyl;
$R^5$ is selected from H and F;
d is 0;
Y represents —$C(O)NR^{16}R^{17}$;
$R^{16}$ is —$(C_2-C_6)$alkyl substituted with —$NR^{25}R^{26}$;
$R^{17}$ is selected from H and —$(C_1-C_6)$alkyl
or
$R^{16}$ and $R^{17}$ together with the nitrogen atom to which they are attached form a 5 to 7 membered ring, optionally containing a further heteroatom $NR^{27}$, wherein $R^{27}$ is selected from H and —$(C_1-C_6)$alkyl wherein said —$(C_1-C_6)$alkyl is optionally substituted by —OH; and
wherein said ring is optionally substituted on carbon by —$NR^{25}R^{26}$;
$R^{25}$ and $R^{26}$ are independently selected from H and —$(C_1-C_6)$alkyl;
or a pharmaceutically acceptable salt or N-oxide thereof.

In one embodiment, the present invention provides a compound of formula (ID),

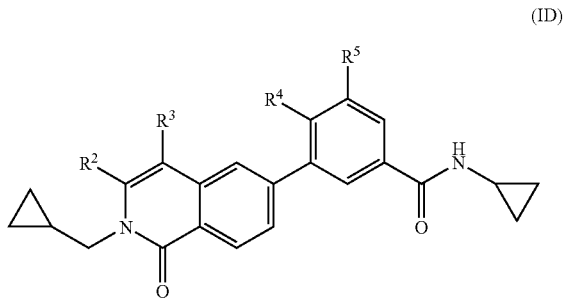

(ID)

wherein
$R^2$ is hydrogen;
$R^3$ is $(CH_2)_d$—Y;
$R^4$ is methyl;
$R^5$ is selected from H and F;
d is 1
Y represents $NR^{16}R^{17}$;
$R^{16}$ and $R^{17}$ together with the nitrogen atom to which they are attached form a 6 to 7 membered ring, optionally containing a further heteroatom $NR^{27}$, wherein said ring is optionally substituted on carbon by 1 or 2 substituents independently selected from —$(C_1-C_6)$alkyl wherein said —$(C_1-C_6)$alkyl is optionally substituted by —OH; and wherein $R^{27}$ is selected from H and $(C_1-C_6)$alkyl wherein said $(C_1-C_6)$alkyl is optionally substituted by —OH;
or a pharmaceutically acceptable salt or N-oxide thereof.

In one embodiment, the present invention provides a compound of formula (ID), wherein $R^5$ is H.

In one embodiment, the present invention provides a compound of formula (ID), wherein $R^5$ is F.

In one embodiment, the present invention provides a compound of formula (ID), wherein
$R^3$ is —$CH_2NR^{16}R^{17}$ wherein $R^{16}$ and $R^{17}$ together with the nitrogen atom to which they are attached form a 6 to 7 membered ring, containing a further heteroatom $NR^{27}$, wherein said ring is optionally substituted on carbon by —($C_1$-$C_2$)alkyl wherein said —($C_1$-$C_2$)alkyl is optionally substituted by —OH; and
$R^{27}$ is H.

In one embodiment, the present invention provides a compound of formula (IE), (IE)

wherein
$R^4$ is methyl:
$R^5$ is selected from H and F; and
$R^{103}$ is selected from H and —($C_1$-$C_4$)alkyl wherein said —($C_1$-$C_4$)alkyl is optionally substituted by —OH;
or a pharmaceutically acceptable salt or N-oxide thereof.

In one embodiment, the present invention provides a compound of formula (IE), wherein $R^5$ is H.

In one embodiment, the present invention provides a compound of formula (IE), wherein $R^5$ is F.

In one embodiment, the present invention provides a compound of formula (IE), wherein $R^{103}$ is selected from H, methyl, ethyl, —$CH_2OH$ and —$CH_2CH_2OH$.

In one embodiment, the present invention provides a compound of formula (IE) selected from:

(S)—N-Cyclopropyl-3-(2-(cyclopropylmethyl)-4-((3-methylpiperazin-1-yl)methyl)-1-oxo-1,2-dihydroisoquinolin-6-yl)-4-methylbenzamide (S)—N-Cyclopropyl-3-(2-(cyclopropylmethyl)-4-((3-methylpiperazin-1-yl)methyl)-1-oxo-1,2-dihydroisoquinolin-6-yl)-5-fluoro-4-methylbenzamide (R)—N-Cyclopropyl-3-(2-(cyclopropylmethyl)-4-((3-(hydroxymethyl)piperazin-1-yl)methyl)-1-oxo-1,2-dihydroisoquinolin-6-yl)-5-fluoro-4-methylbenzamide (R)—N-Cyclopropyl-3-(2-(cyclopropylmethyl)-4-((2-methylpiperazin-1-yl)methyl)-1-oxo-1,2-dihydroisoquinolin-6-yl)-5-fluoro-4-methylbenzamide N-Cyclopropyl-3-(2-(cyclopropylmethyl)-1-oxo-4-(piperazin-1-ylmethyl)-1,2-dihydroisoquinolin-6-yl)-5-fluoro-4-methylbenzamide, dihydrochloride (S)—N-Cyclopropyl-3-(2-(cyclopropylmethyl)-4-((3-(hydroxymethyl)piperazin-1-yl)methyl)-1-oxo-1,2-dihydroisoquinolin-6-yl)-5-fluoro-4-methylbenzamide (R)—N-Cyclopropyl-3-(2-(cyclopropylmethyl)-4-((3-methylpiperazin-1-yl)methyl)-1-oxo-1,2-dihydroisoquinolin-6-yl)-5-fluoro-4-methylbenzamide (S)—N-Cyclopropyl-3-(2-(cyclopropylmethyl)-4-((2-(hydroxymethyl)piperazin-1-yl)methyl)-1-oxo-1,2-dihydroisoquinolin-6-yl)-5-fluoro-4-methylbenzamide (S)—N-Cyclopropyl-3-(2-(cyclopropylmethyl)-4-((3-methylpiperazin-1-yl)methyl)-1-oxo-1,2-dihydroisoquinolin-6-yl)-5-fluoro-4-methylbenzamide (S)—N-Cyclopropyl-3-(2-(cyclopropylmethyl)-4-((3-(2-hydroxyethyl)piperazin-1-yl)methyl)-1-oxo-1,2-dihydroisoquinolin-6-yl)-5-fluoro-4-methylbenzamide and (S)—N-Cyclopropyl-3-(2-(cyclopropylmethyl)-4-((2-methylpiperazin-1-yl)methyl)-1-oxo-1,2-dihydroisoquinolin-6-yl)-5-fluoro-4-methylbenzamide or a pharmaceutically acceptable salt or N-oxide thereof.

In one embodiment, the present invention provides a compound of formula (IF), (IF)

wherein
$R^4$ is methyl:
$R^5$ is selected from H and F; and
$R^{103}$ is selected from H and —($C_1$-$C_4$)alkyl wherein said —($C_1$-$C_4$)alkyl is optionally substituted by —OH;
or a pharmaceutically acceptable salt or N-oxide thereof.

In one embodiment, the present invention provides a compound of formula (IF), wherein $R^5$ is H.

In one embodiment, the present invention provides a compound of formula (IF), wherein $R^5$ is F.

In one embodiment, the present invention provides a compound of formula (IF), wherein $R^{103}$ is selected from H, and —$CH_2OH$.

In one embodiment, the present invention provides a compound of formula (IF) selected from:

N-Cyclopropyl-3-(2-cyclopropylmethyl-4-[1,4]diazepan-1-ylmethyl-1-oxo-1,2-dihydro-isoquinolin-6-yl)-4-methylbenzamide 3-(4-((1,4-Diazepan-1-yl)methyl)-2-(cyclopropylmethyl)-1-oxo-1,2-dihydroisoquinolin-6-yl)-N-cyclopropyl-5-fluoro-4-methylbenzamide and N-Cyclopropyl-3-[2-cyclopropylmethyl-4-(5-hydroxymethyl-[1,4]diazepan-1-ylmethyl)-1-oxo-1,2-dihydro-isoquinolin-6-yl]-5-fluoro-4-methyl-benzamide or a pharmaceutically acceptable salt or N-oxide thereof.

In one embodiment, the present invention provides a compound of formula (IG),

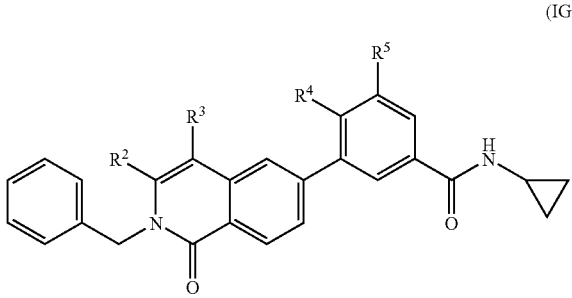

(IG)

wherein
R² is hydrogen;
R³ is (CH₂)_d—Y;
R⁴ is methyl;
R⁵ is selected from H and F;
d is 0;
Y represents —C(O)NR¹⁶R¹⁷;
R¹⁶ is —(C₂-C₆)alkyl substituted with —NR²⁵R²⁶;
R¹⁷ is selected from H and —(C₁-C₆)alkyl
or
R¹⁶ and R¹⁷ together with the nitrogen atom to which they are attached form a 5 to 7 membered ring, optionally containing a further heteroatom NR²⁷, wherein R²⁷ is selected from H and —(C₁-C₆)alkyl wherein said —(C₁-C₆)alkyl is optionally substituted by —OH; and
wherein said ring is optionally substituted on carbon by —NR²⁵R²⁶;
R²⁵ and R²⁶ are independently selected from H and —(C₁-C₆)alkyl;
or a pharmaceutically acceptable salt or N-oxide thereof.

In one embodiment, the present invention provides a compound of formula (IH),

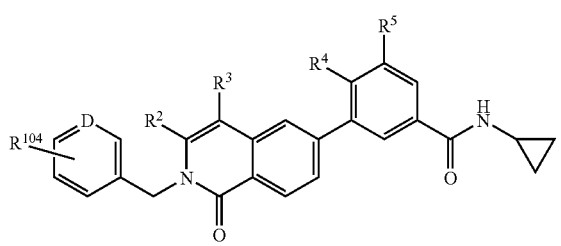

(IH)

wherein
R² and R³ are independently selected from hydrogen or methyl;
R⁴ is methyl;
R⁵ is H;
D is CH or N;
R¹⁰⁴ is —NR⁸R⁹, —O—(C₂-C₆)alkyl-NR¹²R¹³ or a C-linked 5 to 7 membered non-aromatic cyclic ring containing a further heteroatom NR²⁸;
R⁸ and R⁹ together with the nitrogen atom to which they are attached form a 5 to 7 membered ring, optionally containing a further heteroatom NR²¹;
R¹² and R¹³ are independently selected from H and (C₁-C₆)alkyl or R¹² and R¹³ together with the nitrogen atom to which they are attached form a 5 to 7 membered ring;

R²¹ and R²⁸ are each independently selected from H and (C₁-C₆)alkyl;
or a pharmaceutically acceptable salt thereof or N-oxide thereof.

In one embodiment, the present invention provides a compound of formula (IH), which is selected from:
N-Cyclopropyl-4-methyl-3-{2-[4-(4-methyl-piperazin-1-yl)-benzyl]-1-oxo-1,2-dihydro-isoquinolin-6-yl}-benzamide N-Cyclopropyl-4-methyl-3-[1-oxo-2-(4-piperidin-4-yl-benzyl)-1,2-dihydro-isoquinolin-6-yl]-benzamide N-Cyclopropyl-3-{2-[3-(3-dimethylamino-propoxy)-benzyl]-1-oxo-1,2-dihydro-isoquinolin-6-yl}-4-methyl-benzamide N-Cyclopropyl-3-(2-((6-(3-(dimethylamino)propoxy)pyridin-3-yl)methyl)-1-oxo-1,2-dihydroisoquinolin-6-yl)-4-methylbenzamide N-Cyclopropyl-3-(2-((6-(2-(dimethylamino)ethoxy)pyridin-3-yl)methyl)-1-oxo-1,2-dihydroisoquinolin-6-yl)-4-methylbenzamide N-Cyclopropyl-4-methyl-3-(1-oxo-2-((6-(2-(pyrrolidin-1-yl)ethoxy)pyridin-3-yl)methyl)-1,2-dihydroisoquinolin-6-yl)benzamide N-Cyclopropyl-3-(2-(4-(2-(dimethylamino)ethoxy)benzyl)-1-oxo-1,2-dihydroisoquinolin-6-yl)-4-methylbenzamide N-Cyclopropyl-4-methyl-3-{1-oxo-2-[3-(2-pyrrolidin-1-ylethoxy)benzyl]-1,2-dihydroisoquinolin-6-yl}benzamide N-Cyclopropyl-4-methyl-3-(2-{3-[2-(methylamino)ethoxy]benzyl}-1-oxo-1,2-dihydroisoquinolin-6-yl)benzamide and N-Cyclopropyl-4-methyl-3-(2-(4-(2-(methylamino)ethoxy)benzyl)-1-oxo-1,2-dihydroisoquinolin-6-yl)benzamide or a pharmaceutically acceptable salt or N-oxide thereof.

In one embodiment, the present invention provides a compound of formula (I), wherein:
R¹ is selected from H, (C₁-C₆)alkyl, (C₂-C₆)alkenyl and (CH₂)_a—X—Ar, wherein said (C₁-C₆)alkyl is optionally substituted with a substituent selected from (C₃-C₇)cycloalkyl and NR⁸R⁹;
R² and R³ are independently selected from H and (CH₂)_d—Y;
R⁴ and R⁵ are independently selected from H, (C₁-C₆)alkyl and halo;
R⁶ is selected from (C₁-C₆)alkyl, (C₁-C₆)alkoxy and (C₃-C₇)cycloalkyl;
R⁷ is H;
Ar is an aryl or heteroaryl ring optionally substituted with a substituent selected from —(C₁-C₆)alkyl, —(CH₂)_e—O—(C₁-C₆)alkyl,
—(CH₂)_e—S(O)_f—(C₁-C₆)alkyl, —(CH₂)_e-Z-(C₁-C₆)alkyl, -halo, -heterocycloalkyl, C(O)NR⁸R⁹ and —NR⁸R⁹, wherein each occurrence of (C₁-C₆)alkyl is, independently, optionally substituted with NR¹²R¹³;
X is a single bond;
Y is selected from NR¹⁶R¹⁷ and C(O)NR¹⁶R¹⁷;
Z is C(O)N(R¹⁸);
R⁸ and R⁹ are independently selected from H and (C₁-C₆)alkyl; or R⁸ and R⁹ together with the nitrogen atom to which they are attached form a 3 to 7 membered ring, optionally containing a further heteroatom selected from NR²¹;
R¹² and R¹³ are independently selected from H and (C₁-C₆)alkyl wherein said (C₁-C₆)alkyl is optionally substituted with —OH; or R¹² and R¹³ together with the nitrogen atom to which they are attached form a 3 to 7 membered ring, optionally containing a further heteroatom selected from NR²⁴;

R$^{16}$ is selected from H, (C$_1$-C$_6$)alkyl and heterocycloalkyl, wherein said (C$_1$-C$_6$)alkyl is optionally substituted with —NR$^{25}$R$^{26}$;

R$^{17}$ is selected from H and (C$_1$-C$_6$)alkyl;

or R$^{16}$ and R$^{17}$ together with the nitrogen atom to which they are attached form a 3 to 7 membered ring, optionally containing a further heteroatom selected from NR$^{27}$; wherein said ring is optionally substituted on carbon by NR$^{25}$R$^{26}$;

R$^{25}$ and R$^{26}$ are independently selected from H and (C$_1$-C$_6$)alkyl; or R$^{25}$ and R$^{26}$ together with the nitrogen atom to which they are attached form a 3 to 7 membered ring, optionally containing a further heteroatom selected from NR$^{24}$;

R$^{27}$ is selected from H and (C$_1$-C$_6$)alkyl wherein said (C$_1$-C$_6$)alkyl is optionally substituted with a substituent selected from —OH and —NR$^{22}$R$^{23}$;

R$^{18}$, R$^{21}$, R$^{22}$, R$^{23}$ and R$^{24}$ are independently selected from H and (C$_1$-C$_6$)alkyl;

a is selected from 0 and 1;

d and e are independently selected from 0 and 1;

f is 2;

heterocycloalkyl is a C-linked 3 to 7 membered non-aromatic cyclic ring, containing from 1 to 2 NR$^{28}$ atoms;

R$^{28}$ is selected from H, (C$_1$-C$_6$)alkyl and —C(O)O—(C$_1$-C$_6$)alkyl;

or a pharmaceutically acceptable salt thereof.

In one embodiment, the present invention provides a compound of formula (I), wherein:

R$^1$ is selected from H, (C$_1$-C$_6$)alkyl, (C$_2$-C$_6$)alkenyl and (CH$_2$)$_a$—X—Ar, wherein said (C$_1$-C$_6$)alkyl is optionally substituted with a substituent selected from (C$_3$-C$_7$)cycloalkyl and NR$^8$R$^9$;

R$^2$ and R$^3$ are independently selected from H and (CH$_2$)$_d$—Y;

R$^4$ and R$^5$ are independently selected from H, (C$_1$-C$_6$)alkyl and halo;

R$^6$ is selected from (C$_1$-C$_6$)alkyl, (C$_1$-C$_6$)alkoxy and (C$_3$-C$_7$)cycloalkyl;

R$^7$ is H;

Ar is an aryl or heteroaryl ring optionally substituted with a substituent selected from —(C$_1$-C$_6$)alkyl, —(CH$_2$)$_e$—O—(C$_1$-C$_6$)alkyl, —(CH$_2$)$_e$—S(O)$_f$—(C$_1$-C$_6$)alkyl, —(CH$_2$)$_e$-Z-(C$_1$-C$_6$)alkyl, -halo, -heterocycloalkyl, C(O)NR$^8$R$^9$ and —NR$^8$R$^9$, wherein each occurrence of (C$_1$-C$_6$)alkyl is, independently, optionally substituted with NR$^{12}$R$^{13}$;

X is a single bond;

Y is selected from NR$^{16}$R$^{17}$ and C(O)NR$^{16}$R$^{17}$;

Z is C(O)N(R$^{18}$);

R$^8$ and R$^9$ are independently selected from H and (C$_1$-C$_6$)alkyl; or R$^8$ and R$^9$ together with the nitrogen atom to which they are attached form a 3 to 7 membered ring, optionally containing a further heteroatom selected from NR$^{21}$;

R$^{12}$ and R$^{13}$ are independently selected from H and (C$_1$-C$_6$)alkyl wherein said (C$_1$-C$_6$)alkyl is optionally substituted with —OH; or R$^{12}$ and R$^{13}$ together with the nitrogen atom to which they are attached form a 3 to 7 membered ring, optionally containing a further heteroatom selected from NR$^{24}$;

R$^{16}$ is selected from H, (C$_1$-C$_6$)alkyl and heterocycloalkyl, wherein said (C$_1$-C$_6$)alkyl is optionally substituted with —NR$^{25}$R$^{26}$;

R$^{17}$ is selected from H and (C$_1$-C$_6$)alkyl;

or R$^{16}$ and R$^{17}$ together with the nitrogen atom to which they are attached form a 3 to 7 membered ring, optionally containing a further heteroatom selected from NR$^{27}$, S and O; and optionally containing, where possible, 1 or 2 double bonds; wherein said ring is optionally substituted on carbon by 1 or 2 substituents independently selected from —(C$_1$-C$_6$)alkyl, (C$_1$-C$_6$)alkoxy, (C$_2$-C$_6$)alkenyl, —OH, —CN, halo and —NR$^{25}$R$^{26}$, wherein said —(C$_1$-C$_6$)alkyl is optionally substituted by —OH;

R$^{25}$ and R$^{26}$ are independently selected from H and (C$_1$-C$_6$)alkyl; or R$^{25}$ and R$^{26}$ together with the nitrogen atom to which they are attached form a 3 to 7 membered ring, optionally containing a further heteroatom selected from NR$^{24}$;

R$^{27}$ is selected from H and (C$_1$-C$_6$)alkyl wherein said (C$_1$-C$_6$)alkyl is optionally substituted with a substituent selected from —OH and —NR$^{22}$R$^{23}$;

R$^{18}$, R$^{21}$, R$^{22}$, R$^{23}$ and R$^{24}$ are independently selected from H and (C$_1$-C$_6$)alkyl;

a is selected from 0 and 1;

d and e are independently selected from 0 and 1;

f is 2;

heterocycloalkyl is a C-linked 3 to 7 membered non-aromatic cyclic ring, containing from 1 to 2 NR$^{28}$ atoms;

R$^{28}$ is selected from H, (C$_1$-C$_6$)alkyl and —C(O)O—(C$_1$-C$_6$)alkyl;

or a pharmaceutically acceptable salt thereof.

In one embodiment, the present invention provides a compound of formula (IA),

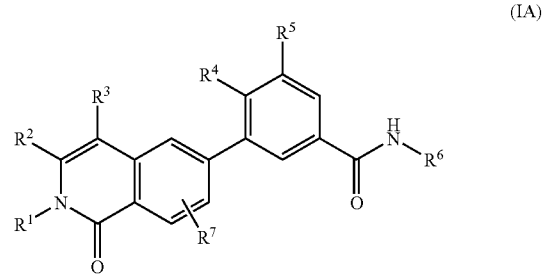

wherein:

R$^1$ is selected from H, (C$_1$-C$_6$)alkyl, (C$_2$-C$_6$)alkenyl, (C$_3$-C$_6$)alkynyl and (CH$_2$)$_a$—X—Ar, wherein said (C$_1$-C$_6$)alkyl is optionally substituted with 1, 2 or 3 groups independently selected from —(C$_1$-C$_6$)alkoxy, -halo, —OH, -heterocycloalkyl and —NR$^8$R$^9$;

R$^2$ and R$^3$ are independently selected from H, halo, (C$_1$-C$_6$)alkyl, (C$_1$-C$_6$)alkoxy and (CH$_2$)$_d$—Y; wherein said (C$_1$-C$_6$)alkyl is optionally substituted with 1, 2 or 3 groups independently selected from —(C$_1$-C$_6$)alkoxy, -halo and —OH; and wherein said (C$_1$-C$_6$)alkoxy is optionally substituted with 1, 2 or 3 groups independently selected from -halo and —OH; and provided that when R$^2$ is (CH$_2$)$_d$—Y, R$^3$ is selected from H, halo, (C$_1$-C$_6$)alkyl and (C$_1$-C$_6$)alkoxy; and provided that when R$^3$ is (CH$_2$)$_d$—Y, R$^2$ is selected from H, halo, (C$_1$-C$_6$)alkyl and (C$_1$-C$_6$)alkoxy;

R$^4$ and R$^5$ are independently selected from H, (C$_1$-C$_6$)alkyl, (C$_1$-C$_6$)alkoxy, halo, CF$_3$, and CN;

R$^6$ is selected from (C$_1$-C$_6$)alkyl, (C$_1$-C$_6$)alkoxy, (C$_3$-C$_7$)cycloalkyl, aryl, heteroaryl and OH, wherein said (C$_1$-C$_6$)alkyl, (C$_1$-C$_6$)alkoxy, (C$_3$-C$_7$)cycloalkyl, aryl or heteroaryl group may be substituted by 1 or more halo atoms;

R$^7$ is selected from H, (C$_1$-C$_6$)alkyl, (C$_1$-C$_6$)alkoxy and halo;

Ar is an aryl or heteroaryl ring optionally substituted with 1, 2 or 3 groups independently selected from —(C$_1$-C$_6$)alkyl, —(C$_2$-C$_6$)alkenyl, —(C$_3$-C$_6$)alkynyl, —(CH$_2$)$_e$—O—(C$_1$-C$_6$)alkyl, —(CH$_2$)$_e$—S(O)$_f$—(C$_1$-C$_6$)alkyl, —(CH$_2$)$_e$—N(R$^{10}$)—(C$_1$-C$_6$)alkyl, —(CH$_2$)$_e$-Z-(C$_1$-C$_6$)

alkyl, —O-heterocycloalkyl, —S—(O)$_b$-heterocycloalkyl, —N(R$^{11}$)-heterocycloalkyl, —CN, —OH, -halo, -phenyl, -heterocycloalkyl, —(C$_3$-C$_7$)cycloalkyl and —NR$^8$R$^9$, wherein each occurrence of (C$_1$-C$_6$)alkyl is, independently, optionally substituted with 1, 2 or 3 groups independently selected from -halo, —OH, —(C$_1$-C$_6$)alkoxy, —NR$^{12}$R$^{13}$ and heterocycloalkyl;

X is selected from a single bond, O, NR$^{14}$ and S(O)$_g$;

Y is selected from heterocycloalkyl, O-heterocycloalkyl, O—(CH$_2$)$_h$—NR$^{16}$R$^{17}$, S—(O)$_j$-heterocycloalkyl, S—(O)$_j$—(CH$_2$)$_h$—NR$^{16}$R$^{17}$, NR$^{16}$R$^{17}$, NR$^{15}$C(O)R$^{16}$, NR$^{15}$SO$_2$R$^{16}$, C(O)NR$^{16}$R$^{17}$, OC(O)NR$^{16}$R$^{17}$, OC(O)R$^{16}$, C(O)OR$^{16}$ and NR$^{15}$C(O)OR$^{16}$;

Z is selected from C(O)N(R$^{18}$), N(R$^{18}$)C(O), C(O)O, OC(O), SO$_2$N(R$^{18}$), N(R$^{18}$)SO$_2$, OC(O)N(R$^{18}$), N(R$^{18}$)C(O)O, and OC(O)O;

R$^8$ and R$^9$ are independently selected from H and (C$_1$-C$_6$)alkyl, wherein said (C$_1$-C$_6$)alkyl is optionally substituted with 1, 2 or 3 groups independently selected from —(C$_1$-C$_6$)alkoxy, -halo, —OH and NR$^{19}$R$^{20}$; or R$^8$ and R$^9$ together with the nitrogen atom to which they are attached form a 3 to 7 membered ring, optionally containing a further heteroatom selected from NR$^{21}$, S and O; and optionally containing, where possible, 1 or 2 double bonds; wherein said ring is optionally substituted on carbon by 1 or 2 substituents independently selected from —(C$_1$-C$_6$)alkyl, (C$_1$-C$_6$)alkoxy, (C$_2$-C$_6$)alkenyl, —OH, —CN, halo and —NR$^{19}$R$^{20}$;

R$^{12}$ and R$^{13}$ are independently selected from H and (C$_1$-C$_6$)alkyl wherein said (C$_1$-C$_6$)alkyl is optionally substituted with —(C$_1$-C$_6$)alkoxy, —OH, -halo, —(C$_3$-C$_7$)cycloalkyl and —NR$^{22}$R$^{23}$;

or R$^{12}$ and R$^{13}$ together with the nitrogen atom to which they are attached form a 3 to 7 membered ring, optionally containing a further heteroatom selected from NR$^{24}$, S and O; and optionally containing, where possible, 1 or 2 double bonds; wherein said ring is optionally substituted on carbon by 1 or 2 substituents independently selected from —(C$_1$-C$_6$)alkyl, (C$_1$-C$_6$)alkoxy, (C$_2$-C$_6$)alkenyl, —OH, —CN, halo and —NR$^{22}$R$^{23}$;

R$^{16}$ is selected from H, (C$_1$-C$_6$)alkyl and heterocycloalkyl, wherein said (C$_1$-C$_6$)alkyl is optionally substituted with —(C$_1$-C$_6$)alkoxy, —OH, -halo, —(C$_3$-C$_7$)cycloalkyl and —NR$^{25}$R$^{26}$;

R$^{17}$ is selected from H and (C$_1$-C$_6$)alkyl;

or R$^{16}$ and R$^{17}$ together with the nitrogen atom to which they are attached form a 3 to 7 membered ring, optionally containing a further heteroatom selected from NR$^{27}$, S and O; and optionally containing, where possible, 1 or 2 double bonds; wherein said ring is optionally substituted on carbon by 1 or 2 substituents independently selected from —(C$_1$-C$_6$)alkyl, (C$_1$-C$_6$)alkoxy, (C$_2$-C$_6$)alkenyl, —OH, —CN, halo and —NR$^{25}$R$^{26}$;

R$^{10}$, R$^{11}$, R$^{14}$, R$^{15}$, R$^{18}$, R$^{19}$, R$^{20}$R$^{21}$, R$^{22}$, R$^{23}$, R$^{24}$, R$^{25}$, R$^{26}$ and R$^{27}$ are independently selected from H and (C$_1$-C$_6$)alkyl;

a is selected from 0, 1, 2, 3, 4, 5 and 6;

d, e and h are independently selected from 0, 1, 2 and 3;

b, f, g and j are independently selected from 0, 1 and 2;

heterocycloalkyl is a C-linked 3 to 7 membered non-aromatic cyclic ring, containing from 1 to 2 NR$^{28}$ atoms, or one NR$^{28}$ atom and an S or an O atom, or one S atom, or one O atom; optionally containing, where possible, 1 or 2 double bonds; and optionally substituted with 1 to 3 substituents independently selected from (C$_1$-C$_6$)alkyl, (C$_1$-C$_6$)alkoxy, (C$_2$-C$_6$)alkenyl, —OH, —CN, halo and —NR$^{29}$R$^{30}$;

heteroaryl is a 5, 6, 9 or 10 membered aromatic ring, containing from 1 to 2 N atoms and, optionally, an NR$^{31}$ atom, or one NR$^{31}$ atom and an S or an O atom, or one S atom, or one O atom;

R$^{28}$ and R$^{31}$ are each independently selected from H, (C$_1$-C$_6$)alkyl and —C(O)O—(C$_1$-C$_6$)alkyl, wherein said (C$_1$-C$_6$)alkyl may be optionally substituted with (C$_1$-C$_6$)alkoxy, —OH, halo, (C$_3$-C$_7$)cycloalkyl and —NR$^{32}$R$^{33}$;

R$^{29}$, R$^{30}$, R$^{32}$ and R$^{33}$ are each independently selected from H and (C$_1$-C$_6$)alkyl;

or a pharmaceutically acceptable salt thereof.

In a further aspect the present invention provides a compound of formula (IB):

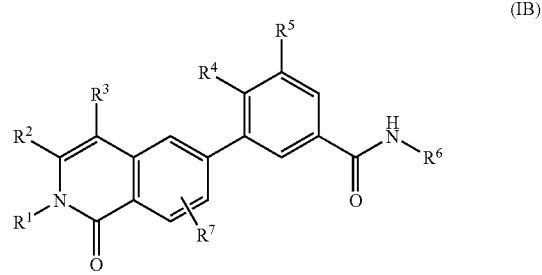

wherein:

R$^1$ is selected from H, (C$_1$-C$_6$)alkyl, (C$_2$-C$_6$)alkenyl, (C$_3$-C$_6$)alkynyl and (CH$_2$)$_a$—X—Ar, wherein said (C$_1$-C$_6$)alkyl is optionally substituted with 1, 2 or 3 groups independently selected from —(C$_1$-C$_6$)alkoxy, -halo, —OH, -heterocycloalkyl, (C$_3$-C$_7$)cycloalkyl and —NR$^8$R$^9$;

R$^2$ and R$^3$ are independently selected from H, halo, (C$_1$-C$_6$)alkyl, (C$_1$-C$_6$)alkoxy and (CH$_2$)$_d$—Y; wherein said (C$_1$-C$_6$)alkyl is optionally substituted with 1, 2 or 3 groups independently selected from —(C$_1$-C$_6$)alkoxy, -halo and —OH; and wherein said (C$_1$-C$_6$)alkoxy is optionally substituted with 1, 2 or 3 groups independently selected from -halo and —OH; and provided that when R$^2$ is (CH$_2$)$_d$—Y, R$^3$ is selected from H, halo, (C$_1$-C$_6$)alkyl and (C$_1$-C$_6$)alkoxy; and provided that when R$^3$ is (CH$_2$)$_d$—Y, R$^2$ is selected from H, halo, (C$_1$-C$_6$)alkyl and (C$_1$-C$_6$)alkoxy;

R$^4$ and R$^5$ are independently selected from H, (C$_1$-C$_6$)alkyl, (C$_1$-C$_6$)alkoxy, halo, CF$_3$, and CN;

R$^6$ is selected from (C$_1$-C$_6$)alkyl, (C$_1$-C$_6$)alkoxy, (C$_3$-C$_7$)cycloalkyl, aryl, heteroaryl and OH, wherein said (C$_1$-C$_6$)alkyl, (C$_1$-C$_6$)alkoxy, (C$_3$-C$_7$)cycloalkyl, aryl or heteroaryl group may be substituted by 1 or more halo atoms;

R$^7$ is selected from H, (C$_1$-C$_6$)alkyl, (C$_1$-C$_6$)alkoxy and halo;

Ar is an aryl or heteroaryl ring optionally substituted with 1, 2 or 3 groups independently selected from —(C$_1$-C$_6$)alkyl, —(C$_2$-C$_6$)alkenyl, —(C$_3$-C$_6$)alkynyl, —(CH$_2$)$_e$—O—(C$_1$-C$_6$)alkyl, —(CH$_2$)$_e$—S(O)$_f$—(C$_1$-C$_6$)alkyl, —(CH$_2$)$_e$—N(R$^{10}$)—(C$_1$-C$_6$)alkyl, —(CH$_2$)$_e$-Z-(C$_1$-C$_6$)alkyl, —O-heterocycloalkyl, —S—(O)$_b$-heterocycloalkyl, —N(R$^{11}$)-heterocycloalkyl, —CN, —OH, -halo, -phenyl, -heterocycloalkyl, —(C$_3$-C$_7$)cycloalkyl, C(O)NR$^8$R$^9$ and —NR$^8$R$^9$, wherein each occurrence of (C$_1$-C$_6$)alkyl is, independently, optionally substituted with 1, 2 or 3 groups independently selected from -halo, —OH, —(C$_1$-C$_6$)alkoxy, —NR$^{12}$R$^{13}$ and heterocycloalkyl;

X is selected from a single bond, O, NR$^{14}$ and S(O)$_g$;

Y is selected from heterocycloalkyl, O-heterocycloalkyl, O—(CH$_2$)$_h$—NR$^{16}$R$^{17}$, S—(O)$_j$-heterocycloalkyl, S—(O)$_j$—(CH$_2$)$_h$—NR$^{16}$R$^{17}$, NR$^{16}$R$^{17}$, NR$^{15}$C(O)R$^{16}$, NR$^{15}$SO$_2$R$^{16}$, C(O)NR$^{16}$R$^{17}$, OC(O)NR$^{16}$R$^{17}$, OC(O)

R$^{16}$, C(O)OR$^{16}$ and NR$^{15}$C(O)OR$^{16}$; Z is selected from C(O)N(R$^{18}$), N(R$^{18}$)C(O), C(O)O, OC(O), SO$_2$N(R$^{18}$), N(R$^{18}$)SO$_2$, OC(O)N(R$^{18}$), N(R$^{18}$)C(O)O, and OC(O)O;

R$^8$ and R$^9$ are independently selected from H and (C$_1$-C$_6$)alkyl, wherein said (C$_1$-C$_6$)alkyl is optionally substituted with 1, 2 or 3 groups independently selected from —(C$_1$-C$_6$)alkoxy, -halo, —OH and NR$^{19}$R$^{20}$; or R$^8$ and R$^9$ together with the nitrogen atom to which they are attached form a 3 to 7 membered ring, optionally containing a further heteroatom selected from NR$^{21}$, S and O; and optionally containing, where possible, 1 or 2 double bonds; wherein said ring is optionally substituted on carbon by 1 or 2 substituents independently selected from —(C$_1$-C$_6$)alkyl, (C$_1$-C$_6$)alkoxy, (C$_2$-C$_6$)alkenyl, —OH, —CN, halo and —NR$^{19}$R$^{20}$;

R$^{12}$ and R$^{13}$ are independently selected from H and (C$_1$-C$_6$)alkyl wherein said (C$_1$-C$_6$)alkyl is optionally substituted with —(C$_1$-C$_6$)alkoxy, —OH, -halo, —(C$_3$-C$_7$)cycloalkyl and —NR$^{22}$R$^{23}$; or R$^{12}$ and R$^{13}$ together with the nitrogen atom to which they are attached form a 3 to 7 membered ring, optionally containing a further heteroatom selected from NR$^{24}$, S and O; and optionally containing, where possible, 1 or 2 double bonds; wherein said ring is optionally substituted on carbon by 1 or 2 substituents independently selected from —(C$_1$-C$_6$)alkyl, (C$_1$-C$_6$)alkoxy, (C$_2$-C$_6$)alkenyl, —OH, —CN, halo and —NR$^{22}$R$^{23}$;

R$^{16}$ is selected from H, (C$_1$-C$_6$)alkyl and heterocycloalkyl, wherein said (C$_1$-C$_6$)alkyl is optionally substituted with —(C$_1$-C$_6$)alkoxy, —OH, -halo, —(C$_3$-C$_7$)cycloalkyl and —NR$^{25}$R$^{26}$ R$^{17}$ is selected from H and (C$_1$-C$_6$)alkyl;

or R$^{16}$ and R$^{17}$ together with the nitrogen atom to which they are attached form a 3 to 7 membered ring, optionally containing a further heteroatom selected from NR$^{27}$, S and O; and optionally containing, where possible, 1 or 2 double bonds; wherein said ring is optionally substituted on carbon by 1 or 2 substituents independently selected from —(C$_1$-C$_6$)alkyl, (C$_1$-C$_6$)alkoxy, (C$_2$-C$_6$)alkenyl, —OH, —CN, halo and —NR$^{25}$R$^{26}$;

R$^{25}$ and R$^{26}$ are independently selected from H and (C$_1$-C$_6$)alkyl wherein said (C$_1$-C$_6$)alkyl is optionally substituted with —(C$_1$-C$_6$)alkoxy, —OH, -halo, —(C$_3$-C$_7$)cycloalkyl and —NR$^{22}$R$^{23}$;

or R$^{25}$ and R$^{26}$ together with the nitrogen atom to which they are attached form a 3 to 7 membered ring, optionally containing a further heteroatom selected from NR$^{24}$, S and O; and optionally containing, where possible, 1 or 2 double bonds; wherein said ring is optionally substituted on carbon by 1 or 2 substituents independently selected from —(C$_1$-C$_6$)alkyl, (C$_1$-C$_6$)alkoxy, (C$_2$-C$_6$)alkenyl, —OH, —CN, halo and —NR$^{22}$R$^{23}$;

R$^{27}$ is selected from H, (C$_1$-C$_6$)alkyl and heterocycloalkyl, wherein said (C$_1$-C$_6$)alkyl is optionally substituted by a substituent selected from —OH, -halo and —NR$^{22}$R$^{23}$R$^{10}$, R$^{11}$, R$^{14}$, R$^{15}$, R$^{18}$, R$^{19}$, R$^{20}$R$^{21}$, R$^{22}$, R$^{23}$ and R$^{24}$ are independently selected from H and (C$_1$-C$_6$)alkyl;

a is selected from 0, 1, 2, 3, 4, 5 and 6;

d, e and h are independently selected from 0, 1, 2 and 3;

b, f, g and j are independently selected from 0, 1 and 2;

heterocycloalkyl is a C-linked 3 to 7 membered non-aromatic cyclic ring, containing from 1 to 2 NR$^{28}$ atoms, or one NR$^{28}$ atom and an S or an O atom, or one S atom, or one O atom; optionally containing, where possible, 1 or 2 double bonds; and optionally substituted with 1 to 3 substituents independently selected from (C$_1$-C$_6$)alkyl, (C$_1$-C$_6$)alkoxy, (C$_2$-C$_6$)alkenyl, —OH, —CN, halo and —NR$^{29}$R$^{30}$;

heteroaryl is a 5, 6, 9 or 10 membered aromatic ring, containing from 1 to 2 N atoms and, optionally, an NR$^{31}$ atom, or one NR$^{31}$ atom and an S or an O atom, or one S atom, or one O atom;

R$^{28}$ and R$^{31}$ are each independently selected from H, (C$_1$-C$_6$)alkyl and —C(O)O—(C$_1$-C$_6$)alkyl, wherein said (C$_1$-C$_6$)alkyl may be optionally substituted with (C$_1$-C$_6$)alkoxy, —OH, halo, (C$_3$-C$_7$)cycloalkyl and —NR$^{32}$R$^{33}$;

R$^{29}$, R$^{30}$, R$^{32}$ and R$^{33}$ are each independently selected from H and (C$_1$-C$_6$)alkyl;

or a pharmaceutically acceptable salt thereof.

In one embodiment, the present invention provides a compound of formula (I) selected from:

3-(2-Benzyl-1-oxo-1,2-dihydro-isoquinolin-6-yl)-N-cyclopropyl-4-methyl-benzamide;

3-(2-Benzyl-1-oxo-1,2-dihydro-isoquinolin-6-yl)-N-ethyl-4-methyl-benzamide;

3-[2-(4-Bromo-benzyl)-1-oxo-1,2-dihydro-isoquinolin-6-yl-N-cyclopropyl-4-methyl-benzamide;

N-Cyclopropyl-4-methyl-3-{2-[4-(4-methyl-piperazin-1-yl)-benzyl]-1-oxo-1,2-dihydro-isoquinolin-6-yl}-benzamide;

N-Cyclopropyl-3-[2-(4-methanesulfonyl-benzyl)-1-oxo-1,2-dihydro-isoquinolin-6-yl]-4-methyl-benzamide;

4-{4-[6-(5-Cyclopropylcarbamoyl-2-methyl-phenyl)-1-oxo-1H-isoquinolin-2-ylmethyl]-phenyl}-3,6-dihydro-2H-pyridine-1-carboxylic acid, tert-butyl ester;

N-Cyclopropyl-4-methyl-3-[1-oxo-2-{4-(1,2,3,6-tetrahydro-pyridin-4-yl)-benzyl}-1,2-dihydro-isoquinolin-4-yl]-benzamide;

N-Cyclopropyl-4-methyl-3-[1-oxo-2-(4-piperidin-4-yl-benzyl)-1,2-dihydro-isoquinolin-6-yl]-benzamide;

N-Methoxy-4-methyl-3-{1-oxo-2-[4-(1,2,3,6-tetrahydro-pyridin-4-yl)-benzyl]-1,2-dihydro-isoquinolin-6-yl}-benzamide;

N-Cyclopropyl-3-{2-[3-(3-dimethylamino-propoxy)-benzyl]-1-oxo-1,2-dihydro-isoquinolin-6-yl}-4-methyl-benzamide;

N-Cyclopropyl-4-methyl-3-(1-oxo-1,2-dihydro-isoquinolin-6-yl)-benzamide;

3-(2-Allyl-1-oxo-1,2-dihydro-isoquinolin-6-yl)-N-cyclopropyl-4-methyl-benzamide;

N-Cyclopropyl-4-methyl-3-[1-oxo-2-(3-pyrrolidin-1-yl-propyl)-1,2-dihydro-isoquinolin-6-yl]-benzamide;

N-Cyclopropyl-3-[2-(4-dimethylaminomethyl-benzyl)-1-oxo-1,2-dihydro-isoquinolin-6-yl]-4-methyl-benzamide;

N-Cyclopropyl-3-[2-(3-dimethylaminomethyl-benzyl)-1-oxo-1,2-dihydro-isoquinolin-6-yl]-4-methyl-benzamide;

N-Cyclopropyl-3-[2-(2-dimethylaminomethyl-benzyl)-1-oxo-1,2-dihydro-isoquinolin-6-yl]-4-methyl-benzamide;

N-Cyclopropyl-3-[2-(4-methoxy-benzyl)-1-oxo-1,2-dihydro-isoquinolin-6-yl]-4-methyl-benzamide;

N-Cyclopropyl-3-(2-(4-((2-(dimethylamino)ethyl)(methyl)carbamoyl)benzyl)-1-oxo-1,2-dihydroisoquinolin-6-yl)-4-methylbenzamide;

N-Cyclopropyl-3-(2-(4-(2-(dimethylamino)ethylcarbamoyl)benzyl)-1-oxo-1,2-dihydroisoquinolin-6-yl)-4-methyl-benzamide;

N-Cyclopropyl-4-methyl-3-(2-(4-(4-methylpiperazine-1-carbonyl)benzyl)-1-oxo-1,2-dihydroisoquinolin-6-yl)benzamide;

N-Cyclopropyl-3-(2-(4-((3-(dimethylamino)propyl)(methyl)carbamoyl)benzyl)-1-oxo-1,2-dihydroisoquinolin-6-yl)-4-methylbenzamide;

N-Cyclopropyl-4-methyl-3-(1-oxo-2-(4-(2-(pyrrolidin-1-yl)ethylcarbamoyl)benzyl)-1,2-dihydroisoquinolin-6-yl)benzamide;

N-Cyclopropyl-4-methyl-3-(2-(4-(methyl(2-(methylamino) ethyl)carbamoyl)benzyl)-1-oxo-1,2-dihydroisoquinolin-6-yl)benzamide;
N-Cyclopropyl-4-methyl-3-(1-oxo-2-(4-(3-(pyrrolidin-1-yl) propylcarbamoyl)benzyl)-1,2-dihydroisoquinolin-6-yl) benzamide;
N-Cyclopropyl-4-methyl-3-(1-oxo-2-(4-(pyrrolidin-1-ylmethyl)benzyl)-1,2-dihydroisoquinolin-6-yl)benzamide;
N-Cyclopropyl-4-methyl-3-(2-(4-((4-methylpiperazin-1-yl) methyl)benzyl)-1-oxo-1,2-dihydroisoquinolin-6-yl)benzamide;
3-(2-(4-((Tert-butyl(methyl)amino)methyl)benzyl)-1-oxo-1, 2-dihydroisoquinolin-6-yl)-N-cyclopropyl-4-methylbenzamide;
3-(2-(4-((Tert-butylamino)methyl)benzyl)-1-oxo-1,2-dihydroisoquinolin-6-yl)-N-cyclopropyl-4-methylbenzamide;
N-Cyclopropyl-3-(2-((6-(3-(dimethylamino)propoxy)pyridin-3-yl)methyl)-1-oxo-1,2-dihydroisoquinolin-6-yl)-4-methylbenzamide;
N-Cyclopropyl-3-(2-((6-(2-(dimethylamino)ethoxy)pyridin-3-yl)methyl)-1-oxo-1,2-dihydroisoquinolin-6-yl)-4-methylbenzamide;
N-Cyclopropyl-4-methyl-3-(1-oxo-2-((6-(2-(pyrrolidin-1-yl)ethoxy)pyridin-3-yl)methyl)-1,2-dihydroisoquinolin-6-yl)benzamide;
N-Cyclopropyl-3-(2-(4-(2-(dimethylamino)ethoxy)benzyl)-1-oxo-1,2-dihydroisoquinolin-6-yl)-4-methylbenzamide;
N-cyclopropyl-4-methyl-3-{1-oxo-2-[3-(2-pyrrolidin-1-ylethoxy)benzyl]-1,2-dihydroisoquinolin-6-yl}benzamide;
N-Cyclopropyl-4-methyl-3-(2-{3-[2-(methylamino)ethoxy] benzyl}-1-oxo-1,2-dihydroisoquinolin-6-yl)benzamide;
N-Cyclopropyl-3-[2-(3-{2-[(2-hydroxyethyl)amino] ethoxy}benzyl)-1-oxo-1,2-dihydroisoquinolin-6-yl]-4-methylbenzamide;
N-Cyclopropyl-4-methyl-3-(2-(4-(2-(methylamino)ethoxy) benzyl)-1-oxo-1,2-dihydroisoquinolin-6-yl)benzamide;
6-(5-(Cyclopropylcarbamoyl)-2-methylphenyl)-2-(cyclopropylmethyl)-1-oxo-N-(piperidin-4-yl)-1,2-dihydroisoquinoline-4-carboxamide;
3-(4-(4-Aminopiperidine-1-carbonyl)-2-(cyclopropylmethyl)-1-oxo-1,2-dihydroisoquinolin-6-yl)-N-cyclopropyl-4-methylbenzamide;
N-Cyclopropyl-3-(2-(cyclopropylmethyl)-4-(4-(dimethylamino)piperidine-1-carbonyl)-1-oxo-1,2-dihydroisoquinolin-6-yl)-4-methylbenzamide;
2-Benzyl-6-(5-(cyclopropylcarbamoyl)-2-methylphenyl)-N-(2-(dimethylamino)ethyl)-1-oxo-1,2-dihydroisoquinoline-4-carboxamide;
2-Benzyl-6-(5-(cyclopropylcarbamoyl)-2-methylphenyl)-1-oxo-N-(2-(piperidin-1-yl)ethyl)-1,2-dihydroisoquinoline-4-carboxamide;
2-Benzyl-6-{5-[(cyclopropylamino)carbonyl]-2-methylphenyl}-1-oxo-N-(2-pyrrolidin-1-ylethyl)-1,2-dihydroisoquinoline-4-carboxamide;
2-Benzyl-6-{5-[(cyclopropylamino)carbonyl]-2-methylphenyl}-N-(1-methylpiperidin-4-yl)-1-oxo-1,2-dihydroisoquinoline-4-carboxamide;
2-Benzyl-6-{5-[(cyclopropylamino)carbonyl]-2-methylphenyl}-N-[3-(dimethylamino)propyl]-1-oxo-1,2-dihydroisoquinoline-4-carboxamide;
(R)-3-(4-(3-Aminopyrrolidine-1-carbonyl)-2-benzyl-1-oxo-1,2-dihydroisoquinolin-6-yl)-N-cyclopropyl-4-methylbenzamide;
6-(5-(Cyclopropylcarbamoyl)-2-methylphenyl)-1-oxo-N-(piperidin-4-yl)-2-(pyridin-4-ylmethyl)-1,2-dihydroisoquinoline-4-carboxamide;
3-(4-(4-Aminopiperidine-1-carbonyl)-1-oxo-2-(pyridin-4-ylmethyl)-1,2-dihydroisoquinolin-6-yl)-N-cyclopropyl-4-methylbenzamide;
N-Cyclopropyl-3-[2-cyclopropylmethyl-4-(4-methyl-[1,4] diazepan-1-ylmethyl)-1-oxo-1,2-dihydro-isoquinoiin-6-yl]-4-methyl-benzamide; and
2-Benzyl-6-(5-(cyclopropylcarbamoyl)-3-fluoro-2-methylphenyl)-N-(2-(dimethylamino)ethyl)-1-oxo-1,2-dihydroisoquinoline-4-carboxamide
(S)—N-Cyclopropyl-3-(2-(cyclopropylmethyl)-4-((3-methylpiperazin-1-yl)methyl)-1-oxo-1,2-dihydroisoquinolin-6-yl)-4-methylbenzamide
N-Cyclopropyl-3-(2-cyclopropylmethyl-4-[1,4]diazepan-1-ylmethyl-1-oxo-1,2-dihydro-isoquinolin-6-yl)-4-methylbenzamide
N-Cyclopropyl-3-(2-(cyclopropylmethyl)-4-((4-(2-hydroxyethyl)-1,4-diazepan-1-yl)methyl)-1-oxo-1,2-dihydroisoquinolin-6-yl)-4-methylbenzamide
N-Cyclopropyl-3-(2-(cyclopropylmethyl)-4-((4-methylpiperazin-1-yl)methyl)-1-oxo-1,2-dihydroisoquinolin-6-yl)-4-methylbenzamide
N-Cyclopropyl-3-(2-(cyclopropylmethyl)-4-((4-methyl-1,4-diazepan-1-yl)methyl)-1-oxo-1,2-dihydroisoquinolin-6-yl)-5-fluoro-4-methylbenzamide
N-Cyclopropyl-3-(2-(cyclopropylmethyl)-4-((4-(2-hydroxyethyl)-1,4-diazepan-1-yl)methyl)-1-oxo-1,2-dihydroisoquinolin-6-yl)-5-fluoro-4-methylbenzamide
N-Cyclopropyl-3-(2-(cyclopropylmethyl)-4-(((3S,5R)-3,5-dimethylpiperazin-1-yl)methyl)-1-oxo-1,2-dihydroisoquinolin-6-yl)-5-fluoro-4-methylbenzamide
(S)—N-Cyclopropyl-3-(2-(cyclopropylmethyl)-4-((3-methylpiperazin-1-yl)methyl)-1-oxo-1,2-dihydroisoquinolin-6-yl)-5-fluoro-4-methylbenzamide
(R)—N-Cyclopropyl-3-(2-(cyclopropylmethyl)-4-((3-(hydroxymethyl)piperazin-1-yl)methyl)-1-oxo-1,2-dihydroisoquinolin-6-yl)-5-fluoro-4-methylbenzamide
(R)—N-Cyclopropyl-3-(2-(cyclopropylmethyl)-4-((2-methylpiperazin-1-yl)methyl)-1-oxo-1,2-dihydroisoquinolin-6-yl)-5-fluoro-4-methylbenzamide
(R)—N-Cyclopropyl-3-(2-(cyclopropylmethyl)-4-((3-(hydroxymethyl)-4-methylpiperazin-1-yl)methyl)-1-oxo-1,2-dihydroisoquinolin-6-yl)-5-fluoro-4-methylbenzamide
N-Cyclopropyl-3-(2-(cyclopropylmethyl)-1-oxo-4-(piperazin-1-ylmethyl)-1,2-dihydroisoquinolin-6-yl)-5-fluoro-4-methylbenzamide
N-Cyclopropyl-3-(2-(cyclopropylmethyl)-4-((4-(2-hydroxyethyl)piperazin-1-yl)methyl)-1-oxo-1,2-dihydroisoquinolin-6-yl)-5-fluoro-4-methylbenzamide
3-(4-((1,4-Diazepan-1-yl)methyl)-2-(cyclopropylmethyl)-1-oxo-1,2-dihydroisoquinolin-6-yl)-N-cyclopropyl-5-fluoro-4-methylbenzamide
(S)—N-Cyclopropyl-3-(2-(cyclopropylmethyl)-4-((3-(hydroxymethyl)piperazin-1-yl)methyl)-1-oxo-1,2-dihydroisoquinolin-6-yl)-5-fluoro-4-methylbenzamide
(R)—N-Cyclopropyl-3-(2-(cyclopropylmethyl)-4-((3-methylpiperazin-1-yl)methyl)-1-oxo-1,2-dihydroisoquinolin-6-yl)-5-fluoro-4-methylbenzamide
(S)—N-Cyclopropyl-3-(2-(cyclopropylmethyl)-4-((2-(hydroxymethyl)piperazin-1-yl)methyl)-1-oxo-1,2-dihydroisoquinolin-6-yl)-5-fluoro-4-methylbenzamide
(S)—N-Cyclopropyl-3-(2-(cyclopropylmethyl)-4-((3-ethylpiperazin-1-yl)methyl)-1-oxo-1,2-dihydroisoquinolin-6-yl)-5-fluoro-4-methylbenzamide
(S)—N-Cyclopropyl-3-(2-(cyclopropylmethyl)-4-((3-(2-hydroxyethyl)piperazin-1-yl)methyl)-1-oxo-1,2-dihydroisoquinolin-6-yl)-5-fluoro-4-methylbenzamide (S)—N-Cyclopropyl-3-(2-(cyclopropylmethyl)-4-((2-methylpiperazin-1-yl)methyl)-1-oxo-1,2-dihydroisoquinolin-6-yl)-5-fluoro-4-methylbenzamide 3-(4-(((2R,4S)-4-Amino-2-(hydroxymethyl)pyrrolidin-1-yl)methyl)-2-(cyclopropylmethyl)-1-oxo-1,2-dihydroisoquinolin-6-yl)-N-cyclopropyl-5-fluoro-4-methylbenzamide or a pharmaceutically acceptable salt or N-oxide thereof.

DEFINITIONS

Unless otherwise stated, halo is Cl, F, Br or I;

Unless otherwise stated, cycloalkyl is a non-aromatic carbocyclic ring containing the requisite number of carbon atoms, optionally containing, where possible, up to 3 double bonds, and optionally substituted with 1 to 3 substituents selected from ($C_1$-$C_6$)alkyl, ($C_1$-$C_6$)alkoxy, ($C_2$-$C_6$)alkenyl, —OH, —CN, halo and —$NR^{34}R^{35}$, each substituent may be the same or different. Examples of suitable cycloalkyl groups include cyclopropyl, cyclobutyl, cyclopentyl, cyclohexyl, cycloheptyl, cyclopentene, cyclopenta-1,3-diene, cyclohexene and cyclohexa-1,4-diene (optionally substituted as stated above).

Examples of suitable heterocycloalkyl groups include oxiranyl, aziridinyl, azetidinyl, tetrahydrofuranyl, pyrrolidinyl, tetrahydropyranyl, piperidinyl, N-methylpiperidinyl, azepinyl, homopiperidinyl, piperazinyl, homopiperazinyl, 1,2,3,6-tetrahydropyridinyl and 1,2,3,4-tetrahydropyridinyl (optionally substituted as stated above).

Unless otherwise stated, aryl is an aromatic ring containing 6 or 10 carbon atoms, optionally substituted with 1 to 3 substituents selected from ($C_1$-$C_6$)alkyl, ($C_1$-$C_6$)alkoxy, ($C_2$-$C_6$)alkenyl, —OH, —CN, halo and —$NR^{36}R^{37}$, each substituent may be the same or different. Examples of suitable aryl groups include phenyl and naphthyl (optionally substituted as stated above).

Unless otherwise stated, heteroaryl may be optionally substituted with 1 to 3 substituents selected from ($C_1$-$C_6$)alkyl, ($C_1$-$C_6$)alkoxy, ($C_2$-$C_6$)alkenyl, —OH, —CN, halo and —$NR^{38}R^{39}$, each substituent may be the same or different. Examples of suitable heteroaryl groups include thienyl, furanyl, pyrrolyl, pyrazolyl, imidazoyl, oxazolyl, isoxazolyl, thiazolyl, isothiazolyl, triazolyl, oxadiazolyl, thiadiazolyl, tetrazolyl, pyridinyl, pyridazinyl, pyrimidinyl, pyrazinyl, indolyl, benzimidazolyl, benzotriazolyl, quinolinyl, benzothiophenyl, benzofuranyl, quinazolinyl, quinoxalinyl, benzoxazolyl, benzisoxazolyl, and isoquinolinyl (optionally substituted as stated above).

Unless otherwise stated alkyl, alkoxy, alkenyl and alkynyl groups containing the requisite number of carbon atoms can be branched or unbranched. Examples of suitable alkyl groups include methyl, ethyl, n-propyl, i-propyl, n-butyl, sec-butyl and t-butyl. Examples of suitable alkoxy groups include methoxy (—$OCH_3$), ethoxy (—$OCH_2CH_3$), n-propoxy, i-propoxy, n-butoxy, sec-butoxy and t-butoxy. Examples of suitable alkenyl groups include 1,1-ethylenyl, 1,2-ethylenyl, 1,1-propylenyl, 1,2-propylenyl, 1,3-propylenyl and 2,2-propylene. Examples of suitable alkynyl groups include prop-1-ynyl, but-1-ynyl, but-2-ynyl, pent-1-ynyl, pent-2-ynyl and hex-1-ynyl.

In the above definitions, $R^{34}$, $R^{35}$, $R^{36}$, $R^{37}$, $R^{38}$ and $R^{39}$ are each independently selected from H, and ($C_1$-$C_6$)alkyl.

The term 'C-linked', such as in 'C-linked heterocycloalkyl', means that the heterocycloalkyl group is joined via a ring carbon atom.

Unless otherwise stated, in groups of the type $NR^aR^b$ wherein $R^a$ and $R^b$ together with the nitrogen atom to which they are attached form a ring (e.g. as may be the case for $NR^{16}R^{17}$ in compounds of formula (I)), where the ring is 7-membered or larger the ring may be mono or polycyclic.

Examples of monocyclic rings include pyrrolidinyl, piperidinyl, piperazinyl and diazepanyl. An example of a 7-membered polycyclic ring is a 2,5-diazabicyclo[2.2.1]heptan-2-yl ring.

"Pharmaceutically acceptable salt" means a physiologically or toxicologically tolerable salt and includes, when appropriate, pharmaceutically acceptable base addition salts and pharmaceutically acceptable acid addition salts. For example (i) where a compound of the invention contains one or more acidic groups, for example carboxy groups, pharmaceutically acceptable base addition salts that can be formed include sodium, potassium, calcium, magnesium and ammonium salts, or salts with organic amines, such as, diethylamine, N-methyl-glucamine, diethanolamine or amino acids (e.g. lysine) and the like; (ii) where a compound of the invention contains a basic group, such as an amino group, pharmaceutically acceptable acid addition salts that can be formed include hydrochlorides, hydrobromides, sulfates, phosphates, acetates, citrates, lactates, tartrates, mesylates, tosylates, benzenesulfonates, maleates, fumarates, xinafoates, p-acetamidobenzoates, succinates, ascorbates, oleates, bisulfates, furoates, propionates, stearates, isethionates and the like.

Hemisalts of acids and bases can also be formed, for example, hemisulfate and hemicalcium salts.

For a review of suitable salts, see "Handbook of Pharmaceutical Salts: Properties, Selection and Use" by Stahl and Wermuth (Wiley-VCH, Weinheim, Germany, 2002).

"Prodrug" refers to a compound which is convertible in vivo by metabolic means (e.g. by hydrolysis, reduction or oxidation) to a compound of the invention. Suitable groups for forming pro-drugs are described in 'The Practice of Medicinal Chemistry, $2^{nd}$ Ed. pp 561-585 (2003) and in F. J. Leinweber, Drug Metab. Res., 18, 379. (1987).

The compounds of the invention can exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when the solvent is water.

Where compounds of the invention exist in one or more geometrical, optical, enantiomeric, diastereomeric and tautomeric forms, including but not limited to cis- and trans-forms, E- and Z-forms, R-, S- and meso-forms, keto-, and enol-forms. Unless otherwise stated a reference to a particular compound includes all such isomeric forms, including racemic and other mixtures thereof. Where appropriate such isomers can be separated from their mixtures by the application or adaptation of known methods (e.g. chromatographic techniques and recrystallisation techniques). Where appropriate such isomers can be prepared by the application of adaptation of known methods (e.g. asymmetric synthesis).

The skilled person will recognise that the compounds of the invention may be prepared, in known manner, in a variety of ways. The routes below are merely illustrative of some of the methods that can be employed for the synthesis of compounds of formula (I).

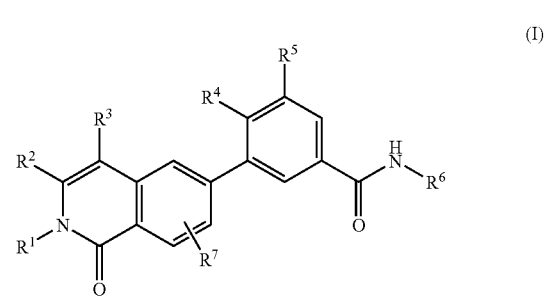

A compound of formula (I), or a pharmaceutically-acceptable salt thereof, wherein $R^1$, $R^2$, $R^3$, $R^4$, $R^5$, $R^6$ and $R^7$ are as previously defined, may be prepared by reacting a compound of formula (II), wherein $R^1$, $R^2$, $R^3$, $R^4$, $R^5$ and $R^7$ are as previously defined in formula (I) and $R^{50}$ is a carboxylic acid or a derivative thereof, with an amine of formula (III), wherein $R^6$ is as previously defined in formula (I).

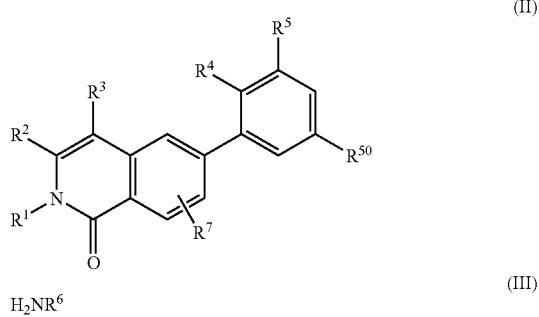

A suitable reactive derivative of a carboxylic acid of the formula (II) is, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an ester, formed by reaction with an alcohol in the presence of acid or base; an active ester, for example an ester formed by the reaction of the acid with a phenol such as pentafluorophenol, with an ester such as pentafluorophenyl trifluoroacetate or with an alcohol such as N-hydroxybenzotriazole; or the product of the reaction of the acid and an amide coupling agent such as dicyclohexylcarbodiimide.

Typically, the carboxylic acid is converted to an acid chloride by treatment with oxalyl chloride at a temperature between −5° C. and 35° C. in an inert solvent such as dichloromethane. Typically, the acid chloride is then treated with the amine in an inert solvent such as dichloromethane in the presence of a non-nucleophilic base such as N,N-diisopropylethylamine.

In the case where $R^{50}$ is a carboxylic ester such as a methyl ester, the reaction with an amine of formula (III) may be carried out in the presence of a Grignard reagent in an inert solvent. Preferentially a methyl ester is used in the presence of isopropylmagnesium bromide in tetrahydrofuran.

A compound of formula (II) may be prepared as shown in scheme 1 below, wherein $R^1$, $R^2$, $R^3$, $R^4$, $R^5$ and $R^7$ are as previously defined in formula (I), W is a leaving group such as a halide (for example bromide or iodide) or an sulfonate ester (for example a trifluoromethane sulfonate) or a boronate ester or boronic acid and $R^{50}$ is a carboxylic acid or derivative thereof. Suitable derivatives of the carboxylic acid $R^{50}$ include a $C_1$-$C_6$ alkyl ester such as a methyl ester or an amide such that $R^{50}$ is equivalent to $CONHR^6$ where $R^6$ is as previously defined in formula (I).

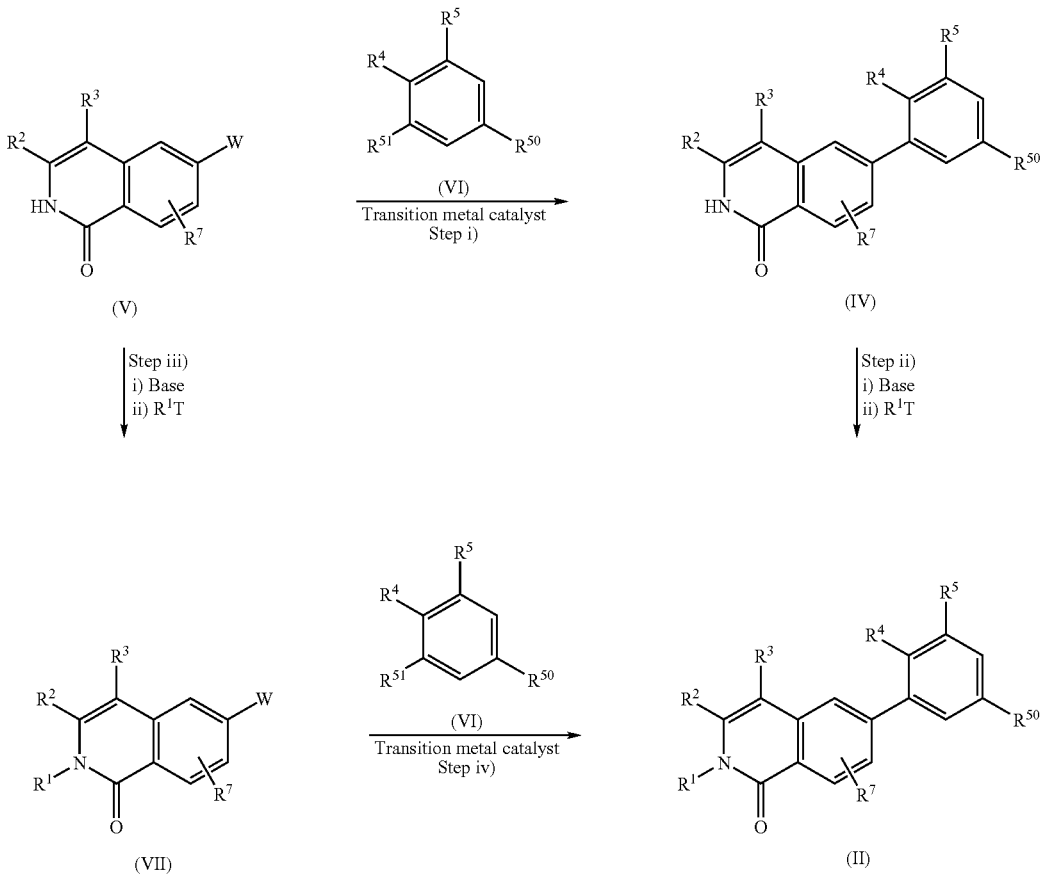

Scheme 1, Step i)

A compound of formula (IV) may be prepared by treating a compound of formula (V), wherein W is a leaving group such as a halide (for example bromide or iodide) or an sulfonate ester (for example a trifluoromethane sulfonate) or an boronate ester or boronic acid, with a compound of formula (VI), wherein $R^{50}$ is a carboxylic acid or protected derivative thereof and $R^{51}$ is a leaving group such as a halide (for example bromide or iodide) or an sulfonate ester (for example a trifluoromethane sulfonate) or an boronate ester or boronic acid. The reaction may be carried out in the presence of a transition metal catalyst such as tetrakis(triphenylphosphine) palladium(0) or 1,1-bis(di-tert-butylphosphino)ferrocene palladium dichloride (Pd-118) in an inert solvent such as N,N-dimethylformamide at a temperature of 0° C. to 150° C. in the presence of a base such as potassium carbonate.

Typically, the reaction is carried out where W is bromide, $R^{51}$ is $B(OH)_2$ or 4,4,5,5-tetramethyl-[1,3,2]dioxaborolane and $R^{50}$ is $CO_2Me$ or $CONHR^6$ where $R^6$ is as defined in formula (I) and the reaction is carried out in N,N-dimethylformamide at 95° C. in the presence of potassium carbonate and either tetrakis(triphenylphosphine) palladium(0) or 1,1-bis(di-tert-butylphosphino)ferrocene palladium dichloride (Pd-118).

Scheme 1 Step ii)

A compound of formula (II) may be prepared by treating a compound of formula (IV) with a compound of formula $R^1T$ wherein T is a leaving group such as halide, in an inert solvent in the presence of a base at a temperature of −20° C. to 150° C.

Typically, the reaction is carried out where T is iodide, bromide or chloride, the base is sodium hydride, potassium carbonate or cesium carbonate and the reaction is carried out in N,N-dimethylformamide or 1-methylpyrrolidine at 60-80° C.

Scheme 1 Step iii)

A compound of formula (VII) wherein W is a leaving group such as a halide (for example bromide or iodide) or an sulfonate ester (for example a trifluoromethane sulfonate) or an boronate ester or boronic acid, may be prepared by treating a compound of formula (V) with a compound of formula $R^1T$ as described in scheme 1 step ii).

Typically, the reaction is carried out where T is iodide, bromide or chloride, W is a leaving group such as a halide, for example bromide or iodide and the base is sodium hydride, potassium carbonate or cesium carbonate and the reaction is carried out in N,N-dimethylformamide or 1-methylpyrrolidine at 60-80° C.

Scheme 1 Step iv)

A compound of formula (II) may be prepared by treating a compound of formula (VII) with a compound of formula (VI) wherein $R^{51}$ is a leaving group as a halide (for example bromide or iodide) or an sulfonate ester (for example a trifluoromethane sulfonate) or a boronate ester or boronic acid using the method described in scheme 1 step (i).

Typically, the reaction is carried out where W is bromide, $R^{51}$ is $B(OH)_2$ or 4,4,5,5-tetramethyl-[1,3,2]dioxaborolane and $R^{50}$ is $CO_2Me$ or $CONHR^6$, wherein $R^6$ is as defined in formula (I), and the reaction is carried out in N,N-dimethylformamide at 95° C. in the presence of potassium carbonate and either tetrakis(triphenylphosphine) palladium(0) or 1,1-bis(di-tert-butylphosphino)ferrocene palladium dichloride (Pd-118).

Compounds of formula (VI) wherein $R^{51}$ is a boronate ester or boronic acid, may be prepared as described in the literature, see for example WO07000339, WO06134382, WO06118256, WO06110173, WO06104889, WO06104915, WO06104917, J. Med. Chem. 2006, 49, 5671, WO05073217, WO05073189, WO05014550 or WO0368747. Compounds of formula $R^1T$ are commercially available or are prepared by known experimental methods.

A compound of formula (V) may be prepared from a compound of formula (VIII) as shown in scheme 2, wherein $R^2$, $R^3$ and $R^7$ are as previously defined in formula (I) and W is a leaving group such as a halide (for example bromide or iodide).

Scheme 2

(VIII)

1. Activate Acid
2. Metal azide
3. Heat (V)

Typically, the acid (VIII) is activated by conversion to the acid chloride by treatment with oxalyl chloride in an inert solvent such as dichloromethane. Typically, the acid chloride is then treated with an inorganic azide such as sodium azide in an inert solvent such as tetrahydrofuran/water. Typically, the rearrangement/cyclisation is carried out in an inert solvent such as dichlorobenzene at 170° C.

A compound of formula (XII) may be prepared from a compound of formula (IX), as shown in scheme 3, wherein $R^1$, $R^3$ and $R^7$ are as defined in formula (I) or are protected derivatives thereof, $R^2$ is H and W is a leaving group such as a halide, for example chloride, bromide or iodide.

Scheme 3

(IX) → Step i) Dehydrating agent → (X)

Step ii)
$R^1NH_2$

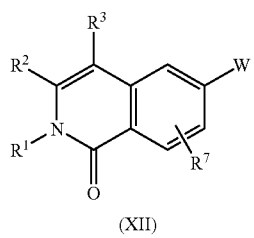 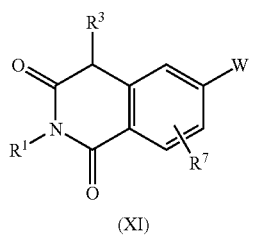

(XII)    (XI)

Step iii)
i) Reduction
ii) Acid

Scheme 3 Step i)

A compound of formula (X) may be prepared from a compound of formula (IX) by treatment with a dehydrating agent, such as dicyclohexylcarbodiimide or acetic anhydride, in an inert solvent, such as toluene, at a temperature of −30° C. to 100° C. Typically, the reaction is carried out using acetyl chloride in acetone at 25° C.

sodium borohydride in dichloromethane/methanol at 25° C., followed by treatment with cHCl.

Amines of formula $H_2NR^1$ are commercially available or are prepared by known experimental methods.

A compound of formula (IX) may be prepared as shown in Scheme 4, wherein $R^3$ is H or $C_1$-$C_6$ alkyl, $R^7$ is as previously defined in formula (I) and W is a leaving group such as a halide, for example chloride, bromide or iodide.

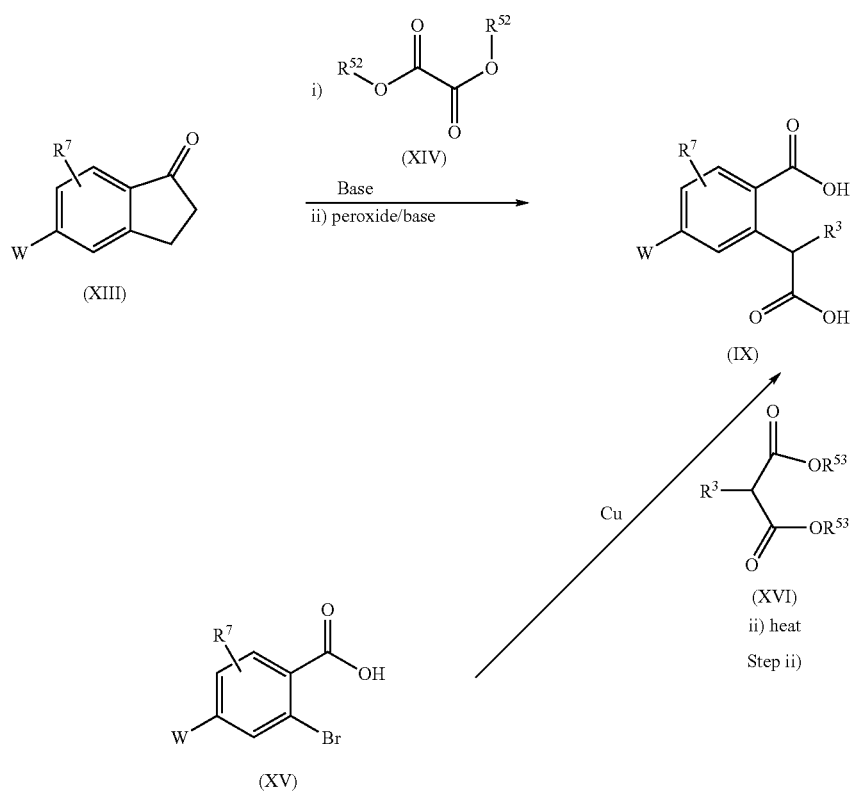

Scheme 3 Step ii)

A compound of formula (XI) may be prepared by treating a compound of formula (X) with an amine of formula $H_2NR^1$, an inert solvent at a temperature of −20° C. to 150° C. Typically, the reaction is carried out in toluene/acetic acid at reflux.

Scheme 3 Step iii)

A compound of formula (XII) may be prepared from a compound of formula (XI) by treatment with a reducing agent, such as lithium triethylborohydride, in an inert solvent, such as tetrahydrofuran, at a temperature between −100° C. and 100° C. followed by treatment with an acid, such as trifluoroacetic acid. Typically, the reaction is carried out with

Scheme 4 Step i)

A compound of formula (IX), wherein $R^3$ is H, may be prepared by treating a compound of formula (XIII) with a compound of formula (XIV), wherein $R^{52}$ is $C_1$-$C_6$ alkyl (such as methyl or ethyl) or a benzyl group, in the presence of a base such as potassium ethoxide, followed by treatment with an organic or inorganic peroxide such as t-butylhydrogen peroxide in the presence of a base such as sodium hydroxide in an inert solvent such as methanol at a temperature between 0° C. and 150° C. Typically, the reaction is carried out with diethyl oxalate and sodium methoxide in toluene at 0° C. to 25° C. followed by treatment with hydrogen peroxide and potassium hydroxide in methanol at 50-65° C.

Scheme 4 Step ii)

A compound of formula (IX) may also be prepared by treating a compound of formula (XV) with a compound of formula (XVI), wherein $R^{53}$ is $C_1$-$C_6$ alkyl (such as methyl or ethyl) or benzyl, in the presence of a base such as sodium hydride, and a copper catalyst such as copper (I) bromide, followed by a decarboxylation reaction. Typically, the decarboxylation is carried out in cHCl at reflux.

Compounds of formula (XII), (XIII), (XIV) (XV) and (XVI) are commercially available or are prepared by known experimental methods.

Compounds of formula (I) may be converted into other compounds of formula (I) using known chemistry.

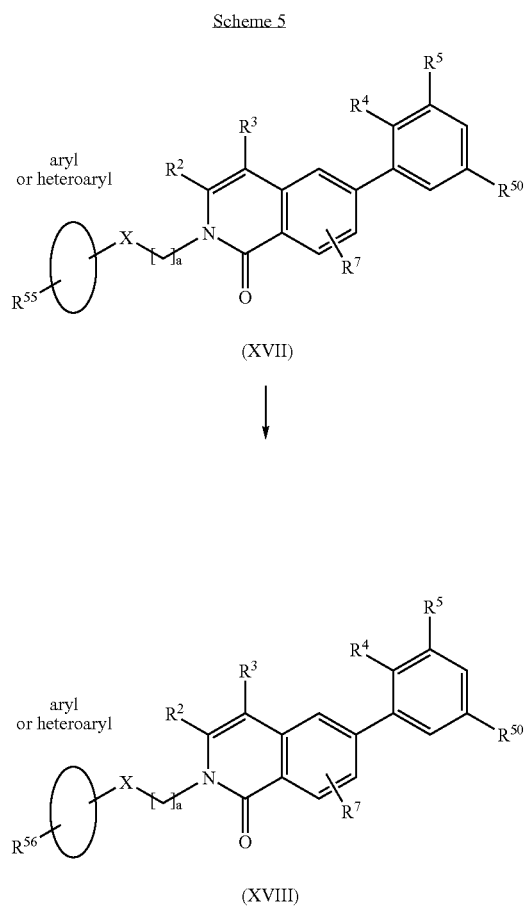

For example, as shown in scheme 5, compounds of formula (XVII) wherein $R^{55}$ is a halide such as bromide or chloride may be converted into compounds of formula (XVIII), wherein $R^{56}$ is an amine or heterocyclylalkyl. The reaction is carried out in the presence of a suitable amine or activated heterocyclylalkyl group in the presence of a transition metal catalyst such as $Pd(dppf)_2Cl_2$ in the presence of a base such as potassium carbonate. Suitable amines include N-methyl-piperazine, while suitably activated heterocyclylalkyls include 4-(4,4,5,5-tetramethyl-[1,3,2]-dioxaborolan-2-yl)-3,6-dihydro-2H-pyridine-1-carboxylic acid, tert-butyl ester (prepared as described in Tetrahedron Lett., 2000, 41, 3705. Double bonds in structure (XVIII) may optionally then be reduced by treatment with hydrogen in the presence of a transition metal catalyst such a palladium on carbon.

A compound of formula (XXV) wherein where $R^1$, $R^2$, $R^4$, $R^5$, $R^7$, $R^{16}$ and $R^{17}$ are as defined in formula (I), $R^2$ is H and $R^{50}$ is a carboxylic acid or derivative thereof may be prepared as shown in scheme 6. Suitable derivatives of the carboxylic acid $R^{50}$ include a $C_1$-$C_6$ alkyl ester such as a methyl ester or an amide such that $R^{50}$ is equivalent to $CONHR^6$ where $R^6$ is as defined in formula (I).

Scheme 6 Step i)

A compound of formula (XXI) wherein $R^{54}$ is $C_1$-$C_6$ alkyl or benzyl and W is a leaving group (such as bromide or iodide) may be prepared from a compound of formula (XX) by treatment with an activating reagent, such as acetic anhydride or acetyl chloride and a trialkyl orthoformate, at temperatures between 100° C. and 200° C. The reaction may be carried out in acetic anhydride or an inert solvent. Typically the reaction is carried out using trimethyl orthoformate in acetic anhydride at 120° C.

Scheme 6 Step ii)

A compound of formula (XXII) may be prepared by treating a compound of formula (XXI) with an aqueous inorganic acid such as sulphuric acid or hydrochloric acid in water or an alcoholic solvent at temperatures of 80° C. to 200° C. Typically the reaction is carried out using sulphuric acid in methanol at reflux.

Scheme 6 Step iii)

A compound of formula (XXIII) may be prepared by reacting a compound of formula (XXII) with an amine of formula $NH_2R^1$. The reaction may be carried out using an alcohol as a solvent at temperatures of 50° C. to 200° C. Typically the reaction is carried out in methanol at reflux.

Scheme 6 Step iv)

A compound of formula (XXIV) may be prepared by reaction of a compound of formula (XXIII) with a compound of formula (VI), where $R^{51}$ is boronate ester or acid, as described for scheme 1 step i).

Scheme 6 Step v)

A compound of formula (XXV) may be prepared from a compound of formula (XXIV) using the method as described for the reaction between compounds of formula (II) and (III). The carboxylic ester $COOR^{54}$ may first be hydrolysed to the carboxylic acid by treatment with acid or base. Typically the ester is hydrolysed using sodium hydroxide in methanol at 50° C. then the acid reacted with the amine $HNR^{16}R^{17}$ in the presence of O-(7-azabenzotriazol-1-yl)-N,N,N',N'-tetramethyluronium hexafluorophosphate (HATU) and N,N-diisopropylethylamine in tetrahydrofuran.

Scheme 6

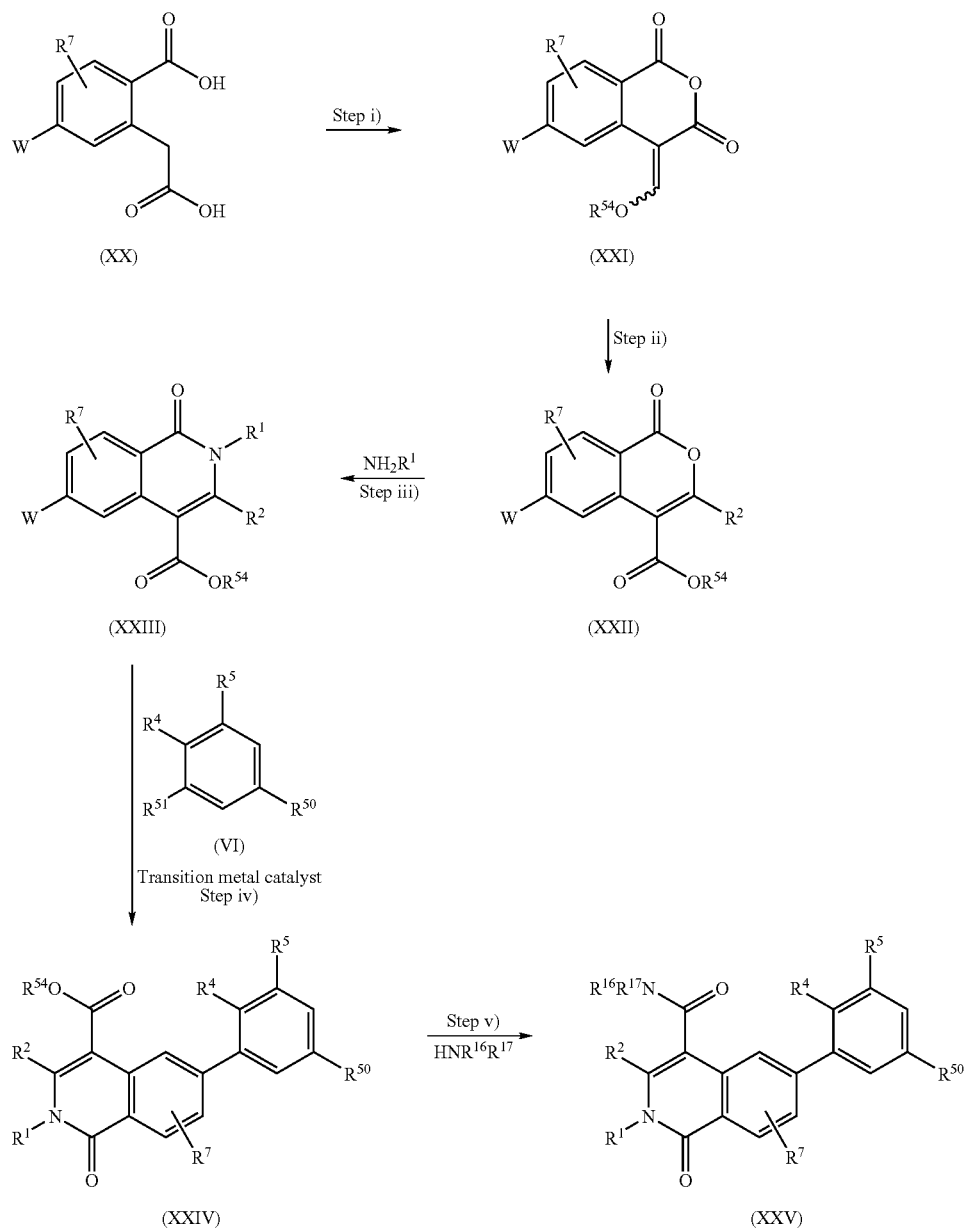

Compounds of formula (XX) may be prepared as described in scheme 4.

A compound of formula (XXVIII) wherein $R^1$, $R^2$, $R^4$, $R^5$, $R^7$, $R^{16}$ and $R^{17}$ are as defined in formula (I), $R^{50}$ is a carboxylic acid or derivative thereof may be prepared as shown in scheme 7. Suitable derivatives of the carboxylic acid $R^{50}$ include a $C_1$-$C_6$ alkyl ester such as a methyl ester or an amide such that $R^{50}$ is equivalent to $CONHR^6$ where $R^6$ is as defined in formula (I).

Scheme 7, Step i)

A compound of formula (IV) where $R^3$ is H may be prepared by reaction of a compound of formula (V) where $R^3$ is H and W is a leaving group (such as bromide or iodide) with a compound of formula (VI) where $R^{51}$ is boronate ester or acid, using the method described for scheme 1 step i).

Scheme 7, Step ii)

A compound of formula (XXVI) may be prepared from a compound of formula (IV) where $R^3$ is H by first reacting a formamide such as N,N-dimethylformamide or N-phenyl-N-methylformamide with an activating agent such as phosphorous oxychloride or oxalyl chloride in a solvent at a temperature of −20 to 80° C. followed by treatment with a compound of formula (IV) at a temperature of 25 to 100° C. Preferably the reaction is carried out with N,N-dimethyl formamide and phosphorous oxychloride in N,N-dimethyl formamide at 0° C. then heated at 80° C. in the presence of (IV).

Scheme 7, Step iii)

A compound of formula (XXVII) may be prepared from a compound of formula (V) where $R^3$ is H using the method described for scheme 7 step ii).

Scheme 7, Step iv)

A compound of formula (XXVI) may be prepared by reaction of a compound of formula (XXVII) with a compound of formula (VI) using the method as described for scheme 1 step i).

Scheme 7, Step v)

A compound of formula (XXVIII) may be prepared by a reductive amination reaction between compounds of formula (XXVI) and $HNR^{16}R^{17}$. The reductive amination is carried out in the presence of suitable reducing agent such as sodium cyanoborohydride, sodium triacetoxyborohydride or sodium borohydride, in a polar solvent such as methanol, ethanol or dichloromethane either alone or in combination with acetic acid. Typically the reaction is carried out using sodium triacetoxyborohydride in dichloromethane at room temperature.

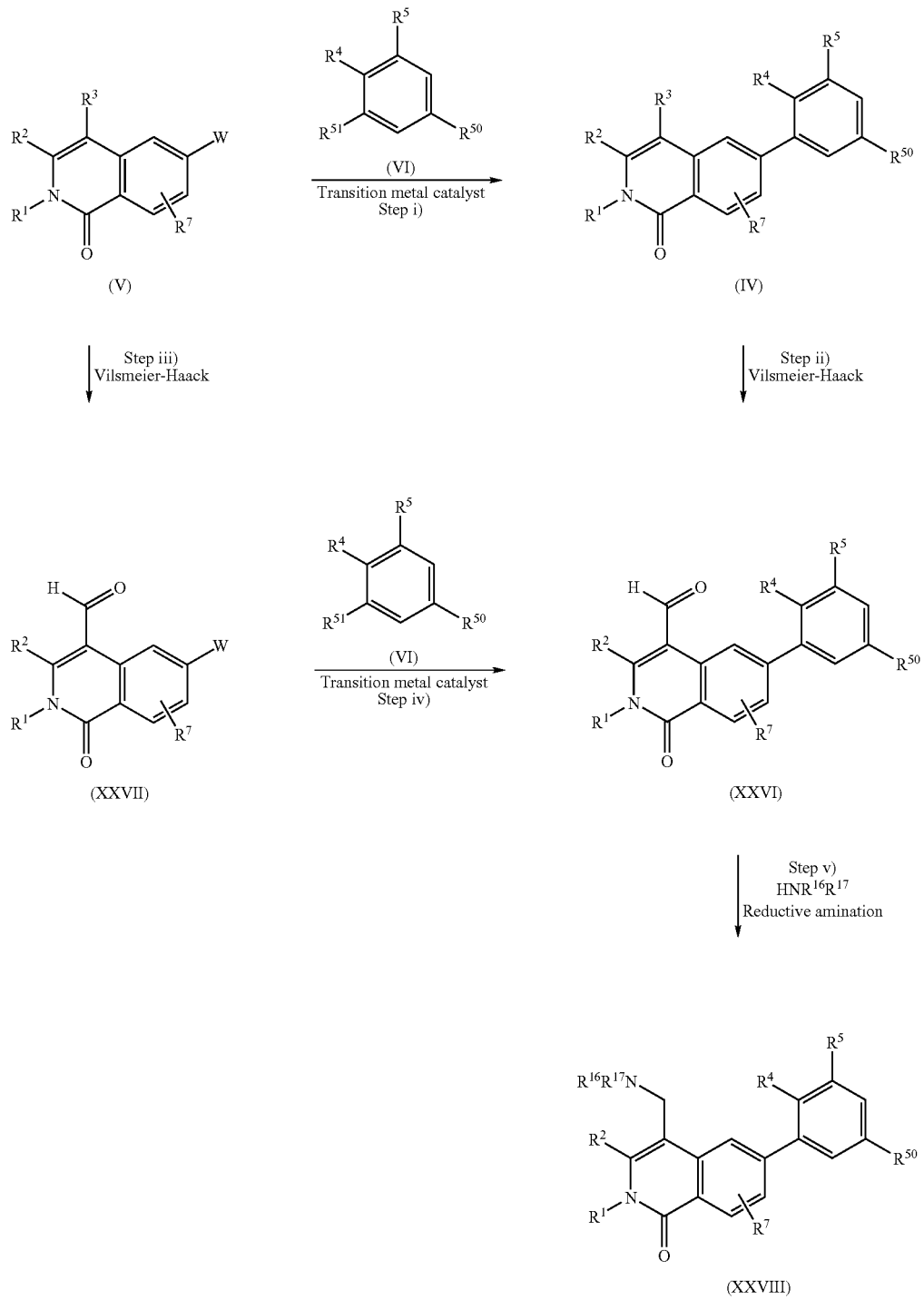

A compound of formula (XXX) wherein $R^1$, $R^2$, $R^4$, $R^5$, $R^7$, $R^{16}$ and $R^{17}$ are as described in formula (I) and $R^{50}$ are as described above, may be prepared as shown in scheme 8.

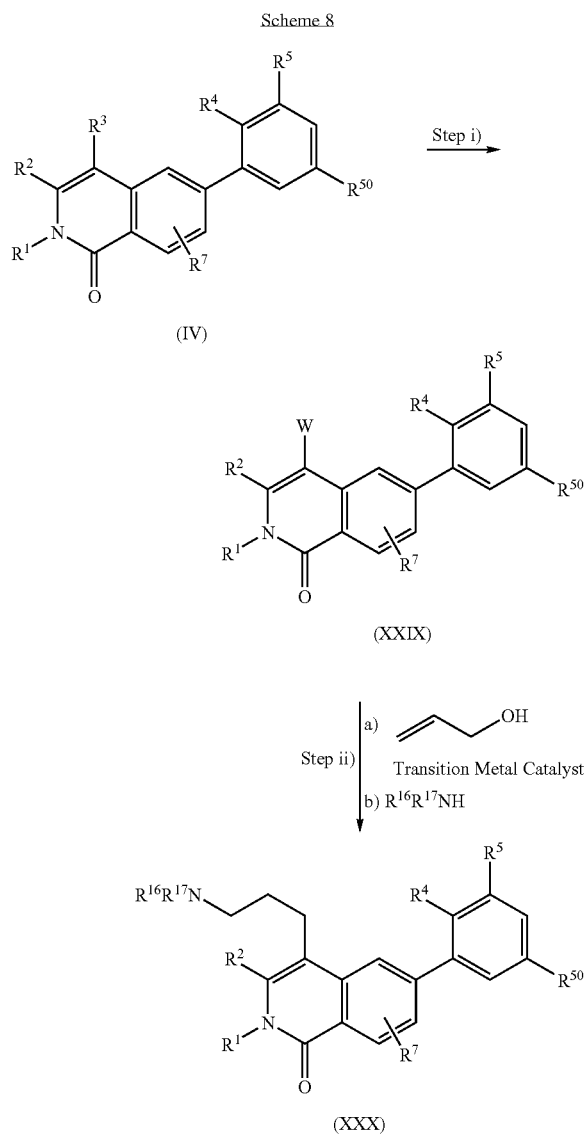

Scheme 8, Step i)

A compound of formula (XXIX) wherein W is a leaving group such as a halide (for example bromide or iodide) may be prepared by electrophilic substitution of a compound of formula (IV) where $R^3$ is H. The electrophilic substitution is carried out with a suitable source of electrophilic halogen such as bromine, iodine, N-bromosuccinimide, N-iodosuccinimide HOBr or iodine monochloride. Usually an acid catalyst is required such as ferric chloride or acetic acid. Typically the reaction is carried out where W is Br, using bromine in acetic acid at room temperature.

Scheme 8, Step ii)

A compound of formula (XXX) may be prepared from a compound of formula (XXIX) by treating with allylic alcohol in the presence of a transition metal catalyst such as 1,1-bis (di-tert-butylphosphino)ferrocene palladium dichloride (Pd-118) under an inert atmosphere and in an inert solvent such as N,N-dimethylformamide at temperatures between 0° C. and 150° C., followed by an in-situ reductive amination. The reductive amination is usually carried out by the addition of a suitable amine of formula $R^{16}R^{17}NH$ and a reducing agent such as sodium cyanoborohydride, sodium triacetoxyborohydride or sodium borohydride. Typically the reaction is carried out in N,N-dimethylformamide using 1,1-bis(di-tert-butylphosphino)ferrocene palladium dichloride (Pd-118) at 70° C. Following addition of aqueous hydrochloric acid and filtration, a suitable amine of formula $R^{16}R^{17}NH$ and sodium triacetoxyborohydride are added.

Amines of formula $HNR^{16}R^{17}$ are commercially available or are prepared by known experimental methods.

In a further aspect the present invention provides a process for the preparation of a compound of formula (I), or a pharmaceutically-acceptable salt or N-oxide thereof, by
(a) reacting a compound of formula (II):

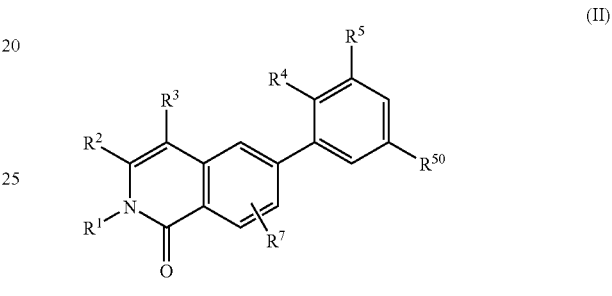

wherein $R^1$, $R^2$, $R^3$, $R^4$, $R^5$ and $R^7$ are as defined in formula (I) and $R^{50}$ is a carboxylic acid or a derivative thereof (such as a methyl ester or an acid chloride);
with an amine of formula (III)

$$H_2NR^6 \quad (III)$$

wherein $R^6$ is as defined formula (I), in an inert solvent (e.g. dichloromethane or tetrahydrofuran); or
(b) when $R^3$ is $CH_2NR^6R^7$, reacting a compound of formula (XXXI) wherein $R^1$, $R^2$, $R^4$, $R^5$, $R^6$ and $R^7$ are as defined in formula (I)

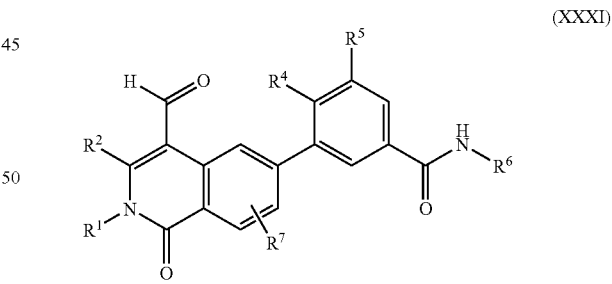

with an amine of formula $HNR^{16}R^{17}$, wherein $R^{16}$ and $R^{17}$ are as defined in formula (I), in the presence of a suitable reducing agent (e.g. sodium triacetoxyborohydride) in an inert solvent (e.g. dichloromethane);
and optionally after (a) or (b) converting the compound obtained to a pharmaceutically acceptable salt or N-oxide of the compound.

It will be appreciated by those skilled in the art that in the processes of the present invention certain functional groups such as hydroxyl, carboxyl, amino or lactam groups in the starting reagents or intermediate compounds may need to be protected by protecting groups. Thus, the preparation of the compounds of formula (I) may involve at a certain stage the removal of one or more protecting groups. The protection and deprotection of functional groups is described in 'Protective Groups in Organic Synthesis', 2nd edition, T. W. Greene and P. G. M. Wuts, Wiley-Interscience (1991) and 'Protecting Groups', P. J. Kocienski, Georg Thieme Verlag (1994).

The compounds of the invention have activity as pharmaceuticals, in particular as p38 kinase inhibitors. Diseases and conditions which may be treated with the compounds include:

1. respiratory tract obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus;
2. bone and joints: arthritides associated with or including osteoarthritis/osteoarthrosis, both primary and secondary to, for example, congenital hip dysplasia; cervical and lumbar spondylitis, and low back and neck pain; rheumatoid arthritis and Still's disease; seronegative spondyloarthropathies including ankylosing spondylitis, psoriatic arthritis, reactive arthritis and undifferentiated spondarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositits and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthalgias, tendonititides, and myopathies;
3. pain and connective tissue remodelling of musculoskeletal disorders due to injury [for example sports injury] or disease: arthritides (for example rheumatoid arthritis, osteoarthritis, gout or crystal arthropathy), other joint disease (such as intervertebral disc degeneration or temporomandibular joint degeneration), bone remodelling disease (such as osteoporosis, Paget's disease or osteonecrosis), polychondritis, scleroderma, mixed connective tissue disorder, spondyloarthropathies or periodontal disease (such as periodontitis);
4. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia greata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;
5. eyes: blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; infections including viral, fungal, and bacterial;
6. gastrointestinal tract glossitis, gingivitis, periodontitis; oesophagitis, including reflux; eosinophilic gastro-enteritis, mastocytosis, Crohn's disease, colitis including ulcerative colitis, proctitis, pruritis ani; coeliac disease, irritable bowel syndrome, and food-related allergies which may have effects remote from the gut (for example migraine, rhinitis or eczema);
7. abdominal: hepatitis, including autoimmune, alcoholic and viral; fibrosis and cirrhosis of the liver; cholecystitis; pancreatitis, both acute and chronic;
8. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);
9. allograft rejection: acute and chronic following, for example, transplantation of kidney, heart, liver, lung, bone marrow, skin or cornea or following blood transfusion; or chronic graft versus host disease;
10. CNS: Alzheimer's disease and other dementing disorders including CJD and nvCJD; amyloidosis; multiple sclerosis and other demyelinating syndromes; cerebral atherosclerosis and vasculitis; temporal arteritis; myasthenia gravis; acute and chronic pain (acute, intermittent or persistent, whether of central or peripheral origin) including visceral pain, headache, migraine, trigeminal neuralgia, atypical facial pain, joint and bone pain, pain arising from cancer and tumor invasion, neuropathic pain syndromes including diabetic, post-herpetic, and HIV-associated neuropathies; neurosarcoidosis; central and peripheral nervous system complications of malignant, infectious or autoimmune processes;
11. other auto-immune and allergic disorders including Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome;

12. other disorders with an inflammatory or immunological component; including acquired immune deficiency syndrome (AIDS), leprosy, Sezary syndrome, and paraneoplastic syndromes;
13. cardiovascular atherosclerosis, affecting the coronary and peripheral circulation; pericarditis; myocarditis, inflammatory and auto-immune cardiomyopathies including myocardial sarcoid; ischaemic reperfusion injuries; endocarditis, valvulitis, and aortitis including infective (for example syphilitic); vasculitides; disorders of the proximal and peripheral veins including phlebitis and thrombosis, including deep vein thrombosis and complications of varicose veins;
14. oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and,
15. gastrointestinal tract. Coeliac disease, proctitis, eosinopilic gastro-enteritis, mastocytosis, Crohn's disease, ulcerative colitis, microscopic colitis, indeterminant colitis, irritable bowel disorder, irritable bowel syndrome, non-inflammatory diarrhea, food-related allergies which have effects remote from the gut, e.g., migraine, rhinitis and eczema.

Accordingly, the present invention further provides a compound of formula (I), (IA), (IB), (IC), (ID), (IE), (IF), (IG) or (IH) as hereinbefore defined for use in therapy.

In another aspect, the invention provides the use of a compound of formula (I), as hereinbefore defined, in the manufacture of a medicament for use in therapy.

In the context of the present specification, the term "therapy" also includes "prophylaxis" unless there are specific indications to the contrary. The terms "therapeutic" and "therapeutically" should be construed accordingly.

A further aspect of the invention provides a method of treating a disease state in a mammal suffering from, or at risk of, said disease, which comprises administering to a mammal in need of such treatment a therapeutically effective amount of a compound of formula (I) as hereinbefore defined.

The present invention also provides the use of a compound of formula (I), (IA), (IB), (IC), (ID), (IE), (IF), (IG) or (IH) as hereinbefore defined, in the manufacture of a medicament for use in the treatment of chronic obstructive pulmonary disease (COPD) (such as irreversible COPD).

The present invention also provides the use of a compound of formula (I), (IA), (IB), (IC), (ID), (IE), (IF), (IG) or (IH) as hereinbefore defined, in the manufacture of a medicament for use in the treatment of asthma.

The present invention also provides a compound of formula (I), (IA), (IB), (IC), (ID), (IE), (IF), (IG) or (IH) as hereinbefore defined, for treating chronic obstructive pulmonary disease (COPD) (such as irreversible COPD).

The present invention also provides a compound of formula (I), (IA), (IB), (IC), (ID), (IE), (IF), (IG) or (IH) as hereinbefore defined, for treating asthma.

The present invention further provides a method of treating chronic obstructive pulmonary disease (COPD) (such as irreversible COPD), in a warm-blooded animal, such as man, which comprises administering to a mammal in need of such treatment an effective amount of a compound of formula (I), (IA), (IB), (IC), (ID), (IE), (IF), (IG) or (IH) as hereinbefore defined.

The present invention further provides a method of treating asthma in a warm-blooded animal, such as man, which comprises administering to a mammal in need of such treatment an effective amount of a compound of formula (I), (IA), (IB), (IC), (ID), (IE), (IF), (IG) or (IH) as hereinbefore defined.

In order to use a compound of the invention for the therapeutic treatment of a warm-blooded animal, such as man, said ingredient is normally formulated in accordance with standard pharmaceutical practice as a pharmaceutical composition.

Therefore in another aspect the present invention provides a pharmaceutical composition that comprises a compound of the invention as hereinbefore defined and a pharmaceutically acceptable adjuvant, diluent or carrier. In a further aspect the present invention provides a process for the preparation of said composition, which comprises mixing active ingredient with a pharmaceutically acceptable adjuvant, diluent or carrier. Depending on the mode of administration, the pharmaceutical composition will, for example, comprise from 0.05 to 99% w (percent by weight), such as from 0.05 to 80% w, for example from 0.10 to 70% w, such as from 0.10 to 50% w, of active ingredient, all percentages by weight being based on total composition.

The pharmaceutical compositions of this invention may be administered in standard manner for the disease condition that it is desired to treat, for example by topical (such as to the lung and/or airways or to the skin), oral, rectal or parenteral administration. For these purposes the compounds of this invention may be formulated by means known in the art into the form of, for example, aerosols, dry powder formulations, tablets, capsules, syrups, powders, granules, aqueous or oily solutions or suspensions, (lipid) emulsions, dispersible powders, suppositories, ointments, creams, drops and sterile injectable aqueous or oily solutions or suspensions.

A suitable pharmaceutical composition of this invention is one suitable for oral administration in unit dosage form, for example a tablet or capsule, which contains between 0.1 mg and 1 g of active ingredient.

In another aspect a pharmaceutical composition of the invention is one suitable for intravenous, subcutaneous or intramuscular injection. Each patient may receive, for example, an intravenous, subcutaneous or intramuscular dose of 0.01 mgkg$^{-1}$ to 100 mgkg$^{-1}$ of the compound, for example in the range of 0.1 mgkg$^{-1}$ to 20 mgkg$^{-1}$ of this invention, the composition being administered 1 to 4 times per day. The intravenous, subcutaneous and intramuscular dose may be given by means of a bolus injection. Alternatively the intravenous dose may be given by continuous infusion over a period of time. Alternatively each patient will receive a daily oral dose, which is approximately equivalent to the daily parenteral dose, the composition being administered 1 to 4 times per day Another suitable pharmaceutical composition of this invention is one suitable for inhaled administration, inhalation being a particularly useful method for administering the compounds of the invention when treating respiratory diseases such as chronic obstructive pulmonary disease (COPD) or asthma. When administered by inhalation the compounds of formula (I) may be used effectively at doses in the µg range, for example 0.1 to 500 µg, 0.1 to 50 µg, 0.1 to 40 µg, 0.1 to 30 µg, 0.1 to 20 µg, 0.1 to 10 µg, 5 to 10 µg, 5 to 50 µg, 5 to 40 µg, 5 to 30 µg, 5 to 20 µg, 5 to 10 µg, 10 to 50 µg, 10 to 40 µg 10 to 30 µg, or 10 to 20 µg of active ingredient.

In an embodiment of the invention, there is provided a pharmaceutical composition comprising a compound of the invention as hereinbefore defined, in association with a pharmaceutically acceptable adjuvant, diluent or carrier, which is formulated for inhaled administration.

When administered by inhalation, metered dose inhaler devices may be used to administer the active ingredient, dispersed in a suitable propellant and with or without additional excipients such as ethanol, surfactants, lubricants or stabilising agents. Suitable propellants include hydrocarbon, chlorofluorocarbon and hydrofluoroalkane (e.g. heptafluoroalkane) propellants, or mixtures of any such propellants. Preferred propellants are P134a and P227, each of which may be used alone or in combination with other propellants and/or surfactant and/or other excipients. Nebulised aqueous suspensions or, preferably, solutions may also be employed, with or without a suitable pH and/or tonicity adjustment, either as a unit-dose or multi-dose formulations.

Dry powder inhalers may be used to administer the active ingredient, alone or in combination with a pharmaceutically acceptable carrier, in the later case either as a finely divided powder or as an ordered mixture. The dry powder inhaler may be single dose or multi-dose and may utilise a dry powder or a powder-containing capsule.

Metered dose inhaler, nebuliser and dry powder inhaler devices are well known and a variety of such devices are available.

The invention further relates to combination therapies wherein a compound of the invention or a pharmaceutical composition or formulation comprising a compound of the invention, is administered concurrently or sequentially or as a combined preparation with another therapeutic agent or agents, for the treatment of one or more of the conditions listed.

In particular, for the treatment of the inflammatory diseases such as (but not restricted to) rheumatoid arthritis, osteoarthritis, asthma, allergic rhinitis, chronic obstructive pulmonary disease (COPD), psoriasis, and inflammatory bowel disease, the compounds of the invention may be combined with agents listed below.

Non-steroidal anti-inflammatory agents (hereinafter NSAIDs) including non-selective cyclo-oxygenase COX-1/COX-2 inhibitors whether applied topically or systemically (such as piroxicam, diclofenac, propionic acids such as naproxen, flurbiprofen, fenoprofen, ketoprofen and ibuprofen, fenamates such as mefenamic acid, indomethacin, sulindac, azapropazone, pyrazolones such as phenylbutazone, salicylates such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticosteroids (whether administered by topical, oral, intramuscular, intravenous, or intra-articular routes); methotrexate; leflunomide; hydroxychloroquine; d-penicillamine; auranofin or other parenteral or oral gold preparations; analgesics; diacerein; intra-articular therapies such as hyaluronic acid derivatives; and nutritional supplements such as glucosamine.

The present invention still further relates to the combination of a compound of the invention together with a cytokine or agonist or antagonist of cytokine function, (including agents which act on cytokine signalling pathways such as modulators of the SOCS system) including alpha-, beta-, and gamma-interferons; insulin-like growth factor type I (IGF-1); interleukins (IL) including IL1 to 17, and interleukin antagonists or inhibitors such as anakinra; tumour necrosis factor alpha (TNF-α) inhibitors such as anti-TNF monoclonal antibodies (for example infliximab; adalimumab, and CDP-870) and TNF receptor antagonists including immunoglobulin molecules (such as etanercept) and low-molecular-weight agents such as pentoxyfylline.

In addition the invention relates to a combination of a compound of the invention with a monoclonal antibody targeting B-Lymphocytes (such as CD20 (rituximab), MRA-aILI6R and T-Lymphocytes, CTLA4-Ig, HuMax II-15).

The present invention still further relates to the combination of a compound of the invention with a modulator of chemokine receptor function such as an antagonist of CCR1, CCR2, CCR2A, CCR2B, CCR3, CCR4, CCR5, CCR6, CCR7, CCR8, CCR9, CCR10 and CCR11 (for the C-C family); CXCR1, CXCR2, CXCR3, CXCR4 and CXCR5 (for the C-X-C family) and $CX_3CR1$ for the $C-X_3-C$ family.

The present invention further relates to the combination of a compound of the invention with an inhibitor of matrix metalloprotease (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11) and MMP-9 and MMP-12, including agents such as doxycycline.

The present invention still further relates to the combination of a compound of the invention and a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; a N-(5-substituted)-thiophene-2-alkylsulfonamide; 2,6-di-tert-butylphenolhydrazones; a methoxytetrahydropyrans such as Zeneca ZD-2138; the compound SB-210661; a pyridinyl-substituted 2-cyanonaphthalene compound such as L-739,010; a 2-cyanoquinoline compound such as L-746,530; or an indole or quinoline compound such as MK-591, MK-886, and BAY x 1005.

The present invention further relates to the combination of a compound of the invention and a receptor antagonist for leukotrienes (LT) B4, LTC4, LTD4, and LTE4 selected from the group consisting of the phenothiazin-3-1s such as L-651,392; amidino compounds such as CGS-25019c; benzoxalamines such as ontazolast; benzenecarboximidamides such as BIIL 2841260; and compounds such as zafirlukast, ablukast, montelukast, pranlukast, verlukast (MK-679), RG-12525, Ro-245913, iralukast (CGP 45715A), and BAY x 7195.

The present invention still further relates to the combination of a compound of the invention and a phosphodiesterase (PDE) inhibitor such as a methylxanthanine including theophylline and aminophylline; a selective PDE isoenzyme inhibitor including a PDE4 inhibitor an inhibitor of the isoform PDE4D, or an inhibitor of PDE5.

The present invention further relates to the combination of a compound of the invention and a histamine type 1 receptor antagonist such as cetirizine, loratadine, desloratadine, fexofenadine, acrivastine, terfenadine, astemizole, azelastine, levocabastine, chlorpheniramine, promethazine, cyclizine, or mizolastine; applied orally, topically or parenterally.

The present invention still further relates to the combination of a compound of the invention and a proton pump inhibitor (such as omeprazole) or a gastroprotective histamine type 2 receptor antagonist.

The present invention further relates to the combination of a compound of the invention and an antagonist of the histamine type 4 receptor.

The present invention still further relates to the combination of a compound of the invention and an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride or ethylnorepinephrine hydrochloride.

The present invention further relates to the combination of a compound of the invention, or a pharmaceutically acceptable salt thereof, and an anticholinergic agent including a muscarinic receptor (M1, M2, and M3) antagonist such as atropine, hyoscine, glycopyrrrolate, ipratropium bromide, tiotropium bromide, oxitropium bromide, pirenzepine or telenzepine.

The present invention still further relates to the combination of a compound of the invention and a beta-adrenoceptor agonist (including beta receptor subtypes 1-4) such as isoprenaline, salbutamol, formoterol, salmeterol, terbutaline, orciprenaline, bitolterol mesylate, pirbuterol, or indacaterol or a chiral enantiomer thereof.

The present invention further relates to the combination of a compound of the invention and a chromone, such as sodium cromoglycate or nedocromil sodium.

The present invention still further relates to the combination of a compound of the invention with a glucocorticoid, such as flunisolide, triamcinolone acetonide, beclomethasone dipropionate, budesonide, fluticasone propionate, ciclesonide or mometasone furoate.

The present invention further relates to the combination of a compound of the invention with an agent that modulates a nuclear hormone receptor such as PPARs.

The present invention still further relates to the combination of a compound of the invention together with an immunoglobulin (Ig) or Ig preparation or an antagonist or antibody modulating Ig function such as anti-IgE (for example omalizumab).

The present invention further relates to the combination of a compound of the invention and another systemic or topically-applied anti-inflammatory agent, such as thalidomide or a derivative thereof, a retinoid, dithranol or calcipotriol.

The present invention still further relates to the combination of a compound of the invention and combinations of aminosalicylates and sulfapyridine such as sulfasalazine, mesalazine, balsalazide, and olsalazine; and immunomodulatory agents such as the thiopurines, and corticosteroids such as budesonide.

The present invention further relates to the combination of a compound of the invention together with an antibacterial agent such as a penicillin derivative, a tetracycline, a macrolide, a beta-lactam, a fluoroquinolone, metronidazole, an inhaled aminoglycoside; an antiviral agent including acyclovir, famciclovir, valaciclovir, ganciclovir, cidofovir, amantadine, rimantadine, ribavirin, zanamavir and oseltamavir; a protease inhibitor such as indinavir, nelfinavir, ritonavir, and saquinavir; a nucleoside reverse transcriptase inhibitor such as didanosine, lamivudine, stavudine, zalcitabine or zidovudine; or a non-nucleoside reverse transcriptase inhibitor such as nevirapine or efavirenz.

The present invention still further relates to the combination of a compound of the invention and a cardiovascular agent such as a calcium channel blocker, a beta-adrenoceptor blocker, an angiotensin-converting enzyme (ACE) inhibitor, an angiotensin-2 receptor antagonist; a lipid lowering agent such as a statin or a fibrate; a modulator of blood cell morphology such as pentoxyfylline; thrombolytic, or an anticoagulant such as a platelet aggregation inhibitor.

The present invention further relates to the combination of a compound of the invention and a CNS agent such as an antidepressant (such as sertraline), an anti-Parkinsonian drug (such as deprenyl, L-dopa, ropinirole, pramipexole, a MAOB inhibitor such as selegine and rasagiline, a comP inhibitor such as tasmar, an A-2 inhibitor, a dopamine reuptake inhibitor, an NMDA antagonist, a nicotine agonist, a dopamine agonist or an inhibitor of neuronal nitric oxide synthase), or an anti-Alzheimer's drug such as donepezil, rivastigmine, tacrine, a COX-2 inhibitor, propentofylline or metrifonate.

The present invention still further relates to the combination of a compound of the invention and an agent for the treatment of acute or chronic pain, such as a centrally or peripherally-acting analgesic (for example an opioid or derivative thereof), carbamazepine, phenyloin, sodium valproate, amitryptiline or other anti-depressant agent-s, paracetamol, or a non-steroidal anti-inflammatory agent.

The present invention further relates to the combination of a compound of the invention together with a parenterally or topically-applied (including inhaled) local anaesthetic agent such as lignocaine or a derivative thereof.

A compound of the present invention can also be used in combination with an anti-osteoporosis agent including a hormonal agent such as raloxifene, or a biphosphonate such as alendronate.

The present invention still further relates to the combination of a compound of the invention together with a: (i) tryptase inhibitor; (ii) platelet activating factor (PAF) antagonist; (iii) interleukin converting enzyme (ICE) inhibitor; (iv) IMPDH inhibitor; (v) adhesion molecule inhibitors including VLA-4 antagonist; (vi) cathepsin; (vii) kinase inhibitor such as an inhibitor of tyrosine kinase (such as Btk, Itk, Jak3 or MAP, for example Gefitinib or Imatinib mesylate), a serine/threonine kinase (such as an inhibitor of a MAP kinase such as p38, JNK, protein kinase A, B or C, or IKK), or a kinase involved in cell cycle regulation (such as a cyclin dependent kinase): (viii) glucose-6 phosphate dehydrogenase inhibitor; (ix) kinin-B1.- or B2.-receptor antagonist; (x) anti-gout agent, for example colchicine; (xi) xanthine oxidase inhibitor, for example allopurinol; (xii) uricosuric agent, for example probenecid, sulfinpyrazone or benzbromarone; (xiii) growth hormone secretagogue; (xiv) transforming growth factor (TGFβ); (xv) platelet-derived growth factor (PDGF); (xvi) fibroblast growth factor for example basic fibroblast growth factor (bFGF); (xvii) granulocyte macrophage colony stimulating factor (GM-CSF); (xviii) capsaicin cream; (xix) tachykinin NK1 or NK3 receptor antagonist such as NKP-608C, SB-233412 (talnetant) or D-4418; (xx) elastase inhibitor such as UT-77 or ZD-0892; (xxi) TNF-alpha converting enzyme inhibitor (TACE); (xxii) induced nitric oxide synthase (iNOS) inhibitor; (xxiii) chemoattractant receptor-homologous molecule expressed on TH2 cells, (such as a CRTH2 antagonist); (xxiv) inhibitor of P38; (xxv) agent modulating the function of Toll-like receptors (TLR), (xxvi) agent modulating the activity of purinergic receptors such as P2X7; or (xxvii) inhibitor of transcription factor activation such as NFkB, API, or STATS.

A compound of the invention can also be used in combination with an existing therapeutic agent for the treatment of cancer, for example suitable agents include:
(i) an antiproliferative/antineoplastic drug or a combination thereof, as used in medical oncology, such as an alkylating agent (for example cis-platin, carboplatin, cyclophosphamide, nitrogen mustard, melphalan, chlorambucil, busulphan or a nitrosourea); an antimetabolite (for example an antifolate such as a fluoropyrimidine like 5-fluorouracil or tegafur, raltitrexed, methotrexate, cytosine arabinoside, hydroxyurea, gemcitabine or paclitaxel); an antitumour antibiotic (for example an anthracycline such as adriamycin, bleomycin, doxorubicin, daunomycin, epirubicin, idarubicin, mitomycin-C, dactinomycin or mithramycin); an antimitotic agent (for example a vinca alkaloid such as vincristine, vinblastine, vindesine or vinorelbine, or a taxoid such as taxol or taxotere); or a topoisomerase inhibitor (for example an epipodophyllotoxin such as etoposide, teniposide, amsacrine, topotecan or a camptothecin);

(ii) a cytostatic agent such as an antioestrogen (for example tamoxifen, toremifene, raloxifene, droloxifene or iodoxyfene), an oestrogen receptor down regulator (for example fulvestrant), an antiandrogen (for example bicalutamide, flutamide, nilutamide or cyproterone acetate), a LHRH antagonist or LHRH agonist (for example goserelin, leuprorelin or buserelin), a progestogen (for example megestrol acetate), an aromatase inhibitor (for example as anastrozole, letrozole, vorazole or exemestane) or an inhibitor of 5α-reductase such as finasteride;

(iii) an agent which inhibits cancer cell invasion (for example a metalloproteinase inhibitor like marimastat or an inhibitor of urokinase plasminogen activator receptor function);

(iv) an inhibitor of growth factor function, for example: a growth factor antibody (for example the anti-erbb2 antibody trastuzumab, or the anti-erbb1 antibody cetuximab [C225]), a farnesyl transferase inhibitor, a tyrosine kinase inhibitor or a serine/threonine kinase inhibitor, an inhibitor of the epidermal growth factor family (for example an EGFR family tyrosine kinase inhibitor such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) or 6-acrylamido-N-(3-chloro-4-fluorophenyl)-7-(3-morpholinopropoxy) quinazolin-4-amine (CI 1033)), an inhibitor of the platelet-derived growth factor family, or an inhibitor of the hepatocyte growth factor family;

(v) an antiangiogenic agent such as one which inhibits the effects of vascular endothelial growth factor (for example the anti-vascular endothelial cell growth factor antibody bevacizumab, a compound disclosed in WO 97/22596, WO 97/30035, WO 97/32856 or WO 98/13354), or a compound that works by another mechanism (for example linomide, an inhibitor of integrin αvβ3 function or an angiostatin);

(vi) a vascular damaging agent such as combretastatin A4, or a compound disclosed in WO 99/02166, WO 00/40529, WO 00/41669, WO 01/92224, WO 02/04434 or WO 02/08213;

(vii) an agent used in antisense therapy, for example one directed to one of the targets listed above, such as ISIS 2503, an anti-ras antisense;

(viii) an agent used in a gene therapy approach, for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; or (ix) an agent used in an immunotherapeutic approach, for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

In a further embodiment the present invention provides a pharmaceutical product comprising, in combination, a first active ingredient which is a compound of formula (I), (IA), (IB), (IC), (ID), (IE), (IF), (IG) or (IH) or a pharmaceutically acceptable salt or N-oxide thereof, as hereinbefore described, and at least one further active ingredient selected from:—
  a phosphodiesterase inhibitor
  a β2 adrenoceptor agonist
  a modulator of chemokine receptor function
  a protease inhibitor
  a steroidal glucocorticoid receptor agonist
  an anticholinergic agent, and a
  a non-steroidal glucocorticoid receptor agonist.

The pharmaceutical product according to this embodiment may, for example, be a pharmaceutical composition comprising the first and further active ingredients in admixture. Alternatively, the pharmaceutical product may, for example, comprise the first and further active ingredients in separate pharmaceutical preparations suitable for simultaneous, sequential or separate administration to a patient in need thereof.

The pharmaceutical product of this embodiment is of particular use in treating respiratory diseases such as asthma, COPD or rhinitis.

Examples of a phosphodiesterase inhibitor that may be used in the pharmaceutical product according to this embodiment include a PDE4 inhibitor such as an inhibitor of the isoform PDE4D, a PDE3 inhibitor and a PDE5 inhibitor. Examples include the compounds
(Z)-3-(3,5-dichloro-4-pyridyl)-2-[4-(2-indanyloxy-5-methoxy-2-pyridyl]propenenitrile,
N-[9-amino-4-oxo-1-phenyl-3,4,6,7-tetrahydropyrrolo[3,2,1-jk][1,4]benzodiazepin-3(R)— yl]pyridine-3-carboxamide (CI-1044),
3-(benzyloxy)-1-(4-fluorobenzyl)-N-[3-(methylsulphonyl)phenyl]-1H-indole-2-carboxamide,
(1S-exo)-5-[3-(bicyclo[2.2.1]hept-2-yloxy)-4-methoxyphenyl]tetrahydro-2(1H)-pyrimidinone (Atizoram),
N-(3,5,dichloro-4-pyridinyl)-2-[1-(4-fluorobenzyl)-5-hydroxy-1H-indol-3-yl]-2-oxoacetamide (AWD-12-281),
β-[3-(cyclopentyloxy)-4-methoxyphenyl]-1,3-dihydro-1,3-dioxo-2H-isoindole-2-propanamide (CDC-801),
N-[9-methyl-4-oxo-1-phenyl-3,4,6,7-tetrahydropyrrolo[3,2,1-jk][1,4]benzodiazepin-3(R)-yl]pyridine-4-carboxamide (CI-1018),
cis-[4-cyano-4-(3-cyclopentyloxy-4-methoxyphenyl)cyclohexane-1-carboxylic acid (Cilomilast),
8-amino-1,3-bis(cyclopropylmethyl)xanthine (Cipamfylline),
N-(2,5-dichloro-3-pyridinyl)-8-methoxy-5-quinolinecarboxamide (D-4418),
5-(3,5-di-tert-butyl-4-hydroxybenzylidene)-2-iminothiazolidin-4-one (Darbufelone),
2-methyl-1-[2-(1-methylethyl)pyrazolo[1,5-a]pyridin-3-yl]-1-propanone (Ibudilast),
2-(2,4-dichlorophenylcarbonyl)-3-ureidobenzofuran-6-yl methanesulphonate (Lirimilast),
(−)-(R)-5-(4-methoxy-3-propoxyphenyl)-5-methyloxazolidin-2-one (Mesopram),
(−)-cis-9-ethoxy-8-methoxy-2-methyl-1,2,3,4,4a,10b-hexahydro-6-(4-diisopropylaminocarbonylphenyl)-benzo[c][1,6]naphthyridine (Pumafentrine),
3-(cyclopropylmethoxy)-N-(3,5-dichloro-4-pyridyl)-4-(difluoromethoxy)benzamide (Roflumilast),
the N-oxide of Roflumilast,
5,6-diethoxybenzo[b]thiophene-2-carboxylic acid (Tibenelast),
2,3,6,7-tetrahydro-2-(mesitylimino)-9,10-dimethoxy-3-methyl-4H-pyrimido[6,1-a]isoquinolin-4-one (trequinsin) and
3-[[3-(cyclopentyloxy)-4-methoxyphenyl]-methyl]-N-ethyl-8-(1-methylethyl)-3H-purine-6-amine (V-11294A).

Examples of a β₂-adrenoceptor agonist that may be used in the pharmaceutical product according to this embodiment include metaproterenol, isoproterenol, isoprenaline, albuterol, salbutamol (e.g. as sulphate), formoterol (e.g. as fumarate), salmeterol (e.g. as xinafoate), terbutaline, orciprenaline, bitolterol (e.g. as mesylate), pirbuterol or indacaterol. The β₂-adrenoceptor agonist of this embodiment may be a long-acting β₂-agonists, for example salmeterol (e.g. as xinafoate), formoterol (e.g. as fumarate), bambuterol (e.g. as hydrochloride), carmoterol (TA 2005, chemically identified as 2(1H)-Quinolone, 8-hydroxy-5-[1-hydroxy-2-[[2-(4-methoxy-phenyl)-1-methylethyl]-amino]ethyl]-monohydrochloride, [R-(R*,R*)] also identified by Chemical Abstract Service Registry Number 137888-11-0 and disclosed in U.S. Pat. No. 4,579,854), indacaterol (CAS no 312753-06-3; QAB-149), formanilide derivatives e.g. 3-(4-{[6-({(2R)-2-[3-(formylamino)-4-hydroxyphenyl]-2-hydroxyethyl}amino)hexyl]oxy}-butyl)-benzenesulfonamide as disclosed in WO 2002/76933, benzenesulfonamide derivatives e.g. 3-(4-{[6-({(2R)-2-hydroxy-2-[4-hydroxy-3-(hydroxy-methyl)phenyl]ethyl}amino)-hexyl]oxy}butyl)benzenesulfonamide as disclosed in WO 2002/88167, aryl aniline receptor agonists as disclosed in WO 2003/042164 and WO 2005/025555, indole derivatives as disclosed in WO 2004/032921, in US 2005/222144, compounds GSK 159797, GSK 159802, GSK 597901, GSK 642444 and GSK 678007.

Examples of a modulator of chemokine receptor function that may be used in the pharmaceutical product according to this embodiment include a CCR1 receptor antagonist.

Examples of a protease inhibitor that may be used in the pharmaceutical product according to this embodiment include an inhibitor of neutrophil elastase or an inhibitor of MMP12.

Examples of a steroidal glucocorticoid receptor agonist that may be used in the pharmaceutical product according to this embodiment include budesonide, fluticasone (e.g. as propionate ester), mometasone (e.g. as furoate ester), beclomethasone (e.g. as 17-propionate or 17,21-dipropionate esters), ciclesonide, loteprednol (as e.g. etabonate), etiprednol (as e.g. dicloacetate), triamcinolone (e.g. as acetonide), flunisolide, zoticasone, flumoxonide, rofleponide, butixocort (e.g. as propionate ester), prednisolone, prednisone, tipredane, steroid esters e.g. 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-propionyloxy-androsta-1,4-diene-17β-carbothioic acid S-(2-oxo-tetrahydro-furan-3S-yl) ester and 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, steroid esters according to DE 4129535, steroids according to WO 2002/00679, WO 2005/041980, or steroids GSK 870086, GSK 685698 and GSK 799943.

Examples of an anticholinergic agent that may be used in the pharmaceutical product according to this embodiment include for example a muscarinic receptor antagonist (for example a M1, M2 or M3 antagonist, such as a M3 antagonist) for example ipratropium (e.g. as bromide), tiotropium (e.g. as bromide), oxitropium (e.g. as bromide), tolterodine, pirenzepine, telenzepine, glycopyrronium bromide (such as R,R-glycopyrronium bromide or a mixture of R,S- and S,R-glycopyrronium bromide); mepensolate (e.g. as bromide), a quinuclidine derivative such as 3(R)-(2-hydroxy-2,2-dithien-2-ylacetoxy)-1-(3-phenoxypropyl)-1-azonia-bicyclo[2.2.2] octane bromide as disclosed in US 2003/0055080, quinuclidine derivatives as disclosed in WO 2003/087096 and WO 2005/115467 and DE 10050995; or GSK 656398 or GSK 961081.

Examples of a modulator of a non-steroidal glucocorticoid receptor agonist that may be used in the pharmaceutical product according to this embodiment include those described in WO2006/046916.

The present invention is further illustrated by the non-limiting examples that follow below. In these examples the NMR spectra were measured on a Varian Unity Inova spectrometer at a proton frequency of either 300 or 400 MHz. The MS spectra were measured on a Hewlett Packard HP1100 MSD G1946A spectrometer. Preparative HPLC separations were performed using a Waters Symmetry® or XBridge® column or a Phenomenex Gemini® column using 0.1% aqueous trifluoroacetic acid, 0.1% aqueous ammonia or 0.1% ammonium acetate as the aqueous phase and either acetonitrile or methanol as the organic phase. SCX and NH₂ resin were obtained from Varian Incorporated. Reactions that were heated by microwave irradiation were performed using a CEM Discover Microwave. Compounds were named using the MDL Information Systems AutoNom program.

The following abbreviations have been used:—
DMF N,N-dimethylformamide
DMSO dimethylsulphoxide
THF tetrahydrofuran
DMA N,N-dimethylacetamide
DCM dichloromethane
HATU O-(7-Azabenzotriazol-1-yl)-N,N,N',N'-tetramethyluronium hexafluorophosphate
Pd-118 1,1-bis(di-tert-butylphosphino)ferrocene palladium dichloride
Pd(dppf)₂Cl₂ [1,1'-Bis(diphenylphosphino)ferrocene]dichloropalladium(II) complex with CH₂Cl₂

INTERMEDIATE 1

6-Bromo-2H-isoquinolin-1-one

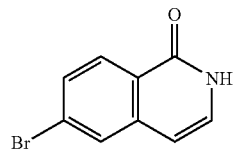

The title compound was prepared as described in EP0526402.

INTERMEDIATE 2

3-Borono-4-methyl-benzoic acid, methyl ester

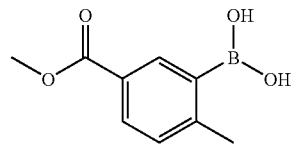

The title compound was prepared as described in Organic Letts., 2006, 8, 305.

INTERMEDIATE 3

4-Methyl-3-(1-oxo-1,2-dihydro-isoquinolin-6-yl)-benzoic acid, methyl ester

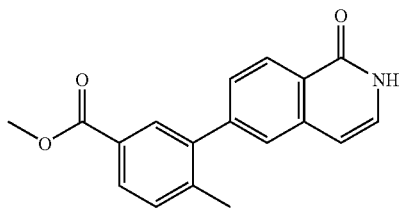

6-Bromo-2H-isoquinolin-1-one (0.5 g) (intermediate 1), 3-borono-4-methyl-benzoic acid methyl ester (0.5 g) (intermediate 2), potassium carbonate (0.69), and dry DMF (10 mL) were stirred under nitrogen at room temperature. Tetrakis(triphenylphosphine)palladium(0) (200 mg) was then added and the mixture heated at 95° C. for 12 hours. The mixture was allowed to cool to room temperature and then poured into dilute hydrochloric acid. The aqueous was extracted with ethyl acetate. The organics were combined, dried over magnesium sulfate then filtered and evaporated under reduced pressure. Purification (SiO$_2$ with 1:1 ethyl acetate/isohexane eluant) gave the title compound (0.45 g).

MS: APCI (+ve) 294 (M+H)$^+$ $^1$H NMR DMSO-d$_6$ 11.30 (1H, s broad), 8.25 (1H, d), 7.96-7.85 (1H, m), 7.72-7.48 (4H, m), 7.25 (1H, t), 6.62 (1H, d), 3.86 (3H, s), 2.33 (3H, s).

INTERMEDIATE 4

3-(2-Benzyl-1-oxo-1,2-dihydro-isoquinolin-6-yl)-4-methyl-benzoic acid, methyl ester

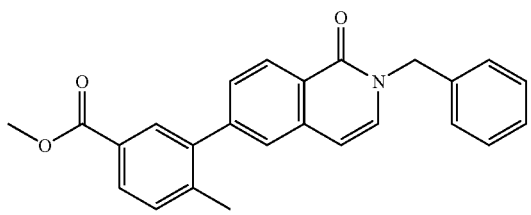

Intermediate 3 (0.45 g) was dissolved in dry DMF (10 mL) then 60% sodium hydride (70 mg) was added under nitrogen. The mixture was allowed to stir for 30 minutes at room temperature then benzyl bromide (0.2 mL) was added. The mixture was then stirred at room temperature for a further 12 hours. The reaction mixture was then poured into water and extracted with ethyl acetate. The organics were combined, dried over magnesium sulfate then filtered and evaporated under reduced pressure. Purification (SiO$_2$ with 1:4 ethyl acetate: isohexane as eluant) gave the title compound (0.5 g).

MS: APCI (+ve) 384 (M+H)$^+$ $^1$H NMR DMSO-d$_6$ 8.29 (1H, d), 7.98-7.90 (1H, m), 7.82 (1H, m), 7.72 (1H, s), 7.64 (1H, d), 7.54 (1H, d), 7.42 (1H, m), 7.38-7.30 (5H, m), 6.72 (1H, d), 5.21 (2H, s), 3.85 (3H, s), 2.32 (3H, s).

INTERMEDIATE 5

3-(2-Benzyl-1-oxo-1,2-dihydro-isoquinolin-6-yl)-methyl-benzoic acid

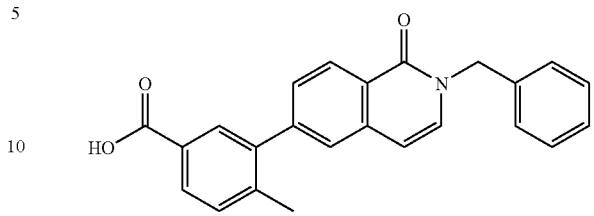

Intermediate 4 (0.5 g), lithium hydroxide monohydrate (0.1 g), methanol (20 mL) and water (4 mL) were stirred at room temperature for one hour then heated at 50° C. for two hours. On cooling to room temperature the reaction was poured into dilute hydrochloric acid and extracted with ethyl acetate. The organics were combined, dried over magnesium sulfate then filtered and evaporated under reduced pressure to give the title compound (0.4 g).

INTERMEDIATE 6

3-(2-Benzyl-1-oxo-1,2-dihydro-isoquinolin-6-yl)-4-methyl-benzoyl chloride

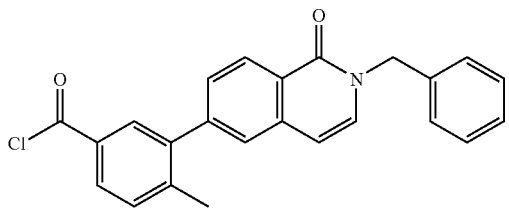

Intermediate 5 (0.4 g) was dissolved in dichloromethane (25 mL) then oxalyl chloride (0.5 mL) and one drop of N,N-dimethylformamide were added. The mixture was stirred at room temperature for twelve hours. The volatiles were removed under reduced pressure to give the title compound which was used directly without further purification.

EXAMPLE 1

3-(2-Benzyl-1-oxo-1,2-dihydro-isoquinolin-6-yl)-N-cyclopropyl-4-methyl-benzamide

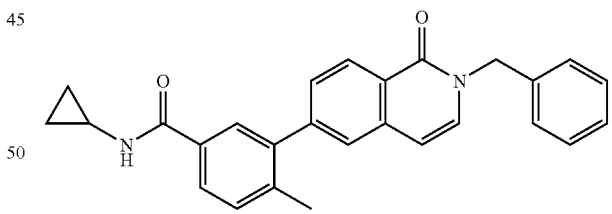

Intermediate 6 (0.29) in dichloromethane (5 mL) was added to a solution of cyclopropylamine (1 mL) in dichloromethane (5 mL). The reaction mixture was stirred at room temperature for 12 hours then poured into water and extracted with ethyl acetate. The organics were combined, dried over magnesium sulfate then filtered and evaporated under reduced pressure. Purification (SiO$_2$ with 1:1 ethyl acetate: isohexane as eluant) gave the title compound as a solid (120 mg).

MS: APCI (+ve) 409 (M+H)$^+$ $^1$H NMR DMSO-d$_6$ 8.42 (1H, d), 8.29 (1H, d), 7.79 (1H, d), 7.75 (1H, s), 7.67 (1H, s), 7.62 (1H, d), 7.51 (1H, d), 7.41 (1H, d), 7.33-7.30 (5H, m), 6.71 (1H, d), 5.22 (1H, s), 2.28 (3H, s), 2.90-2.84 (1H, m), 0.71-0.66 (2H, m), 0.61-0.56 (2H, m).

EXAMPLE 2

3-(2-Benzyl-1-oxo-1,2-dihydro-isoquinolin-6-yl)-N-ethyl-4-methyl-benzamide

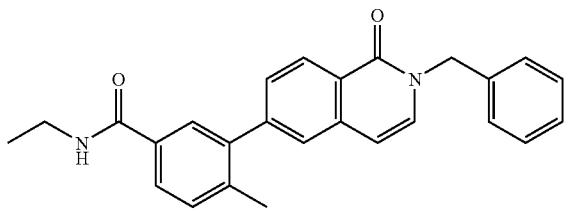

Intermediate 6 (0.2 g) in dichloromethane (5 mL) was added to a solution of 2.0M ethylamine in THF (5 mL). The solution was stirred for 12 hours at room temperature. The reaction mixture was poured into water and extracted with ethyl acetate. The organics were combined, dried over magnesium sulfate then filtered and evaporated under reduced pressure. Purification (SiO$_2$ with 1:1 ethyl acetate:isohexane as eluant) gave the title compound as a solid (100 mg).

MS: APCI (+ve) 397 (M+H)$^+$ $^1$H NMR DMSO-d$_6$ 8.47 (1H, t), 8.31 (1H, d), 7.82 (1H, s), 7.79-7.78 (1H, m), 7.69 (1H, s), 7.63 (1H, d), 7.54 (1H, d), 7.43 (1H, d), 7.37-7.29 (5H, m), 6.72 (1H, d), 5.21 (2H, d), 3.31-3.24 (2H, m), 2.30 (3H, s), 1.13 (3H, t).

EXAMPLE 3

3-[2-(4-Bromo-benzyl)-1-oxo-1,2-dihydro-isoquinolin-6-yl]-N-cyclopropyl-4-methyl-benzamide

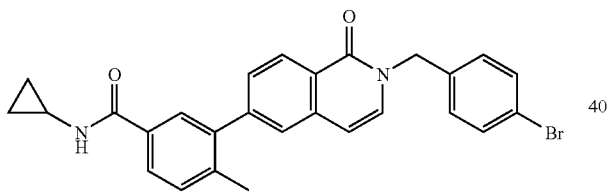

i) 3-[2-(4-Bromo-benzyl)-1-oxo-1,2-dihydro-isoquinolin-6-yl]-4-methyl-benzoic acid, methyl ester

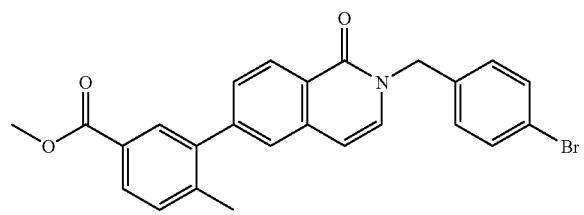

60% Sodium hydride (70 mg,) was added to a solution of intermediate 3 (0.45 g) in dry DMF (10 mL). The reaction mixture was stirred for 30 minutes at room temperature then 4-bromobenzyl bromide (0.45 g) added. The reaction mixture was then stirred at room temperature for a further 12 hours. The reaction mixture was poured into water and extracted with ethyl acetate. The organics were combined, dried over magnesium sulfate then filtered and evaporated under reduced pressure. Purification (SiO$_2$ with 4:1 ethyl acetate: isohexane as eluant) gave the sub-title compound (0.45 g).

MS: APCI (+ve) 462,464 (M+H)$^+$ $^1$H NMR DMSO-d$_6$ 8.29 (1H, d), 7.92 (1H, d3, 7.83 (1H, s), 7.69 (1H, s), 7.63 (1H, d), 7.57-7.49 (4H, m), 7.30 (2H, d), 6.73 (1H, d), 5.18 (2H, s), 3.86 (3H, s), 2.32 (3H, s).

ii) 3-[2-(4-Bromo-benzyl)-1-oxo-1,2-dihydro-isoquinolin-4-yl-N-cyclopropyl-4-methyl-benzamide

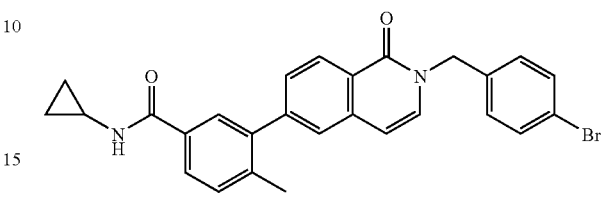

2.0M Isopropylmagnesium chloride in THF (0.9 mL) was added dropwise to a solution of cyclopropylamine (0.18 mL) in THF (5 mL). The reaction mixture was stirred for 5 minutes then Example 3 step (i) (0.2 g) in dry THF (3 mL) was added dropwise. The reaction mixture was stirred for 3 hours at room temperature. The reaction mixture was then poured into saturated ammonium chloride solution and extracted with dichloromethane. The organics were combined, dried over magnesium sulfate then filtered and evaporated under reduced pressure. Purification (SiO$_2$ with 1:1 ethyl acetate: isohexane as eluant) gave the title compound as a solid (0.18 g).

MS: APCI (+ve) 487,489 (M+H)$^+$ $^1$H NMR DMSO-d$_6$ 8.45 (1H, s), 8.28 (1H, d), 7.79 (1H, dd), 7.75 (1H, s), 7.67 (1H, s), 7.63 (1H, d), 7.57-7.51 (3H, m), 7.42 (1H, d), 7.30 (1H, d), 6.72 (1H, d), 5.19 (2H, s), 2.87-2.82 (1H, m), 0.71-0.64 (2H, m), 0.58-0.52 (2H, m).

EXAMPLE 4

N-Cyclopropyl-4-methyl-3{2-[4-(4-methyl-piperazin-1-yl)-benzyl]-1-oxo-1,2-dihydro-isoquinolin-6-yl}-benzamide

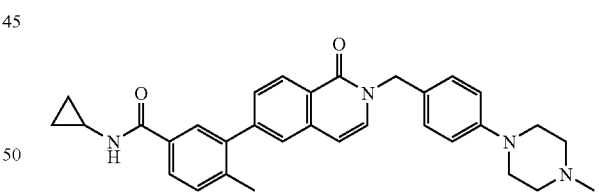

(i) 4-Methyl-3-{2-[4-(4-methyl-piperazin-1-yl)-benzyl]-1-oxo-1,2-dihydro-isoquinolin-6-yl}-benzoic acid, methyl ester

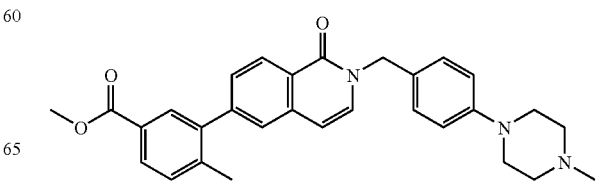

Example 3 step (i) (0.2 g), N-methylpiperazine (0.13 g), cesium carbonate (0.42 g), palladium (II) acetate (10 mg), BINAP (30 mg), in 1,4-dioxane (10 mL) were heated at 100° C. for 18 hours. The reaction mixture was allowed to cool and then evaporated under reduced pressure. Purification (SiO$_2$ 5:95 methanol:dichloromethane as eluant) gave the sub-title compound (40 mg) which was used directly in the next step.

(ii) N-Cyclopropyl-4-methyl-3{-2-[4-(4-methyl-piperazin-1-yl)-benzyl]-1-oxo-1,2-dihydro-isoquinolin-6-yl}-benzamide

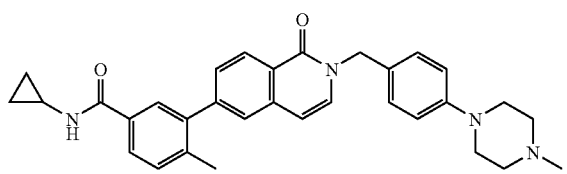

The title compound was prepared as described in Example 3 step (ii) using the product of step (i). Purification (SiO$_2$ 5:95 methanol:dichloromethane as eluant) gave the title compound as a solid (17 mg).

MS: APCI (+ve) 507 (M+H)$^+$ $^1$H NMR DMSO-d$_6$ 8.45 (1H, d), 8.29 (1H, d), 7.79 (1H, dd), 7.74 (1H, d), 7.65 (1H, d) 7.59 (1H, D), 7.51 (1H, dd), 7.41 (1H, d), 7.25 (2H, d), 6.91 (2H, d), 6.68 (1H, d), 5.09 (2H, s) 3.30-3.26 (4H, m), 3.17-3.11 (4H, m) 2.67-2.62 (1H, m), 2.34 (3H, s), 2.27 (3H, s), 0.70-0.66 (2H, m), 0.55-0.52 (2H, m).

EXAMPLE 5

N-Cyclopropyl-3-[2-(4-methanesulfonyl-benzyl)-1-oxo-1,2-dihydro-isoquinolin-6-yl]-4-methyl-benzamide

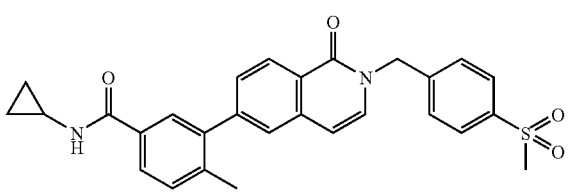

(i) 3-[2-(4-Methanesulfonyl-benzyl)-1-oxo-1,2-dihydro-isoquinolin-6-yl]-4-methyl-benzoic acid, methyl ester

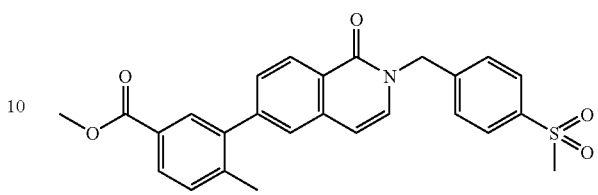

The sub-title compound was prepared as described for Example 3 step (i) using intermediate 3 and 1-chloromethyl-4-methanesulfonyl-benzene.

Purification (SiO$_2$ with 1:1 ethyl acetate:isohexane as eluant) gave the sub-title compound (0.4 g).

MS: APCI (+ve) 462 (M+H)$^+$ $^1$H NMR CDCl$_3$ 8.49 (1H, d), 7.99-7.92 (4H, m), 7.53 (2H, d), 7.49-7.47 (2H, m), 7.35 (1H, d), 7.14 (1H, d), 6.58 (1H, d), 5.31 (2H, s), 3.92 (3H, s), 3.02 (3H, s).

(ii) N-Cyclopropyl-3-[2-(4-methanesulfonyl-benzyl)-1-oxo-1,2-dihydro-isoquinolin-6-yl]-4-methyl-benzamide

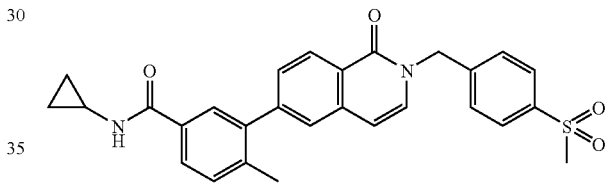

The title compound was prepared as described in Example 3 step (ii) using product of step (i). Purification (SiO$_2$ with 2:98 methanol:dichloromethane as eluant) gave the title compound as a solid (0.12 g).

MS: APCI (+ve) 487 (M+H)$^+$ $^1$H NMR DMSO-d$_6$ 8.43 (1H, d), 8.29 (1H, d), 7.91 (2H, d), 7.79 (1H, dd), 7.75 (1H, m), 7.70-7.66 (2H, m), 7.57-7.52 (3H, m), 7.42 (1H, d), 6.76 (1H, d), 5.33 (2H, s), 3.19 (3H, s), 2.87-2.83 (1H, m), 2.29 (3H, s), 0.70-0.65 (2H, m), 0.58-0.53 (2H, m).

EXAMPLE 6

4-{4-[6-(5-Cyclopropylcarbamoyl-2-methyl-phenyl)-1-oxo-1H-isoquinolin-2-ylmethyl]-phenyl}-3,6-dihydro-2H-pyridine-1-carboxylic acid, tert-butyl ester

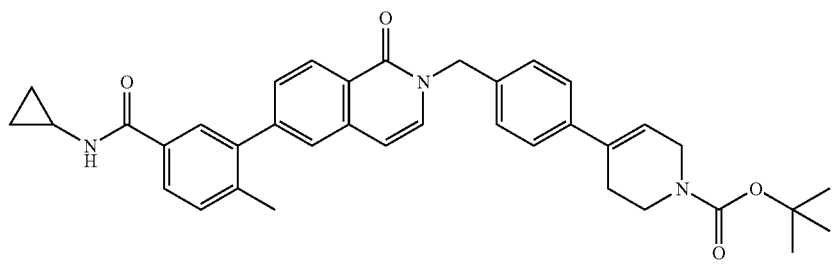

(i) 4-(4,4,5,5-Tetramethyl-[1,3,2]-dioxaborolan-2-yl)-3,6-dihydro-2H-pyridine-1-carboxylic acid, tert-butyl ester

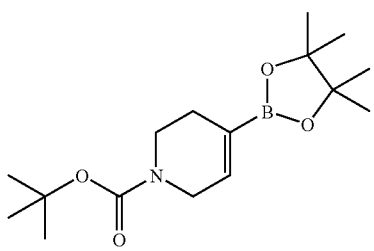

The sub-title compound was prepared as described in Tetrahedron Lett., 2000, 41, 3705.

(ii) 4-{4-[6-(5-Methoxycarbonyl-2-methyl-phenyl)-1-oxo-1H-isoquinolin-2-yl methyl]-phenyl}-3,6-dihydro-2H-pyridine-1-carboxylic acid, tert-butyl ester

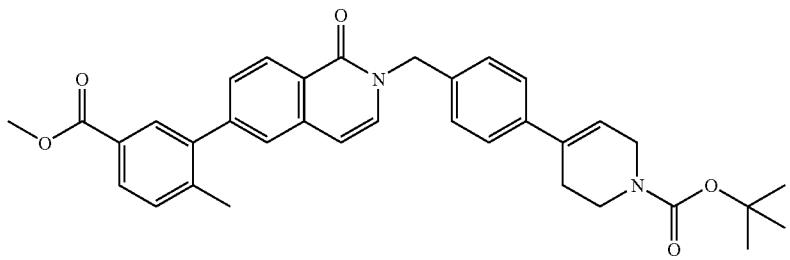

Example 3 step (i) (0.59 g), 4-(4,4,5,5-tetramethyl-[1,3,2]-dioxaborolan-2-yl)-3,6-dihydro-2H-pyridine-1-carboxylic acid, tert-butyl ester (step (i)) (0.4 g), potassium carbonate (0.53 g), Pd(dppf)$_2$Cl$_2$ (100 mg) in DMF (10 mL) were heated at 75° C. for 12 hours. The reaction mixture was allowed to cool then poured into water and extracted with dichloromethane. The organics were combined, dried over magnesium sulfate, then filtered and evaporated under reduced pressure. Purification (SiO$_2$ with 1:3 ethyl acetate:isohexane as eluant) gave the sub-title compound (0.4 g).

MS: APCI (+ve) 565 (M+H)$^+$ $^1$H NMR CDCl$_3$ 8.51 (1H, d), 7.98-7.94 (2H, m), 7.47-7.29 (7H, m), 7.13 (1H, d), 6.51 (1H, d), 6.02 (1H, s), 5.23 (2H, s), 4.09-4.04 (2H, m), 3.91 (3H, s), 3.62 (2H, t), 2.53-2.45 (2H, m), 2.31 (3H, s) 1.48 (9H, s).

(iii) 4-{4-[6-(5-Cyclopropylcarbamoyl-2-methyl-phenyl)-1-oxo-1H-isoquinolin-2-ylmethyl]-phenyl}-3,6-dihydro-2H-pyridine-1-carboxylic acid, tert-butyl ester

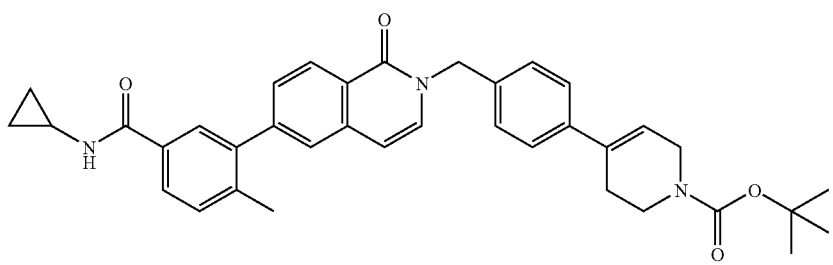

The title compound was prepared as described in Example 3 step (ii) using the product of step (ii). Purification (SiO$_2$ with 1:1 ethyl acetate:isohexane as eluant) gave the title compound as a solid (0.24 g).

MS: APCI (+ve) 590 (M+H)$^+$ $^1$H NMR CDCl$_3$ 8.49 (1H, d), 7.67 (1H, d), 7.62 (1H, s), 7.46-7.40 (2H, m), 7.37-7.31 (5H, m), 7.14 (1H, m), 6.50 (1H, d), 6.21 (1H, s), 6.02 (1H, s), 5.23 (2H, s), 4.07-4.03 (2H, m), 3.62 (2H, t), 2.93-2.87 (1H, m), 2.52-2.46 (2H, m), 2.30 (3H, s), 1.46 (9H, s), 0.90-0.84 (2H, m), 0.64-0.59 (2H, m).

EXAMPLE 7

N-Cyclopropyl-4-methyl-3-[1-oxo-2-{4-(1,2,3,6-tetrahydro-pyridin-4-yl)-benzyl}-1,2-dihydro-isoquinolin-6-yl]-benzamide, hydrochloride

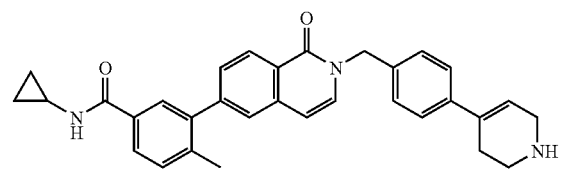

A solution of Example 6 step (iii) (0.2 g) in methanol (10 mL) was treated with 4.0M HCl in 1,4-dioxane (10 mL) and the solution stirred at room temperature for 2 hours. The volatiles were then removed under reduced pressure and the residue triturated with diethyl ether to give the product, after filtration as a solid (80 mg).

MS: APCI (+ve) 490 (M+H)$^+$ $^1$H NMR DMSO-d$_6$ δ 9.04 (2Hs), 8.44 (1H, d), 8.29 (1H, d), 7.79 (1H, d), 7.75 (1H, s), 7.68 (1H, s), 7.64 (1H, d), 7.53 (1H, d), 7.46 (2H, d), 7.42 (1H, d), 7.35 (2H, d), 6.72 (1H, d), 6.17 (1H, s), 5.22 (2H, s), 3.75-3.73 (2H, m), 3.32-3.26 (2H, m), 2.87-2.82 (1H, m), 2.66-2.63 (2H, m), 2.29 (3H, s), 0.69-0.66 (2H, m), 0.57-0.54 (2H, m).

EXAMPLE 8

N-Cyclopropyl-4-methyl-3-[1-oxo-2-(4-piperidin-4-yl-benzyl)-1,2-dihydro-isoquinolin-6-yl]-benzamide

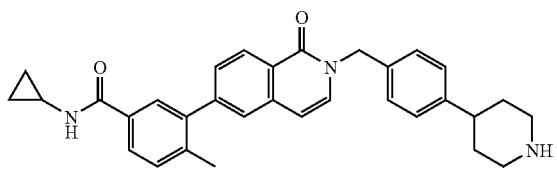

10% Pd/C (20 mg) was added to a solution of Example 7 (60 mg) in ethanol (20 mL) and the mixture subjected to hydrogenation at 3 Barr for 2 hours. The reaction mixture was filtered and evaporated under reduced pressure to give the title compound as the hydrochloride salt as a solid (50 mg).
MS: APCI (+ve) 492 (M+H)$^+$
$^1$H NMR DMSO-d$_6$ 8.77 (2H, s), 8.44 (1H, d), 8.28 (1H, d), 7.79 (1H, d), 7.75 (1H, s), 7.67 (1H, s), 7.63 (1H, d), 7.52 (1H, d), 7.42 (1H, d), 7.31 (2H, d), 7.21 (2H, d), 6.71 (1H, d), 5.19 (2H, s), 3.321-3.28 (2H, m), 3.01-2.92 (2H, m), 2.87-2.79 (2H, m), 2.28 (3H, s), 1.90-1.75 (4H, m), 0.70-0.65 (2H, m), 0.57-0.53 (2H, m).

Further purification of the above material (40 mg) (HPLC using acetonitrile: 0.1% aqueous ammonia as eluant) gave the title compound as a solid as the free base (30 mg).

MS: APCI (+ve) 492 (M+H)$^+$
$^1$H NMR DMSO-d$_6$ 8.41 (1H, d), 8.29 (1H, d), 7.79 (1H, d), 7.75 (1H, s), 7.66 (1H, s), 7.61 (1H, d), 7.51 (1H, d), 7.41 (1H, d), 7.26 (2H, d), 7.19 (2H, d), 6.69 (1H, d), 5.17 (2H, s), 3.01-2.98 (2H, m), 2.86-2.83 (1H, m), 2.56-2.52 (3H, m), 2.28 (3H, s), 1.65-1.62 (2H, m), 1.51-1.42 (2H, m), 0.70-0.66 (2H, m), 0.57-0.54 (2H, m)

EXAMPLE 9

N-Methoxy-4-methyl-3-[1-oxo-2-[4-(1,2,3,6-tetrahydro-pyridin-4-yl)-benzyl]-1,2-dihydro-isoquinolin-6-yl]-benzamide

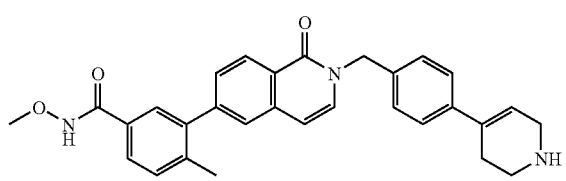

Methoxylamine hydrochloride (0.12 g) was added to a solution of Example 6 step (ii) (0.4 g) in THF (10 mL). The mixture was stirred at room temperature then 2.0M isopropylmagnesium chloride in THF (1 mL) added. The mixture was stirred for 1 hour then a further portion of 2.0M isopropylmagnesium chloride in THF (1 mL) was added. The mixture was stirred for a further 1 hour then poured into saturated aqueous ammonium chloride and extracted with dichloromethane. The organics were combined and evaporated under reduced pressure. The residue was dissolved in methanol (20 mL) and 2.0M HCl in diethyl ether added (20 mL). This solution was stirred at room temperature for 12 hours. The volatiles were removed under reduced pressure and the residue purified (SiO$_2$ 10:90:1 methanol:dichoromethane: aqueous ammonia as eluant) to give the title compound as a solid (22 mg).
MS: APCI (+ve) 480 (M+H)$^+$
$^1$H NMR DMSO-d$_6$ 8.30 (1H, d), 7.72 (1H, d), 7.68 (2H, s), 7.63 (1H, d), 7.52 (1H, d), 7.45 (1H, d), 7.39 (2H, d), 7.30 (2H, d), 6.72 (1H, d), 6.17 (1H, s), 5.20 (2H, s), 3.71 (3H, s), 3.40-3.32 (2H, m), 2.90 (2H t), 2.35-2.31 (2H, m), 2.30 (3H, s).

EXAMPLE 10

N-Cyclopropyl-3-{2-[3-(3-dimethylamino-propoxy)-benzyl]-1-oxo-1,2-dihydro-isoquinolin-6-yl}-4-methyl-benzamide

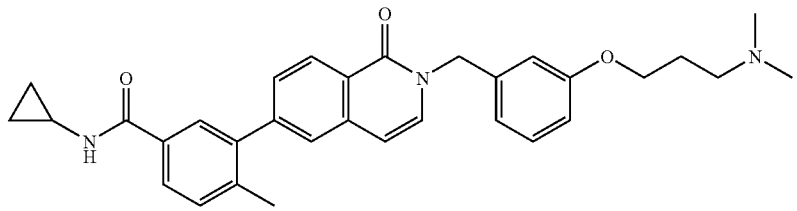

(i) [3-(3-Dimethylamino-propoxy)-phenyl]-methanol

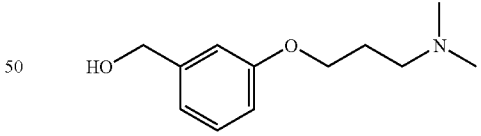

Cesium carbonate (15.4 g) was added to a solution of 3-hydroxymethyl-phenol (3 g) in DMF (80 mL). To this mixture was added (3-chloro-propyl)-dimethyl-amine hydrochloride (4 g). The mixture was heated at 80° C. for 20 hours then allowed to cool. The reaction mixture was poured into water and extracted with ethyl acetate.

The organics were combined, dried over magnesium sulfate then filtered and evaporated under reduced pressure. Purification (SiO$_2$ with 5:95 methanol:dichloromethane as eluant) gave the sub-title compound (1 g).

¹H NMR CDCl₃ 6.93-6.90 (2H, m), 6.82-6.79 (1H, m), 4.65 (2H, m), 4.00 (2H, t), 2.45 (2H, t), 2.26 (6H, s), 1.95 (2H, quintet).

(ii) [3-(3-Chloromethyl-phenoxy)-propyl]-dimethyl-amine

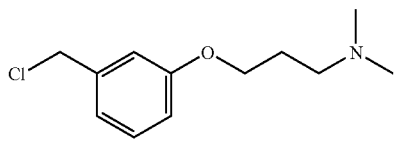

Thionyl chloride (0.5 mL) was added to a solution of Example 10 step (i) (1 g) in dichloromethane (20 mL) and the solution stirred at room temperature for 4 hours. The volatiles were then removed under reduced pressure to give the product as the hydrochloride salt (1 g) that was used directly in the next step without further purification.

(iii) 3-(2-[3-(3-Dimethylamino-propoxy)-benzyl]-1-oxo-1,2-dihydro-isoquinolin-6-yl}-4-methyl-benzoic acid, methyl ester

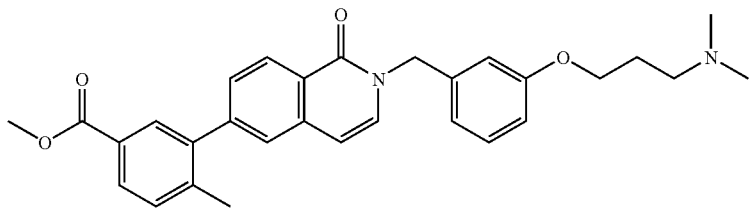

The sub-titled compound was prepared as described for intermediate 4 using intermediate 3 and product of step (ii). Purification (SiO₂ with 5:95 methanol:dichloromethane as eluant) gave the sub-title compound (0.1 g).
MS: APCI (+ve) 485 (M+H)⁺
¹H NMR CDCl₃ 8.51 (1H, d), 7.97-7.94 (2H, m), 7.46-7.44 (2H, m), 7.37 (1H, d), 7.24 (1H, d), 7.12 (1H, d), 6.92-6.82 (3H, m), 6.50 (1H, d), 5.21 (2H, s), 4.00 (2H, t), 3.91 (3H, s), 2.48 (2H, t), 2.33 (3H, s), 2.27 (6H, s), 1.95 (2H, quintet).

(iv) N-Cyclopropyl-3-[2-[3-(3-dimethylamino-propoxy)-benzyl]-1-oxo-1,2-dihydro-isoquinolin-6-yl]-4-methyl-benzamide

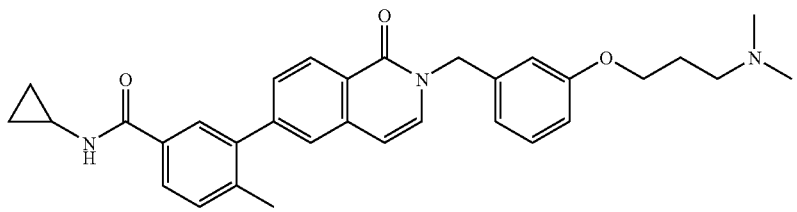

The title compound was prepared as described for Example 3 step (ii) using product from step (iii). Purification (SiO₂ with 10:90 methanol:dichloromethane as eluant) gave the title compound as a solid (0.35 g).

MS: APCI (+ve) 510 (M+H)⁺
¹H NMR DMSO-d₆ 8.44 (1H, d), 7.70 (1H, dd), 7.65-7.64 (1H, m), 7.41 (1H, d), 7.39 (1H, s), 7.34 (1H, dd), 7.24 (1H, dd), 7.11 (1H, d), 6.91 (1H, d), 6.89-6.88 (1H, m), 6.81 (1H, dd), 6.45) 1H, d), 6.43 (1H, s), 5.20 (2H, s), 4.99 (2H, t), 2.95-2.88 (1H, m), 2.62 (2H, t), 2.36 (6H, s), 2.29 (3H, s), 2.02 (2H, quintet), 0.87-0.84 (2H, m), 0.63-0.60 (2H, m).

EXAMPLE 11

N-Cyclopropyl-4-methyl-3-(1-oxo-1,2-dihydro-iso-quinolin-6-yl)-benzamide

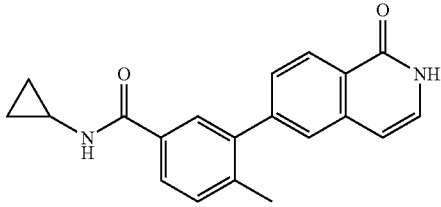

A solution of isopropylmagnesium chloride (2M, 0.4 mL) in THF was added dropwise to a stirred solution of 4-methyl-3-(1-oxo-1,2-dihydro-isoquinolin-6-yl)-benzoic acid, methyl ester (Intermediate 3) (76 mg) and cyclopropylamine (0.15 mL) in THF (2 mL). The mixture was stirred for 10 min., quenched with sat. aqueous NH₄Cl and extracted into ethyl acetate. The organic phase was dried (Na₂SO₄) and concentrated in vacuo and the residue was purified by HPLC to give the title compound as a solid (40 mg).

MS: APCI (+ve) 319 (M+H)⁺

¹H NMR DMSO-d₆ 11.27 (1H, s), 8.42 (1H, d), 8.24 (1H, d), 7.79 (1H, d), 7.75 (1H, s), 7.65 (1H, s), 7.48 (1H, d), 7.42 (1H, d), 7.22 (1H, d), 6.60 (1H, d), 2.85 (1H, m), 2.29 (3H, s), 0.68 (2H, m), 0.56 (2H, m)

EXAMPLE 12

3-(2-Allyl-1-oxo-1,2-dihydro-isoquinolin-6-yl)-N-cyclopropyl-4-methyl-benzamide

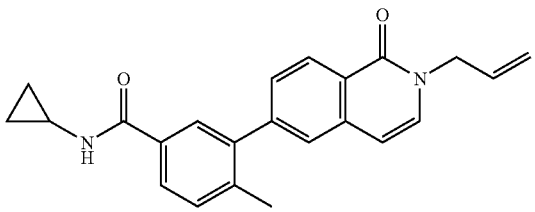

Sodium hydride (75 mg, 60% in oil) was added to a stirred mixture of 4-methyl-3-(1-oxo-1,2-dihydro-isoquinolin-6-yl)-benzoic acid, methyl ester (Intermediate 3) (250 mg), methyl acetate (0.5 mL) and DMF (5 mL). The mixture was stirred for 15 minutes. Allyl bromide (0.5 mL) was added via syringe and the mixture was stirred for 30 minutes, then quenched with sat. aqueous NH$_4$Cl solution and extracted into ethyl acetate. The organic phase was dried (Na$_2$SO$_4$), filtered and concentrated in vacuo to give crude ester. The ester was treated with THF (5 mL) and cyclopropylamine (0.3 mL). A solution of isopropylmagnesium chloride (2M, 0.4 mL) in THF was added dropwise. The reaction mixture was stirred for 10 minutes, quenched with sat. aqueous NH$_4$Cl solution and extracted into ethyl acetate. The phases were separated, the organic phase was dried (Na$_2$SO$_4$), filtered and concentrated in vacuo to give crude product (380 mg). A sample (80 mg) of crude product was purified by HPLC to give an analytical sample of the title compound as a solid (45 mg).

MS: APCI (+ve) 359 (M+H)$^+$ $^1$H NMR DMSO-d$_6$ 8.48 (1H, d), 7.68 (1H, dd), 7.62 (1H, d), 7.45-7.40 (3H, m), 7.35 (1H, d), 7.10 (1H, d), 6.52 (1H, d), 6.23 (1H, s), 6.00 (1H, ddt), 5.28 (1H, dq), 5.24 (1H, dq), 4.67 (2H, dq), 2.90 (1H, m), 2.30 (3H, s), 0.86 (2H, m), 0.61 (2H, m)

EXAMPLE 13

N-Cyclopropyl-4-methyl-3-[1-oxo-2-(3-pyrrolidin-1-yl-propyl)-1,2-dihydro-isoquinolin-6-yl]-benzamide

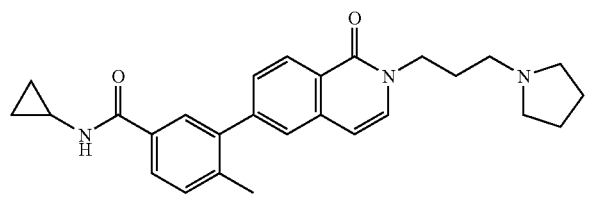

Borane-tetrahydrofuran complex (1M, 3 mL) was added to a stirred solution of 3-(2-allyl-1-oxo-1,2-dihydro-isoquinolin-6-yl)-N-cyclopropyl-4-methyl-benzamide (Example 12) (0.3 g) in THF (5 mL) at −78° C. The mixture was stirred at −78° C.–−10° C. for 2.5 hours, then left in the freezer overnight. Water (3 mL) was added carefully (strong gas evolution) to the reaction mixture at 0° C., followed by 5M NaOH (3 mL) and hydrogen peroxide (35%, 1 mL). The mixture was stirred at 0° C. for 1 hour. Solid sodium thiosulphate (5 g) was added, followed by water (20 mL). The mixture was stirred for 5 minutes and extracted into ethyl acetate. The organic was washed with water, dried (Na$_2$SO$_4$), filtered and concentrated in vacuo to give a mixture alcohols. Methanesulphonyl chloride (0.1 mL) was added to the mixture of alcohols, triethylamine (0.5 mL) and dichloromethane (4 mL) at 0° C. The mixture was stirred for 10 min and pyrrolidine (0.5 mL) was added. The mixture was stirred at room temperature for 72 hours, then concentrated in vacuo. Purification by HPLC gave the title compound as a solid (50 mg).

MS: APCI (+ve) 430 (M+H)$^+$ $^1$H NMR DMSO-d$_6$ 8.43 (1H, d), 8.28 (1H, d), 7.79 (1H, dd), 7.75 (1H, d), 7.65 (1H, d), 7.50 (2H, m), 7.42 (1H, d), 6.66 (1H, d), 4.02 (2H, t), 2.84 (1H, m), 2.41 (4H, m), 2.28 (3H, s), 1.85 (2H, m), 1.68 (4H, m), 0.67 (2H, m), 0.56 (2H, m)

EXAMPLE 14

N-Cyclopropyl-3-[2-(4-dimethylaminomethyl-benzyl)-1-oxo-1,2-dihydro-isoquinolin-6-yl]-4-methyl-benzamide

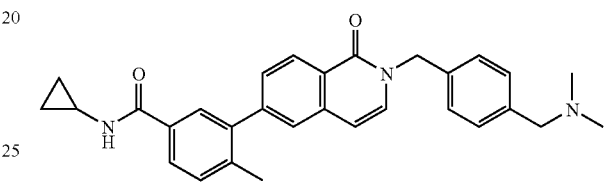

Sodium hydride (34 mg, 60% in oil) was added to a stirred mixture of 4-methyl-3-(1-oxo-1,2-dihydro-isoquinolin-6-yl)-benzoic acid, methyl ester (Intermediate 3) (100 mg), methyl acetate (0.25 mL) and DMF (2 mL). The mixture was stirred for 15 min., then α,α'-dichloro-para-xylene (250 mg) was added. The mixture was stirred for 30 minutes and dimethylamine hydrochloride (330 mg) was added followed by triethylamine (1.5 mL). The mixture was stirred overnight, then concentrated in vacuo and azeotroped with toluene. The ester was treated with THF (5 mL) and cyclopropylamine (0.3 mL). A solution of isopropylmagnesium chloride (2M, 10 mL) in THF was added dropwise. The reaction mixture was stirred for 10 min., quenched with sat. aqueous NH$_4$Cl solution and extracted into ethyl acetate. The phases were separated. The organic phase was dried (Na$_2$SO$_4$), filtered and concentrated in vacuo to give crude product (380 mg). A sample (80 mg) was purified by HPLC to give an analytical sample of the title compound as a solid (56 mg).

MS: APCI (+ve) 466 (M+H)$^+$ $^1$H NMR DMSO-d$_6$ 8.43 (1H, d), 8.29 (1H, d), 7.79 (1H, d), 7.75 (1H, d), 7.67 (1H, d), 7.62 (1H, d), 7.52 (1H, dd), 7.42 (1H, d), 7.29 (4H, m), 6.71 (1H, d), 5.20 (2H, s), 3.29 (2H, s), 2.84 (1H, m), 2.25 (3H, s), 2.18 (6H, br), 0.68 (2H, m), 0.55 (2H, m)

EXAMPLE 15

N-Cyclopropyl-3-[2-(3-dimethylaminomethyl-benzyl)-1-oxo-1,2-dihydro-isoquinolin-6-yl]-4-methyl-benzamide

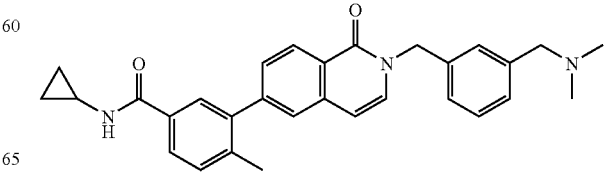

The title compounds was prepared as a solid by the method of Example 14 from 4-methyl-3-(1-oxo-1,2-dihydro-isoquinolin-6-yl)-benzoic acid methyl ester (Intermediate 3) and α,α'-dichloro-meta-xylene.

MS: APCI (+ve) 466 (M+H)+

¹H NMR DMSO-d₆ 8.42 (1H, d), 8.30 (1H, d), 7.79 (1H, dd), 7.75 (1H, d), 7.67 (1H, d), 7.61 (1H, d), 7.52 (1H, dd), 7.42 (1H, d), 7.29 (2H, m), 7.19 (2H, d), 6.71 (1H, d), 5.21 (2H, s), 3.35 (2H, s), 2.84 (1H, m), 2.29 (3H, s), 2.11 (6H, s), 0.68 (2H, m), 0.56 (2H, m)

EXAMPLE 16

N-Cyclopropyl-3-[2-(2-dimethylaminomethyl-benzyl)-1-oxo-1,2-dihydro-isoquinolin-6-yl]-4-methyl-benzamide

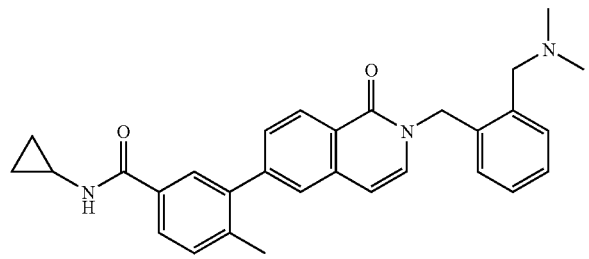

The title compounds was prepared as a solid by the method of Example 14 from 4-methyl-3-(1-oxo-1,2-dihydro-isoquinolin-6-yl)-benzoic acid methyl ester (Intermediate 3) and α,α'-dichloro-ortho-xylene.

MS: APCI (+ve) 466 (M+H)+

¹H NMR DMSO-d₆ 8.43 (1H, d), 8.28 (1H, d), 7.80 (1H, d), 7.77-7.69 (3H, m), 7.55 (2H, m), 7.47-7.39 (3H, m), 7.16 (1H, m), 6.85 (1H, d), 5.38 (2H, s), 4.60 (2H, m), 2.90 (6H, s), 2.29 (3H, s), 0.68 (2H, m), 0.54 (2H, m)

EXAMPLE 17

N-Cyclopropyl-3-[2-(4-methoxy-benzyl)-1-oxo-1,2-dihydro-isoquinolin-6-yl]-4-methyl-benzamide

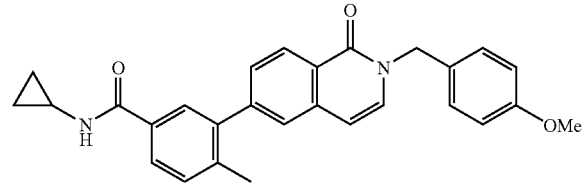

i) 4-Bromo-2-carboxymethyl-benzoic acid

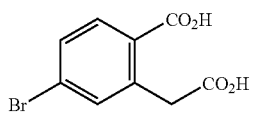

A solution of 5-bromo-1-indanone (25 g) and diethyl oxalate (27.7 g) in toluene (500 mL) was added to a suspension of sodium methoxide (13.1 g) in toluene (50 mL) at 0° C. The mixture was warmed to room temperature and stirred for 90 minutes. The solvent was removed and the residue suspended in methanol (800 mL). Potassium hydroxide (53.1 g) was added portionwise keeping the temp below 50° C. Hydrogen peroxide solution (30% w/w, 135 mL) was then added keeping the temperature below 64° C., the reaction mixture was then stirred at room temperature for 17 hours. Sodium sulfite (5% aqueous solution) was added and the reaction stirred for 30 minutes. The reaction mixture was filtered and the filtrate was reduced to half volume then washed with 2-methoxy-2-methyl-propane. The aqueous layer was then acidified with hydrochloric acid and extracted into ethyl acetate. The organic phase was dried, filtered and evaporated then triturated with diethyl ether to yield sub-title compound (9.0 g).

¹H NMR DMSO-d₆ 7.82 (1H, d), 7.62 (1H, d), 7.59 (1H, dd), 3.95 (2H, s).

ii) 6-Bromo-isochroman-1,3-dione

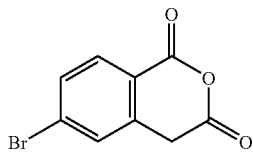

A solution of 4-bromo-2-carboxymethyl-benzoic acid (product of step i)) (11.0 g) in acetone (200 mL) was treated with acetyl chloride (13.3 g) and the solution stirred at room temperature for 17 hours. The reaction mixture was evaporated then azeotroped with toluene to yield the sub-title compound (9.8 g).

¹H NMR DMSO-d₆ 7.95 (1H, d), 7.74 (1H, s), 7.72 (1H, d), 4.27 (2H, s).

iii) 6-Bromo-2-(4-methoxy-benzyl)-4H-isoquinoline-1,3-dione

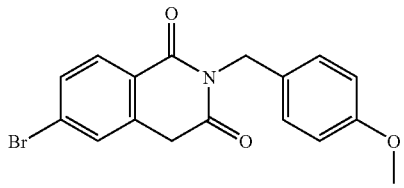

A mixture of 6-bromo-isochroman-1,3-dione (0.6 g) (product of step ii)) and 4-methoxybenzylamine (0.313 g) in toluene:acetic acid (4:1, 20 mL) was heated at reflux for 17 hours. The reaction mixture was evaporated and the residue was dissolved in dichloromethane before washing with 2N hydrochloric acid. The organic phase was dried, filtered and evaporated then triturated with diethyl ether to yield the sub-title compound (680 mg).

¹H NMR DMSO-d 7.95 (1H, d), 7.68 (1H, s), 7.67 (1H, d), 7.25 (2H, d), 6.84 (2H, d), 4.96 (2H, s), 4.22 (2H, s), 3.70 (3H, s)

iv) 6-Bromo-2-(4-methoxy-benzyl)-2H-isoquinolin-1-one

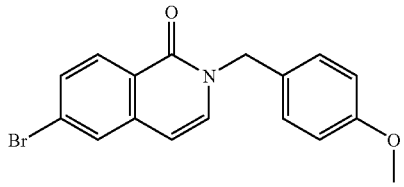

To a solution of 6-bromo-2-(4-methoxy-benzyl)-4H-iso-quinoline-1,3-dione (product of step iii)) (2.6 g) in dichloromethane:methanol (3:1, 80 mL) was added sodium borohydride (1.0 g) portionwise over 2 hours. The reaction mixture was acidified with hydrochloric acid and stirred for 30 minutes. The reaction mixture was evaporated and the residue partitioned between dichloromethane and water. The organic phase was washed with brine, dried, filtered and evaporated. The residue was purified (SiO$_2$, 1:4 ethyl acetate:iso-hexane as eluent) to yield the sub-title compound (1.2 g).

$^1$H NMR DMSO-d$_6$ 8.13 (1H, d), 7.94 (1H, d), 7.65 (1H, dd), 7.63 (1H, d), 7.30 (2H, d), 6.89 (2H, d), 6.62 (1H, d), 5.09 (2H, s), 3.71 (3H, s)

v) 3-[2-(4-Methoxy-benzyl)-1-oxo-1,2-dihydro-iso-quinolin-6-yl]-4-methyl-benzoic acid, methyl ester

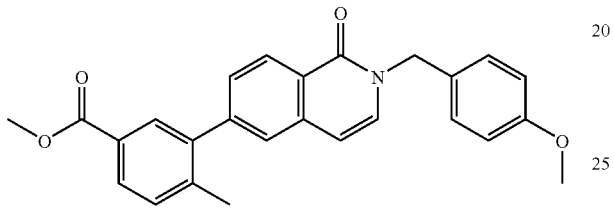

A mixture of 6-bromo-2-(4-methoxy-benzyl)-2H-iso-quinolin-1-one (product of step iv)) (1.2 g), intermediate 2 (0.7 g), potassium carbonate (1.0 g) and tetrakis(triphenylphosphine)palladium(0) (0.4 g) in N,N-dimethylformamide (20 mL) was heated to 95° C. for 17 hours. The reaction mixture was diluted with ethyl acetate and washed with water and brine. The organic phase was dried, filtered and evaporated. The residue was purified (SiO$_2$, 1:2 ethyl acetate:isohexane as eluent) to yield the sub-titled compound (1.03 g).

MS: APCI (+ve) 414 [M+H]$^+$ vi) N-Cyclopropyl-3-[2-(4-methoxy-benzyl)-1-oxo-1,2-dihydro-isoquinolin-6-yl]-4-methyl-benzamide

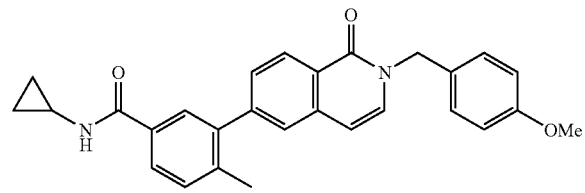

A solution of 3-[2-(4-methoxy-benzyl)-1-oxo-1,2-dihydro-isoquinolin-6-yl]-4-methyl-benzoic acid, methyl ester (product of step v)) (1.0 g) and cyclopropylamine (0.71 g) in tetrahydrofuran (3 mL) was treated with isopropylmagnesium chloride (2M in THF, 0.77 mL) and stirred at room temperature for 1 hour. The reaction mixture was quenched with aqueous ammonium chloride and extracted into ethyl acetate. The organic phase was dried, filtered and evaporated to yield the title compound as a solid (850 mg).

MS: APCI (+ve) 439[M+H]+

$^1$H NMR DMSO-d$_6$ 8.42 (1H, d), 8.29 (1H, d), 7.79 (1H, dd), 7.74 (1H, d), 7.65 (1H, d), 7.61 (1H, d), 7.51 (1H, dd), 7.41 (1H, d), 7.32 (2H, d), 6.91 (2H, d), 6.69 (1H, d), 5.13 (2H, s), 3.72 (3H, s), 2.89-2.80 (1H, m), 2.28 (3H, s), 0.71-0.65 (2H, m), 0.58-0.52 (2H, m)

EXAMPLE 18

N-Cyclopropyl-3-(2-(4-((2-(dimethylamino)ethyl)(methyl)carbamoyl)benzyl)-1-oxo-1,2-dihydroisoquinolin-6-yl)-4-methylbenzamide

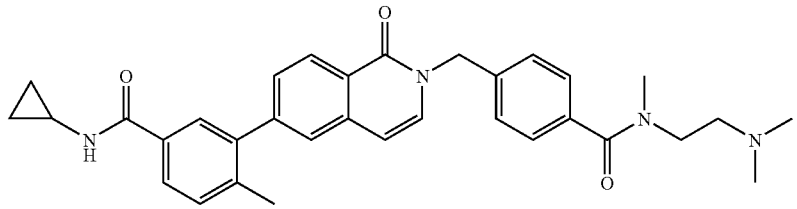

i) Methyl 4-((6-(5-(cyclopropylcarbamoyl)-2-methylphenyl)-1-oxoisoquinolin-2(1H)-yl)methyl)benzoate

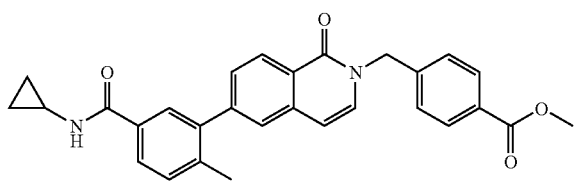

A mixture of N-cyclopropyl-4-methyl-3-(1-oxo-1,2-dihydroisoquinolin-6-yl)benzamide (Example 11) (1.0 g), potassium carbonate (1.3 g) and methyl 4-(bromomethyl)benzoate (0.86 g) in DMF (10 mL) was stirred at room temperature for 17 hours.

The reaction mixture was diluted with ethyl acetate and washed with water and brine. The organic layer was dried over magnesium sulfate, filtered and evaporated. The crude material was purified (SiO$_2$ chromatography eluting with 60 to 80% ethyl acetate in isohexane) to afford the sub-title compound (1.1 g)

MS: APCI (+ve) 467 (M+H)$^+$ ii) 4-((6-(5-(Cyclopropylcarbamoyl)-2-methylphenyl)-1-oxoisoquinolin-2(1H)-yl)methyl)benzoic acid

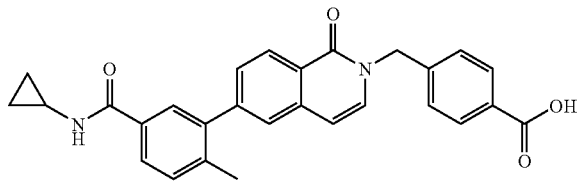

To a slurry of the product of step i) (1 g) in methanol (15 mL) at reflux was added sodium hydroxide solution (1N, 2.4 mL). The reaction mixture was then stirred at reflux for 90 minutes. Additional sodium hydroxide solution (1N, 0.5 mL) was added and heating continued for a further 40 minutes. Acetic acid (0.16 mL) was added and the reaction was stirred at room temperature for 17 hours.

The reaction mixture was filtered and washed with methanol:water (1:1, 5 mL) and methanol (5 mL). The solid was dried under vacuum at 50° C. for 24 hours to yield the sub-title compound (0.93 g).

MS: APCI (+ve) 453 (M+H)$^+$ iii) N-Cyclopropyl-3-(2-(4-((2-(dimethylamino)ethyl)(methyl)carbamoyl)benzyl)-1-oxo-1,2-dihydroisoquinolin-6-yl)-4-methylbenzamide

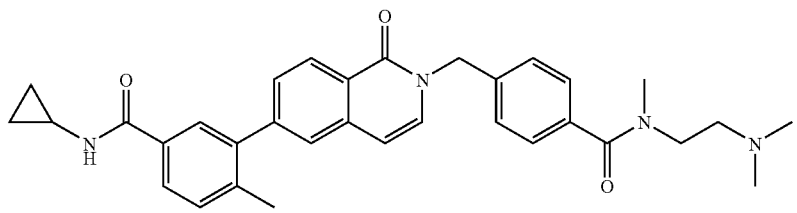

To a solution of the product of step ii) (100 mg), N,N,N'-trimethylethane-1,2-diamine (0.05 mL) and N,N-diisopropylethylamine (0.12 mL) in DMF (2 mL) was added HATU (130 mg) and stirred at room temperature for 15 minutes.

The reaction mixture was filtered and purified by HPLC to afford the title compound as a solid (90 mg).

MS: APCI (+ve) 537 (M+H)$^+$ $^1$H NMR, DMSO-d$_6$, 90° C. 8.31 (d, J=8.2 Hz, 1H), 8.13 (s, 1H), 7.76 (dd, J=7.9, 1.8 Hz, 1H), 7.71 (d, J=1.8 Hz, 1H), 7.60 (d, J=1.5 Hz, 1H), 7.52 (d, J=7.4 Hz, 1H), 7.48 (dd, J=8.3, 1.7 Hz, 1H), 7.39-7.31 (m, 5H), 6.66 (d, J=7.4 Hz, 1H), 5.24 (s, 2H), 3.42-3.34 (m, 2H), 2.91 (s, 3H), 2.89-2.82 (m, 1H), 2.41 (t, J=6.7 Hz, 2H), 2.27 (s, 3H), 2.09 (s, 6H), 0.70-0.62 (m, 2H), 0.62-0.54 (m, 2H)

EXAMPLES 19-24

The following compounds were prepared solids according to the method of Example 18 step (iii) using the product of Example 18 step (ii) and the appropriate amine.

EXAMPLE 19

N-Cyclopropyl-3-(2-(4-(2-(dimethylamino)ethylcarbamoyl)benzyl)-1-oxo-1,2-dihydroisoquinolin-6-yl)-4-methylbenzamide

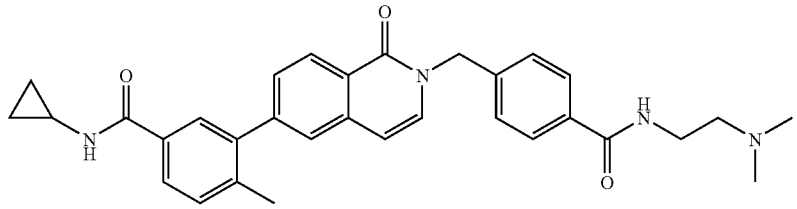

MS: APCI (+ve) 523 (M+H)$^+$ $^1$H NMR, DMSO-d$_6$ 8.43 (d, J=4.1 Hz, 1H), 8.34 (t, J=5.6 Hz, 1H), 8.29 (d, J=8.2 Hz, 1H), 7.83-7.78 (m, 3H), 7.76 (d, J=1.8 Hz, 1H), 7.68 (d, J=1.3 Hz, 1H), 7.63 (d, J=7.4 Hz, 1H), 7.53 (dd, J=8.3, 1.7 Hz, 1H), 7.42 (d, J=8.5 Hz, 1H), 7.39 (d, J=8.5 Hz, 2H), 6.73 (d, J=7.2 Hz, 1H), 5.26 (s, 2H), 3.36-3.30 (m, 2H), 2.89-2.81 (m, 1H), 2.37 (t, J=6.9 Hz, 2H), 2.29 (s, 3H), 2.16 (s, 6H), 0.71-0.65 (m, 2H), 0.59-0.53 (m, 2H)

EXAMPLE 20

N-Cyclopropyl-4-methyl-3-(2-(4-(4-methylpiperazine-1-carbonyl)benzyl)-1-oxo-1,2-dihydroisoquinolin-6-yl)benzamide

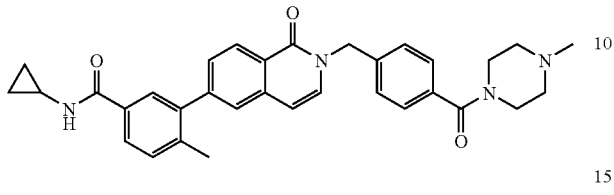

MS: APCI (+ve) 535 (M+H)+

$^1$H NMR, DMSO-d$_6$, 90° C. 8.31 (d, J=8.2 Hz, 1H), 8.13 (s, 1H), 7.76 (dd, J=7.8, 1.9 Hz, 1H), 7.71 (d, J=1.8 Hz, 1H), 7.61 (d, J=1.3 Hz, 1H), 7.54 (d, J=7.4 Hz, 1H), 7.48 (dd, J=8.2, 1.8 Hz, 1H), 7.41-7.31 (m, 5H), 6.67 (d, J=7.2 Hz, 1H), 5.24 (s, 2H), 3.44 (s, 4H), 2.89-2.82 (m, 1H), 2.30 (t, J=5.0 Hz, 4H), 2.27 (s, 3H), 2.19 (s, 3H), 0.70-0.62 (m, 2H), 0.62-0.54 (m, 2H)

EXAMPLE 21

N-Cyclopropyl-3-(2-(4-(((3-(dimethylamino)propyl)(methyl)carbamoyl)benzyl)-1-oxo-1,2-dihydroisoquinolin-6-yl)-4-methylbenzamide

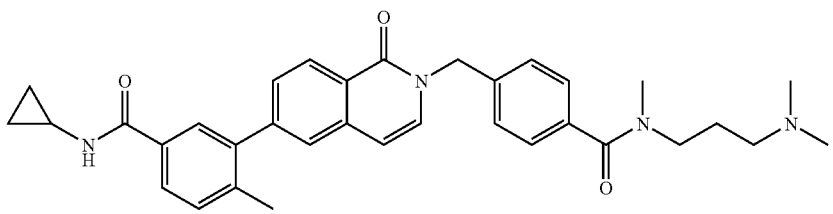

MS: APCI (+ve) 551 (M+H)+

$^1$H NMR, DMSO-d$_6$, 90° C. 8.31 (d, J=8.2 Hz, 1H), 8.13 (s, 1H), 7.76 (dd, J=7.9, 1.8 Hz, 1H), 7.71 (d, J=1.8 Hz, 1H), 7.60 (d, J=1.5 Hz, 1H), 7.53 (d, J=7.4 Hz, 1H), 7.48 (dd, J=8.2, 1.5 Hz, 1H), 7.40-7.30 (m, 5H), 6.67 (d, J=7.2 Hz, 1H), 5.24 (s, 2H), 3.31 (s, 2H), 2.90 (s, 3H), 2.89-2.82 (m, 1H), 2.27 (s, 3H), 2.18-2.10 (m, 2H), 2.04 (s, 6H), 1.63 (quintet, J=7.2 Hz, 2H), 0.70-0.53 (m, 4H)

EXAMPLE 22

N-Cyclopropyl-4-methyl-3-(1-oxo-2-(4-(2-(pyrrolidin-1-yl)ethylcarbamoyl)benzyl)-1,2-dihydroisoquinolin-6-yl)benzamide

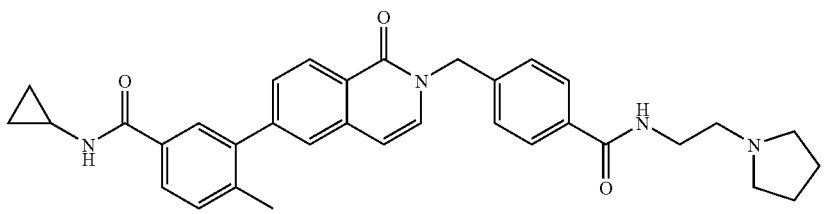

MS: APCI (+ve) 549 (M+H)+

$^1$H NMR, DMSO-d$_6$ 8.43 (d, J=4.1 Hz, 1H), 8.38 (t, J=5.6 Hz, 1H), 8.29 (d, J=8.2 Hz, 1H), 7.83-7.77 (m, 3H), 7.75 (d, J=1.5 Hz, 1H), 7.68 (d, J=1.3 Hz, 1H), 7.64 (d, J=7.2 Hz, 1H), 7.53 (dd, J=8.2, 1.5 Hz, 1H), 7.42 (d, J=8.3 Hz, 1H), 7.39 (d, J=8.3 Hz, 2H), 6.73 (d, J=7.4 Hz, 1H), 5.26 (s, 2H), 3.35 (q, J=6.6 Hz, 2H), 2.89-2.81 (m, 1H), 2.54 (t, J=7.0 Hz, 2H), 2.48-2.42 (m, 4H), 2.29 (s, 3H), 1.70-1.61 (m, 4H), 0.72-0.63 (m, 2H), 0.59-0.52 (m, 2H)

EXAMPLE 23

N-Cyclopropyl-4-methyl-3-(2-(4-(methyl(2-(methylamino)ethyl)carbamoyl)benzyl)-1-oxo-1,2-dihydroisoquinolin-6-yl)benzamide

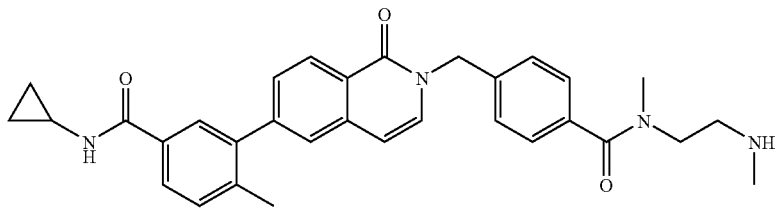

MS: APCI (+ve) 523 (M+H)+

$^1$H NMR, DMSO-$d_6$, 90° C. 8.31 (d, J=8.5 Hz, 1H), 8.14 (s, 1H), 7.76 (dd, J=7.9, 1.8 Hz, 1H), 7.71 (d, J=1.8 Hz, 1H), 7.61 (d, J=1.3 Hz, 1H), 7.53 (d, J=7.5 Hz, 1H), 7.48 (dd, J=8.2, 1.5 Hz, 1H), 7.40-7.32 (m, 5H), 6.67 (d, J=7.4 Hz, 1H), 5.24 (s, 2H), 3.40-3.32 (m, 2H), 2.92 (s, 3H), 2.89-2.82 (m, 1H), 2.64 (t, J=6.4 Hz, 2H), 2.27 (s, 3H), 2.23 (s, 3H), 0.70-0.62 (m, 2H), 0.62-0.54 (m, 2H)

EXAMPLE 24

N-Cyclopropyl-4-methyl-3-(1-oxo-2-(4-(3-(pyrrolidin-1-yl)propylcarbamoyl)benzyl)-1,2-dihydroisoquinolin-6-yl)benzamide

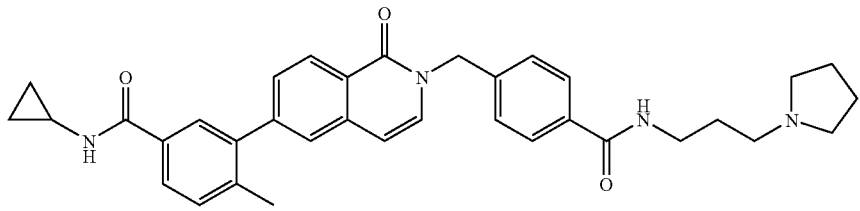

MS: APCI (+ve) 563 (M+H)+

$^1$H NMR, DMSO-$d_6$ 8.50 (s, 1H), 8.43 (d, J=4.4 Hz, 1H), 8.29 (d, J=8.2 Hz, 1H), 7.82-7.77 (m, 3H), 7.75 (d, J=1.8 Hz, 1H), 7.68 (d, J=1.5 Hz, 1H), 7.64 (d, J=7.4 Hz, 1H), 7.53 (dd, J=8.2, 1.8 Hz, 1H), 7.42 (d, J=7.9 Hz, 1H), 7.39 (d, J=7.9 Hz, 2H), 6.73 (d, J=7.4 Hz, 1H), 5.26 (s, 2H), 3.28 (q, J=6.3 Hz, 2H), 2.88-2.81 (m, 1H), 2.44-2.38 (m, 6H), 2.29 (s, 3H), 1.70-1.63 (m, 6H), 0.71-0.65 (m, 2H), 0.58-0.53 (m, 2H)

EXAMPLE 25

N-Cyclopropyl-4-methyl-3-(1-oxo-2-(4-(pyrrolidin-1-ylmethyl)benzyl)-1,2-dihydroisoquinolin-6-yl)benzamide

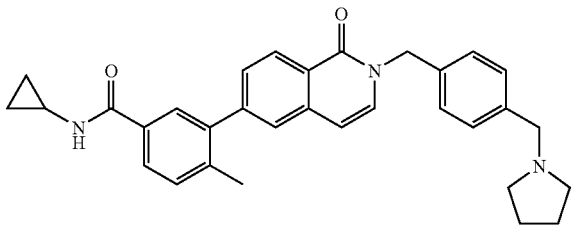

A mixture of potassium carbonate (0.34 g), the product of Example 11 (0.1 g) and 1,4-bis(chloromethyl)benzene (0.220 g) in DMF (2 mL) was stirred at room temperature for 2.5 hours. To the reaction mixture was added pyrrolidine (0.3 mL) and stirring continued for a further 64 hours. The reaction mixture was filtered and the filtrate washed with methanol. The liquors were purified by HPLC to give the title compound as a solid (0.095 g).

MS: APCI (+ve) 492 (M+H)+

$^1$H NMR CDCl$_3$ 8.48 (d, J=8.2 Hz, 1H), 7.68 (d, J=7.7 Hz, 1H), 7.62 (s, 1H), 7.45-7.22 (m, 6H), 7.13 (d, J=7.2 Hz, 1H), 6.47 (d, J=6.9 Hz, 1H), 6.28 (s, 1H), 5.23 (s, 2H), 3.59 (s, 2H), 2.91 (s, 1H), 2.49 (s, 4H), 2.29 (s, 3H), 1.68 (s, 2H), 0.90-0.81 (m, 4H), 0.62 (s, 2H)

EXAMPLES 26-28

The following compounds were prepared as solids according to the method of Example 25 using the product of Example 11 and the appropriate amine.

EXAMPLE 26

N-Cyclopropyl-4-methyl-3-(2-(4-((4-methylpiperazin-1-yl)methyl)benzyl)-1-oxo-1,2-dihydroisoquinolin-6-yl)benzamide

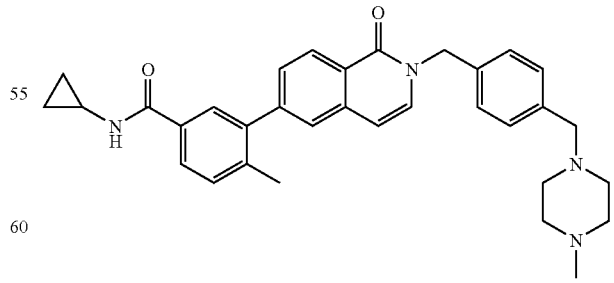

MS: APCI (+ve) 521 (M+H)+

$^1$H NMR DMSO-$d_6$ 8.43 (d, J=3.7 Hz, 1H), 8.29 (d, J=8.3 Hz, 1H), 7.79 (d, J=8.1 Hz, 1H), 7.75 (s, 1H), 7.67 (s, 1H), 7.62 (d, J=7.3 Hz, 1H), 7.52 (d, J=7.9 Hz, 1H), 7.42 (d, J=7.9 Hz, 1H), 7.31-7.21 (m, 4H), 6.71 (d, J=7.3 Hz, 1H), 5.19 (s,

2H), 3.40 (s, 2H), 2.88-2.80 (m, 1H), 2.38-2.20 (m, 11H), 2.12 (s, 3H), 0.72-0.64 (m, 2H), 0.59-0.52 (m, 2H).

EXAMPLE 27

3-(2-(4-((Tert-butyl(methyl)amino)methyl)benzyl)-1-oxo-1,2-dihydroisoquinolin-6-yl)-N-cyclopropyl-4-methylbenzamide

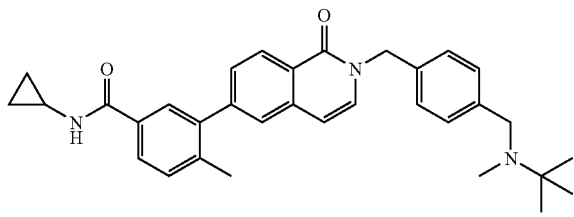

MS: APCI (+ve) 508 (M+H)+

$^1$H NMR DMSO-d$_6$ 8.43 (d, J=3.8 Hz, 1H), 8.29 (d, J=8.3 Hz, 1H), 7.79 (d, J=8.1 Hz, 1H), 7.75 (s, 1H), 7.66 (s, 1H), 7.61 (d, J=7.5 Hz, 1H), 7.52 (d, J=8.3 Hz, 1H), 7.41 (d, J=7.9 Hz, 1H), 7.27 (s, 4H), 6.70 (d, J=7.3 Hz, 1H), 5.19 (s, 2H), 3.43 (s, 2H), 2.90-2.80 (m, 1H), 2.28 (s, 3H), 1.97 (s, 3H), 1.08 (s, 9H), 0.72-0.65 (m, 2H), 0.59-0.52 (m, 2H)

EXAMPLE 28

3-(2-(4-((Tert-butylamino)methyl)benzyl)-1-oxo-1,2-dihydroisoquinolin-6-yl)-N-cyclopropyl-4-methylbenzamide

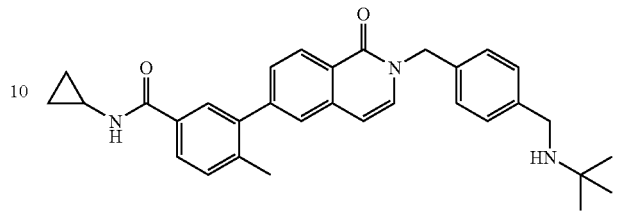

MS: APCI (+ve) 494 (M+H)+

$^1$H NMR DMSO-d$_6$ 8.43 (d, J=3.3 Hz, 1H), 8.29 (d, J=8.2 Hz, 1H), 7.79 (d, J=7.9 Hz, 1H), 7.75 (s, 1H), 7.66 (s, 1H), 7.59 (d, J=7.2 Hz, 1H), 7.52 (d, J=8.2 Hz, 1H), 7.42 (d, J=7.7 Hz, 1H), 7.31 (d, J=8.2 Hz, 2H), 7.26 (d, J=7.9 Hz, 2H), 6.70 (d, J=7.4 Hz, 1H), 5.18 (s, 2H), 3.61 (s, 2H), 2.89-2.81 (m, 1H), 2.28 (s, 3H), 1.06 (s, 9H), 0.71-0.65 (m, 2H), 0.59-0.54 (m, 2H).

EXAMPLE 29

N-Cyclopropyl-3-(2-((6-(3-(dimethylamino)propoxy)pyridin-3-yl)methyl)-1-oxo-1,2-dihydroisoquinolin-6-yl)-4-methylbenzamide

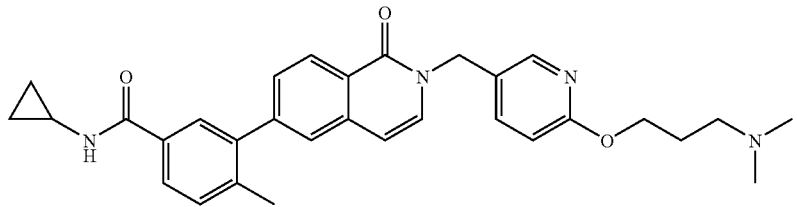

i) 3-(2-((6-Bromopyridin-3-yl)methyl)-1-oxo-1,2-dihydroisoquinolin-6-yl)-N-cyclopropyl-4-methylbenzamide

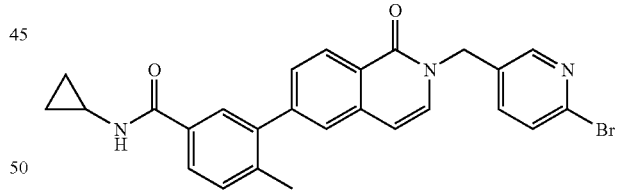

To a solution of the product of Example 11 (400 mg) in DMF (5 mL) was added sodium hydride (60 mg) and the reaction stirred at room temperature for 10 minutes before the addition of a solution of 2-bromo-5-(bromomethyl)pyridine (760 mg) in DMF (5 mL). The reaction mixture was stirred at room temperature for 30 min.

The reaction mixture was diluted with ethyl acetate and washed with water and brine. The organics were dried over magnesium sulphate and evaporated. The residue was purified (SiO$_2$ ethyl acetate:isohexane (1:1) as eluent) to yield the sub-title compound (360 mg).

MS: APCI (+ve) 488, 490 (1:1) (M+H)+ ii) N-Cyclopropyl-3-(2-((6-(3-(dimethylamino)propoxy)pyridin-3-yl)methyl)-1-oxo-1,2-dihydroisoquinolin-6-yl)-4-methylbenzamide

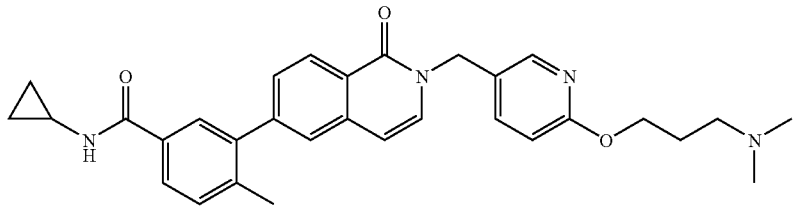

To solution of 3-(dimethylamino)propan-1-ol (0.03 mL) in THF (1 mL) was added potassium tert-butoxide (28 mg) and the reaction stirred at room temperature for 10 minutes. A solution of the product of step i) (100 mg) in THF (2 mL) was added, and the mixture heated at reflux for 100 hours.

The reaction mixture was filtered and the liquors evaporated. The residue was purified (SiO$_2$, Methanol:dichloromethane (15:85) followed by 7N NH3/methanol:dichloromethane (15:85)) to yield the title compound as a solid (52 mg).

MS: APCI (+ve) 511 (M+H)$^+$ $^1$H NMR DMSO-d$_6$ 8.43 (d, J=4.4 Hz, 1H), 8.29 (d, J=8.5 Hz, 1H), 8.24 (d, J=2.1 Hz, 1H), 7.79 (dd, J=7.9, 1.8 Hz, 1H), 7.74 (d, J=2.1 Hz, 1H), 7.72 (dd, J=8.6, 2.4 Hz, 1H), 7.68 (d, J=7.2 Hz, 1H), 7.66 (d, J=1.5 Hz, 1H), 7.52 (dd, J=8.3, 1.7 Hz, 1H), 7.41 (d, J=8.2 Hz, 1H), 6.78 (d, J=8.7 Hz, 1H), 6.71 (d, J=7.4 Hz, 1H), 5.14 (s, 2H), 4.24 (t, J=6.7 Hz, 2H), 2.88-2.81 (m, 1H), 2.30 (t, J=7.1 Hz, 2H), 2.27 (s, 3H), 2.12 (s, 6H), 1.81 (quintet, J=6.9 Hz, 2H), 0.71-0.65 (m, 2H), 0.58-0.53 (m, 2H)

EXAMPLES 30-31

The following compound were prepared as solids according to the method of Example 29 step (ii) using the product of Example 29 step (i) and the appropriate alcohol.

EXAMPLE 30

N-Cyclopropyl-3-(2-((6-(2-(dimethylamino)ethoxy)pyridin-3-yl)methyl)-1-oxo-1,2-dihydroisoquinolin-6-yl)-4-methylbenzamide

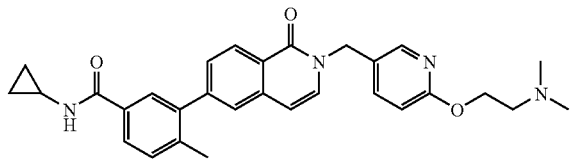

MS: APCI (+ve) 497 (M+H)$^+$
$^1$H NMR DMSO-d$_6$ 8.43 (d, J=4.1 Hz, 1H), 8.29 (d, J=8.5 Hz, 1H), 8.24 (d, J=2.3 Hz, 1H), 7.79 (dd, J=7.9, 1.8 Hz, 1H), 7.74 (s, 1H), 7.73 (dd, J=7.9, 2.6 Hz, 1H), 7.69 (d, J=7.4 Hz, 1H), 7.66 (d, J=1.3 Hz, 1H), 7.52 (dd, J=8.3, 1.7 Hz, 1H), 7.41 (d, J=7.9 Hz, 1H), 6.78 (d, J=8.7 Hz, 1H), 6.71 (d, J=7.2 Hz, 1H), 5.14 (s, 2H), 4.31 (t, J=5.9 Hz, 2H), 2.88-2.81 (m, 1H), 2.59 (t, J=5.9 Hz, 2H), 2.27 (s, 3H), 2.19 (s, 6H), 0.71-0.65 (m, 2H), 0.58-0.53 (m, 2H)

EXAMPLE 31

N-Cyclopropyl-4-methyl-3-(1-oxo-2-((6-(2-(pyrrolidin-1-yl)ethoxy)pyridin-3-yl)methyl)-1,2-dihydroisoquinolin-6-yl)benzamide

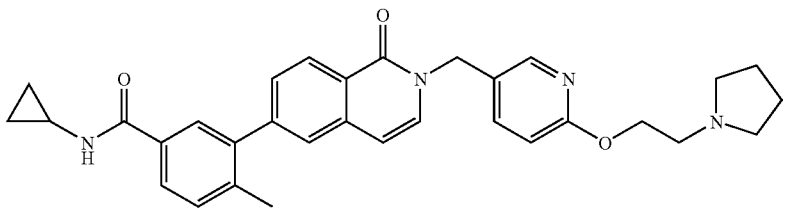

MS: APCI (+ve) 523 (M+H)$^+$
$^1$H NMR DMSO-d$_6$ 8.43 (d, J=4.1 Hz, 1H), 8.29 (d, J=8.2 Hz, 1H), 8.24 (d, J=2.3 Hz, 1H), 7.79 (dd, J=7.9, 1.8 Hz, 1H), 7.75-7.71 (m, 2H), 7.69 (d, J=7.4 Hz, 1H), 7.66 (d, J=1.5 Hz, 1H), 7.52 (dd, J=8.3, 1.7 Hz, 1H), 7.41 (d, J=8.2 Hz, 1H), 6.79 (d, J=8.5 Hz, 1H), 6.71 (d, J=7.4 Hz, 1H), 5.14 (s, 2H), 4.32 (t, J=6.0 Hz, 2H), 2.88-2.80 (m, 1H), 2.75 (t, J=6.0 Hz, 2H), 2.52-2.48 (m, 4H), 2.27 (s, 3H), 1.68-1.64 (m, 4H), 0.71-0.65 (m, 2H), 0.58-0.53 (m, 2H)

EXAMPLE 32

N-Cyclopropyl-3-(2-(4-(2-(dimethylamino)ethoxy)benzyl)-1-oxo-1,2-dihydroisoquinolin-6-yl)-4-methylbenzamide

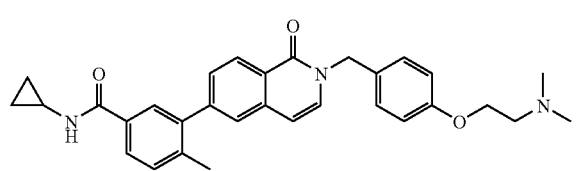

i) N-Cyclopropyl-3-(2-(4-hydroxybenzyl)-1-oxo-1,2-dihydroisoquinolin-6-yl)-4-methylbenzamide

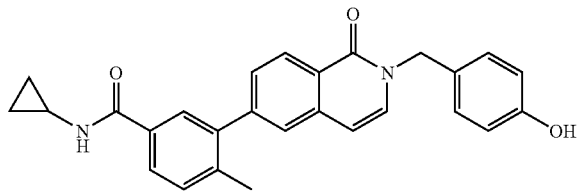

To a solution of the product of Example 11 (460 mg) in DMF (10 mL) was added 60% sodium hydride (38 mg) and the reaction stirred at room temperature for 30 minutes before the addition of 4-(chloromethyl)phenyl acetate (280 mg). The reaction mixture was then stirred at room temperature for 17 hrs. Additional 60% sodium hydride (38 mg) was added and the reaction was stirred for a further 2 hours. NaOH (5N, 2 mL) was added and the reaction was stirred at room temperature for 90 minutes. The reaction mixture was acidified with HCl (2N) and extracted into ethyl acetate. The organics were washed with water and brine, dried over magnesium sulphate and evaporated to yield the sub-titled compound (500 mg).
MS: APCI (+ve) 425 (M+H)$^+$ ii) 3-(2-(4-(2-Chloroethoxy)benzyl)-1-oxo-1,2-dihydroisoquinolin-6-yl)-N-cyclopropyl-4-methylbenzamide

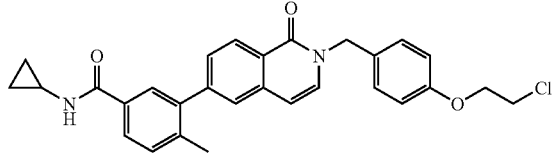

To a solution of the product of step i) (500 mg) in DMF (10 mL) was added potassium carbonate (820 mg) and 1-bromo-2-chloroethane (0.2 mL) and the reaction was heated at 50° C. for 22 hours. Additional 1-bromo-2-chloroethane (0.3 mL) and potassium carbonate (820 mg) were added and heating continued for 40 hours. The reaction mixture was diluted with ethyl acetate and filtered. The filtrate was washed with water and brine, dried over magnesium sulphate and evaporated. The residue was purified (SiO$_2$, ethyl acetate:isohexane (6:4)) to yield the sub-titled compound (280 mg).
MS: APCI (+ve) 488 (M+H)$^+$ iii) N-Cyclopropyl-3-(2-(4-(2-(dimethylamino)ethoxy)benzyl)-1-oxo-1,2-dihydroisoquinolin-6-yl)-4-methylbenzamide

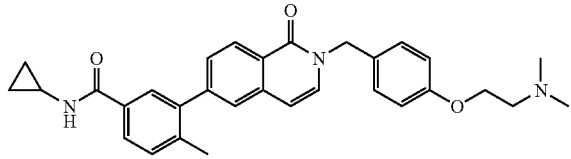

A solution of the product of step ii) (95 mg) in dimethylamine (5M in ethanol, 1.5 mL) was heated using microwave irradiation at 100° C. for 90 minutes.

The reaction mixture was evaporated and purified (SiO$_2$, methanol:DCM (7:93)) to yield the title compound as a solid (85 mg).
MS: APCI (+ve) 496 (M+H)$^+$
$^1$H NMR DMSO-d$_6$ 8.43 (d, J=4.1 Hz, 1H), 8.29 (d, J=8.2 Hz, 1H), 7.79 (dd, J=7.8, 1.9 Hz, 1H), 7.74 (d, J=1.8 Hz, 1H), 7.66 (d, J=1.5 Hz, 1H), 7.62 (d, J=7.4 Hz, 1H), 7.51 (dd, J=8.2, 1.5 Hz, 1H), 7.41 (d, J=7.9 Hz, 1H), 7.32 (d, J=8.7 Hz, 2H), 6.93 (d, J=8.7 Hz, 2H), 6.69 (d, J=7.4 Hz, 1H), 5.14 (s, 2H), 4.10 (t, J=5.5 Hz, 2H), 2.89-2.81 (m, 3H), 2.38 (s, 6H), 2.28 (s, 3H), 0.71-0.65 (m, 2H), 0.58-0.53 (m, 2H)

EXAMPLE 33

N-Cyclopropyl-4-methyl-3-{1-oxo-2-[3-(2-pyrrolidin-1-ylethoxy)benzyl]-1,2-dihydroisoquinolin-6-yl}benzamide

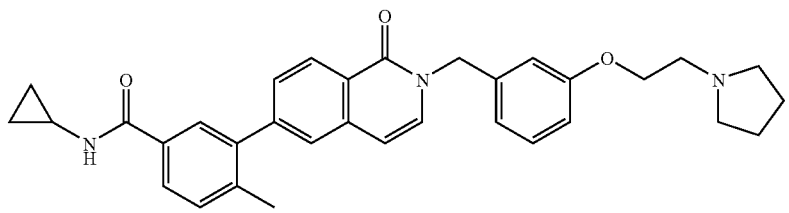

i) N-Cyclopropyl-3-[2-(4-hydroxybenzyl)-1-oxo-1,2-dihydroisoquinolin-6-yl]-4-methylbenzamide

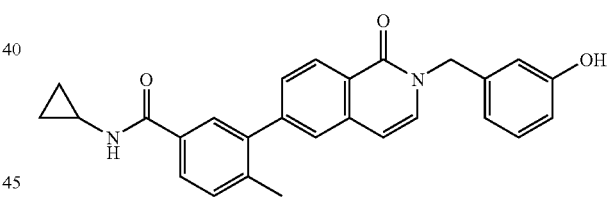

To a solution of the product of Example 11 (0.5 g) in DMF (10 mL) was added 60% sodium hydride in mineral oil (0.1 g) and the mixture stirred at room temperature for 1 hour. To this mixture was then added 3-(bromomethyl)phenol (0.4 g) and the mixture stirred at room temperature for 2 hours. The reaction mixture was concentrated to dryness and the residue purified (SiO$_2$ chromatography 9:1 dichloromethane:methanol) to give the sub-title compound (0.33 g).
MS: APCI (+ve) 425 (M+H)$^+$ ii) 3-[2-[4-(2-Chloroethoxy)benzyl]-1-oxo-1,2-dihydroisoquinolin-6-yl]-N-cyclopropyl-4-methylbenzamide

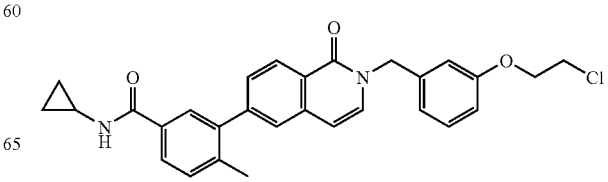

A mixture of the product of step i) (0.33 g), potassium carbonate (1.07 g) and 1-bromo-2-chloroethane (1.12 g) in acetonitrile (10 mL) was heated at reflux for 38 hours. The reaction mixture was concentrated to dryness and the residue partitioned between dichloromethane and water. The organics were collected and purified (SiO$_2$, 9:1 dichloromethane:methanol) to give the sub-title compound (0.31 g).

MS: APCI (+ve) 487/489 (M+H)$^+$ ii) N-Cyclopropyl-4-methyl-3-{1-oxo-2-[3-(2-pyrrolidin-1-ylethoxy)benzyl]-1,2-dihydroisoquinolin-6-yl}benzamide

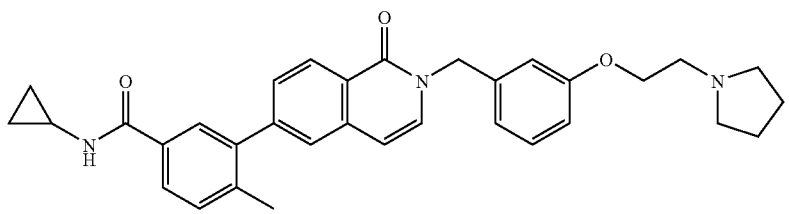

A mixture of the product of step ii) (0.10 g) and pyrrolidine (0.15 g) in acetonitrile (1 mL) was heated by microwave irradiation at 100° C. for 1.5 hours. The reaction mixture was filtered and purified by HPLC to give the title compound as a solid (95 mg).

MS: APCI (+ve) 522 (M+H)$^+$ $^1$H NMR DMSO-d$_6$ 8.43 (d, J=4.0 Hz, 1H), 8.30 (d, J=8.3 Hz, 1H), 7.79 (dd, J=7.9, 1.7 Hz, 1H), 7.75 (s, 1H), 7.67 (d, J=1.3 Hz, 1H), 7.61 (d, J=7.3 Hz, 1H), 7.52 (dd, J=8.3, 1.5 Hz, 1H), 7.42 (d, J=8.1 Hz, 1H), 7.25 (t, J=7.8 Hz, 1H), 6.83-6.91 (m, 3H), 6.71 (d, J=7.3 Hz, 1H), 5.18 (s, 2H), 4.03 (t, J=6.0 Hz, 2H), 2.80-2.89 (m, 1H), 2.74 (t, J=6.0 Hz, 2H), 2.43-2.54 (m, 4H), 2.29 (s, 3H), 1.60-1.71 (m, 4H), 0.65-0.72 (m, 2H), 0.52-0.59 (m, 2H).

EXAMPLES 34-35

The following compounds were prepared as solids according to the method of Example 33 step (iii) using the product of Example 33 step (ii) and the appropriate amine.

EXAMPLE 34

N-Cyclopropyl-4-methyl-3-(2-{3-[2-(methylamino)ethoxy]benzyl}-1-oxo-1,2-dihydroisoquinolin-6-yl)benzamide

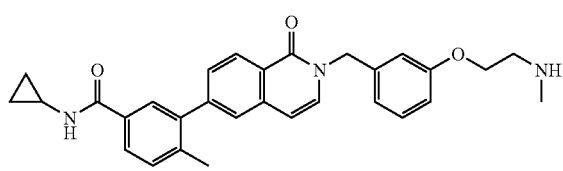

MS: APCI (+ve) 482 (M+H)$^+$ $^1$H NMR DMSO-d$_6$ 8.43 (d, J=4.2 Hz, 1H), 8.30 (d, J=8.3 Hz, 1H), 7.79 (dd, J=7.9, 1.9 Hz, 1H), 7.75 (d, J=1.7 Hz, 1H), 7.67 (d, J=1.5 Hz, 1H), 7.61 (d, J=7.3 Hz, 1H), 7.52 (dd, J=8.3, 1.7 Hz, 1H), 7.42 (d, J=7.9 Hz, 1H), 7.25 (t, J=8.1 Hz, 1H), 6.83-6.90 (m, 3H), 6.71 (d, J=7.3 Hz, 1H), 5.18 (s, 2H), 3.97 (t, J=5.7 Hz, 2H), 2.81-2.89 (m, 1H), 2.78 (t, J=5.6 Hz, 2H), 2.30 (s, 3H), 2.29 (s, 3H), 0.65-0.72 (m, 2H), 0.53-0.58 (m, 2H).

EXAMPLE 35

N-Cyclopropyl-3-[2-(3-{2-[(2-hydroxyethyl)amino]ethoxy}benzyl)-1-oxo-1,2-dihydroisoquinolin-6-yl]-4-methylbenzamide

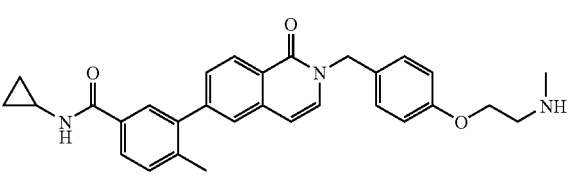

MS: APCI (+ve) 512 (M+H)$^+$ $^1$H NMR DMSO-d$_6$ 8.43 (d, J=4.2 Hz, 1H), 8.30 (d, J=8.3 Hz, 1H), 7.79 (dd, J=7.9, 1.9 Hz, 1H), 7.75 (d, J=1.7 Hz, 1H), 7.67 (d, J=1.5 Hz, 1H), 7.61 (d, J=7.3 Hz, 1H), 7.52 (dd, J=8.3, 1.7 Hz, 1H), 7.42 (d, J=8.1 Hz, 1H), 7.25 (t, J=7.9 Hz, 1H), 6.83-6.92 (m, 3H), 6.71 (d, J=7.3 Hz, 1H), 5.18 (s, 2H), 4.47 (t, J=5.3 Hz, 1H), 3.98 (t, J=5.6 Hz, 2H), 3.45 (q, J=5.5 Hz, 2H), 2.79-2.90 (m, 3H), 2.61 (t, J=5.7 Hz, 2H), 2.29 (s, 3H), 0.64-0.72 (m, 2H), 052-0.59 (m, 2H).

EXAMPLE 36

N-Cyclopropyl-4-methyl-3-(2-(4-(2-(methylamino)ethoxy)benzyl)-1-oxo-1,2-dihydroisoquinolin-6-yl)benzamide The title compound was prepared according to the method of Example 32 step (iii) using the product of Example 32 step (ii) and methylamine.

MS: APCI (+ve) 482 (M+H)$^+$ $^1$H NMR DMSO-d$_6$ 8.55-8.39 (m, 1H), 8.44 (d, J=4.6 Hz, 1H), 8.29 (d, J=8.2 Hz, 1H), 7.79 (dd, J=7.9, 1.8 Hz, 1H), 7.74

(d, J=1.8 Hz, 1H), 7.66 (d, J=1.5 Hz, 1H), 7.62 (d, J=7.4 Hz, 1H), 7.52 (dd, J=8.2, 1.8 Hz, 1H), 7.41 (d, J=8.2 Hz, 1H), 7.34 (d, J=8.7 Hz, 2H), 6.97 (d, J=9.1 Hz, 2H), 6.70 (d, J=7.4 Hz, 1H), 5.15 (s, 2H), 4.19 (t, J=5.1 Hz, 2H), 3.25 (t, J=5.1 Hz, 2H), 2.88-2.80 (m, 1H), 2.57 (s, 3H), 2.28 (s, 3H), 0.71-0.65 (m, 2H), 0.58-0.53 (m, 2H)

EXAMPLE 37

(R)-3-(4-(3-Aminopyrrolidine-1-carbonyl)-2-(cyclopropylmethyl)-1-oxo-1,2-dihydroisoquinolin-6-yl)-N-cyclopropyl-4-methylbenzamide

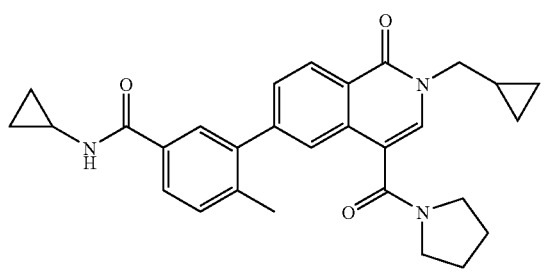

i) (E)-4-Bromo-(methoxymethylene)isochroman-1,3-dione

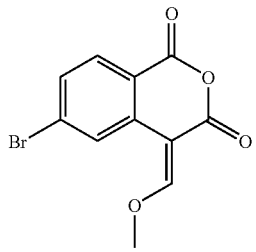

A mixture of the product of Example 17 step (i) (28.9 g), trimethyl orthoformate (30 mL) and acetic anhydride (100 mL) was heated to 120° C. for 2 hours. The reaction mixture was allowed to cool to room temperature and filtered. The solid was washed with methanol and air dried to yield the sub-titled compound (26.1 g).

MS: APCI (+ve) 283, 285 (1:1) (M+H)⁺ ii) 6-Bromo-1-oxo-1H-isochromene-4-carboxylic acid, methyl ester

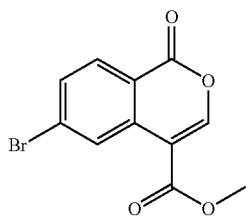

To a stirred slurry of the product of step i) (26 g) in methanol (150 mL) was added sulfuric acid (25 mL). The reaction mixture was heated to reflux for 19 hours. The reaction mixture was cooled to room temperature and filtered. The solid was washed with methanol then water and air dried to yield the sub-titled compound (23 g).

¹H NMR DMSO-d₆ 8.69 (d, J=2.1 Hz, 1H), 8.47 (s, 1H), 8.11 (d, J=8.5 Hz, 1H), 7.87 (dd, J=8.5, 2.1 Hz, 1H), 3.87 (s, 3H).

iii) 6-Bromo-2-(cyclopropylmethyl)-1-oxo-1,2-dihydroisoquinoline-4-carboxylic acid, methyl ester

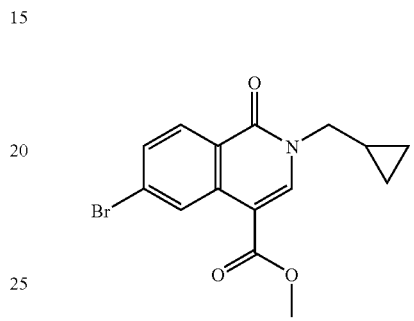

A mixture of the product of step ii) (5.5 g), cyclopropylmethanamine hydrochloride (2.09 g) and N,N-diisopropylethylamine (5.1 mL) in methanol (40 mL) was heated at reflux for 17 hours. The reaction mixture was allowed to cool to room temperature and filtered. The solid was washed with methanol and dried under vacuum at 60° C. to yield the sub-titled compound (4.55 g)

MS: APCI (+ve) 336, 338 (1:1) (M+H)⁺ iv) 6-(5-(Cyclopropylcarbamoyl)-2-methylphenyl)-2-(cyclopropylmethyl)-1-oxo-1,2-dihydroisoquinoline-4-carboxylic acid, methyl ester

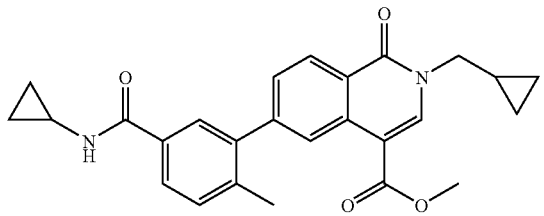

A mixture of N-cyclopropyl-4-methyl-3-(4,4,5,5-tetramethyl-1,3,2-dioxaborolan-2-yl)benzamide (4.24 g) [prepared as described in US2005020590], the product of step iii) (4.3 g), tetrakis(triphenylphosphine)palladium(0) (1.5 g) and potassium carbonate (3.54 g) in DMF (50 mL) was heated to 80° C. for 17 hours. The reaction mixture was diluted with ethyl acetate and washed with water and brine. The organics were dried over magnesium sulphate and evaporated. The crude product was purified (SiO₂, 50 to 70% ethyl acetate in isohexane as eluent) to yield the sub-title compound (2.5 g).

MS: APCI (+ve) 431 (M+H)⁺ v) 6-(5-(Cyclopropylcarbamoyl)-2-methylphenyl)-2-(cyclopropylmethyl)-1-oxo-1,2-dihydroisoquinoline-4-carboxylic acid

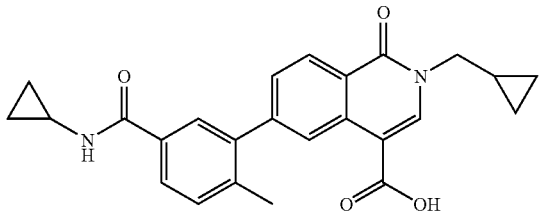

To a solution of the product of step iv) (1.5 g) in methanol (20 mL) at reflux was added sodium hydroxide (1N, 5.23 mL) and the solution stirred at this temperature for 30 min. The reaction mixture was treated with acetic acid (0.34 mL) and water and stirred overnight at room temperature. The solid was filtered and washed with methanol:water (1:1) then water. The solid was dried under vacuum at 60° C. to yield the sub-title compound (1.25 g).

MS: APCI (+ve) 417 (M+H)$^+$ vi) (R)-3-(4-(3-Aminopyrrolidine-1-carbonyl)-2-(cyclopropylmethyl)-1-oxo-1,2-dihydroisoquinolin-6-yl)-N-cyclopropyl-4-methylbenzamide

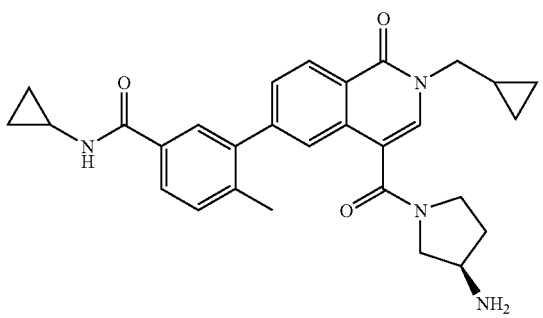

To a solution of the product of step v) (100 mg), (R)-pyrrolidin-3-amine (20 mg) and N,N-diisopropylethylamine (0.13 mL) in DMF (2 mL) was added HATU (140 mg) and the reaction stirred at room temperature for 10 minutes. The reaction mixture was filtered and purified by HPLC to yield the title compound as a solid (65 mg).

MS: APCI (+ve) 485 (M+H)$^+$ $^1$HNMRDMSO-d$_6$ 8.36 (d, J=8.3 Hz, 1H), 8.14 (s, 1H), 7.76 (dd, J=7.9, 1.9 Hz, 1H), 7.70-7.67 (m, 2H), 7.56 (d, J=1.5 Hz, 1H), 7.50 (dd, J=8.3, 1.5 Hz, 2H), 7.37 (d, J=8.1 Hz, 1H), 3.90 (d, J=7.1 Hz, 2H), 3.65-3.37 (m, 4H), 3.17-3.07 (m, 1H), 2.91-2.81 (m, 1H), 2.27-2.21 (m, 3H), 2.04-1.89 (m, 1H), 1.67-1.54 (m, 1H), 1.35-1.22 (m, 2H), 0.71-0.61 (m, 2H), 0.61-0.47 (m, 4H), 0.47-0.38 (m, 2H)

EXAMPLES 38-46

The following compound were prepared as solids according to the method of Example 37 step (vi) using the product of Example 37 step (v) and the appropriate amine.

EXAMPLE 38

6-(5-(Cyclopropylcarbamoyl)-2-methylphenyl)-2-(cyclopropylmethyl)-N-(1-methylpiperidin-4-yl)-1-oxo-1,2-dihydroisoquinoline-4-carboxamide

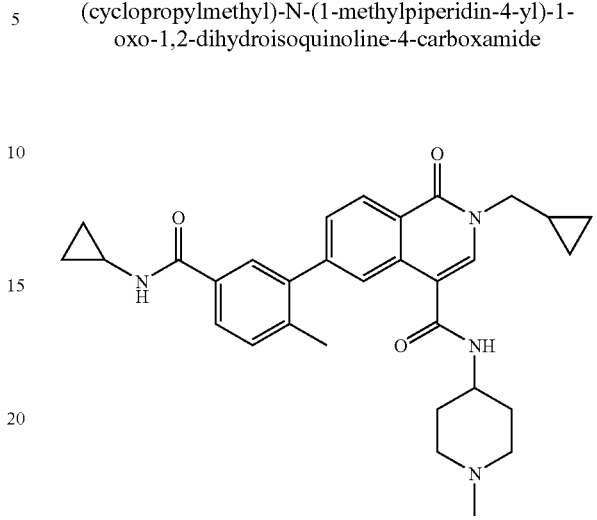

MS: APCI (+ve) 513 (M+H)$^+$ $^1$H NMR DMSO-d$_6$ 8.44 (d, J=4.1 Hz, 1H), 8.34 (d, J=8.5 Hz, 1H), 8.23 (d, J=7.4 Hz, 1H), 8.11 (d, J=1.5 Hz, 1H), 7.87 (s, 1H), 7.79 (dd, J=7.9, 1.8 Hz, 1H), 7.73 (d, J=1.8 Hz, 1H), 7.56 (dd, J=8.2, 1.8 Hz, 1H), 7.42 (d, J=7.9 Hz, 1H), 3.90 (d, J=7.2 Hz, 2H), 3.74-3.63 (m, 1H), 2.89-2.81 (m, 1H), 2.77-2.70 (m, 2H), 2.27 (s, 3H), 2.14 (s, 3H), 1.98-1.89 (m, 2H), 1.85-1.77 (m, 2H), 1.58-1.46 (m, 2H), 1.40-1.30 (m, 1H), 0.71-0.64 (m, 2H), 0.58-0.44 (m, 6H)

EXAMPLE 39

N-Cyclopropyl-3-(2-(cyclopropylmethyl)-4-(4-methylpiperazine-1-carbonyl)-1-oxo-1,2-dihydroisoquinolin-6-yl)-4-methylbenzamide

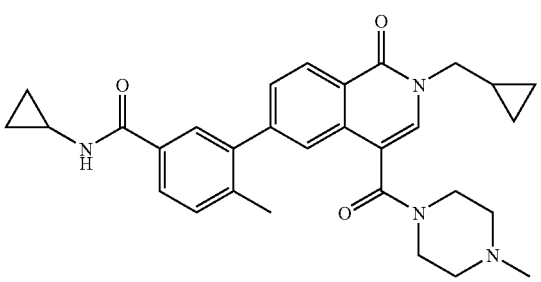

MS: APCI (+ve) 499 (M+H)$^+$ $^1$H NMR DMSO-d$_6$ 8.37 (d, J=7.9 Hz, 1H), 8.17 (s, 1H), 7.77 (d, J=7.7 Hz, 1H), 7.69 (s, 1H), 7.63 (s, 1H), 7.52 (d, J=8.3 Hz, 1H), 7.44 (s, 1H), 7.39 (d, J=7.7 Hz, 1H), 3.90 (d, J=6.9 Hz, 2H), 3.52 (s, 4H), 2.92-2.80 (m, 1H), 2.35-2.27 (m, 4H), 2.25 (s, 3H), 2.18 (s, 3H), 1.35-1.20 (m, 1H), 0.72-0.61 (m, 2H), 0.61-0.46 (m, 4H), 0.46-0.36 (m, 2H)

EXAMPLE 40

6-(5-(Cyclopropylcarbamoyl)-2-methylphenyl)-2-(cyclopropylmethyl)-N-(2-(dimethylamino)ethyl)-1-oxo-1,2-dihydroisoquinoline-4-carboxamide

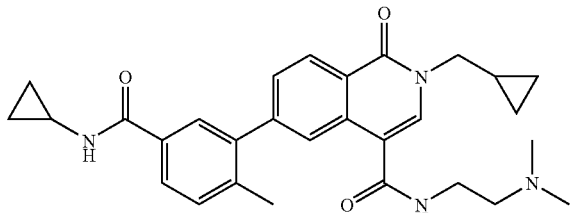

MS: APCI (+ve) 487 (M+H)$^+$ $^1$H NMR DMSO-d$_6$ 8.44 (d, J=4.1 Hz, 1H), 8.35 (d, J=8.5 Hz, 1H), 8.28 (t, J=5.6 Hz, 1H), 8.16 (d, J=1.5 Hz, 1H), 7.88 (s, 1H), 7.79 (dd, J=7.9, 1.8 Hz, 1H), 7.72 (d, J=1.8 Hz, 1H), 7.55 (dd, J=8.3, 1.7 Hz, 1H), 7.42 (d, J=8.2 Hz, 1H), 3.89 (d, J=7.2 Hz, 2H), 3.35-3.29 (m, 2H), 2.88-2.81 (m, 1H), 2.38 (t, J=6.7 Hz, 2H), 2.26 (s, 3H), 2.12 (s, 6H), 1.38-1.29 (m, 1H), 0.71-0.64 (m, 2H), 0.59-0.42 (m, 6H)

EXAMPLE 41

6-(5-(Cyclopropylcarbamoyl)-2-methylphenyl)-2-(cyclopropylmethyl)-1-oxo-N-(piperidin-4-yl)-1,2-dihydroisoquinoline-4-carboxamide

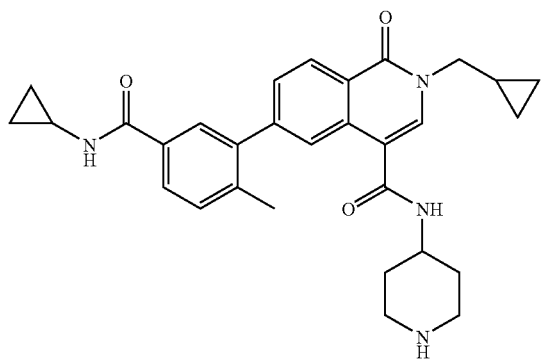

MS: APCI (+ve) 499 (M+H)$^+$ $^1$H NMR DMSO-d$_6$ 8.35 (d, J=8.2 Hz, 1H), 8.15 (s, 1H), 8.11 (s, 1H), 7.91 (s, 1H), 7.80 (s, 1H), 7.76 (d, J=7.9 Hz, 1H), 7.70 (s, 1H), 7.50 (d, J=8.2 Hz, 1H), 7.38 (d, J=7.9 Hz, 1H), 3.90 (d, J=6.9 Hz, 2H), 3.80 (d, J=4.4 Hz, 1H), 3.00-2.91 (m, 2H), 2.89-2.82 (m, 1H), 2.55-2.48 (m, 2H), 2.26 (s, 3H), 1.83-1.74 (m, 2H), 1.44-1.29 (m, 3H), 0.70-0.63 (m, 2H), 0.60-0.55 (m, 2H), 0.55-0.49 (m, 2H), 0.48-0.42 (m, 2H)

EXAMPLE 42

3-(4-(4-Aminopiperidine-1-carbonyl)-2-(cyclopropylmethyl)-1-oxo-1,2-dihydroisoquinolin-6-yl)-N-cyclopropyl-4-methylbenzamide

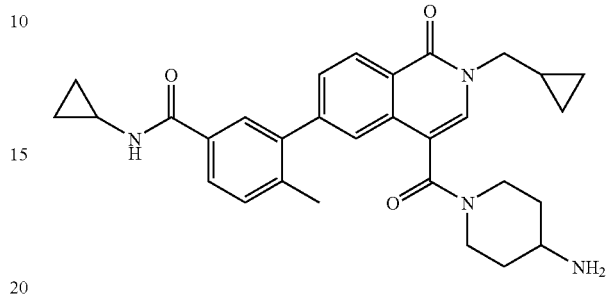

MS: APCI (+ve) 499 (M+H)$^+$ $^1$H NMR DMSO-d$_6$ 8.37 (d, J=8.2 Hz, 1H), 8.17 (s, 1H), 7.76 (d, J=7.9 Hz, 1H), 7.68 (s, 1H), 7.60 (s, 1H), 7.51 (d, J=8.2 Hz, 1H), 7.41 (s, 1H), 7.38 (d, J=7.9 Hz, 1H), 4.00-3.92 (m, 2H), 3.90 (d, J=6.9 Hz, 2H), 3.11-3.00 (m, 2H), 2.89-2.79 (m, 2H), 2.24 (s, 3H), 1.76-1.68 (m, 2H), 1.32-1.22 (m, 1H), 1.22-1.13 (m, 2H), 0.71-0.63 (m, 2H), 0.60-0.54 (m, 2H), 0.54-0.48 (m, 2H), 0.45-0.38 (m, 2H)

EXAMPLE 43

(S)-3-(4-(3-Aminopyrrolidine-1-carbonyl)-2-(cyclopropylmethyl)-1-oxo-1,2-dihydroisoquinolin-6-yl)-N-cyclopropyl-4-methylbenzamide

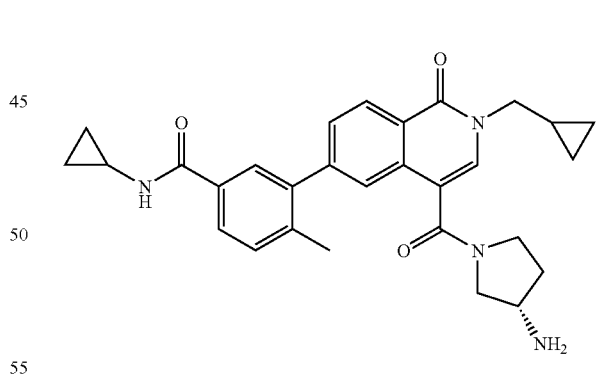

MS: APCI (+ve) 485 (M+H)$^+$ $^1$H NMR DMSO-d$_6$ 8.36 (d, J=8.3 Hz, 1H), 8.14 (s, 1H), 7.76 (dd, J=7.9, 1.9 Hz, 1H), 7.70-7.67 (m, 2H), 7.56 (d, J=1.5 Hz, 1H), 7.50 (dd, J=8.3, 1.5 Hz, 2H), 7.37 (d, J=8.1 Hz, 1H), 3.90 (d, J=7.1 Hz, 2H), 3.65-3.37 (m, 4H), 3.17-3.07 (m, 1H), 2.91-2.81 (m, 1H), 2.27-2.21 (m, 3H), 2.04-1.89 (m, 1H), 1.67-1.54 (m, 1H), 1.35-1.22 (m, 2H), 0.71-0.61 (m, 2H), 0.61-0.47 (m, 4H), 0.47-0.38 (m, 2H)

EXAMPLE 44

6-(5-(Cyclopropylcarbamoyl)-2-methylphenyl)-2-(cyclopropylmethyl)-1-oxo-N-(3-(pyrrolidin-1-yl)propyl)-1,2-dihydroisoquinoline-4-carboxamide

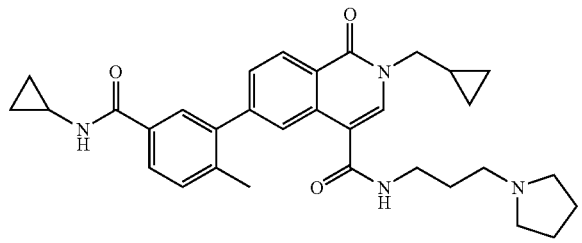

MS: APCI (+ve) 527 (M+H)+

$^1$H NMR DMSO-$d_6$ 8.44 (d, J=4.2 Hz, 1H), 8.38 (t, J=5.4 Hz, 1H), 8.35 (d, J=8.9 Hz, 1H), 8.11 (s, 1H), 7.88 (s, 1H), 7.80 (d, J=8.1 Hz, 1H), 7.73 (s, 1H), 7.55 (d, J=8.5 Hz, 1H), 7.42 (d, J=7.9 Hz, 1H), 3.89 (d, J=7.1 Hz, 2H), 3.27 (q, J=6.1 Hz, 2H), 2.89-2.79 (m, 1H), 2.41 (t, J=6.8 Hz, 2H), 2.39-2.33 (m, 4H), 2.26 (s, 3H), 1.73-1.63 (m, 2H), 1.67-1.59 (m, 4H), 1.40-1.29 (m, 1H), 0.73-0.61 (m, 2H), 0.61-0.42 (m, 6H)

EXAMPLE 45

N-Cyclopropyl-3-(2-(cyclopropylmethyl)-(4-(dimethylamino)piperidine-1-carbonyl)-1-oxo-1,2-dihydroisoquinolin-6-yl)-4-methylbenzamide

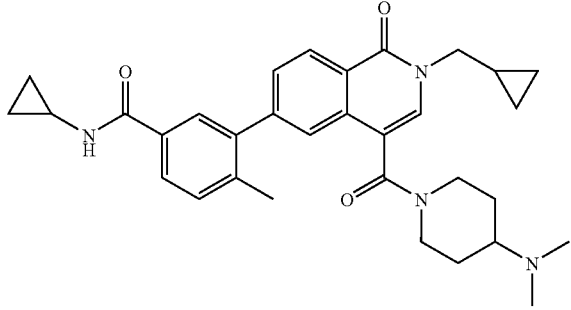

MS: APCI (+ve) 527 (M+H)+

$^1$H NMR DMSO-$d_6$ 8.37 (d, J=8.2 Hz, 1H), 8.14 (s, 1H), 7.76 (dd, J=7.9, 1.5 Hz, 1H), 7.68 (s, 1H), 7.62 (s, 1H), 7.51 (dd, J=8.2, 1.5 Hz, 1H), 7.42 (s, 1H), 7.38 (d, J=8.2 Hz, 1H), 4.13-3.99 (m, 2H), 3.90 (d, J=7.2 Hz, 2H), 3.00-2.92 (m, 2H), 2.88-2.80 (m, 1H), 2.38-2.29 (m, 1H), 2.23 (s, 3H), 2.13 (s, 6H), 1.74 (d, J=12.3 Hz, 2H), 1.38-1.23 (m, 3H), 0.71-0.62 (m, 2H), 0.60-0.54 (m, 2H), 0.54-0.49 (m, 2H), 0.46-0.39 (m, 2H)

EXAMPLE 46

N-Cyclopropyl-3-(2-(cyclopropylmethyl)-4-(4-(2-(dimethylamino)ethyl)piperazine-1-carbonyl)-1-oxo-1,2-dihydroisoquinolin-6-yl)-methylbenzamide

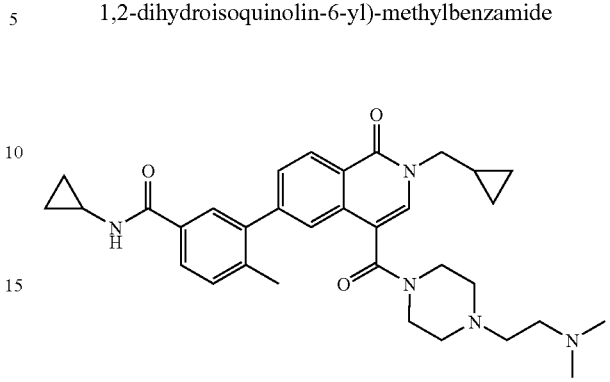

MS: APCI (+ve) 556 (M+H)+

$^1$H NMR DMSO-$d_6$ 8.37 (d, J=8.2 Hz, 1H), 8.15 (s, 1H), 7.76 (dd, J=7.8, 1.9 Hz, 1H), 7.69 (d, J=1.8 Hz, 1H), 7.61 (s, 1H), 7.52 (dd, J=8.3, 1.7 Hz, 1H), 7.44 (d, J=1.3 Hz, 1H), 7.38 (d, J=7.9 Hz, 1H), 3.90 (d, J=7.2 Hz, 2H), 3.51 (t, J=4.6 Hz, 4H), 2.89-2.82 (m, 1H), 2.43-2.37 (m, 6H), 2.36-2.30 (m, 2H), 2.24 (s, 3H), 2.12 (s, 6H), 1.34-1.23 (m, 1H), 0.70-0.64 (m, 2H), 0.59-0.54 (m, 2H), 0.54-0.49 (m, 2H), 0.44-0.39 (m, 2H)

EXAMPLE 47

2-Benzyl-6-(5-(cyclopropylcarbamoyl)-2-methylphenyl)-N-(2-(dimethylamino)ethyl)-1-oxo-1,2-dihydroisoquinoline-4-carboxamide

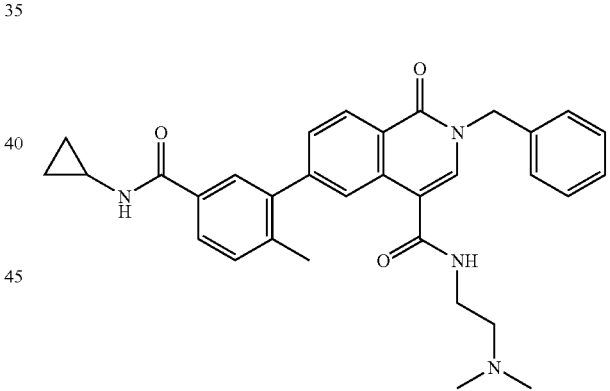

i) 2-Benzyl-6-bromo-1-oxo-1,2-dihydroisoquinoline-4-carboxylic acid, methyl ester

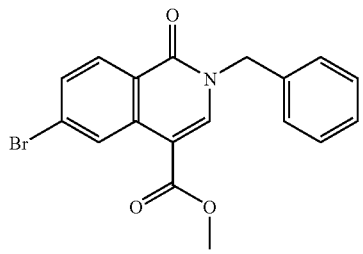

A mixture of the product of Example 37 step ii) (5 g) and benzylamine (3 mL) in methanol (20 mL) was heated at reflux for 40 hours. The reaction was concentrated to half volume, then treated with acetonitrile. The sub-title compound was collected by filtration, washing with acetonitrile (5.30 g).

MS: APCI (+ve) 372/374 (M+H)+ ii) 2-Benzyl-6-(5-(cyclopropylcarbamoyl)-2-methylphenyl)-1-oxo-1,2-dihydroisoquinoline-4-carboxylic acid, methyl ester

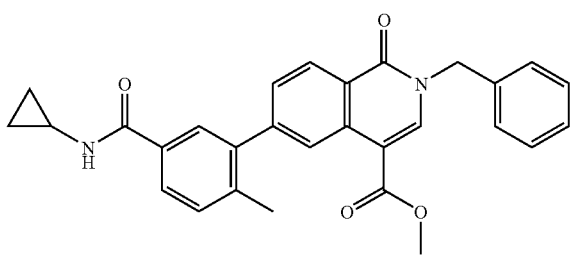

A mixture of the product of step i) (0.37 g), N-cyclopropyl-4-methyl-3-(4,4,5,5-tetramethyl-1,3,2-dioxaborolan-2-yl) benzamide (0.29 g) [prepared as described in US2005020590] and potassium carbonate (0.27 g) in degassed N,N-dimethylformamide (8 mL) was treated with tetrakis(triphenylphosphine)palladium(0) (0.115 g) and the mixture heated at 80° C. under nitrogen for 24 hours. The reaction mixture was concentrated to dryness and the crude product purified (SiO₂, 2% methanol in dichloromethane as eluent) to give the sub-title compound (0.44 g).

MS: APCI (+ve) 467.6 (M+H)+ iii) 2-Benzyl-6-(5-(cyclopropylcarbamoyl)-2-methylphenyl)-1-oxo-1,2-dihydroisoquinoline-4-carboxylic acid

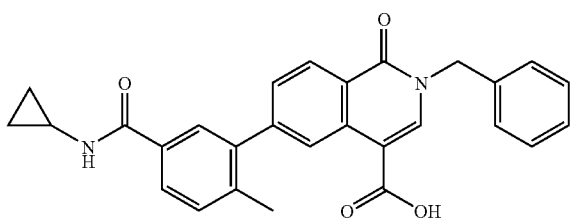

A mixture of the product of step ii) (0.88 g) and 5N sodium hydroxide (2.3 mL) in methanol (20 mL) was heated at 50° C. for 2 hours and then allowed to cool to room temperature. The reaction mixture was treated with glacial acetic acid (1 mL) and then water (20 mL). The precipitate was collected by filtration, washed with water and dried under vacuum to afford the sub-title compound (0.77 g).

MS: APCI (+ve) 452 (M+H)+ iv) 2-Benzyl-6-(5-(cyclopropylcarbamoyl)-2-methylphenyl)-N-(2-(dimethylamino)ethyl)-1-oxo-1,2-dihydroisoquinoline-4-carboxamide

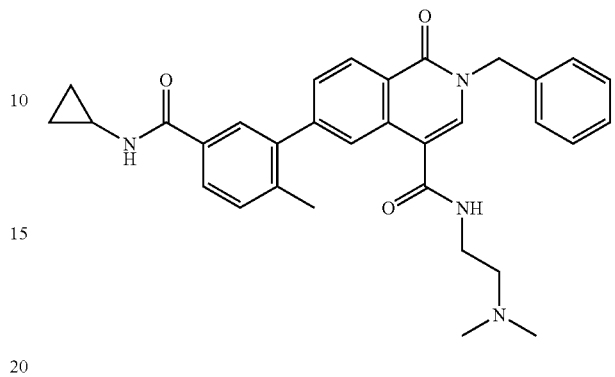

To a mixture of the product of step iii) (0.48 g) and N,N-dimethylethane-1,2-diamine (0.17 mL) in THF (20 mL) was added N,N-diisopropylethylamine (0.56 mL) followed by HATU (0.60 g) and the reaction stirred at room temperature for 3 hours. The reaction mixture was concentrated to dryness and the crude product purified by SiO₂ chromatography (eluting with 90:10:0.1 dichloromethane:methanol:triethylamine). The fractions containing product were concentrated to dryness and the residue triturated with acetonitrile to give the title compound as a solid (0.35 g).

MS: APCI (+ve) 523 (M+H)+

$^1$H NMR DMSO-$d_6$ 8.44 (d, J=4.2 Hz, 1H), 8.34 (dd, J=8.3, 0.9 Hz, 1H), 8.30 (d, J=5.6 Hz, 1H), 8.14 (s, 1H), 7.96 (s, 1H), 7.79 (d, J=8.1 Hz, 1H), 7.72 (s, 1H), 7.57 (d, J=8.3 Hz, 1H), 7.42 (d, J=8.1 Hz, 1H), 7.39-7.34 (m, 4H), 7.34-7.26 (m, 1H), 5.24 (s, 2H), 3.36-3.28 (m, 2H), 2.89-2.79 (m, 1H), 2.37 (t, J=6.6 Hz, 2H), 2.26 (s, 3H), 2.10 (s, 6H), 0.72-0.64 (m, 2H), 0.59-0.52 (m, 2H)

EXAMPLES 48-53

The following compounds were prepared as solids according to the method of Example 18 step (iii) using the product of Example 47 step (iii) and the appropriate amine.

EXAMPLE 48

2-Benzyl-6-(5-(cyclopropylcarbamoyl)-2-methylphenyl)-1-oxo-N-(2-(piperidin-1-yl)ethyl)-1,2-dihydroisoquinoline-4-carboxamide

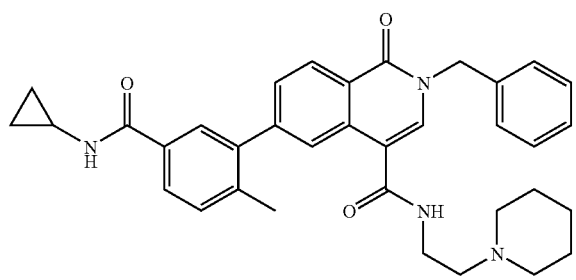

MS: APCI (+ve) 563 (M+H)+
¹H NMR DMSO-d₆ 8.49-8.19 (m, 3H), 8.12-8.00 (m, 1H), 7.98-7.85 (m, 1H), 7.80-7.63 (m, 2H), 7.59-7.46 (m, 1H), 7.43-7.22 (m, 6H), 5.28-5.13 (m, 2H), 3.35-3.20 (m, 2H), 2.88-2.74 (m, 1H), 2.49-2.35 (m, 2H), 2.35-2.17 (m, 4H), 2.23 (s, 3H), 1.39-1.16 (m, 6H), 0.70-0.57 (m, 2H), 0.57-0.44 (m, 2H)

EXAMPLE 49

2-Benzyl-6-{5-[(cyclopropylamino)carbonyl]-2-methylphenyl}-1-oxo-N-(2-pyrrolidin-1-ylethyl)-1,2-dihydroisoquinoline-4-carboxamide

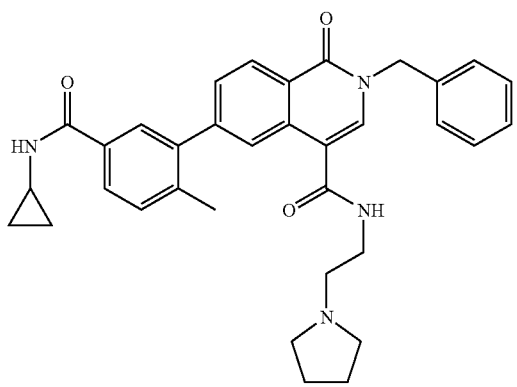

MS: APCI (+ve) 549 (M+H)+
¹H NMR DMSO-d₆ 9.56 (s, 1H), 8.63 (t, J=5.8 Hz, 1H), 8.43 (d, J=4.4 Hz, 1H), 8.33 (d, J=8.2 Hz, 1H), 8.21 (d, J=1.5 Hz, 1H), 8.06 (s, 1H), 7.77 (dd, J=7.9, 1.8 Hz, 1H), 7.71 (d, J=1.8 Hz, 1H), 7.58 (dd, J=8.3, 1.7 Hz, 1H), 7.41-7.26 (m, 4H), 5.23 (s, 2H), 3.62-3.50 (m, 4H), 3.07-2.99 (m, 2H), 3.03 (m, 2H), 2.97 (s, 2H), 2.82 (octet, J=4.0 Hz, 1H), 2.25 (s, 3H), 1.98 (m, 2H), 1.82 (m, 2H), 0.66 (dd, J=6.9, 2.3 Hz, 2H), 0.52 (m, 2H)

EXAMPLE 50

2-Benzyl-6-{5-[(cyclopropylamino)carbonyl]-2-methylphenyl}-N-(1-methylpiperidin-4-yl)-1-oxo-1,2-dihydroisoquinoline-4-carboxamide

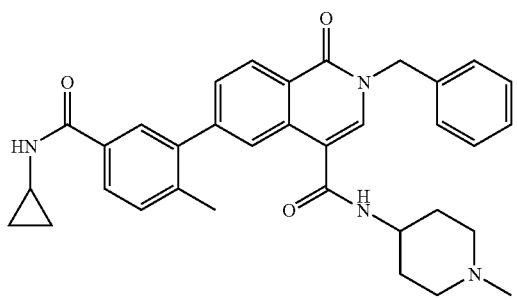

MS: APCI (+ve) 549 (M+H)+
¹H NMR DMSO-d₆ 8.41 (d, J=4.1 Hz, 1H), 8.31 (d, J=8.2 Hz, 1H), 8.26 (d, J=7.7 Hz, 1H), 8.06 (d, J=1.5 Hz, 1H), 7.94 (s, 1H), 7.77 (dd, J=7.9, 1.8 Hz, 1H), 7.70 (d, J=1.8 Hz, 1H), 7.55 (dd, J=8.2, 1.8 Hz, 1H), 7.42-7.31 (m, 4H), 5.22 (s, 2H), 3.66 (m, 1H), 2.97 (s, 2H), 2.82 (q, J=3.7 Hz, 1H), 2.70 (d, J=11.0 Hz, 2H), 2.24 (s, 3H), 2.11 (s, 3H), 1.90 (t, J=11.9 Hz, 2H), 1.77 (d, J=15.3 Hz, 2H), 1.48 (dd, J=11.5, 3.3 Hz, 2H), 0.65 (m, 2H), 0.53 (m, Hz, 2H)

EXAMPLE 51

2-Benzyl-6-{5-[(cyclopropylamino)carbonyl]-2-methylphenyl}-N-[3-(dimethylamino)propyl]-1-oxo-1,2-dihydroisoquinoline-4-carboxamide

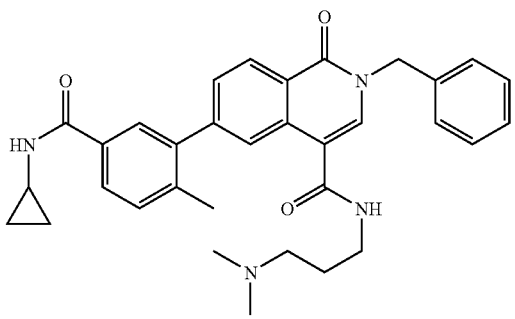

MS: APCI (+ve) 537 (M+H)+
¹H NMR DMSO-d₆ 9.39 (s, 1H), 8.55 (t, J=5.6 Hz, 1H), 8.43 (d, J=4.4 Hz, 1H), 8.32 (d, J=8.5 Hz, 1H), 8.13 (d, J=1.5 Hz, 1H), 8.02 (s, 1H), 7.78 (dd, J=7.9, 2.1 Hz, 2H), 7.71 (d, J=1.5 Hz, 1H), 7.57 (dd, J=8.2, 1.8 Hz, 1H), 7.40 (d, J=7.9 Hz, 1H), 7.37-7.25 (m, 3H), 5.22 (s, 2H), 3.29 (m, 2H), 3.08 (m, 2H), 2.82 (quintet, J=3.7 Hz, 1H), 2.73 (s, 6H), 2.25 (s, 3H), 1.85 (t, J=7.8 Hz, 2H), 0.66 (td, J=7.0, 4.8 Hz, 2H), 0.53 (m, 2H)

EXAMPLE 52

3-(2-Benzyl-4-{[4-(2-hydroxyethyl)piperazin-1-yl]carbonyl}-1-oxo-1,2-dihydroisoquinolin-6-yl)-N-cyclopropyl-4-methylbenzamide

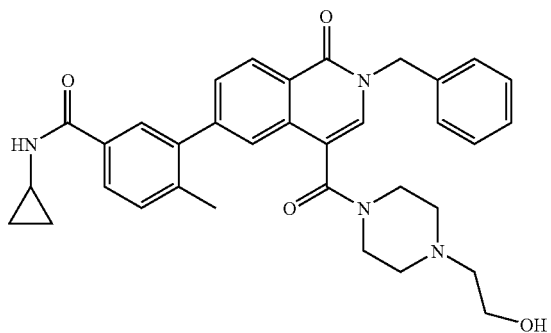

MS: APCI (+ve) 565 (M+H)+
¹H NMR DMSO-d₆ 8.41 (d, J=4.4 Hz, 1H), 8.34 (d, J=8.2 Hz, 1H), 7.76 (m, 2H), 7.68 (d, J=1.8 Hz, 1H), 7.56 (dd, J=8.3, 1.7 Hz, 1H), 7.40 (m, 2H), 7.36-7.24 (m, 4H), 5.21 (s, 2H), 4.37 (t, J=5.4 Hz, 1H), 3.45 (q, J=5.7 Hz, 2H), 2.97 (s, 1H), 2.81 (quintet, J=3.6 Hz, 1H), 2.54-2.44 (m, 8H), 2.35 (t, J=6.2 Hz, 2H), 2.23 (s, 3H), 0.65 (td, J=6.9, 4.8 Hz, 2H), 0.51 (m, 2H)

EXAMPLE 53

(R)-3-(4-(3-Aminopyrrolidine-1-carbonyl)-2-benzyl-1-oxo-1,2-dihydroisoquinolin-6-yl)-N-cyclopropyl-4-methylbenzamide

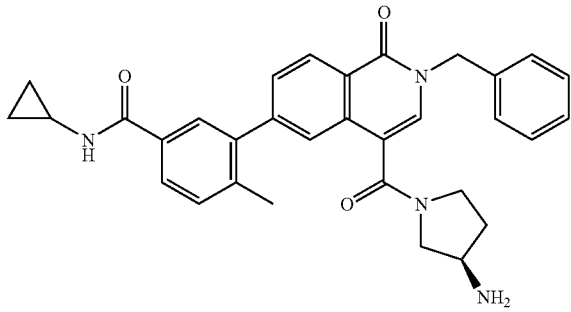

MS: APCI (+ve) 520 (M+H)⁺

¹H NMR DMSO-d₆ 8.43 (d, J=2.6 Hz, 1H), 8.36 (d, J=8.7 Hz, 1H), 7.90 (d, J=10.5 Hz, 1H), 7.78 (d, J=7.9 Hz, 1H), 7.70 (s, 1H), 7.59-7.55 (m, 2H), 7.41 (d, J=7.9 Hz, 1H), 7.38-7.34 (m, 4H), 7.30 (q, J=4.1 Hz, 1H), 5.24 (s, 2H), 3.68-3.32 (m, 3H), 3.23-2.98 (m, 1H), 2.88-2.80 (m, 1H), 2.25 (s, 3H), 1.99-1.84 (m, 1H), 1.66-1.53 (m, 2H), 0.71-0.65 (m, 2H), 0.58-0.53 (m, 2H).

EXAMPLE 54

N-Cyclopropyl-4-methyl-3-(1-oxo-2-(pyridin-4-ylmethyl)-4-(4-(pyrrolidin-1-yl)piperidine-1-carbonyl)-1,2-dihydroisoquinolin-6-yl)benzamide

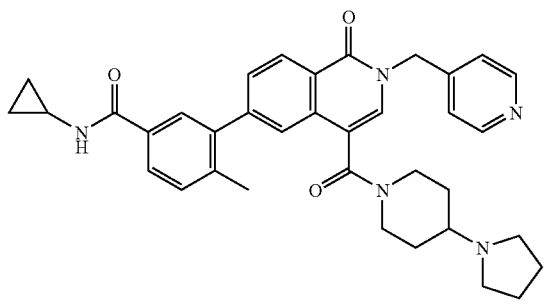

i) 6-Bromo-1-oxo-2-(pyridin-4-ylmethyl)-1,2-dihydroisoquinoline-4-carboxylic acid, methyl ester

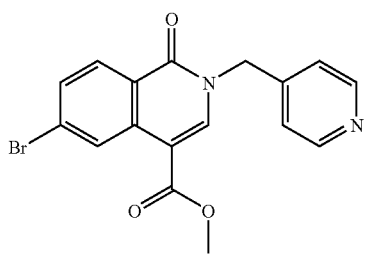

A mixture of the product of Example 37 step ii) (0.78 g) and pyridin-4-ylmethanamine (0.298 g) in methanol (5 mL) was heated at reflux for 24 hours. The reaction was concentrated to dryness and the crude product triturated with acetonitrile before being purified (SiO₂, 5% methanol in dichloromethane as eluent) to give the sub-title compound (0.70 g).

MS: APCI (+ve) 372/374 (M+H)⁺ ii) 6-(5-(Cyclopropylcarbamoyl)-2-methylphenyl)-1-oxo-2-(pyridin-4-ylmethyl)-1,2-dihydroisoquinoline-4-carboxylic acid, methyl ester

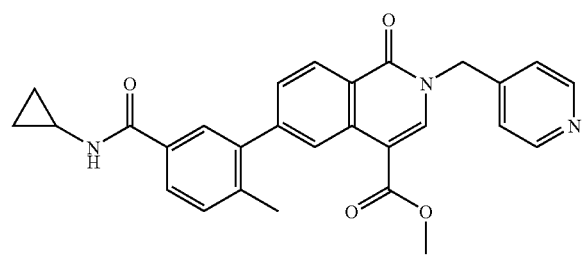

A mixture of the product of step i) (0.7 g), N-cyclopropyl-4-methyl-3-(4,4,5,5-tetramethyl-1,3,2-dioxaborolan-2-yl)benzamide (0.565 g) and potassium carbonate (0.518 g) in degassed N,N-dimethylformamide (15 mL) was treated with tetrakis(triphenylphosphine)palladium(0) (0.25 g) and the mixture heated at 80° C. under nitrogen for 40 hours. The reaction mixture was concentrated to dryness and the residue purified (SiO₂, 5% methanol in dichloromethane as eluent) to give the sub-title compound (0.70 g).

MS: APCI (+ve) 468 (M+H)⁺ iii) 6-(5-(Cyclopropylcarbamoyl)-2-methylphenyl)-1-oxo-2-(pyridin-4-ylmethyl)-1,2-dihydroisoquinoline-4-carboxylic acid

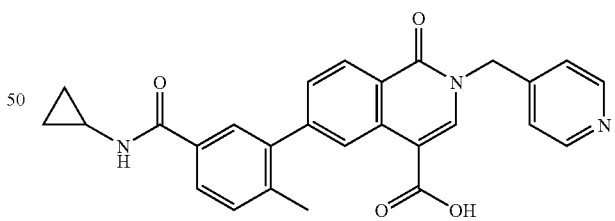

To a mixture of the product of step ii) (0.7 g) in methanol (15 mL) was added a 5M aqueous solution of sodium hydroxide (1.8 mL) and the reaction heated at 50° C. for 6 hours. The reaction mixture was allowed to cool to room temperature and then treated with water (20 mL). The precipitate was collected by filtration, washed with water and dried to give the sub-title compound (0.52 g).

MS: APCI (+ve) 454 (M+H)⁺ iv) N-Cyclopropyl-4-methyl-3-(1-oxo-2-(pyridin-4-ylmethyl)-4-(4-(pyrrolidin-1-yl)piperidine-1-carbonyl)-1,2-dihydroisoquinolin-6-yl)benzamide

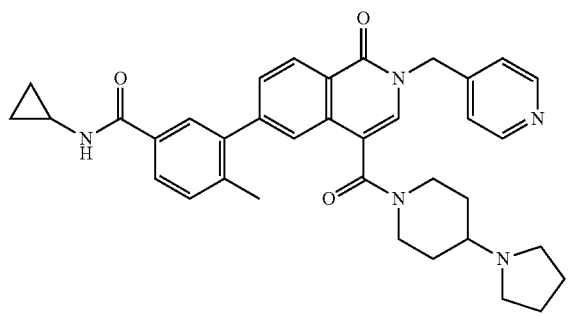

To a mixture of the product of step iii) (0.1 g), 4-(N-pyrrolidin-1-yl)piperidine (0.037 g) and N,N-diisopropylethylamine (0.25 mL) in tetrahydrofuran (10 mL) was added HATU (0.17 g) and then stirred at room temperature for 3 hours. The reaction mixture was then concentrated to dryness and the crude product purified by HPLC to afford the title compound as a solid (0.07 g).
MS: APCI (+ve) 564 (M+H)$^+$
$^1$H NMR DMSO-d$_6$ 8.54 (d, J=5.8 Hz, 2H), 8.45 (d, J=4.0 Hz, 1H), 8.36 (d, J=8.3 Hz, 1H), 7.83 (s, 1H), 7.80 (dd, J=8.1, 1.5 Hz, 1H), 7.70 (s, 1H), 7.59 (dd, J=8.3, 1.3 Hz, 1H), 7.45-7.39 (m, 2H), 7.28 (d, J=5.8 Hz, 2H), 5.28 (s, 2H), 4.31-4.18 (m, 1H), 3.74-3.61 (m, 1H), 3.12-3.00 (m, 2H), 2.90-2.80 (m, 1H), 2.47-2.40 (m, 4H), 2.25 (s, 3H), 2.23-2.16 (m, 1H), 1.91-1.70 (m, 2H), 1.68-1.58 (m, 4H), 1.44-1.29 (m, 2H), 0.72-0.63 (m, 2H), 0.59-0.52 (m, 2H).

EXAMPLES 55-56

The following compounds were prepared as solids according to the method of Example 18 step (iii) using the product of Example 54 step (iii) and the appropriate amine.

EXAMPLE 55

6-(5-(Cyclopropylcarbamoyl)-2-methylphenyl)-N-methyl-N-(1-methylpiperidin-4-yl)-1-oxo-2-(pyridin-4-ylmethyl)-1,2-dihydroisoquinoline-4-carboxamide

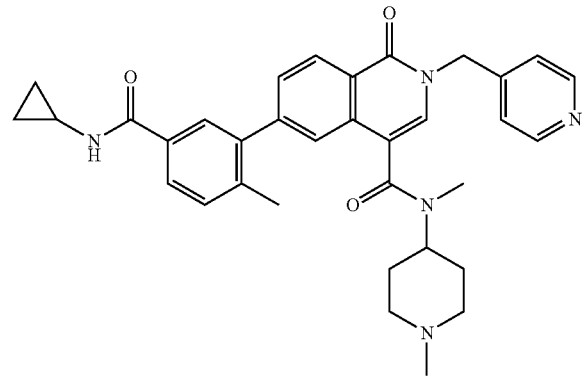

MS: APCI (+ve) 564 (M+H)$^+$
$^1$H NMR DMSO-d$_6$ 8.54 (dd, J=4.6, 1.3 Hz, 2H), 8.45 (d, J=4.2 Hz, 1H), 8.37 (d, J=8.3 Hz, 1H), 7.83-7.77 (m, 2H), 7.69 (s, 1H), 7.60 (dd, J=8.3, 1.3 Hz, 1H), 7.42 (d, J=8.1 Hz, 1H), 7.38 (s, 1H), 7.27 (d, J=6.0 Hz, 2H), 5.26 (s, 2H), 4.31 (s, 1H), 2.86 (s, 3H), 2.85-2.78 (m, 1H), 2.78-2.61 (m, 2H), 2.24 (s, 3H), 2.16-2.02 (m, 2H), 2.07-2.02 (m, 3H), 1.87-1.71 (m, 2H), 1.61-1.47 (m, 2H), 0.71-0.65 (m, 2H), 0.58-0.51 (m, 2H)

EXAMPLE 56

N-Cyclopropyl-3-(4-(4-(dimethylamino)piperidine-1-carbonyl)-1-oxo-2-(pyridin-4-ylmethyl)-1,2-dihydroisoquinolin-6-yl)-4-methylbenzamide

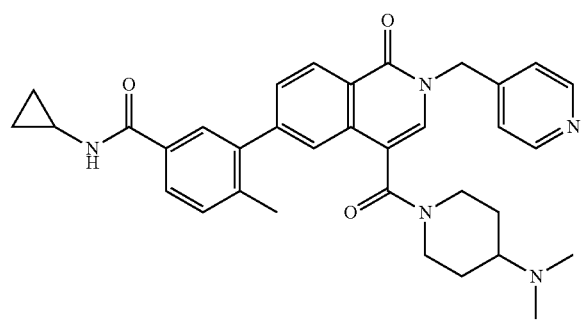

MS: APCI (+ve) 564 (M+H)$^+$
$^1$H NMR DMSO-d$_6$ 8.54 (dd, J=4.6, 1.3 Hz, 2H), 8.44 (d, J=4.0 Hz, 1H), 8.36 (d, J=8.3 Hz, 1H), 7.82 (s, 1H), 7.79 (d, J=7.9 Hz, 1H), 7.70 (d, J=1.2 Hz, 1H), 7.60 (dd, J=8.3, 1.3 Hz, 1H), 7.44-7.39 (m, 2H), 7.28 (d, J=6.0 Hz, 2H), 5.27 (s, 2H), 4.52-4.38 (m, 1H), 3.82-3.66 (m, 1H), 2.91-2.78 (m, 3H), 2.37-2.27 (m, 1H), 2.25 (s, 3H), 2.10 (s, 6H), 1.80-1.65 (m, 2H), 1.35-1.20 (m, 2H), 0.71-0.65 (m, 2H), 0.57-0.52 (m, 2H)

EXAMPLE 57

6-(5-Cyclopropylcarbamoyl-2-methyl-phenyl)-1-oxo-2-pyridin-4-ylmethyl-1,2-dihydro-isoquinoline-4-carboxylic acid piperidin-4-ylamide

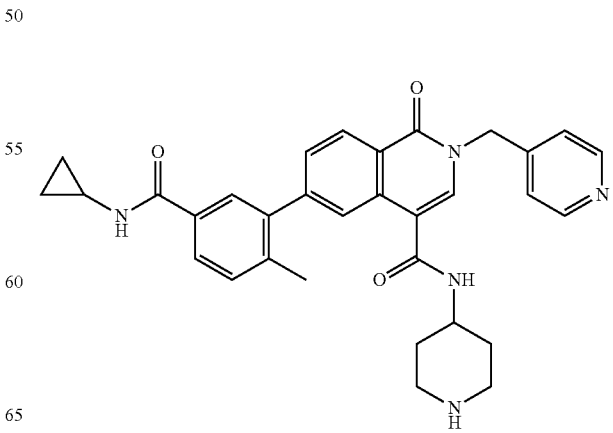

i) 4-{[6-(5-Cyclopropylcarbamoyl-2-methyl-phenyl)-1-oxo-2-pyridin-4-ylmethyl-1,2-dihydro-isoquinoline-4-carbonyl]-amino}-piperidine-1-carboxylic acid tert-butyl ester

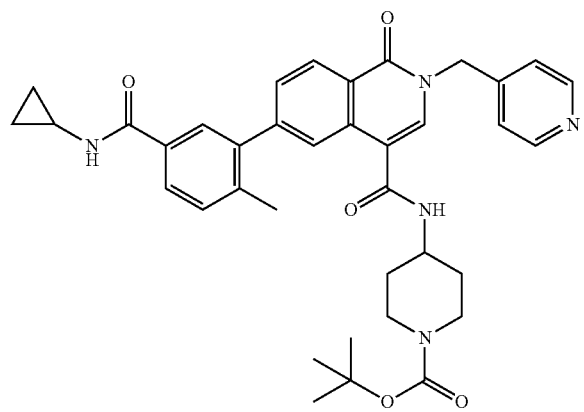

To a mixture of the product of Example 54 step iii) (0.1 g), 4-amino-N-boc-piperadine (0.05 g) and N,N-diisopropylethylamine (0.25 mL) in tetrahydrofuran (10 mL) was added HATU (0.16 g) and the mixture stirred at room temperature for 3 hours. The reaction mixture was then concentrated to dryness and the crude product purified HPLC to give the sub-title compound (0.09 g).
MS: APCI (−ve) 634 (M−H)⁻ ii) 6-(5-Cyclopropylcarbamoyl-2-methyl-phenyl)-1-oxo-2-pyridin-4-ylmethyl-1,2-dihydro-isoquinoline-4-carboxylic acid piperidin-4-ylamide

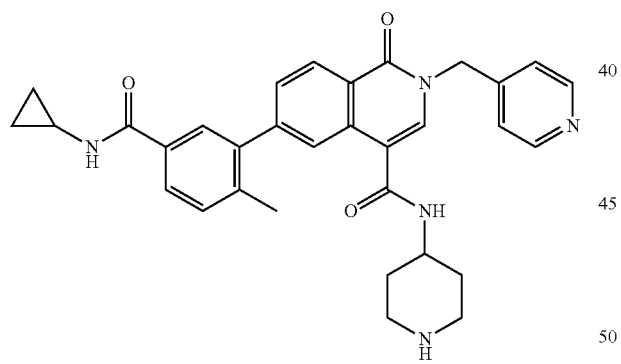

To a solution of the product of step i) (0.1 g) in dichloromethane (9 mL) was added trifluoroacetic acid (1 mL) and the mixture stirred at room temperature for 1 hour. The reaction was basified by the addition of 0.88 ammonia and washed with water. The organics were dried over magnesium sulphate, filtered and concentrated to dryness to yield the title compound as a solid (0.08 g).
MS: APCI (−ve) 536 (M−H)⁻
¹H NMR DMSO-d₆ 8.60 (dd, J=3.9, 1.8 Hz, 2H), 8.50 (s, 1H), 8.40-8.34 (m, 1H), 8.38 (dd, J=8.0, 2.0 Hz, 1H), 8.16 (s, 1H), 8.05 (s, 1H), 7.85 (d, J=7.7 Hz, 1H), 7.79 (s, 1H), 7.64 (d, J=7.9 Hz, 1H), 7.49 (d, J=7.9 Hz, 1H), 7.34 (t, J=2.0 Hz, 2H), 5.33 (s, 2H), 3.92-3.78 (m, 1H), 3.05-2.97 (m, 2H), 2.94-2.87 (m, 1H), 2.61-2.51 (m, 2H), 2.33 (s, 3H), 1.89-1.78 (m, 2H), 1.50-1.33 (m, 2H), 1.32-1.26 (m, 1H), 0.78-0.70 (m, 2H), 0.65-0.58 (m, 2H)

EXAMPLE 58

3-(4-(4-Aminopiperidine-1-carbonyl)-1-oxo-2-(pyridin-4-ylmethyl)-1,2-dihydroisoquinolin-6-yl)-N-cyclopropyl-4-methylbenzamide

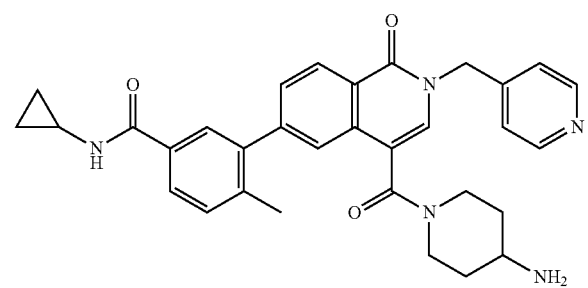

i) [1-[6-(5-Cyclopropylcarbamoyl-2-methyl-phenyl)-1-oxo-2-pyridin-4-ylmethyl-1,2-dihydro-isoquinoline-4-carbonyl]-piperidin-4-yl]-carbamic acid, tert-butyl ester

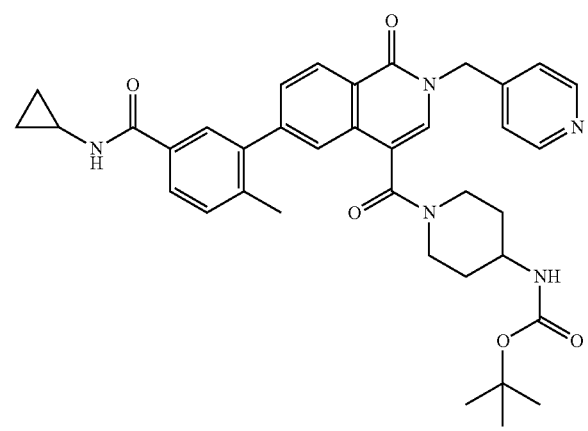

The sub-title compound was prepared using the method of Example 57 step i) and piperidin-4-yl-carbamic acid, tert-butyl ester.
MS: APCI (−ve) 634 (M−H)⁻ ii) 3-(4-(4-Aminopiperidine-1-carbonyl)-1-oxo-2-(pyridin-4-ylmethyl)-1,2-dihydroisoquinolin-6-yl)-N-cyclopropyl-4-methylbenzamide

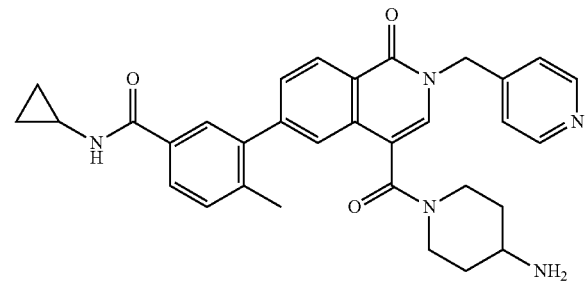

The title compound was prepared as a solid by using the method of Example 57 step ii).

MS: APCI (−ve) 536 (M−H)⁻

$^1$H NMR DMSO-$d_6$ 8.54 (d, J=4.6 Hz, 2H), 8.46 (d, J=3.8 Hz, 1H), 8.36 (d, J=8.3 Hz, 1H), 7.83-7.78 (m, 2H), 7.71 (s, 1H), 7.61 (d, J=8.3 Hz, 1H), 7.45-7.41 (m, 2H), 7.28 (d, J=4.8 Hz, 2H), 5.28 (s, 2H), 4.36-4.25 (m, 1H), 3.75-3.65 (m, 1H), 3.09-2.95 (m, 2H), 2.91-2.79 (m, 2H), 2.27 (s, 3H), 1.80-1.63 (m, 2H), 1.26-1.12 (m, 2H), 0.95 (dd, J=6.5, 1.2 Hz, 2H), 0.72-0.65 (m, 2H), 0.58-0.53 (m, 2H).

EXAMPLE 59

N-Cyclopropyl-3-[2-cyclopropylmethyl-4-(4-methyl-[1,4]diazepan-1-ylmethyl)-1-oxo-1,2-dihydro-isoquinolin-6-yl]-4-methyl-benzamide

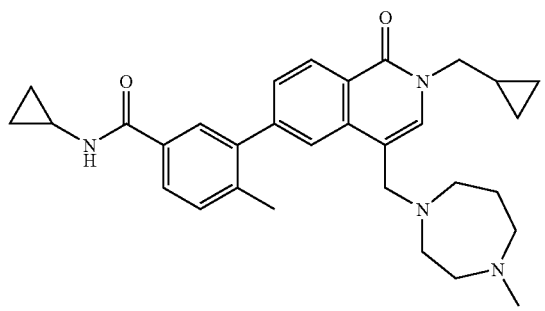

i) 6-Bromo-2-cyclopropylmethyl-2H-isoquinolin-1-one

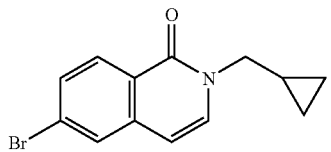

Cesium carbonate (2.62 g), intermediate 1 (1.5 g) and (bromomethyl)cyclopropane (0.8 mL) were stirred and heated at 50° C. for 4 hours. The mixture was allowed to cool then poured into water and extracted with ethyl acetate. The organic extracts were combined dried and evaporated under reduced pressure. The residue was triturated with ether and the sub-titled compound isolated by filtration (1.0 g).

MS: APCI (+ve) 277, 279 (M+H)⁺ ii) 6-Bromo-2-cyclopropylmethyl-1-oxo-1,2-dihydro-isoquinoline-4-carbaldehyde

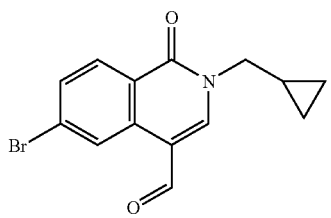

DMF (10 mL) was cooled in an ice bath and phosphorus oxychloride (0.40 mL) was added over 20 seconds. The solution was stirred for 10 minutes at room temperature and then the product of step i) (0.6 g) in DMF (2 mL) was added over 5 minutes. The mixture was heated at 80° C. overnight. The mixture was allowed to cool then poured onto ice/water and stirred for 20 minutes. The aqueous was extracted with ethyl acetate, the organics were combined and evaporated under reduced pressure. The residue was purified (SiO₂, eluting with 1:4 ethyl acetate:isohexane) to give the sub-title compound (0.4 g).

$^1$H NMR DMSO-$d_6$ 9.78 (s, 1H), 9.24 (s, 1H), 8.28 (d, J=8.7 Hz, 1H), 7.83 (s, 1H), 7.69 (dd, J=8.6, 1.9 Hz, 1H), 3.97 (d, J=7.2 Hz, 2H), 1.36-1.27 (m, 1H), 0.73-0.67 (m, 2H), 0.51-0.44 (m, 2H).

iii) N-Cyclopropyl-3-(2-cyclopropylmethyl-4-formyl-1-oxo-1,2-dihydro-isoquinolin-6-yl)-4-methyl-benzamide

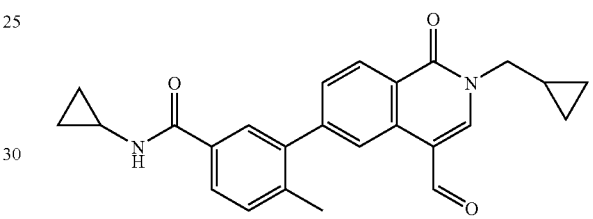

A mixture of N-cyclopropyl-4-methyl-3-(4,4,5,5-tetramethyl-1,3,2-dioxaborolan-2-yl)benzamide (0.47 g) [prepared as described in US2005020590], the product of step ii) (0.4 g), tetrakis(triphenylphosphine)palladium(0) (0.15 g) and potassium carbonate (0.54 g) in DMF (10 mL) were heated at 80° C. for 5 hours. The reaction mixture was diluted with ethyl acetate and washed with water and brine. The organics were dried over magnesium sulphate and evaporated. The residue was purified (SiO₂, eluting with 1:1 ethyl acetate: isohexane) to give the sub-title compound (0.2 g).

MS: APCI (+ve) 401 (M+H)⁺ iv) N-Cyclopropyl-3-[2-cyclopropylmethyl-4-(4-methyl-[1,4]diazepan-1-ylmethyl)-1-oxo-1,2-dihydro-isoquinolin-6-yl]-4-methyl-benzamide

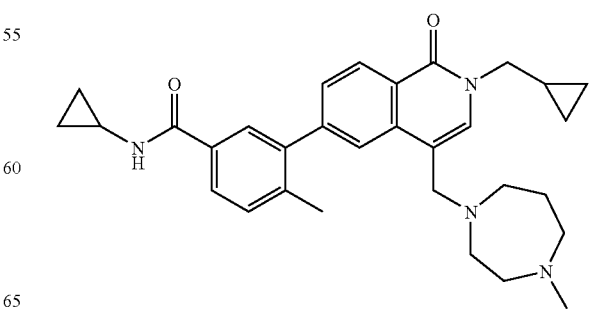

The product of step iii) (0.1 g) was dissolved in dichloromethane (10 mL) and 1-methyl-1,4-diazepane (0.062 mL) added. The mixture was stirred at room temperature for 5 minutes then sodium triacetoxyborohydride (0.16 g) was added. The mixture was allowed to stand and the solvent allowed to evaporate. Methanol (5 mL) was added and the solution purified directly by HPLC to give the title compound as a solid (30 mg).

MS: APCI (+ve) 499 (M+H)⁺

¹H NMR DMSO-d₆ 8.43 (d, J=4.1 Hz, 1H), 8.32 (d, J=8.2 Hz, 1H), 7.97 (s, 1H), 7.80-7.74 (m, 2H), 7.51 (dd, J=8.3, 1.7 Hz, 1H), 7.47 (s, 1H), 7.43 (d, J=7.7 Hz, 1H), 3.85 (d, J=7.2 Hz, 2H), 3.63 (s, 2H), 2.88-2.81 (m, 1H), 2.68-2.61 (m, 4H), 2.50-2.48 (m, 2H), 2.46-2.42 (m, 2H), 2.33 (s, 3H), 2.19 (s, 3H), 1.71-1.65 (m, 2H), 1.28-1.24 (m, 1H), 0.70-0.65 (m, 2H), 0.58-0.53 (m, 2H), 0.51-0.46 (m, 2H), 0.44-0.40 (m, 2H).

EXAMPLE 60

2-Benzyl-6-(5-(cyclopropylcarbamoyl)-3-fluoro-2-methylphenyl)-N-(2-(dimethylamino)ethyl)-1-oxo-1,2-dihydroisoquinoline-4-carboxamide

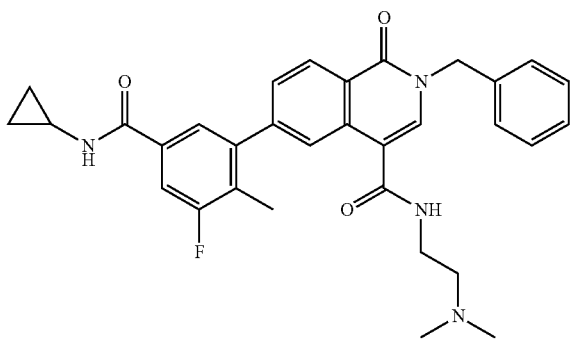

i) 2-Benzyl-6-bromo-1-oxo-1,2-dihydroisoquinoline-4-carboxylic acid

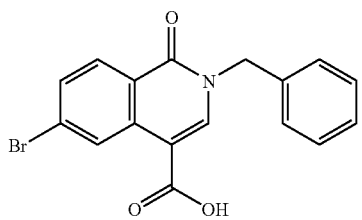

To a solution of the product of Example 47 step i) (0.65 g) in methanol (10 mL) was added a 5M aqueous solution of sodium hydroxide (3.53 mL) and the mixture stirred at 70° C. for 2 hours. The reaction was concentrated to approximately half volume and acidified with acetic acid. The sub-title compound was collected by filtration (0.36 g).

¹H NMR DMSO-d₆ 13.05 (s, 1H), 9.06 (d, J=1.9 Hz, 1H), 8.59 (s, 1H), 8.20 (d, J=8.7 Hz, 1H), 7.75 (dd, J=8.7, 1.9 Hz, 7H), 7.39-7.23 (m, 5H), 5.30 (s, 2H).

ii) 2-Benzyl-6-bromo-N-(2-(dimethylamino)ethyl)-1-oxo-1,2-dihydroisoquinoline-4-carboxamide

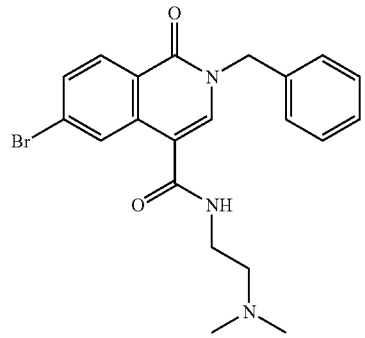

To a suspension of the product of step ii) (359 mg) in dichloromethane (10 mL) containing 1 drop of DMF, was added oxalyl chloride (0.3 mL) and the mixture stirred at room temperature for 16 hours. The reaction was cooled in an ice bath and treated with N,N-diisopropylethylamine (1 mL) followed by N,N-dimethylethylenediamine (0.5 mL). After stirring at room temperature for 15 minutes, the reaction mixture was purified (SiO₂, elution gradient 7 to 10% methanol in dichloromethane) to give the sub-title compound (300 mg).

MS: APCI (+ve) 428/430 (M+H)⁺ iii) 2-Benzyl-6-(5-(cyclopropylcarbamoyl)-3-fluoro-2-methylphenyl)-N-(2-(dimethylamino)ethyl)-1-oxo-1,2-dihydroisoquinoline-4-carboxamide

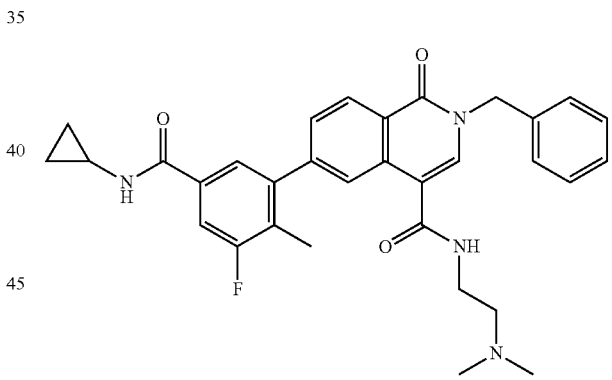

To a degassed mixture of N-cyclopropyl-3-fluoro-4-methyl-5-(4,4,5,5-tetramethyl-1,3,2-dioxaborolan-2-yl)benzamide (0.1 g) [prepared as described in WO 06110173], the product of step ii) (0.09 g) and potassium carbonate (0.06 g) in DMF (5 mL) under nitrogen, was added tetrakis(triphenylphosphine)palladium(0) (0.02 g) and the mixture stirred at 80° C. for 16 hours. The reaction mixture was concentrated to dryness and the crude product was purified (SiO₂, elution with 90:10:0.1 dichloromethane: methanol: triethylamine) and by HPLC. The fractions containing product were concentrated to dryness and the residue crystallised from acetonitrile to afford the title compound as a solid (0.04 g).

MS: APCI (+ve) 541 (M+H)⁺

¹H NMR DMSO-d₆ 8.53 (d, J=4.0 Hz, 1H), 8.40-8.30 (m, 2H), 8.17 (s, 1H), 7.99 (s, 1H), 7.67 (d, J=10.6 Hz, 1H), 7.63 (s, 1H), 7.58 (d, J=8.3 Hz, 1H), 7.41-7.26 (m, 5H), 5.24 (s, 2H), 3.40-3.26 (m, 2H), 2.89-2.82 (m, 1H), 2.43 (t, J=6.2 Hz, 2H), 2.16 (s, 3H), 2.14 (s, 6H), 0.73-0.65 (m, 2H), 0.60-0.52 (m, 2H).

EXAMPLE 61

3-(2-Benzyl-1-oxo-4-(pyrrolidin-1-ylmethyl)-1,2-dihydroisoquinolin-6-yl)-N-cyclopropyl-4-methylbenzamide

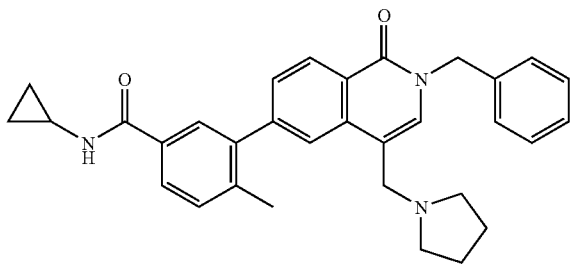

i) 3-(2-Benzyl-4-formyl-1-oxo-1,2-dihydroisoquinolin-6-yl)-N-cyclopropyl-4-methylbenzamide

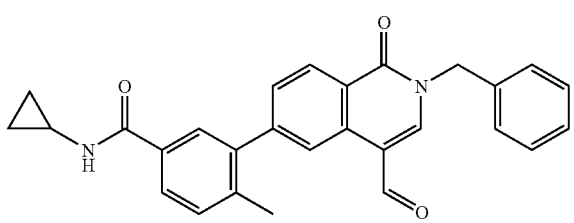

DMF (5 mL) was cooled in an ice bath and phosphorus oxychloride (0.11 mL) added. The solution was stirred for 10 minutes. 3-(2-Benzyl-1-oxo-1,2-dihydroisoquinolin-6-yl)-N-cyclopropyl-4-methylbenzamide, Example 1 (0.4 g) was then added in one portion and the mixture heated at 80° C. for 6 hours. The mixture was allowed to cool then poured onto ice and stirred for 10 minutes. This was then extracted with ethyl acetate. The organics were combined and evaporated under reduced pressure. The residue was purified (SiO$_2$, 1:1 isohexane/ethyl acetate) to give the sub titled compound (0.15 g).
MS: APCI (+ve) 437 (M+H)$^+$ ii) 3-(2-Benzyl-1-oxo-4-(pyrrolidin-1-ylmethyl)-1,2-dihydroisoquinolin-6-yl)-N-cyclopropyl-4-methylbenzamide

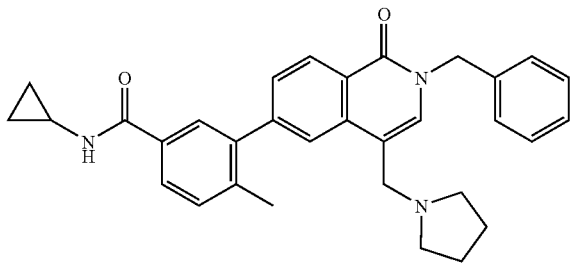

3-(2-Benzyl-4-formyl-1-oxo-1,2-dihydroisoquinolin-6-yl)-N-cyclopropyl-4-methylbenzamide (0.13 g) was dissolved in dichloromethane (10 mL). Pyrrolidine (0.064 g) was then added and the mixture stirred for 10 minutes before adding sodium triacetoxyborohydride (0.25 g). The mixture was stirred at room temperature overnight. The volatiles were removed under reduced pressure and the residue purified (SiO$_2$, eluting with 5% methanol in dichloromethane) to give the title compound as a solid (0.038 g).
MS: APCI (+ve) 492 (M+H)$^+$
$^1$H NMR DMSO-d$_6$ 8.44 (d, J=4.1 Hz, 1H), 8.34 (d, J=8.5 Hz, 1H), 7.94 (d, J=1.3 Hz, 1H), 7.80 (d, J=1.8 Hz, 1H), 7.77 (s, 1H), 7.58 (s, 1H), 7.55 (dd, J=8.2, 1.5 Hz, 1H), 7.43 (d, J=7.7 Hz, 1H), 7.37-7.25 (m, 5H), 5.22 (s, 2H), 3.68 (s, 2H), 2.91-2.80 (m, 1H), 2.52-2.42 (m, 4H), 2.30 (s, 3H), 1.72-1.62 (m, 4H), 0.71-0.66 (m, 2H), 0.59-0.50 (m, 2H)

EXAMPLE 62

3-(4-(1,4'-Bipiperidin-1'-ylmethyl)-2-(cyclopropylmethyl)-1-oxo-1,2-dihydroisoquinolin-6-yl)-N-cyclopropyl-4-methylbenzamide

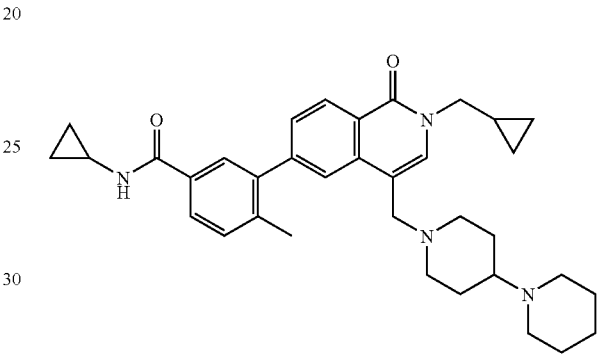

The title compound was prepared as a solid by the method of Example 59 step iv) using product of Example 59 step iii) and 1,4'-bipiperidine.
MS: APCI (+ve) 553 (M+H)$^+$
$^1$H NMR CDCl$_3$ 8.50 (d, J=8.2 Hz, 1H), 7.85 (s, 1H), 7.70 (d, J=7.7 Hz, 1H), 7.65 (s, 1H), 7.42 (d, J=8.2 Hz, 1H), 7.36 (d, J=7.9 Hz, 1H), 7.12 (s, 1H), 6.32 (s, 1H), 3.90 (d, J=6.9 Hz, 2H), 3.52-3.46 (m, 3H), 3.03-2.90 (m, 3H), 2.52-2.44 (m, 3H), 2.34 (s, 3H), 2.28-2.19 (m, 1H), 2.00-1.92 (m, 2H), 1.82-1.72 (m, 3H), 1.61-1.39 (m, 6H), 1.32-1.17 (m, 3H), 0.89-0.85 (m, 2H), 0.65-0.58 (m, 3H), 0.45-0.41 (m, 2H)

EXAMPLE 63

(S)—N-Cyclopropyl-3-(2-(cyclopropylmethyl)-4-((3-methylpiperazin-1-yl)methyl)-1-oxo-1,2-dihydroisoquinolin-6-yl)-4-methylbenzamide

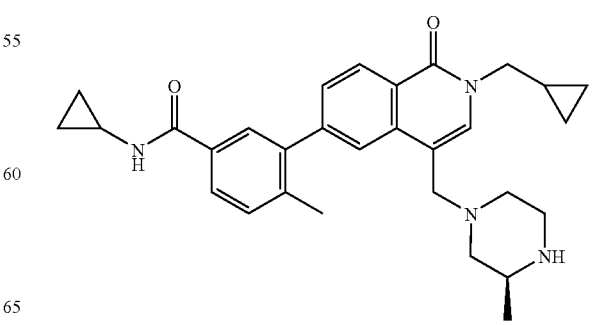

The product of Example 59 step iii) (0.25 g), (S)-2-methylpiperazine-1-carboxylic acid, tert-butyl ester (0.37 g) and sodium triacetoxyborohydride (0.40 g) were stirred in dichloromethane (20 mL) under nitrogen for 16 hours. Water (20 mL) and dichloromethane (20 mL) were then added and the organics separated. The organics were evaporated under reduced pressure. The residue was dissolved in methanol (5 mL) and 4M HCl in 1,4-dioxane (2 mL) added. The mixture was stirred overnight at room temperature. The volatiles were removed under vacuum and the residue purified by HPLC to give the title compound as a solid (0.11 g).

MS: APCI (+ve) 485 (M+H)$^+$ $^1$H NMR DMSO-d$_6$ 8.43 (d, J=4.1 Hz, 1H), 8.33 (d, J=8.2 Hz, 1H), 7.95 (d, J=1.5 Hz, 1H), 7.79-7.76 (m, 2H), 7.52 (dd, J=8.2, 1.5 Hz, 1H), 7.47 (s, 1H), 7.43 (d, J=11.3 Hz, 1H), 3.85 (d, J=6.7 Hz, 2H), 3.49 (d, J=16.6 Hz, 1H), 3.45 (d, J=18.1 Hz, 1H), 2.88-2.81 (m, 1H), 2.80-2.66 (m, 3H), 2.61-2.54 (m, 2H), 2.34 (s, 3H), 1.92-1.83 (m, 2H), 1.60-1.51 (m, 1H), 1.31-1.21 (m, 1H), 0.88 (d, J=6.4 Hz, 3H), 0.71-0.65 (m, 2H), 0.58-0.53 (m, 2H), 0.51-0.46 (m, 2H), 0.43-0.39 (m, 2H)

EXAMPLE 64

N-Cyclopropyl-3-(2-(cyclopropylmethyl)-4-((methyl (2-(methylamino)ethyl)amino)methyl)-1-oxo-1,2-dihydroisoquinolin-6-yl)-4-methylbenzamide

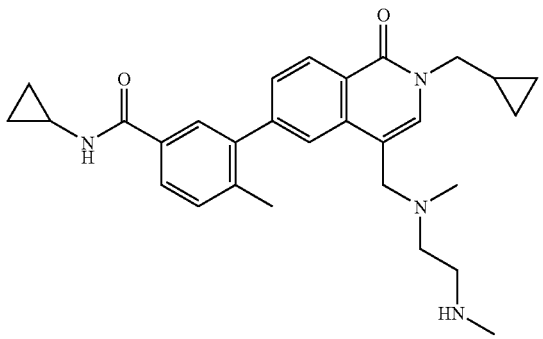

The title compound was prepared as a solid by the method of Example 59 step iv) using product of Example 59 step iii) and N$^1$,N$^2$-dimethylethane-1,2-diamine.

MS: APCI (+ve) 473 (M+H)$^+$ $^1$H NMR DMSO-d$_6$ 8.43 (d, J=4.1 Hz, 1H), 8.32 (d, J=8.5 Hz, 1H), 7.91 (d, J=1.5 Hz, 1H), 7.78 (dd, J=7.9, 1.8 Hz, 1H), 7.75 (d, J=1.8 Hz, 1H), 7.52-7.48 (m, 2H), 7.42 (d, J=7.9 Hz, 1H), 3.86 (d, J=6.9 Hz, 2H), 3.53 (s, 2H), 2.88-2.81 (m, 1H), 2.48-2.43 (m, 4H), 2.29 (s, 3H), 2.14 (s, 3H), 2.07 (s, 3H), 1.31-1.23 (m, 1H), 0.71-0.65 (m, 2H), 0.58-0.53 (m, 2H), 0.51-0.45 (m, 2H), 0.44-0.39 (m, 2H)

EXAMPLE 65

N-Cyclopropyl-3-(2-(cyclopropylmethyl)-4-((1-methylpiperidin-4-ylamino)methyl)-1-oxo-1,2-dihydroisoquinolin-6-yl)-4-methylbenzamide

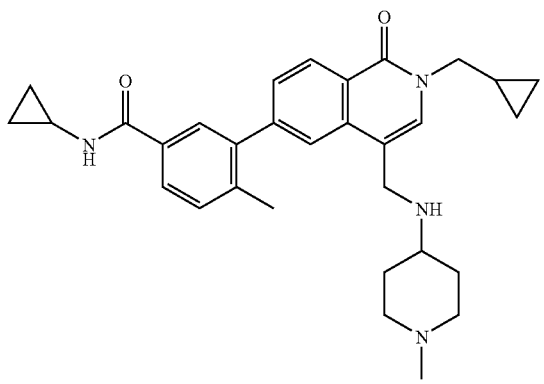

The title compound was prepared as a solid by the method of Example 59 step iv) using product of Example 59 step iii) and 1-methylpiperidin-4-amine.

MS: APCI (+ve) 499 (M+H)$^+$ $^1$H NMR DMSO-d$_6$ 8.42 (d, J=4.1 Hz, 1H), 8.32 (d, J=8.2 Hz, 1H), 7.90 (d, J=1.5 Hz, 1H), 7.80-7.75 (m, 2H), 7.53-7.48 (m, 2H), 7.43 (d, J=7.7 Hz, 1H), 3.84 (d, J=6.9 Hz, 2H), 3.90-3.80 (m, 2H), 2.89-2.82 (m, 1H), 2.68-2.61 (m, 2H), 2.44-2.37 (m, 1H), 2.31 (s, 3H), 2.09 (s, 3H), 1.88-1.76 (m, 5H), 1.32-1.22 (m, 3H), 0.71-0.66 (m, 2H), 0.58-0.53 (m, 2H), 0.51-0.46 (m, 2H), 0.44-0.40 (m, 2H)

EXAMPLE 66

3-(4-((4-Aminopiperidin-1-yl)methyl)-2-(cyclopropylmethyl)-1-oxo-1,2-dihydroisoquinolin-6-yl)-N-cyclopropyl-4-methylbenzamide

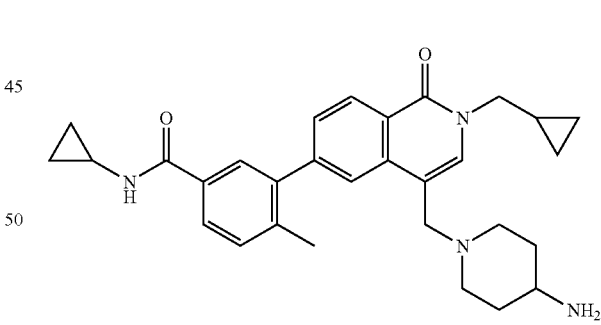

The title compound was prepared as a solid by the method of Example 63 using product of Example 59 step iii) and piperidin-4-yl-carbamic acid, tert-butyl ester.

MS: APCI (+ve) 485 (M+H)$^+$ $^1$H NMR DMSO-d$_6$ 8.44 (d, J=4.4 Hz, 1H), 8.33 (d, J=8.2 Hz, 1H), 7.96 (d, J=1.5 Hz, 1H), 7.80-7.77 (m, 1H), 7.77 (s, 1H), 7.53 (dd, J=8.2, 1.5 Hz, 1H), 7.45 (s, 1H), 7.44-7.42 (m, 1H), 3.85 (d, J=7.2 Hz, 2H), 3.48 (s, 2H), 2.89-2.82 (m, 1H), 2.82-2.76 (m, 2H), 2.56-2.51 (m, 1H), 2.35 (s, 3H), 2.01-1.91 (m, 2H), 1.68-1.61 (m, 2H), 1.30-1.22 (m, 1H), 1.21-1.08 (m, 2H), 0.71-0.65 (m, 2H), 0.59-0.54 (m, 2H), 0.51-0.45 (m, 2H), 0.44-0.38 (m, 2H)

EXAMPLE 67

N-Cyclopropyl-3-(2-(cyclopropylmethyl)-4-((2-(dimethylamino)ethylamino)methyl)-1-oxo-1,2-dihydroisoquinolin-6-yl)-4-methylbenzamide

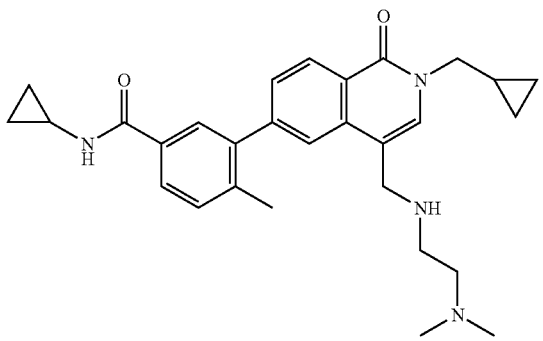

The title compound was prepared as a solid by the method of Example 59 step iv) using product of Example 59 step iii) and $N^1,N^1$-dimethylethane-1,2-diamine.
MS: APCI (+ve) 473 (M+H)$^+$
$^1$H NMR DMSO-d$_6$ 8.43 (d, J=4.1 Hz, 1H), 8.33 (d, J=13.3 Hz, 1H), 7.87 (d, J=4.9 Hz, 1H), 7.78 (dd, J=7.9, 1.8 Hz, 1H), 7.75 (d, J=1.8 Hz, 1H), 7.52-7.50 (m, 1H), 7.50 (s, 1H), 7.42 (d, J=8.2 Hz, 1H), 3.85 (d, J=6.9 Hz, 2H), 3.80 (s, 2H), 2.89-2.82 (m, 1H), 2.62 (t, J=6.4 Hz, 2H), 2.32-2.27 (m, 2H), 2.29 (s, 3H), 2.05 (s, 6H), 1.29-1.22 (m, 1H), 0.71-0.65 (m, 2H), 0.58-0.53 (m, 2H), 0.51-0.46 (m, 2H), 0.44-0.39 (m, 2H)

EXAMPLE 68

N-Cyclopropyl-3-(2-(cyclopropylmethyl)-4-(((2-(dimethylamino)ethyl)(methyl)amino)methyl)-1-oxo-1,2-dihydroisoquinolin-6-yl)-4-methylbenzamide

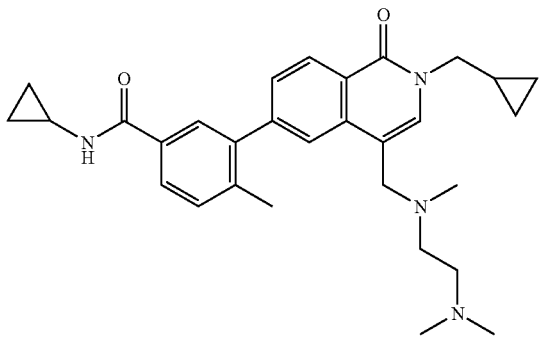

The product of Example 67 (0.050 g) and formaldehyde (0.079 mL) were stirred in dichloromethane (10 mL). Sodium triacetoxyborohydride (0.067 g) was then added and the mixture stirred at room temperature for 12 hours. The volatiles were removed under reduced pressure and the residue purified by HPLC to give the title compound as a solid (0.035 g).
MS: APCI (+ve) 487 (M+H)$^+$
$^1$H NMR DMSO-d$_6$ 8.43 (d, J=4.2 Hz, 1H), 8.31 (d, J=8.3 Hz, 1H), 8.07 (s, 1H), 7.80-7.74 (m, 2H), 7.52-7.46 (m, 2H), 7.42 (d, J=7.9 Hz, 1H), 3.86 (d, J=7.1 Hz, 2H), 3.52 (s, 2H), 2.90-2.80 (m, 1H), 2.48-2.42 (m, 2H), 2.33 (t, J=3.3 Hz, 2H), 2.28 (s, 3H), 2.12 (s, 3H), 1.97 (s, 6H), 1.30-1.21 (m, 1H), 0.72-0.64 (m, 2H), 0.58-0.52 (m, 2H), 0.51-0.45 (m, 2H), 0.44-0.39 (m, 2H)

EXAMPLE 69

N-Cyclopropyl-3-(2-(cyclopropylmethyl)-4-((4-(dimethylamino)piperidin-1-yl)methyl)-1-oxo-1,2-dihydroisoquinolin-6-yl)-4-methylbenzamide

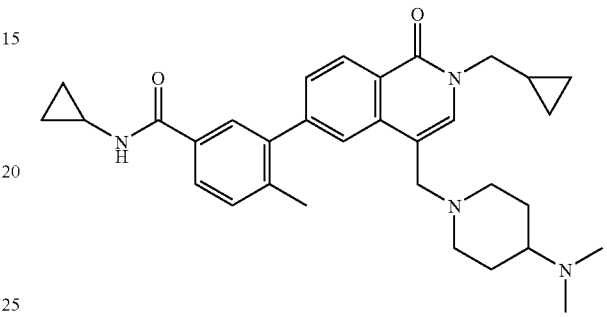

The product of Example 66 (50 mg) and formaldehyde (0.15 mL) were stirred in dichloromethane (10 mL). Sodium triacetoxyborohydride (109 mg) was then added and the mixture stirred at room temperature overnight. The volatiles were removed under vacuum and the residue purified by HPLC to give the title compound as a solid (39 mg).
MS: APCI (+ve) 513 (M+H)$^+$
1H NMR DMSO-d$_6$ 8.43 (d, J=4.1 Hz, 1H), 8.33 (d, J=8.5 Hz, 1H), 7.94 (d, J=1.5 Hz, 1H), 7.80-7.75 (m, 2H), 7.52 (dd, J=8.2, 1.5 Hz, 1H), 7.45 (s, 1H), 7.44 (d, J=7.7 Hz, 1H), 3.85 (d, J=7.2 Hz, 2H), 3.49 (s, 2H), 2.93-2.81 (m, 3H), 2.35 (s, 3H), 2.35 (s, 6H), 2.06-1.98 (m, 1H), 1.96-1.86 (m, 2H), 1.72-1.65 (m, 2H), 1.34-1.22 (m, 3H), 0.71-0.64 (m, 2H), 0.59-0.54 (m, 2H), 0.51-0.45 (m, 2H), 0.44-0.39 (m, 2H)

EXAMPLE 70

N-Cyclopropyl-3-(2-cyclopropylmethyl-4-[1,4]diazepan-1-ylmethyl-1-oxo-1,2-dihydro-isoquinolin-6-yl)-4-methyl-benzamide

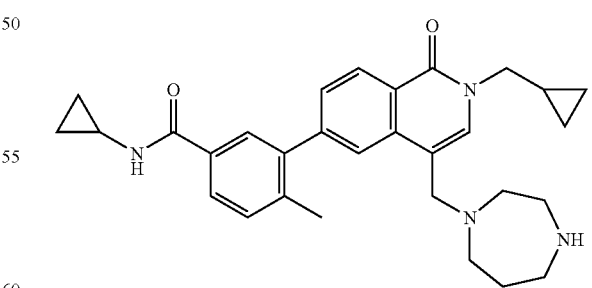

The title compound was prepared as a solid by the method of Example 59 step iv) using product of Example 59 step iii) and 1,4-diazepane.
MS: APCI (+ve) 485 (M+H)$^+$
$^1$H NMR DMSO-d$_6$ 8.44 (d, J=4.1 Hz, 1H), 8.32 (d, J=8.2 Hz, 1H), 7.98 (d, J=1.3 Hz, 1H), 7.80-7.75 (m, 2H), 7.52 (dd, J=8.2, 1.5 Hz, 1H), 7.48 (s, 1H), 7.43 (d, J=7.9 Hz, 1H), 3.85 (d, J=7.2 Hz, 2H), 3.65 (s, 2H), 2.88-2.82 (m, 1H), 2.78 (t, J=6.2 Hz, 2H), 2.72-2.65 (m, 4H), 2.62-2.58 (m, 2H), 2.33 (s, 3H), 1.66-1.59 (m, 2H), 1.30-1.22 (m, 1H), 0.71-0.65 (m, 2H), 0.58-0.53 (m, 2H), 0.50-0.45 (m, 2H), 0.43-0.39 (m, 2H)

EXAMPLE 71

N-Cyclopropyl-3-(2-(cyclopropylmethyl)-4-((3-(dimethylamino)propylamino)methyl)-1-oxo-1,2-dihydroisoquinolin-6-yl)-4-methylbenzamide

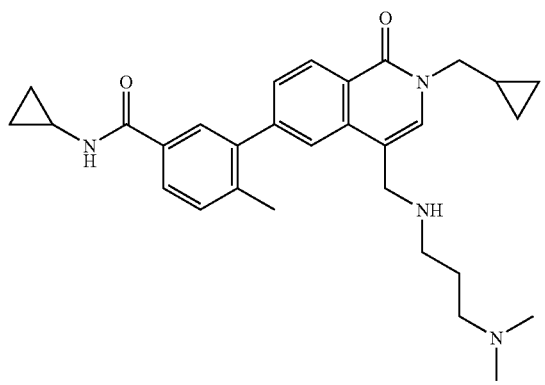

The title compound was prepared as a solid by the method of Example 59 step iv) using product of Example 59 step iii) and $N^1,N^1$-dimethylpropane-1,3-diamine.

MS: APCI (+ve) 487 (M+H)$^+$ $^1$H NMR DMSO-$d_6$ 8.42 (d, J=4.1 Hz, 1H), 8.33 (d, J=8.2 Hz, 1H), 7.87 (d, J=1.3 Hz, 1H), 7.78 (dd, J=7.8, 1.9 Hz, 1H), 7.76 (d, J=1.8 Hz, 1H), 7.50 (dd, J=8.3, 1.7 Hz, 1H), 7.48 (s, 1H), 7.42 (d, J=7.9 Hz, 1H), 3.85 (d, J=7.2 Hz, 2H), 3.77 (s, 2H), 2.88-2.82 (m, 1H), 2.57 (t, J=6.8 Hz, 2H), 2.30 (s, 3H), 2.17 (t, J=7.2 Hz, 2H), 1.52 (quintet, J=7.0 Hz, 2H), 1.30-1.21 (m, 1H), 0.71-0.65 (m, 2H), 0.58-0.54 (m, 2H), 0.52-0.46 (m, 2H), 0.44-0.40 (m, 2H), 2.02 (s, 6H)

EXAMPLE 72

N-Cyclopropyl-3-(2-(cyclopropylmethyl)-4-((4-(2-hydroxyethyl)-1,4-diazepan-1-yl)methyl)-1-oxo-1,2-dihydroisoquinolin-6-yl)-4-methylbenzamide

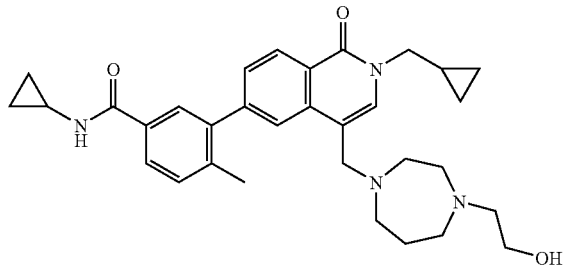

The title compound was prepared as a solid by the method of Example 59 step iv) using product of Example 59 step iii) and 2-(1,4-diazepan-1-yl)ethanol.

MS: APCI (+ve) 529 (M+H)$^+$ $^1$H NMR DMSO-$d_6$ d 8.43 (d, J=4.4 Hz, 1H), 8.32 (d, J=8.2 Hz, 1H), 7.96 (s, 1H), 7.80-7.74 (m, 2H), 7.51 (d, J=8.5 Hz, 1H), 7.47 (s, 1H), 7.43 (d, J=7.7 Hz, 1H), 4.24 (t, J=7.1 Hz, 1H), 3.85 (d, J=6.9 Hz, 2H), 3.62 (s, 2H), 3.43-3.38 (m, 2H), 2.88-2.82 (m, 1H), 2.68-2.56 (m, 8H), 2.50-2.44 (m, 2H), 2.32 (s, 3H), 1.71-1.61 (m, 2H), 1.30-1.21 (m, 1H), 0.71-0.65 (m, 2H), 0.58-0.54 (m, 2H), 0.51-0.47 (m, 2H), 0.44-0.39 (m, 2H)

EXAMPLE 73

N-Cyclopropyl-3-(2-(cyclopropylmethyl)-4-((4-isopropyl-1,4-diazepan-1-yl)methyl)-1-oxo-1,2-dihydroisoquinolin-6-yl)-4-methylbenzamide

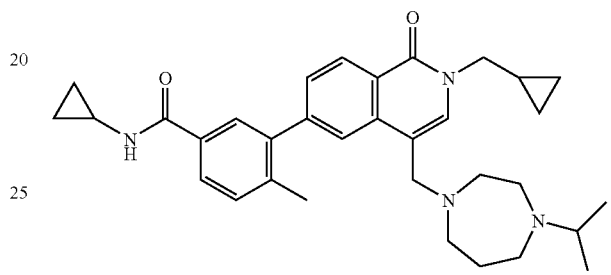

The product of Example 70 (50 mg) was dissolved in dichloromethane (10 mL) and acetone (0.15 mL) added. The mixture was stirred for 2 minutes then sodium triacetoxyborohydride (109 mg) added. The mixture was stirred at room temperature for 12 hours. The volatiles were removed under reduced pressure and the residue purified by HPLC to give the title compound as a solid (33 mg).

MS: APCI (+ve) 527 (M+H)$^+$ $^1$H NMR DMSO-$d_6$ 8.42 (d, J=4.4 Hz, 1H), 8.32 (d, J=8.2 Hz, 1H), 7.98 (d, J=1.5 Hz, 1H), 7.77 (dd, J=7.9, 1.8 Hz, 1H), 7.75 (s, 1H), 7.51 (dd, J=8.2, 1.5 Hz, 1H), 7.46 (s, 1H), 7.42 (d, J=7.7 Hz, 1H), 3.85 (d, J=6.9 Hz, 2H), 3.62 (s, 2H), 2.88-2.80 (m, 1H), 2.80-2.73 (m, 1H), 2.67-2.62 (m, 2H), 2.61-2.57 (m, 4H), 2.54-2.50 (m, 2H), 2.49 (s, 3H), 1.67-1.60 (m, 2H), 1.29-1.22 (m, 1H), 0.88 (d, J=6.4 Hz, 6H), 0.71-0.65 (m, 2H), 0.58-0.53 (m, 2H), 0.51-0.46 (m, 2H), 0.44-0.39 (m, 2H)

EXAMPLE 74

N-Cyclopropyl-3-(2-(cyclopropylmethyl)-4-((4-methylpiperazin-1-yl)methyl)-1-oxo-1,2-dihydroisoquinolin-6-yl)-4-methylbenzamide

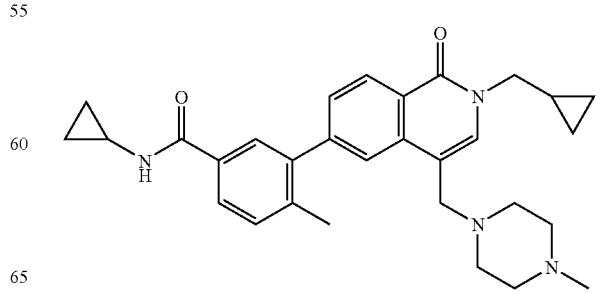

The title compound was prepared as a solid by the method of Example 59 step iv) using product of Example 59 step iii) and 1-methylpiperazine.

MS: APCI (+ve) 485 (M+H)$^+$ $^1$H NMR DMSO-d$_6$ 8.44 (d, J=4.1 Hz, 1H), 8.33 (d, J=8.2 Hz, 1H), 7.95 (d, J=5.1 Hz, 1H), 7.80-7.76 (m, 2H), 7.53 (dd, J=8.2, 1.8 Hz, 1H), 7.48 (s, 1H), 7.44 (d, J=7.7 Hz, 1H), 3.85 (d, J=7.2 Hz, 2H), 3.52 (s, 2H), 2.89-2.82 (m, 1H), 2.51-2.29 (m, 8H), 2.35 (s, 3H), 2.16 (s, 3H), 1.29-1.23 (m, 1H), 0.72-0.65 (m, 2H), 0.59-0.54 (m, 2H), 0.51-0.46 (m, 2H), 0.44-0.39 (m, 2H)

EXAMPLE 75

N-Cyclopropyl-3-(2-(cyclopropylmethyl)-4-((4-methyl-1,4-diazepan-1-yl)methyl)-1-oxo-1,2-dihydroisoquinolin-6-yl)-5-fluoro-4-methylbenzamide

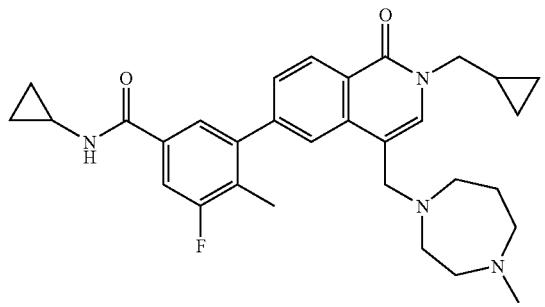

i) N-Cyclopropyl-3-(2-(cyclopropylmethyl)-4-formyl-1-oxo-1,2-dihydroisoquinolin-6-yl)-5-fluoro-4-methylbenzamide

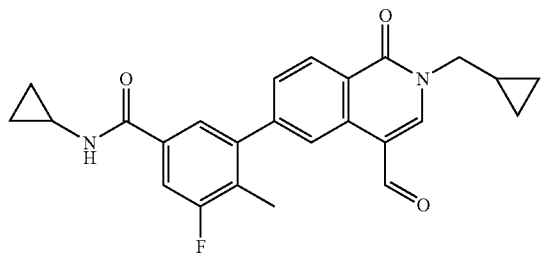

To a mixture of the product of Example 59 step ii) (3.17 g), N-cyclopropyl-3-fluoro-4-methyl-5-(4,4,5,5-tetramethyl-1,3,2-dioxaborolan-2-yl)benzamide (3.3 g) [prepared as described in WO06110173] and potassium carbonate (2.86 g) in DMF (40 mL) was added Pd-118 (0.20 g) and the mixture heated at 60° C. under nitrogen for 11 hours. The reaction mixture was diluted with ethyl acetate and washed with water and brine. The organics were dried over magnesium sulphate, filtered and evaporated. The residue was purified (SiO$_2$, eluting with 3:2 ethyl acetate:isohexane) to give the sub-title compound (4.24 g).

$^1$H NMR DMSO-d$_6$ 9.80 (s, 1H), 8.92 (d, J=1.8 Hz, 1H), 8.60 (s, 1H), 8.55 (d, J=4.1 Hz, 1H), 8.39 (d, J=8.2 Hz, 1H), 7.70 (dd, J=10.5, 1.5 Hz, 1H), 7.67-7.64 (m, 2H), 3.99 (d, J=7.2 Hz, 2H), 2.89-2.82 (m, 1H), 2.17 (d, J=2.3 Hz, 3H), 1.39-1.32 (m, 1H), 0.72-0.67 (m, 2H), 0.59-0.53 (m, 4H), 0.51-0.47 (m, 2H)

ii) N-Cyclopropyl-3-(2-(cyclopropylmethyl)-4-((4-methyl-1,4-diazepan-1-yl)methyl)-1-oxo-1,2-dihydroisoquinolin-6-yl)-5-fluoro-4-methylbenzamide

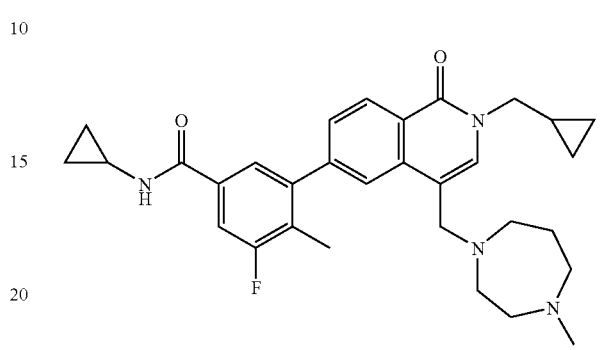

A suspension of the product of step i) (0.45 g) in dichloromethane (50 mL) was treated with 1-methyl-1,4-diazepane (0.61 g) and sodium triacetoxyborohydride (0.68 g) and then stirred at room temperature overnight. Methanol (5 mL) was added and the solution purified directly by SiO$_2$ chromatography (eluting with 0 to 20% methanol in dichloromethane) followed by HPLC to give the title compound as a solid (150 mg).

MS: APCI (+ve) 517 (M+H)$^+$ $^1$H NMR CDCL$_3$ 8.50 (d, J=8.3 Hz, 1H), 7.88 (s, 1H), 7.52 (d, J=9.8 Hz, 1H), 7.44 (s, 1H), 7.40 (d, J=8.1 Hz, 1H), 7.14 (s, 1H), 6.41 (s, 1H), 3.90 (d, J=7.1 Hz, 2H), 3.64 (s, 2H), 2.97-2.85 (m, 1H), 2.78-2.70 (m, 4H), 2.66-2.60 (m, 2H), 2.57-2.52 (m, 2H), 2.33 (s, 3H), 2.23 (s, 3H), 1.85-1.77 (m, 2H), 1.33-1.24 (m, 1H), 0.91-0.83 (m, 2H), 0.65-0.56 (m, 4H), 0.46-0.40 (m, 2H)

EXAMPLE 76

N-Cyclopropyl-3-(2-(cyclopropylmethyl)-4-((4-methylpiperazin-1-yl)methyl)-1-oxo-1,2-dihydroisoquinolin-6-yl)-5-fluoro-4-methylbenzamide

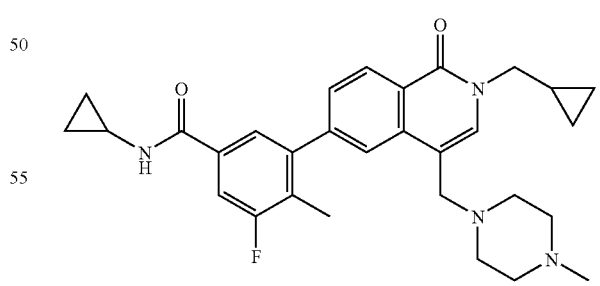

The title compound was prepared as a solid according to the method of Example 75 step ii) using the product of Example 75 step i) and 1-methyl-piperazine.

MS: APCI (+ve) 503 (M+H)$^+$ $^1$H NMR DMSO-d$_6$ 8.54 (d, J=4.1 Hz, 1H), 8.34 (d, J=8.2 Hz, 1H), 7.96 (d, J=1.5 Hz, 1H), 7.67 (s, 1H), 7.66 (d, J=9.8 Hz, 1H), 7.55 (dd, J=8.3, 1.7 Hz, 1H), 7.50 (s, 1H), 3.85 (d,

J=6.9 Hz, 2H), 3.51 (s, 2H), 2.90-2.82 (m, 1H), 2.46-2.35 (m, 4H), 2.34-2.18 (m, 4H), 2.25 (d, J=2.4 Hz, 3H), 2.13 (s, 3H), 1.31-1.20 (m, 1H), 0.73-0.66 (m, 2H), 0.60-0.53 (m, 2H), 0.51-0.44 (m, 2H), 0.44-0.39 (m, 2H)

EXAMPLE 77

N-Cyclopropyl-3-(2-(cyclopropylmethyl)-4-((3-(dimethylamino)propylamino)methyl)-1-oxo-1,2-dihydroisoquinolin-6-yl)-5-fluoro-4-methylbenzamide

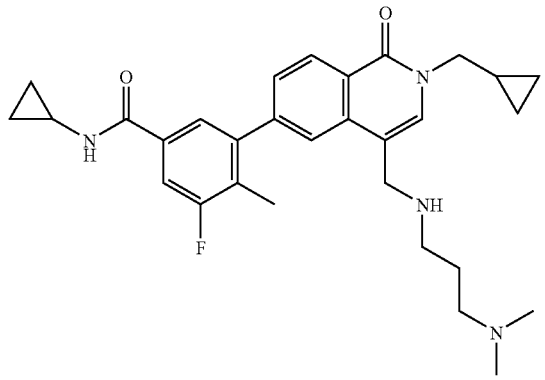

The title compound was prepared as a solid according to the method of Example 75 step ii) using the product of Example 75 step i) and $N^1,N^1$-dimethyl-propane-1,3-diamine.

MS: APCI (+ve) 505 (M+H)$^+$ $^1$H NMR DMSO-d$_6$ 8.52 (d, J=4.1 Hz, 1H), 8.34 (d, J=8.2 Hz, 1H), 7.89 (d, J=1.3 Hz, 1H), 7.66 (s, 1H), 7.66 (d, J=9.5 Hz, 1H), 7.52 (dd, J=8.3, 1.7 Hz, 1H), 7.50 (s, 1H), 3.85 (d, J=7.2 Hz, 2H), 3.77 (s, 2H), 2.89-2.81 (m, 1H), 2.57 (t, J=6.8 Hz, 2H), 2.20 (d, J=2.2 Hz, 3H), 2.17 (t, J=7.2 Hz, 2H), 2.01 (s, 6H), 1.52 (quintet, J=7.0 Hz, 2H), 1.30-1.22 (m, 1H), 0.73-0.66 (m, 2H), 0.60-0.53 (m, 2H), 0.52-0.46 (m, 2H), 0.45-0.39 (m, 2H)

EXAMPLE 78

N-Cyclopropyl-3-(2-(cyclopropylmethyl)-4-((4-(2-hydroxyethyl)-1,4-diazepan-1-yl)methyl)-1-oxo-1,2-dihydroisoquinolin-6-yl)-5-fluoro-4-methylbenzamide

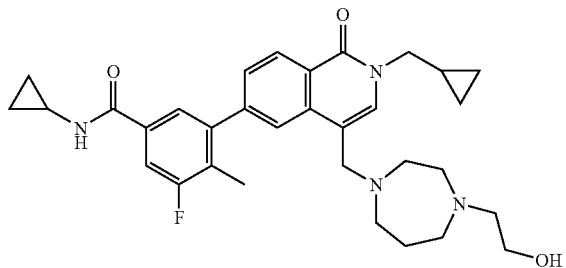

2-(1,4-Diazepan-1-yl)ethanol (311 mg) was added to a suspension of the product of Example 75 step i) (301 mg) in dichloromethane (5 mL). The reaction was stirred at room temperature for 1 hour before the addition of sodium triacetoxyborohydride (457 mg). The reaction was then stirred at room temperature for 1 hour. The reaction mixture was treated with methanol (2 mL) and then concentrated to dryness. The resulting material was purified by HPLC then by SCX ion exchange chromatography (eluting with methanol followed by 1.5M methanolic ammonia). The fractions containing product were concentrated to dryness and the residue triturated with acetonitrile to afford the title compound as a solid (300 mg).

MS: APCI (+ve) 547 (M+H)$^+$ $^1$H NMR DMSO-d$_6$ 8.53 (s, 1H), 8.34 (dd, J=8.3, 2.5 Hz, 1H), 7.98 (s, 1H), 7.70-7.63 (m, 2H), 7.54 (d, J=7.5 Hz, 1H), 7.50 (s, 1H), 4.27 (s, 1H), 3.90-3.80 (m, 2H), 3.64 (s, 2H), 3.46-3.36 (m, 2H), 3.33-3.27 (m, 2H), 2.91-2.79 (m, 1H), 2.70-2.57 (m, 8H), 2.23 (s, 3H), 1.73-1.61 (m, 2H), 1.32-1.20 (m, 1H), 0.74-0.66 (m, 2H), 0.60-0.54 (m, 2H), 0.52-0.46 (m, 2H), 0.44-0.38 (m, 2H)

EXAMPLE 79

4-((6-(5-(Cyclopropylcarbamoyl)-3-fluoro-2-methylphenyl)-2-(cyclopropylmethyl)-1-oxo-1,2-dihydroisoquinolin-4-yl)methyl)-1-(2-hydroxyethyl)-1,4-diazepane 1-oxide

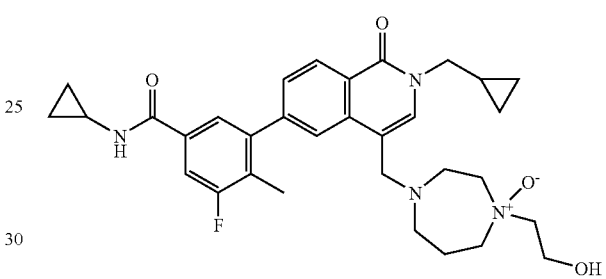

The title compound was isolated as a by-product from the reaction described in Example 78.

MS: APCI (+ve) 563 (M+H)$^+$ $^1$H NMR DMSO-d$_6$ 8.56 (d, J=3.8 Hz, 1H), 8.34 (d, J=8.2 Hz, 1H), 7.91 (d, J=1.3 Hz, 1H), 7.68 (d, J=9.5 Hz, 1H), 7.67 (s, 1H), 7.55 (dd, J=8.3, 1.4 Hz, 1H), 7.52 (s, 1H), 3.86 (d, J=7.4 Hz, 2H), 3.85-3.80 (m, 2H), 3.67 (s, 2H), 3.52-3.45 (m, 1H), 3.37-3.30 (m, 2H), 3.30-3.20 (m, 1H), 3.08-2.99 (m, 1H), 2.89-2.80 (m, 1H), 2.80-2.58 (m, 4H), 2.40-2.27 (m, 1H), 2.22 (d, J=2.1 Hz, 3H), 1.72-1.61 (m, 2H), 1.31-1.21 (m, 1H), 0.73-0.66 (m, 2H), 0.61-0.54 (m, 2H), 0.52-0.45 (m, 2H), 0.45-0.39 (m, 2H)

EXAMPLE 80

N-Cyclopropyl-3-(2-(cyclopropylmethyl)-4-(((3S,5R)-3,5-dimethylpiperazin-1-yl)methyl)-1-oxo-1,2-dihydroisoquinolin-6-yl)-5-fluoro-4-methylbenzamide

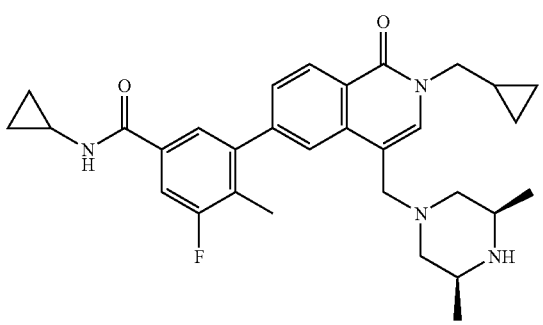

The title compound was prepared as a solid according to the method of Example 75 step ii) using the product of Example 75 step i) and (2R,6S)-2,6-dimethyl-piperazine, and the product purified by SiO$_2$ chromatography (eluting with 5% methanol in dichloromethane followed by 5% of 7M methanolic ammonia in dichloromethane).

MS: APCI (+ve) 517 (M+H)$^+$ $^1$H NMR DMSO-d$_6$ 8.53 (d, J=4.4 Hz, 1H), 8.35 (d, J=8.2 Hz, 1H), 7.95 (d, J=1.5 Hz, 1H), 7.67 (s, 1H), 7.66 (d, J=8.4 Hz, 1H), 7.54 (dd, J=8.2, 1.8 Hz, 1H), 7.48 (s, 1H), 3.86 (d, J=6.9 Hz, 2H), 3.47 (s, 2H), 2.90-2.82 (m, 1H), 2.72 (d, J=10.3 Hz, 2H), 2.69-2.61 (m, 2H), 2.23 (d, J=2.3 Hz, 3H), 1.48 (t, J=10.3 Hz, 2H), 1.31-1.21 (m, 1H), 0.89 (d, J=6.2 Hz, 6H), 0.73-0.67 (m, 2H), 0.59-0.54 (m, 2H), 0.51-0.45 (m, 2H), 0.44-0.39 (m, 2H)

EXAMPLE 81

N-Cyclopropyl-3-(2-(cyclopropylmethyl)-4-((4-(methylamino)piperidin-1-yl)methyl)-1-oxo-1,2-dihydroisoquinolin-6-yl)-5-fluoro-4-methylbenzamide

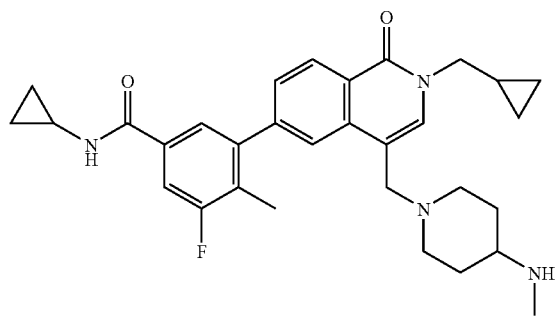

To a solution of the product of Example 75 step i) (320 mg) in dichloromethane (15 mL) was added methylpiperidine-4-yl-carbamic acid, tert-butyl ester (490 mg) and the reaction was stirred at room temperature for 10 minutes before the addition of sodium triacetoxyborohydride (490 mg). The reaction was then stirred at room temperature for 24 hours. The reaction mixture was diluted with dichloromethane (50 mL), washed with water (50 mL), dried over magnesium sulfate, filtered and evaporated in vacuo. The residue was then dissolved in methanol (5 mL) and treated with hydrogen chloride (4N in 1,4-dioxane, 10 mL) and stirred at room temperature for 1 hour. The reaction mixture was evaporated in vacuo and the residue was purified (SiO$_2$, chromatography eluting with 5% methanol in dichloromethane to 5% 7N ammonia/methanol in dichloromethane) to afford the title compound as a solid (250 mg).

MS: APCI (+ve) 517 (M+H)$^+$ $^1$H NMR DMSO-d$_6$ 8.54 (d, J=4.1 Hz, 1H), 8.35 (d, J=8.2 Hz, 1H), 7.96 (d, J=1.5 Hz, 1H), 7.68 (s, 1H), 7.66 (d, J=10.0 Hz, 1H), 7.54 (dd, J=8.2, 1.5 Hz, 1H), 7.47 (s, 1H), 3.85 (d, J=7.2 Hz, 2H), 3.49 (s, 2H), 2.89-2.78 (m, 3H), 2.27-2.21 (m, 7H), 1.97 (t, J=11.2 Hz, 2H), 1.74 (d, J=12.4 Hz, 2H), 1.31-1.20 (m, 1H), 1.20-1.08 (m, 2H), 0.73-0.66 (m, 2H), 0.60-0.55 (m, 2H), 0.52-0.45 (m, 2H), 0.45-0.39 (m, 2H)

EXAMPLE 82

(S)—N-Cyclopropyl-3-(2-(cyclopropylmethyl)-4-((3-methylpiperazin-1-yl)methyl)-1-oxo-1,2-dihydroisoquinolin-6-yl)-5-fluoro-4-methylbenzamide

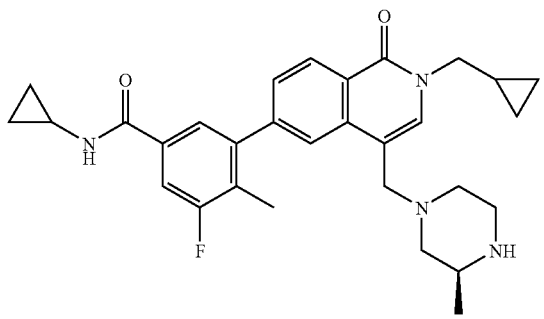

The title compound was prepared as a solid according to the method of Example 81 using the product of Example 75 step i) and (S)-2-methylpiperazine-1-carboxylic acid, tert-butyl ester and purified by HPLC.

MS: APCI (+ve) 503 (M+H)$^+$ $^1$H NMR DMSO-d$_6$ 8.53 (d, J=4.1 Hz, 1H), 8.34 (d, J=8.2 Hz, 1H), 7.96 (d, J=1.3 Hz, 1H), 7.68-7.64 (m, 2H), 7.54 (dd, J=8.3, 1.7 Hz, 1H), 7.53 (s, 1H), 3.90-3.81 (m, 2H), 3.52-3.44 (m, 2H), 2.89-2.82 (m, 1H), 2.81-2.68 (m, 3H), 2.63-2.55 (m, 2H), 2.24 (d, J=2.3 Hz, 3H), 1.93-1.86 (m, 1H), 1.60-1.53 (m, 1H), 1.29-1.22 (m, 1H), 0.89 (d, J=6.4 Hz, 3H), 0.72-0.67 (m, 2H), 0.59-0.54 (m, 2H), 0.51-0.46 (m, 2H), 0.43-0.39 (m, 2H)

EXAMPLE 83

3-(4-((4-Aminopiperidin-1-yl)methyl)-2-(cyclopropylmethyl)-1-oxo-1,2-dihydroisoquinolin-6-yl)-N-cyclopropyl-5-fluoro-4-methylbenzamide

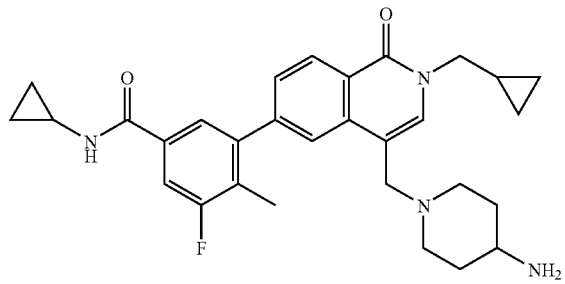

The title compound was prepared as a solid according to the method of Example 81 using the product of Example 75 step i) and piperidin-yl-carbamic acid, tert-butyl ester.

MS: APCI (+ve) 503 (M+H)$^+$ $^1$H NMR DMSO-d$_6$ 8.54 (d, J=4.1 Hz, 1H), 8.34 (d, J=8.5 Hz, 1H), 7.97 (d, J=1.5 Hz, 1H), 7.69-7.65 (m, 2H), 7.55 (dd, J=8.3, 1.7 Hz, 1H), 7.46 (s, 1H), 3.85 (d, J=6.9 Hz, 2H), 3.49 (s, 2H), 2.89-2.78 (m, 3H), 2.54-2.50 (m, 1H), 2.25 (d, J=2.3 Hz, 3H), 1.98-1.92 (m, 2H), 1.67-1.60 (m, 2H), 1.45-1.39 (m,

2H), 1.30-1.21 (m, 1H), 1.19-1.10 (m, 2H), 0.72-0.67 (m, 2H), 0.60-0.55 (m, 2H), 0.51-0.46 (m, 2H), 0.43-0.39 (m, 2H)

EXAMPLE 84

N-Cyclopropyl-3-(2-(cyclopropylmethyl)-4-((4-(isopropylamino)piperidin-1-yl)methyl)-1-oxo-1,2-dihydroisoquinolin-6-yl)-5-fluoro-4-methylbenzamide

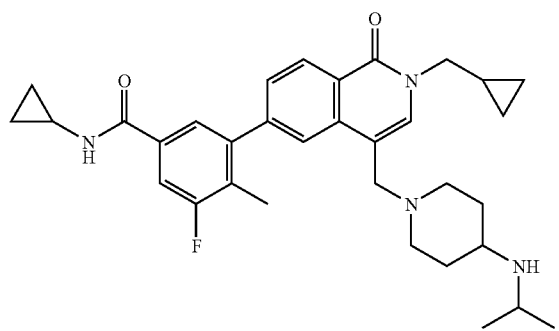

The product of Example 83 (50 mg) was dissolved in dichloromethane (10 mL) and acetone (0.037 mL) added. The solution was stirred for 5 minutes then sodium triacetoxyborohydride (63.3 mg) added. The mixture was stirred at room temperature for 16 hours. The volatiles were removed under reduced pressure and the residue purified by HPLC to give the title compound as a solid (45 mg).

MS: APCI (+ve) 545 (M+H)$^+$ $^1$H NMR DMSO-$d_6$ 8.54 (d, J=4.4 Hz, 1H), 8.34 (d, J=8.2 Hz, 1H), 7.98 (d, J=1.5 Hz, 1H), 7.69-7.64 (m, 2H), 7.55 (dd, J=8.2, 1.5 Hz, 1H), 7.47 (s, 1H), 3.85 (d, J=7.2 Hz, 2H), 3.49 (s, 2H), 2.89-2.79 (m, 4H), 2.47-2.41 (m, 1H), 2.25 (d, J=2.3 Hz, 3H), 2.00-1.92 (m, 2H), 1.76-1.68 (m, 2H), 1.30-1.21 (m, 1H), 1.17-1.07 (m, 2H), 0.93 (d, J=6.2 Hz, 6H), 0.73-0.66 (m, 2H), 0.60-0.55 (m, 2H), 0.51-0.46 (m, 2H), 0.44-0.39 (m, 2H)

EXAMPLE 85

(R)—N-Cyclopropyl-3-(2-(cyclopropylmethyl)-4-((3-(hydroxymethyl)piperazin-1-yl)methyl)-1-oxo-1,2-dihydroisoquinolin-6-yl)-5-fluoro-4-methylbenzamide

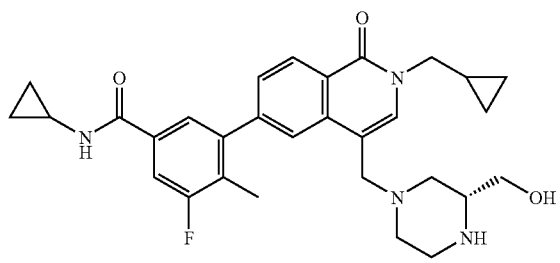

A mixture of the product of Example 75 step i) (300 mg), (R)-2-(hydroxymethyl)piperazine-1-carboxylic acid, tert-butyl ester (465 mg) and sodium triacetoxyborohydride (608 mg) in dichloromethane (20 mL) was stirred under nitrogen for 16 hours. The reaction was partitioned between dichloromethane and water, the organics were then collected and concentrated to dryness. The residue was purified by HPLC to give the title compound (230 mg) as a solid.

MS: APCI (+ve) 519 (M+H)$^+$ $^1$H NMR DMSO-$d_6$ 8.54 (d, J=4.2 Hz, 1H), 8.35 (d, J=8.3 Hz, 1H), 7.97 (d, J=1.5 Hz, 1H), 7.69-7.64 (m, 2H), 7.54 (dd, J=8.2, 1.4 Hz, 1H), 7.49 (s, 1H), 4.46 (t, J=5.4 Hz, 1H), 3.93-3.79 (m, 2H), 3.55-3.44 (m, 2H), 3.28-3.20 (m, 2H), 2.89-2.77 (m, 3H), 2.75-2.67 (m, 1H), 2.63-2.52 (m, 2H), 2.25 (d, J=2.3 Hz, 3H), 2.07-1.87 (m, 2H), 1.67-1.58 (m, 1H), 1.31-1.19 (m, 1H), 0.74-0.66 (m, 2H), 0.60-0.54 (m, 2H), 0.52-0.45 (m, 2H), 0.44-0.38 (m, 2H)

EXAMPLE 86

(R)—N-Cyclopropyl-3-(2-(cyclopropylmethyl)-4-((2-methylpiperazin-1-yl)methyl)-1-oxo-1,2-dihydroisoquinolin-6-yl)-5-fluoro-4-methylbenzamide

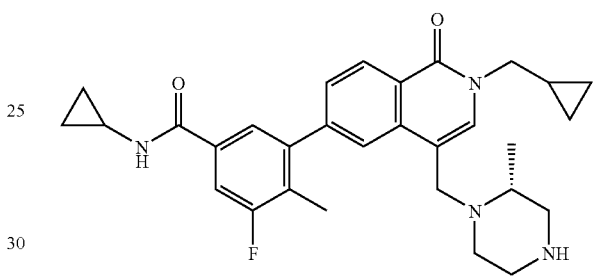

The title compound was prepared as a solid according to the method of Example 81 using the product of Example 75 step i) and (R)-3-methylpiperazine-1-carboxylic acid, tert-butyl ester and the product purified by HPLC.

MS: APCI (+ve) 503 (M+H)$^+$ $^1$H NMR DMSO-$d_6$ 8.53 (d, J=4.1 Hz, 1H), 8.34 (d, J=8.2 Hz, 1H), 8.03 (s, 1H), 7.71-7.64 (m, 2H), 7.55 (dd, J=8.2, 1.3 Hz, 1H), 7.51 (s, 1H), 4.16 (d, J=12.8 Hz, 1H), 3.91-3.80 (m, 2H), 3.05 (d, J=12.8 Hz, 1H), 2.89-2.83 (m, 1H), 2.82-2.76 (m, 1H), 2.73-2.66 (m, 1H), 2.59-2.52 (m, 2H), 2.43-2.33 (m, 2H), 2.26 (d, J=2.1 Hz, 3H), 2.04-1.98 (m, 1H), 1.29-1.22 (m, 1H), 1.09 (d, J=5.9 Hz, 3H), 0.73-0.67 (m, 2H), 0.59-0.54 (m, 2H), 0.51-0.47 (m, 2H), 0.44-0.40 (m, 2H)

EXAMPLE 87

(R)—N-Cyclopropyl-3-(2-(cyclopropylmethyl)-4-((3-(hydroxymethyl)-4-methylpiperazin-1-yl)methyl)-1-oxo-1,2-dihydroisoquinolin-6-yl)-5-fluoro-4-methylbenzamide

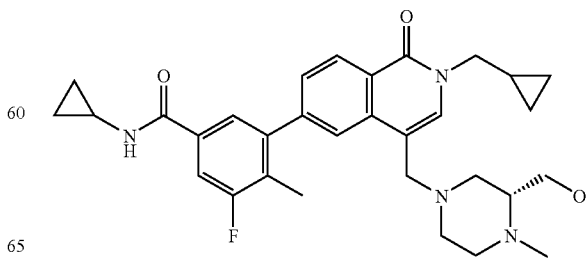

The product of Example 85 (80 mg) was dissolved in dichloromethane (10 mL). Formaldehyde (0.057 mL) and sodium triacetoxyborohydride (98 mg) were then added and the mixture stirred for 4 hours. Water (10 mL) was then added and the mixture extracted with dichloromethane (30 mL). The organics were combined and evaporated under reduced pressure. The residue was purified by HPLC to give the title compound as a solid (70 mg).

MS: APCI (+ve) 533 (M+H)$^+$ $^1$H NMR DMSO-d$_6$ 8.54 (d, J=4.1 Hz, 1H), 8.35 (d, J=8.2 Hz, 1H), 7.96 (d, J=1.5 Hz, 1H), 7.68-7.64 (m, 2H), 7.54 (dd, J=8.2, 1.5 Hz, 1H), 7.50 (s, 1H), 4.41-4.36 (m, 1H), 3.85 (d, J=6.9 Hz, 2H), 3.58-3.51 (m, 1H), 3.51 (s, 2H), 3.26-3.18 (m, 1H), 2.93-2.82 (m, 2H), 2.73-2.63 (m, 2H), 2.25 (d, J=2.3 Hz, 3H), 2.17 (s, 3H), 2.11-2.04 (m, 2H), 1.97-1.80 (m, 2H), 1.31-1.22 (m, 1H), 0.73-0.67 (m, 2H), 0.59-0.54 (m, 2H), 0.51-0.46 (m, 2H), 0.44-0.39 (m, 2H)

EXAMPLE 88

N-Cyclopropyl-3-(2-(cyclopropylmethyl)-1-oxo-4-(piperazin-1-ylmethyl)-1,2-dihydroisoquinolin-6-yl)-5-fluoro-4-methylbenzamide, dihydrochloride

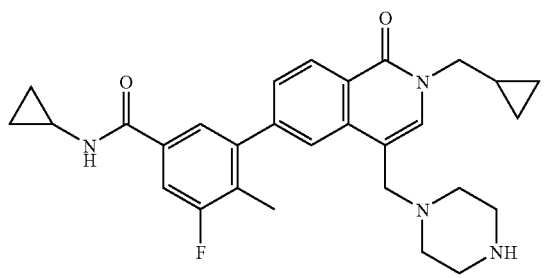

To a solution of the product of Example 75 step i) (400 mg) in dichloromethane (20 mL) was added piperazine-1-carboxylic acid, tert-butyl ester (534 mg) and the mixture stirred at room temperature for 10 minutes before the addition of sodium triacetoxyborohydride (608 mg). After stirring at room temperature for a further 24 hours the reaction mixture was diluted with dichloromethane and washed with water. The organic phase was then evaporated to dryness and the residue treated with 4M HCl in 1,4-dioxane (10 mL) with methanol being added to aid dissolution. The reaction was stirred at room temperature for 1 hour and then concentrated to dryness. The residue was stirred in methanol and the resulting precipitate collected by filtration, washing with methanol to give the title compound as a solid (190 mg).

MS: APCI (+ve) 489 (M+H)$^+$ $^1$H NMR DMSO-d$_6$ 8.62 (s, 1H), 8.37 (d, J=8.2 Hz, 1H), 8.14-7.80 (m, 3H), 7.67 (d, J=10.5 Hz, 1H), 7.59 (d, J=8.2 Hz, 1H), 3.87 (d, J=7.2 Hz, 2H), 3.68 (s, 2H), 3.60-3.24 (m, 8H), 2.93-2.83 (m, 1H), 2.22 (s, 3H), 1.36-1.25 (m, 1H), 0.73-0.58 (m, 4H), 0.56-0.43 (m, 4H)

EXAMPLE 89

N-Cyclopropyl-3-(2-(cyclopropylmethyl)-1-oxo-4-((piperidin-4-ylmethylamino)methyl)-1,2-dihydroisoquinolin-6-yl)-5-fluoro-4-methylbenzamide

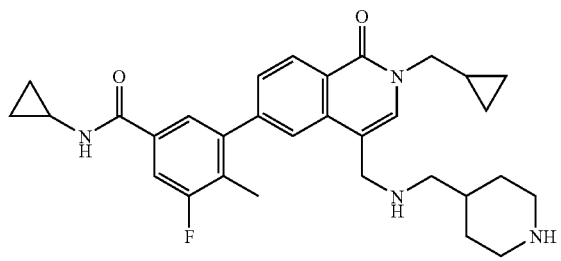

The title compound was prepared as a solid according to the method of Example 81 using the product of Example 75 step i) and 4-aminomethyl-piperidine-1-carboxylic acid tert-butyl ester.

MS: APCI (+ve) 517 (M+H)$^+$ $^1$H NMR DMSO-d$_6$ 8.52 (d, J=4.1 Hz, 1H), 8.34 (d, J=8.2 Hz, 1H), 7.90 (d, J=1.3 Hz, 1H), 7.66 (d, J=9.5 Hz, 1H), 7.65 (s, 1H), 7.51 (dd, J=8.2, 1.5 Hz, 1H), 7.49 (s, 1H), 3.85 (d, J=7.2 Hz, 2H), 3.77 (s, 2H), 2.89-2.80 (m, 3H), 2.40 (d, J=6.4 Hz, 2H), 2.34 (t, J=11.9 Hz, 2H), 2.18 (d, J=2.1 Hz, 3H), 1.57 (d, J=12.0 Hz, 2H), 1.49-1.38 (m, 1H), 1.31-1.22 (m, 1H), 0.97-0.85 (m, 2H), 0.73-0.66 (m, 2H), 0.60-0.54 (m, 2H), 0.52-0.45 (m, 2H), 0.45-0.39 (m, 2H)

EXAMPLE 90

N-Cyclopropyl-3-(2-(cyclopropylmethyl)-4-((4-(2-hydroxyethyl)piperazin-1-yl)methyl)-1-oxo-1,2-dihydroisoquinolin-6-yl)-5-fluoro-4-methylbenzamide

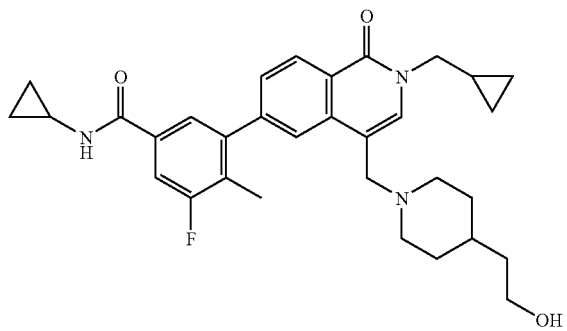

The title compound was prepared as a solid according to the method of Example 75 step ii) using product of Example 75 step i) and 2-piperazin-1-yl-ethanol.

MS: APCI (+ve) 533 (M+H)$^+$ $^1$H NMR DMSO-d$_6$ 8.54 (d, J=4.4 Hz, 1H), 8.34 (d, J=8.2 Hz, 1H), 7.95 (d, J=1.5 Hz, 1H), 7.67 (s, 1H), 7.66 (d, J=10.5 Hz, 1H), 7.55 (dd, J=8.2, 1.5 Hz, 1H), 7.49 (s, 1H), 4.33 (t, J=5.4 Hz, 1H), 3.85 (d, J=7.2 Hz, 2H), 3.51 (s, 2H), 3.46 (q, J=6.0 Hz, 2H), 2.90-2.82 (m, 1H), 2.46-2.31 (m, 8H), 2.34 (t, J=6.3 Hz, 2H), 2.25 (d, J=2.3 Hz, 3H), 1.31-1.21 (m, 1H), 0.73-0.67 (m, 2H), 0.60-0.55 (m, 2H), 0.51-0.45 (m, 2H), 0.45-0.39 (m, 2H)

EXAMPLE 91

N-Cyclopropyl-3-(2-(cyclopropylmethyl)-4-(((1-ethylpiperidin-4-yl)methylamino)methyl)-1-oxo-1,2-dihydroisoquinolin-6-yl)-5-fluoro-4-methylbenzamide

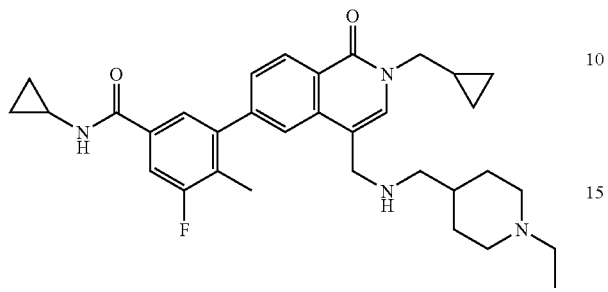

The title compound was prepared as a solid according to the method of Example 75 step ii) using product of Example 75 step i) and C-(1-ethyl-piperidin-4-yl)-methylamine.

MS: APCI (+ve) 545 (M+H)$^+$ $^1$H NMR DMSO-d$_6$ 8.52 (d, J=4.4 Hz, 1H), 8.34 (d, J=8.2 Hz, 1H), 7.89 (d, J=1.5 Hz, 1H), 7.66 (d, J=9.5 Hz, 1H), 7.65 (s, 1H), 7.51 (dd, J=8.2, 1.5 Hz, 1H), 7.49 (s, 1H), 3.85 (d, J=7.2 Hz, 2H), 3.77 (s, 2H), 2.89-2.82 (m, 1H), 2.74 (d, J=11.3 Hz, 2H), 2.42 (d, J=6.7 Hz, 2H), 2.22 (q, J=7.2 Hz, 2H), 2.18 (d, J=2.1 Hz, 3H), 1.70 (t, J=11.6 Hz, 2H), 1.62 (d, J=13.6 Hz, 2H), 1.41-1.28 (m, 1H), 1.31-1.21 (m, 1H), 1.03 (q, J=12.4 Hz, 2H), 0.94 (t, J=7.2 Hz, 3H), 0.72-0.66 (m, 2H), 0.59-0.54 (m, 2H), 0.52-0.46 (m, 2H), 0.45-0.39 (m, 2H)

EXAMPLE 92

3-(4-((1,4-Diazepan-1-yl)methyl)-2-(cyclopropylmethyl)-1-oxo-1,2-dihydroisoquinolin-6-yl)-N-cyclopropyl-5-fluoro-4-methylbenzamide

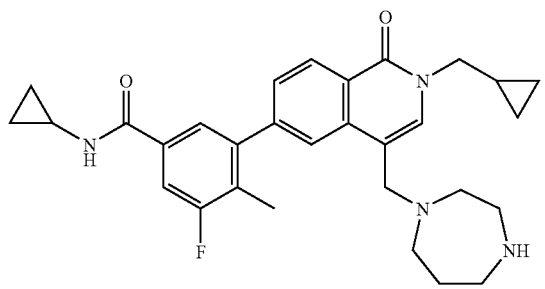

The title compound was prepared as a solid according to the method of Example 75 step ii) using product of Example 75 step i) and [1,4]diazepane.

MS: APCI (+ve) 503 (M+H)$^+$ $^1$H NMR DMSO-d$_6$ 8.58-8.50 (m, 1H), 8.34 (d, J=8.2 Hz, 1H), 8.00-7.94 (m, 1H), 7.66 (s, 1H), 7.66 (d, J=10.1 Hz, 1H), 7.54 (dd, J=8.2, 1.5 Hz, 1H), 7.49 (s, 1H), 3.85 (d, J=7.2 Hz, 2H), 3.66 (s, 2H), 2.90-2.81 (m, 1H), 2.78 (t, J=6.2 Hz, 2H), 2.73-2.65 (m, 4H), 2.65-2.57 (m, 2H), 2.23 (d, J=2.3 Hz, 3H), 1.63 (quintet, J=6.1 Hz, 2H), 1.30-1.21 (m, 1H), 0.73-0.66 (m, 2H), 0.60-0.53 (m, 2H), 0.52-0.45 (m, 2H), 0.45-0.38 (m, 2H)

EXAMPLE 93

N-Cyclopropyl-3-(2-(3-(3-(dimethylamino)propoxy)benzyl)-4-methyl-1-oxo-1,2-dihydroisoquinolin-6-yl)-4-methylbenzamide

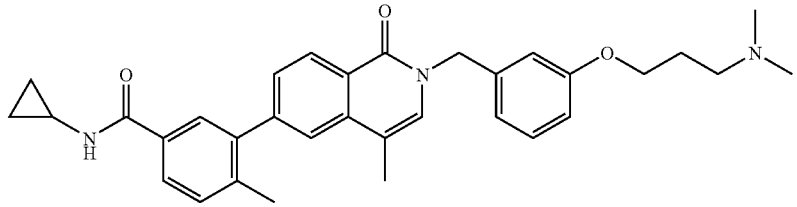

i) 6-Bromo-4-methylisoquinolin-1(2H)-one

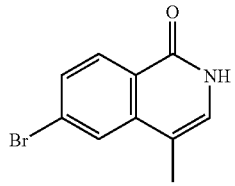

A suspension of 3-(3-bromo-phenyl)-but-2-enoic acid (10.6 g) [prepared as described in WO2007073284] was treated with oxalyl chloride (5.8 mL) and DMF (0.2 mL) and was stirred for 3 hours under a nitrogen atmosphere. The reaction mixture was concentrated in vacuo and azeotroped with toluene. The residue was redissolved in 1,4-dioxane (40 mL) and treated with a solution of sodium azide (8.6 g) in a 1:1 mixture of 1,4-dioxane and water (50 mL) at 0° C. The solution was warmed to room temperature and stirred for a further 1 hour. The reaction mixture was diluted with water (250 mL) and the resulting solution extracted with diethyl ether (2×250 mL). The combined extracts were washed with saturated aqueous sodium hydrogen carbonate (250 mL) and brine (250 mL). The organics were dried over anhydrous magnesium sulphate, filtered and the liquors treated with 1,2-dichlorobenzene (40 mL). The resulting mixture was concentrated to give a solution of the acyl azide in 1,2-dichlorobenzene. This was treated with iodine (2 crystals) and slowly heated to 190° C. After stirring at this temperature overnight the reaction mixture was cooled to room temperature filtered and the solid washed with 1,2-dichlorobenzene, iso-hexane and diethyl ether to give the subtitle compound as a solid (5.8 g).

MS: APCI (−ve) 236, 238 (M−H)$^−$ $^1$H NMR DMSO-d$_6$ 8.13 (d, J=8.7 Hz, 1H), 7.82 (d, J=1.8 Hz, 1H), 7.67 (dd, J=8.5, 2.1 Hz, 1H), 7.07 (d, J=4.6 Hz, 1H), 2.19 (d, J=1.0 Hz, 3H), 11.22 (s, 5H)

ii) 4-Methyl-3-(4-methyl-1-oxo-1,2-dihydro-iso-quinolin-6-yl)-benzoic acid, methyl ester

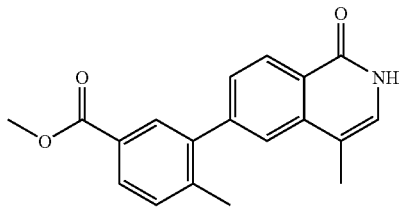

The sub-title compound was prepared by the method of intermediate 3 using the product of step i).
MS: APCI (−ve) 306 (M−H)⁻
¹H NMR DMSO-d₆ 11.15 (s, 1H), 8.30 (d, J=8.2 Hz, 1H), 7.92 (dd, J=7.9, 1.5 Hz, 1H), 7.84 (d, J=1.5 Hz, 1H), 7.58 (s, 1H), 7.52 (dd, J=7.9, 3.8 Hz, 2H), 7.06 (d, J=5.4 Hz, 1H), 3.86 (s, 3H), 2.32 (s, 3H), 2.23 (s, 3H)

iii) 3-(2-(3-(3-Dimethylamino-propoxy)-benzyl)-4-methyl-1-oxo-1,2-dihydro-isoquinolin-6-yl)-4-methyl-benzoic acid methyl ester

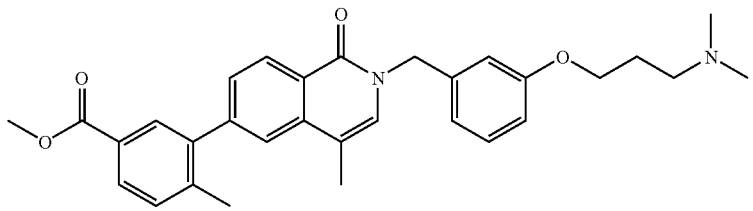

The sub-title compound was prepared by the method of intermediate 4 using the product of step ii) and the product of Example 10 step ii).
MS: APCI (+ve) 499 (M+H)⁺ iv) N-Cyclopropyl-3-(2-(3-(3-(dimethylamino)propoxy)benzyl)-4-methyl-1-oxo-1,2-dihydroisoquinolin-6-yl)-4-methylbenzamide

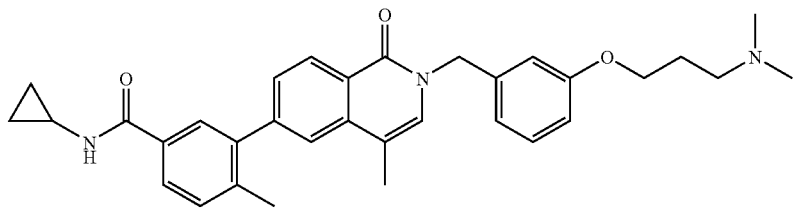

The title compound was prepared as a solid by the method of Example 3 step ii) using the product of step iii).
MS: APCI (+ve) 524 (M+H)⁺
¹H NMR CD₃OD 8.38 (br s, 1H), 7.66 (br s, 2H), 7.60 (br s, 1H), 7.49 (br d, J=5.2 Hz, 1H), 7.34 (br d, J=6.2 Hz, 1H), 7.25-7.14 (m, 2H), 6.95-6.73 (m, 3H), 5.15 (s, 2H), 3.94 (m, 2H), 2.76 (m, 1H), 2.67 (m, 2H), 2.37 (s, 6H), 2.24 (s, 6H), 1.94 (m, 2H), 0.71 (m, 2H), 0.55 (m, 2H)

EXAMPLE 94

N-Cyclopropyl-3-(2-(3-(3-(dimethylamino)propoxy)benzyl)-3-methyl-1-oxo-1,2-dihydroisoquinolin-6-yl)-4-methylbenzamide

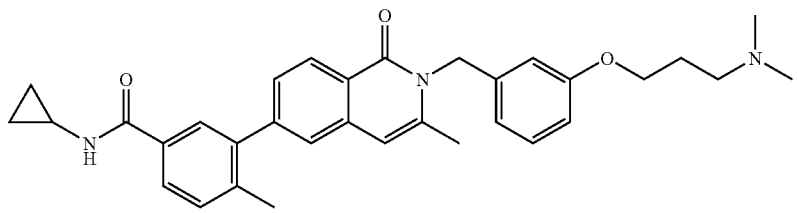

i) 6-Bromo-3-methylisoquinolin-1(2H)-one

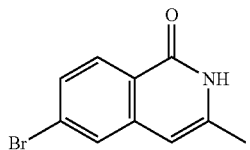

The sub-title compound was prepared by the method of Example 93 step i) using 3-(3-bromo-phenyl)-2-methylacrylic acid (prepared as described in J. Chem. Soc. 1964, 1847).

MS: APCI (−ve) 236, 238 (M−H)⁻
¹H NMR DMSO-d$_6$ 8.02 (d, J=8.7 Hz, 1H), 7.80 (d, J=1.8 Hz, 1H), 7.53 (dd, J=8.6, 1.9 Hz, 1H), 6.30 (s, 1H), 2.21 (s, 3H)

ii) 4-Methyl-3-(3-methyl-1-oxo-1,2-dihydro-isoquinolin-4-yl)-benzoic acid, methyl ester

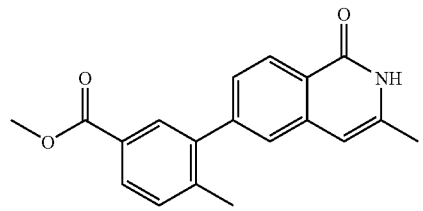

The sub-title compound was prepared by the method of intermediate 3 using the product of step i).

MS: APCI (−ve) 306 (M−H)⁻
¹H NMR DMSO-d$_6$ 8.18 (d, J=8.2 Hz, 1H), 7.91 (dd, J=7.9, 1.8 Hz, 1H), 7.81 (d, J=1.8 Hz, 1H), 7.53 (d, J=1.5 Hz, 1H), 7.50 (d, J=8.2 Hz, 1H), 7.38 (dd, J=8.2, 1.5 Hz, 1H), 6.37 (s, 1H), 3.85 (s, 3H), 2.31 (d, J=6.2 Hz, 3H), 2.23 (s, 3H)

iii) 3-(2-(3-(3-Dimethylamino-propoxy)-benzyl)-3-methyl-1-oxo-1,2-dihydro-isoquinolin-6-yl)-4-methyl-benzoic acid methyl ester

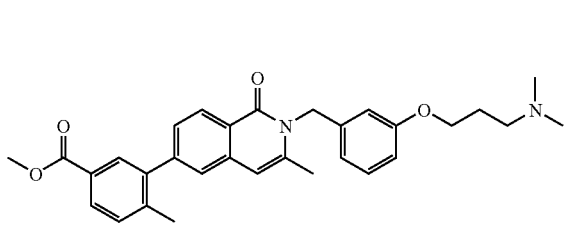

The sub-title compound was prepared by the method of intermediate 4 using the product of step ii) and the product of Example 10 step ii).

MS: APCI (+ve) 499 (M+H)⁺ iv) N-Cyclopropyl-3-(2-(3-(3-(dimethylamino)propoxy)benzyl)-3-methyl-1-oxo-1,2-dihydroisoquinolin-6-yl)-4-methylbenzamide

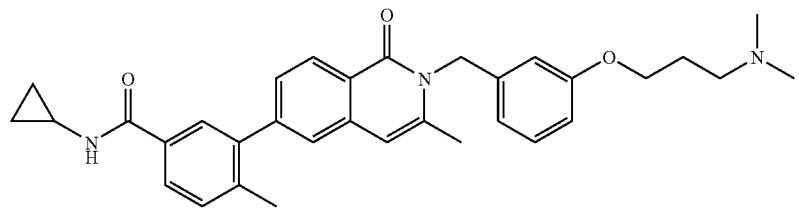

The title compound was prepared as a solid by the method of Example 3 step ii) using the product of step iii).

MS: APCI (+ve) 524 (M+H)⁺
¹H NMR CD$_3$OD 8.34 (d, J=8.2 Hz, 1H), 7.73 (dd, J=7.8, 1.9 Hz, 1H), 7.71 (d, J=1.8 Hz, 1H), 7.51 (d, J=1.5 Hz, 1H), 7.45 (dd, J=8.2, 1.5 Hz, 1H), 7.39 (d, J=7.9 Hz, 1H), 7.21 (t, J=7.9 Hz, 1H), 6.80 (dd, J=8.3, 2.4 Hz, 1H), 6.74-6.66 (m, 2H), 6.63 (s, 1H), 5.45 (s, 2H), 3.94 (t, J=6.2 Hz, 2H), 2.83 (septet, J=5.0 Hz, 1H), 2.45 (t, J=8.8 Hz, 2H), 2.37 (s, 3H), 2.31 (s, 3H), 2.22 (s, 6H), 1.89 (m, 2H), 0.77 (td, J=7.2, 5.0 Hz, 2H), 0.61 (dd, J=4.0, 2.2 Hz, 2H)

EXAMPLE 95

N-Cyclopropyl-3-(2-(4-((dimethylamino)methyl)benzyl)-4-methyl-1-oxo-1,2-dihydroisoquinolin-6-yl)-4-methylbenzamide

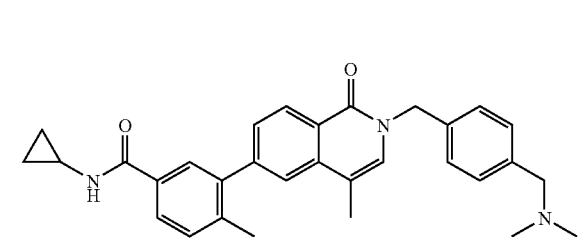

i) 3-(2-(4-Dimethylaminomethyl-benzyl)-4-methyl-1-oxo-1,2-dihydro-isoquinolin-6-yl)-4-methyl-benzoic acid, methyl ester

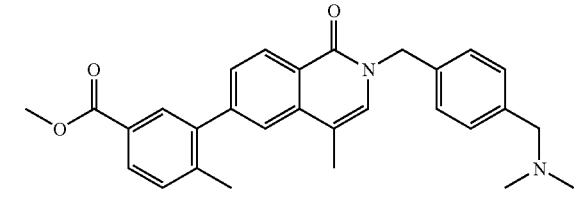

A solution of the product of Example 93 step ii) in DMF (10 mL) was treated with 60% sodium hydride in mineral oil (0.12 g) and the mixture was stirred at room temperature under a nitrogen atmosphere for 20 mins before the addition of 1,4-di(chloromethyl)benzene (0.74 g). After stirring for a further 20 mins the reaction was treated with dimethylamine hydrochloride (0.98 g), followed by triethylamine (5 mL). Stirring was continued for 16 hours before being diluted with ethyl acetate (150 mL) and washing with water (150 mL). The organic layer was dried with anhydrous sodium sulphate and concentrated in vacuo to give a brown oil, which was purified (SiO$_2$, eluting with ethyl acetate containing 2.5% MeOH and 0.25% triethylamine) to give the sub-titled compound (0.25 g).

MS: APCI (+ve) 455 (M+H)$^+$ ii) N-Cyclopropyl-3-(2-(4-((dimethylamino)methyl)benzyl)-4-methyl-1-oxo-1,2-dihydroisoquinolin-6-yl)-4-methylbenzamide

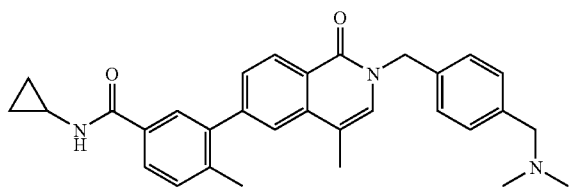

The title compound was prepared as a solid by the method of Example 3 step ii) using the product of step i).

MS: APCI (+ve) 480 (M+H)$^+$ $^1$H NMR CD$_3$OD 8.42 (d, J=7.4 Hz, 1H), 7.73 (m, 2H), 7.65 (d, J=1.5 Hz, 1H), 7.54 (dd, J=8.3, 1.7 Hz, 1H), 7.40 (d, J=7.9 Hz, 1H), 7.29 (m, 5H), 5.24 (s, 2H), 3.43 (s, 2H), 2.83 (septet, J=3.8 Hz, 1H), 2.30 (d, J=1.0 Hz, 6H), 2.19 (s, 6H), 0.77 (m, 2H), 0.61 (m, 2H)

EXAMPLE 96

N-Cyclopropyl-3-(2-(4-((dimethylamino)methyl)benzyl)-3-methyl-1-oxo-1,2-dihydroisoquinolin-6-yl)-4-methylbenzamide

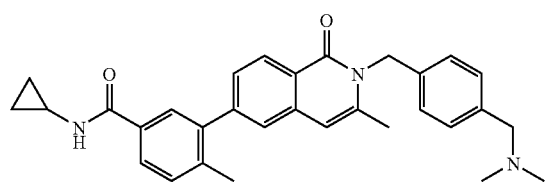

i) 3-(2-(4-Dimethylaminomethyl-benzyl)-3-methyl-1-oxo-1,2-dihydro-isoquinolin-6-yl)-4-methyl-benzoic acid, methyl ester

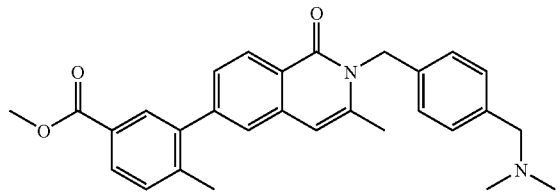

The sub-title compound was prepared by the method of Example 95 step i) using the product of Example 94 step ii).

MS: APCI (+ve) 455 (M+H)$^+$ ii) N-Cyclopropyl-3-(2-(4-((dimethylamino)methyl)benzyl)-3-methyl-1-oxo-1,2-dihydroisoquinolin-6-yl)-4-methylbenzamide

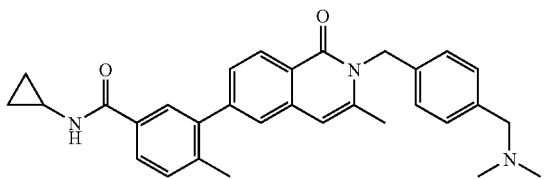

The title compound was prepared as a solid by the method of Example 3 step ii) using the product of step i).

MS: APCI (+ve) 480 (M+H)$^+$ $^1$H NMR DMSO-d$_6$ 8.33 (d, J=8.2 Hz, 1H), 7.73 (dd, J=7.9, 2.1 Hz, 1H), 7.71 (d, J=1.8 Hz, 1H), 7.51 (d, J=1.5 Hz, 1H), 7.45 (dd, J=8.3, 1.7 Hz, 1H), 7.39 (d, J=7.9 Hz, 1H), 7.27 (d, J=8.2 Hz, 2H), 7.13 (d, J=8.2 Hz, 2H), 6.63 (s, 1H), 5.48 (s, 2H), 3.43 (s, 2H), 2.83 (septet, J=3.7 Hz, 1H), 2.38 (s, 3H), 2.31 (s, 3H), 2.20 (s, 6H), 0.77 (m, 2H), 0.61 (m, 2H)

EXAMPLE 97

N-Cyclopropyl-4-methyl-3-(4-methyl-1-oxo-2-(4-(piperidin-4-yl)benzyl)-1,2-dihydroisoquinolin-6-yl)benzamide

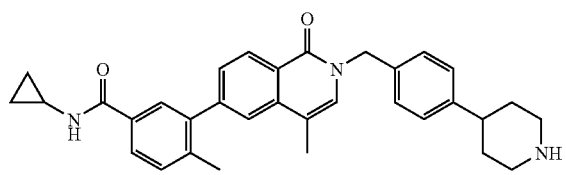

i) 2,2,2-Trifluoro-1-(4-phenyl-piperidin-1-yl)-ethanone

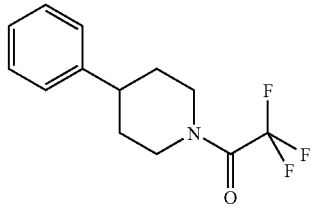

Trifluoroacetic anhydride (70 mL) was added dropwise to 4-phenyl piperidine (25 g) at 0° C. with stirring under nitrogen. The mixture was then heated to reflux for 4 hours before cooling to room temperature and stirring for a further 48 hours. The reaction was concentrated in vacuo, azeotroping with toluene and redissolved ethyl acetate before washing with water and brine. The organic layer was dried using magnesium sulfate and concentrated to give the sub-title compound (40 g).

$^1$H NMR DMSO-d$_6$ 7.34-7.18 (m, 5H), 4.44 (m, 1H), 3.96 (m, 1H), 3.37 (dd, J=26.5, 2.5 Hz, 1H), 3.04-2.81 (m, 2H), 1.90 (dd, J=20.0, 2.9 Hz, 2H), 1.61 (m, 2H)

ii) 1-(4-(4-Chloromethyl-phenyl)-piperidin-1-yl)-2,2,2-trifluoro-ethanone

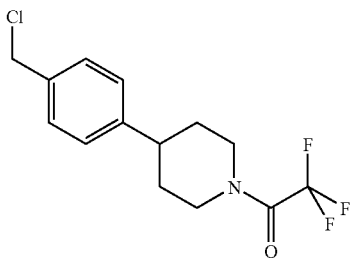

A suspension of the product of step i) (18 g), paraformaldehyde (14 g) and zinc dichloride (14 g) in dichloromethane (700 mL) was stirred at room temperature. Hydrogen chloride gas was bubbled through the reaction for 30 minutes. The reaction was stirred at room temperature under a blanket of nitrogen for a further 18 hours. Water (150 mL) was added and the phases separated. The organic phase was dried using magnesium sulfate and concentrated in vacuo to give a green oil which was purified (SiO$_2$ eluting with 30% i-hexane in dichloromethane) to give the sub-title compound (12 g).
$^1$H NMR DMSO-d$_6$ 7.37 (d, J=9.5 Hz, 2H), 7.28 (d, J=9.0 Hz, 2H), 4.73 (s, 2H), 4.43 (dt, J=13.1, 2.0 Hz, 1H), 3.97 (m, 1H), 3.39 (d, J=10.2 Hz, 1H), 3.06-2.82 (m, 2H), 1.89 (m, 2H), 1.62 (m, 2H)

iii) 4-Methyl-3-(4-methyl-1-oxo-2-(4-(1-(2,2,2-trifluoro-acetyl)-piperidin-4-yl)-benzyl)-1,2-dihydro-isoquinolin-6-yl)-benzoic acid, methyl ester

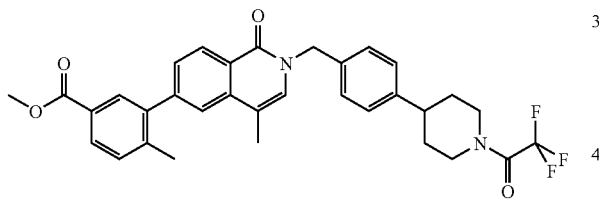

The sub-title compound was prepared by the method of Intermediate 4 using the product of step ii) and the product of Example 93 step ii).
MS: APCI (+ve) 577 (M+H)$^+$
$^1$H NMR CD$_3$OD 8.34 (d, J=8.2 Hz, 1H), 7.93 (dd, J=7.9, 1.8 Hz, 1H), 7.88 (d, J=1.5 Hz, 1H), 7.49 (d, J=1.5 Hz, 1H), 7.42 (dd, J=8.3, 1.9 Hz, 2H), 7.21 (d, J=8.2 Hz, 2H), 7.10 (d, J=8.2 Hz, 2H), 6.63 (s, 1H), 5.46 (d, J=4.1 Hz, 2H), 4.56 (m, 1H), 3.88 (s, 3H), 3.34 (m, 2H), 2.90 (m, 3H), 2.37 (s, 3H), 2.33 (s, 3H), 1.92 (m, 1H), 1.65 (m, 2H)

iv) N-Cyclopropyl-4-methyl-3-(4-methyl-1-oxo-2-(4-(piperidin-4-yl)benzyl)-1,2-dihydroisoquinolin-6-yl)benzamide

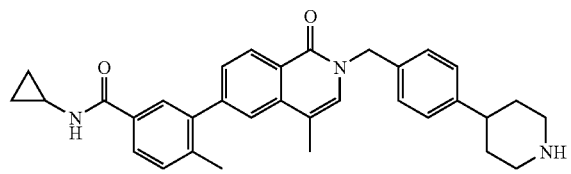

The title compound was prepared as a solid by the method of Example 3 step ii) using the product of step iii).
MS: APCI (+ve) 506 (M+H)$^+$
$^1$H NMR CD$_3$OD 8.41 (d, J=8.2 Hz, 1H), 7.74 (dd, J=7.9, 1.8 Hz, 1H), 7.71 (d, J=1.8 Hz, 1H), 7.63 (d, J=1.5 Hz, 1H), 7.52 (dd, J=8.3, 1.7 Hz, 1H), 7.39 (d, J=7.9 Hz, 1H), 7.23 (dd, J=30.0, 8.2 Hz, 5H), 5.20 (s, 2H), 3.15 (d, J=12.3 Hz, 2H), 2.87-2.60 (m, 4H), 2.30 (s, 3H), 2.27 (d, J=1.3 Hz, 3H), 1.80 (d, J=13.6 Hz, 2H), 1.64 (octet, J=6.2 Hz, 2H), 0.77 (td, J=7.2, 5.1 Hz, 2H), 0.61 (m, 2H)

EXAMPLE 98

N-Cyclopropyl-4-methyl-3-(3-methyl-1-oxo-2-(4-(piperidin-4-yl)benzyl)-1,2-dihydroisoquinolin-6-yl)benzamide

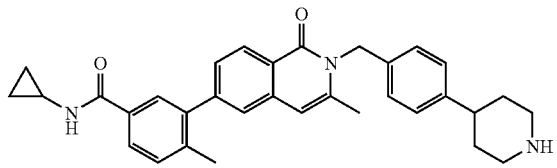

i) 4-Methyl-3-(3-methyl-1-oxo-2-(4-(1-(2,2,2-trifluoroacetyl)piperidin-4-yl)benzyl)-1,2-dihydroisoquinolin-6-yl)benzoic acid, methyl ester

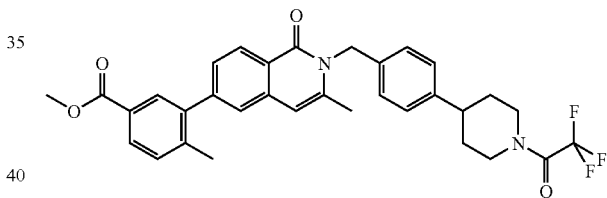

The sub-title compound was prepared by the method of Intermediate 4 using the product of Example 97 step ii) and the product of Example 94 step ii).
MS: APCI (+ve) 577 (M+H)$^+$
$^1$H NMR CD$_3$OD 8.34 (d, J=8.2 Hz, 1H), 7.93 (dd, J=7.9, 1.8 Hz, 1H), 7.88 (d, J=1.5 Hz, 1H), 7.49 (d, J=1.5 Hz, 1H), 7.42 (dd, J=8.3, 1.9 Hz, 2H), 7.16 (dd, J=42.3, 8.2 Hz, 4H), 6.63 (s, 1H), 5.46 (d, J=4.1 Hz, 2H), 4.57 (m, 1H), 4.09 (t, J=7.2 Hz, 1H), 3.88 (s, 3H), 3.32 (m, 1H), 2.90 (m, 2H), 2.37 (s, 3H), 2.32 (s, 3H), 1.92 (m, 2H), 1.65 (m, 2H)

ii) N-Cyclopropyl-4-methyl-3-(3-methyl-1-oxo-2-(4-(piperidin-4-yl)benzyl)-1,2-dihydroisoquinolin-6-yl)benzamide

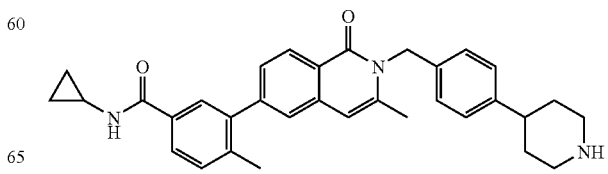

The title compound was prepared as a solid by the method of Example 3 step ii) using the product of step i).

MS: APCI (+ve) 506 (M+H)+

$^1$H NMR CD$_3$OD 8.33 (d, J=8.2 Hz, 1H), 7.73 (dd, J=7.8, 1.9 Hz, 1H), 7.71 (d, J=1.8 Hz, 1H), 7.51 (d, J=1.5 Hz, 1H), 7.44 (dd, J=8.3, 1.7 Hz, 1H), 7.39 (d, J=7.7 Hz, 1H), 7.19 (d, J=8.2 Hz, 2H), 7.08 (d, J=8.2 Hz, 2H), 6.62 (s, 1H), 5.46 (d, J=6.2 Hz, 2H), 3.11 (d, J=12.0 Hz, 2H), 2.83 (septet, J=3.7 Hz, 1H), 2.71 (sextet, J=5.5 Hz, 1H), 2.63 (m, 2H), 2.38 (s, 3H), 2.31 (s, 3H), 1.77 (m, 2H), 1.62 (m, 2H), 0.78 (dd, J=7.2, 2.1 Hz, 2H), 0.61 (m, 2H)

EXAMPLE 99

3-(2-Benzyl-4-(3-(dimethylamino)propyl)-1-oxo-1,2-dihydroisoquinolin-6-yl)-N-cyclopropyl-4-methyl-benzamide

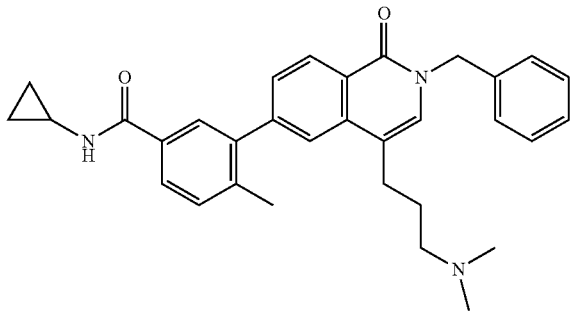

i) 3-(2-Benzyl-4-bromo-1-oxo-1,2-dihydroisoquinolin-6-yl)-4-methylbenzoic acid, methyl ester

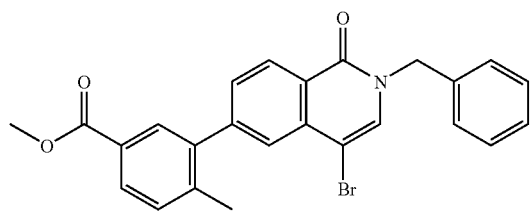

A solution of intermediate 4, (1.3 g) in acetic acid (10 mL) was stirred at room temperature for 10 minutes. Bromine (0.175 mL) was then added and the reaction was stirred at room temperature for 20 minutes. The reaction mixture was diluted with water (100 mL) and extracted into dichloromethane (100 mL). The organics were washed again with water, dried over magnesium sulfate, filtered and evaporated in vacuo. The crude product was purified (SiO$_2$, chromatography, eluting with 10 to 20% ethyl acetate in isohexane) to afford the sub-titled compound (0.72 g).

MS: APCI (+ve) 462, 464 (1:1) (M+H)+ ii) 3-(2-Benzyl-4-(3-(dimethylamino)propyl)-1-oxo-1,2-dihydroisoquinolin-6-yl)-4-methylbenzoic acid, methyl ester

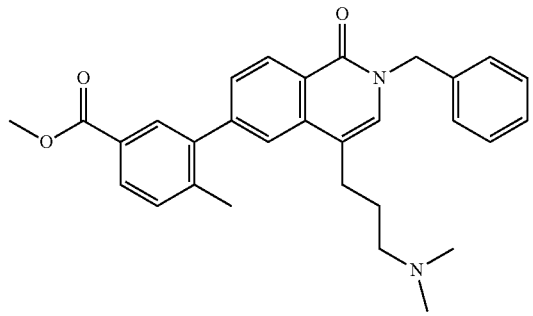

A mixture of the product from step i) (170 mg), tetrabutylammonium chloride (10 mg), Pd-118 (24 mg) and N-methyldicyclohexylamine (0.12 mL) in N,N-dimethylacetamide (3 mL) was evacuated and flushed with nitrogen (×3) before the addition of allyl alcohol (0.05 mL). The resultant solution was stirred under nitrogen at 70° C. for 2 hours. The reaction mixture was cooled to room temperature and dilute hydrochloric acid (1N, 2 mL) was added, followed by dichloromethane (10 mL). The resulting suspension was filtered and the filtrate was washed with water (2×5 mL). The organic phase was separated and treated with dimethylamine hydrochloride (0.181 g) followed by sodium triacetoxyborohydride (0.157 g). The mixture was then stirred at room temperature for 30 minutes. The reaction mixture was filtered and poured directly onto a silica column (10 g) (eluting with 3% methanol in dichloromethane) to afford the sub-titled compound (0.12 g).

MS: APCI (+ve) 469 (M+H)+ iii) 3-(2-Benzyl-4-(3-(dimethylamino)propyl)-1-oxo-1,2-dihydroisoquinolin-6-yl)-N-cyclopropyl-4-methylbenzamide

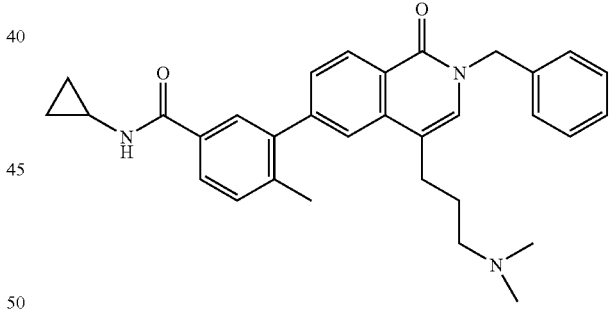

A solution of cyclopropylamine (0.18 mL) and the product from step ii) (120 mg) in THF (5 mL) was treated with isopropylmagnesium chloride (2N/THF, 1 mL) and stirred at room temperature for 1 hour. The reaction mixture was quenched with saturated aqueous ammonium chloride (10 mL), and extracted into ethyl acetate (2×10 mL). The organic layer was dried over magnesium sulfate, filtered and evaporated in vacuo. Purification by HPLC gave the title compound as a solid (31 mg).

MS: APCI (+ve) 494 (M+H)+

$^1$H NMR DMSO-d$_6$ 8.42 (d, J=4.2 Hz, 1H), 8.36 (d, J=8.3 Hz, 1H), 7.80 (d, J=8.5 Hz, 1H), 7.76 (s, 1H), 7.67 (s, 1H), 7.54 (d, J=7.2 Hz, 1H), 7.44 (s, 1H), 7.43 (d, J=7.2 Hz, 1H), 7.37-7.24 (m, 5H), 5.21 (s, 2H), 2.89-2.79 (m, 1H), 2.69 (t, J=7.5 Hz, 2H), 2 2.29 (s, 3H), 2.20 (t, J=7.2 Hz, 2H), 2.05 (s, 6H), 1.67 (quintet, J=7.2 Hz, 2H), 0.72-0.63 (m, 2H), 0.58-0.50 (m, 2H)

EXAMPLE 100

3-(2-Benzyl-1-oxo-4-(3-(pyrrolidin-1-yl)propyl)-1,2-dihydroisoquinolin-6-yl)-N-cyclopropyl-4-methyl-benzamide

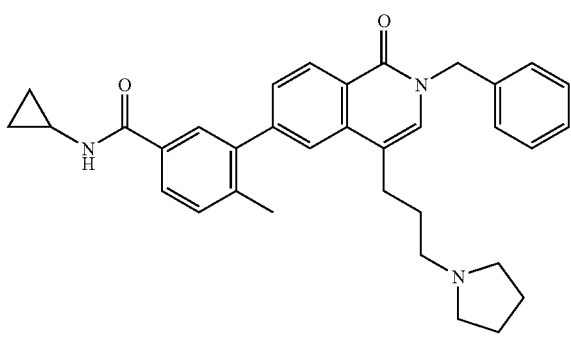

i) 3-(2-Benzyl-1-oxo-4-(3-pyrrolidin-1-yl-propyl)-1,2-dihydro-isoquinolin-6-yl)-4-methyl-benzoic acid, methyl ester

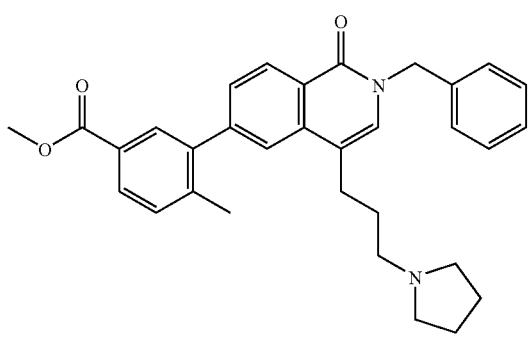

The sub-title compound was prepared according to the method of Example 99 step ii) using the product of Example 99 step i) and pyrrolidine.
MS: APCI (+ve) 495 (M+H)$^+$ ii) 3-(2-Benzyl-1-oxo-4-(3-(pyrrolidin-1-yl)propyl)-1,2-dihydroisoquinolin-6-yl)-N-cyclopropyl-4-methylbenzamide

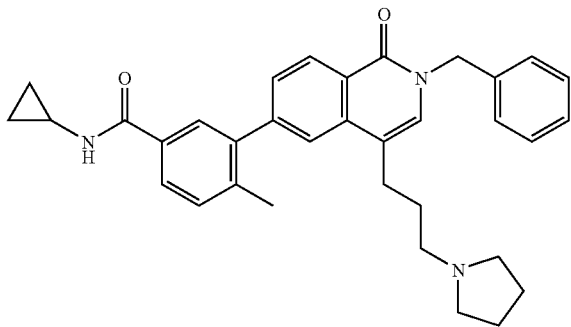

The title compound was prepared as a solid according to the method of Example 99 step iii) using the product of step i).
MS: APCI (+ve) 520 (M+H)$^+$
$^1$H NMR DMSO-d$_6$ 8.42 (d, J=4.1 Hz, 1H), 8.36 (d, J=8.2 Hz, 1H), 7.79 (d, J=7.9 Hz, 1H), 7.76 (s, 1H), 7.69 (s, 1H), 7.54 (d, J=8.6 Hz, 1H), 7.45 (s, 1H), 7.43 (d, J=9.4 Hz, 1H), 7.37-7.24 (m, 5H), 5.23-5.17 (m, 2H), 2.89-2.80 (m, 1H), 2.75-2.68 (m, 2H), 2.37 (t, J=6.9 Hz, 2H), 2.35-2.30 (m, 4H), 2.29 (s, 3H), 1.71 (quintet, J=7.4 Hz, 2H), 1.60-1.53 (m, 4H), 0.71-0.64 (m, 2H), 0.59-0.52 (m, 2H)

EXAMPLE 101

N-Cyclopropyl-3-(2-(cyclopropylmethyl)-4-((2-(dimethylamino)ethoxy)methyl)-1-oxo-1,2-dihydroisoquinolin-6-yl)-4-methylbenzamide

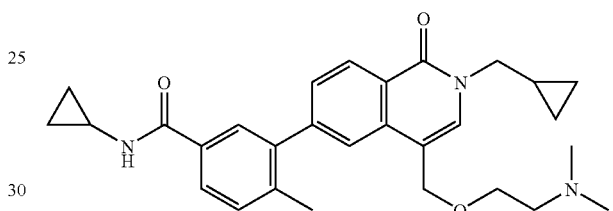

i) N-Cyclopropyl-3-(2-(cyclopropylmethyl)-4-(hydroxymethyl)-1-oxo-1,2-dihydroisoquinolin-6-yl)-4-methylbenzamide

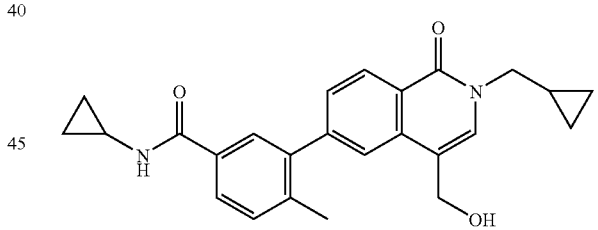

To a solution of the product of Example 37 step v) (500 mg) in THF (12 mL) at 0° C. was added borane tetrahydrofuran complex (1M/THF) (1.6 mL) dropwise. The ice bath was removed once gas evolution had ceased, and the reaction was stirred at room temperature for 1 hour. The reaction mixture was cooled to 0° C. and further borane tetrahydrofuran complex (1M/THF, 750 uL) was added, and the reaction was slowly warmed to room temperature and stirred for 1 hour. The reaction mixture was quenched with water (50 mL) and extracted into ethyl acetate (2×50 mL). The combined organics were dried over magnesium sulfate, filtered and evaporated in vacuo. Purification (SiO$_2$ chromatography, 3% methanol in dichloromethane) gave the sub-titled compound (300 mg).

MS: APCI (+ve) 403 (M+H)$^+$ ii) N-Cyclopropyl-3-(2-(cyclopropylmethyl)-4-((2-(dimethylamino)ethoxy)methyl)-1-oxo-1,2-dihydroisoquinolin-6-yl)-4-methylbenzamide

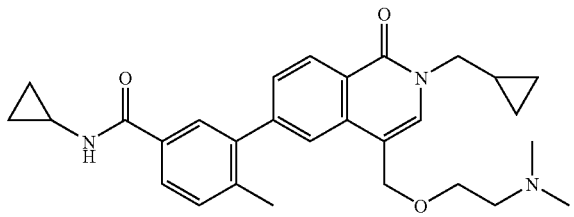

A solution of the product of step i) (130 mg) in dichloromethane (5 mL) was treated with (–/+)-10-camphorsulfonic acid (680 mg) and N,N-dimethylethanolamine (0.32 mL) and stirred at room temperature for 17 hours. 4N Hydrogen chloride in 1,4-dioxane (0.85 mL) was added and the reaction was stirred at room temperature for 6 hrs. Additional N,N-dimethylethanolamine (0.33 mL), (–/+)-10-camphorsulfonic acid (680 mg) and 4N hydrogen chloride in 1,4-dioxane (0.9 mL) were added and the reaction was stirred at room temperature for 60 hours. The reaction mixture was diluted with dichloromethane (100 mL) and washed with saturated sodium bicarbonate (100 mL) solution. The organics were evaporated in vacuo, and the crude product was purified by HPLC to yield the title compound as a solid (25.0 mg).

MS: APCI (+ve) 474 (M+H)$^+$ $^1$H NMR DMSO-d$_6$ 9.32 (s, 1H), 8.43 (s, 1H), 8.35 (d, J=8.2 Hz, 1H), 7.80 (d, J=7.9 Hz, 1H), 7.75 (d, J=7.4 Hz, 1H), 7.70 (s, 1H), 7.57 (d, J=8.2 Hz, 1H), 7.43 (d, J=8.2 Hz, 1H), 4.67 (s, 2H), 3.87 (d, J=6.9 Hz, 2H), 3.74 (s, 2H), 3.27 (s, 2H), 2.90-2.81 (m, 1H), 2.75 (s, 6H), 2.29 (s, 3H), 1.32-1.22 (m, 1H), 0.72-0.65 (m, 2H), 0.60-0.53 (m, 2H), 0.54-0.47 (m, 2H), 0.46-0.40 (m, 2H)

EXAMPLE 102

(S)—N-Cyclopropyl-3-(2-(cyclopropylmethyl)-4-((3-(hydroxymethyl)piperazin-1-yl)methyl)-1-oxo-1,2-dihydroisoquinolin-6-yl)-5-fluoro-4-methylbenzamide

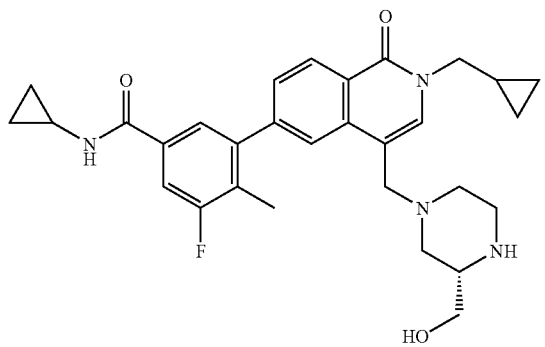

The title compound was prepared as a solid according to the method of Example 81 using the product of Example 75 step i) and (S)-2-(hydroxymethyl)-piperazine-1-carboxylic acid, tert-butyl ester.

MS: APCI (+ve) 519 (M+H)$^+$ $^1$H NMR DMSO-d$_6$ 8.54 (d, J=4.2 Hz, 1H), 8.35 (d, J=8.3 Hz, 1H), 7.97 (d, J=1.5 Hz, 1H), 7.69-7.64 (m, 2H), 7.54 (dd, J=8.2, 1.4 Hz, 1H), 7.49 (s, 1H), 4.46 (t, J=5.4 Hz, 1H), 3.93-3.79 (m, 2H), 3.55-3.44 (m, 2H), 3.28-3.20 (m, 2H), 2.89-2.77 (m, 3H), 2.75-2.67 (m, 1H), 2.63-2.52 (m, 2H), 2.25 (d, J=2.3 Hz, 3H), 2.07-1.87 (m, 2H), 1.67-1.58 (m, 1H), 1.31-1.19 (m, 1H), 0.74-0.66 (m, 2H), 0.60-0.54 (m, 2H), 0.52-0.45 (m, 2H), 0.44-0.38 (m, 2H)

EXAMPLE 103

N-Cyclopropyl-4-methyl-3-(4-((4-methyl-1,4-diazepan-1-yl)methyl)-2-(4-(methylsulfonyl)benzyl)-1-oxo-1,2-dihydroisoquinolin-6-yl)benzamide

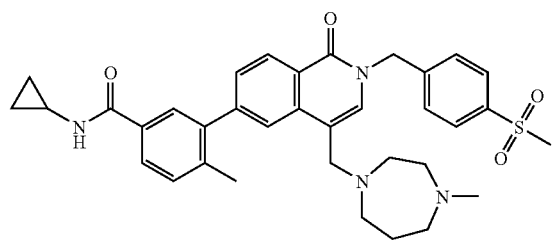

i) 6-Bromo-2-(4-methanesulfonyl-benzyl)-2H-isoquinolin-1-one

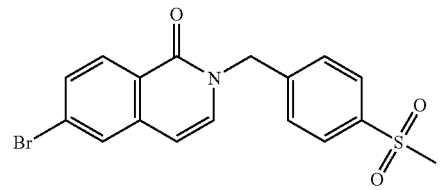

A mixture of intermediate 1 (3.0 g), potassium carbonate (3.70 g), 1-(chloromethyl)-4-(methylsulfonyl)benzene (2.74 g) and DMF (20 mL) was heated at 50° C. for 24 hours. The mixture was allowed to cool then poured into water (50 mL) and extracted with dichloromethane (100 mL). The extracts were combined, evaporated under reduced pressure and the residue purified (SiO$_2$ chromatography, eluting with 2% methanol in dichloromethane) to give the sub-titled compound (2.0 g).

$^1$H NMR DMSO-d$_6$ 8.12 (d, J=8.5 Hz, 1H), 7.99 (d, J=2.1 Hz, 1H), 7.89 (d, J=8.5 Hz, 2H), 7.68 (d, J=0.0 Hz, 1H), 7.68-7.65 (m, 1H), 7.54 (d, J=8.5 Hz, 2H), 6.69 (d, J=7.4 Hz, 1H), 5.28 (s, 2H), 3.18 (s, 3H)

ii) 6-Bromo-2-(4-(methylsulfonyl)benzyl)-1-oxo-1,2-dihydroisoquinoline-4-carbaldehyde

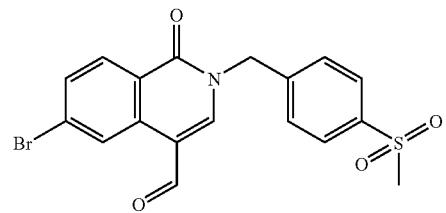

DMF (10 mL) was cooled in an ice bath and phosphorus oxychloride (1.4 mL) added over 20 seconds. The solution was stirred for 10 minutes at room temperature then a solution of the product of step i) (2.0 g) in DMF (4 mL) was added over 5 minutes. The mixture was heated at 95° C. for 16 hours then allowed to cool and poured onto ice/water. The mixture was then extracted into ethyl acetate (100 mL) the organics combined and evaporated under reduced pressure. The residue was purified (SiO$_2$ chromatography, eluting with 1:1 ethyl acetate:isohexane) to give the sub-titled compound (1.5 g).

MS: APCI (+ve) 420 (M+H)$^+$ iii) N-Cyclopropyl-3-(4-formyl-2-(4-(methylsulfonyl)benzyl)-1-oxo-1,2-dihydroisoquinolin-6-yl)-4-methylbenzamide

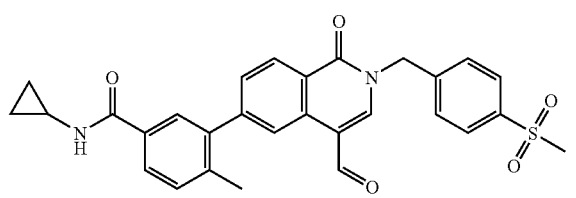

The sub-title compound was prepared by the method of Example 59 step iii) using the product of step ii).

MS: APCI (+ve) 515 (M+H)$^+$ iv) N-Cyclopropyl-4-methyl-3-(4-((4-methyl-1,4-diazepan-1-yl)methyl)-2-(4-(methylsulfonyl)benzyl)-1-oxo-1,2-dihydroisoquinolin-6-yl)benzamide

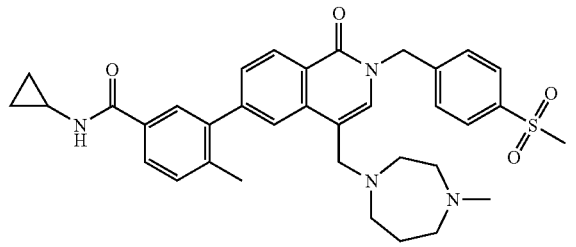

The title compound was prepared as a solid by the method of Example 59 step iv) using the product of step iii) and 1-methyl-1,4-diazepane.

MS: APCI (+ve) 613 (M+H)$^+$

1H NMR DMSO-d$_6$ 8.42 (d, J=4.1 Hz, 1H), 8.32 (d, J=8.2 Hz, 1H), 8.00 (d, J=1.3 Hz, 1H), 7.91 (dd, J=6.7, 1.8 Hz, 2H), 7.79-7.74 (m, 2H), 7.59 (s, 1H), 7.56-7.53 (m, 3H), 7.43 (d, J=7.9 Hz, 1H), 5.31 (s, 2H), 3.63 (s, 2H), 3.18 (s, 3H), 2.88-2.81 (m, 1H), 2.67-2.61 (m, 4H), 2.51-2.48 (m, 2H), 2.45-2.41 (m, 2H), 2.32 (s, 3H), 2.20 (s, 3H), 1.72-1.64 (m, 2H), 0.71-0.65 (m, 2H), 0.58-0.53 (m, 2H).

EXAMPLE 104

4-[6-(5-Cyclopropylcarbamoyl-2-methyl-phenyl)-4-(4-methyl-[1,4]diazepan-1-ylmethyl)-1-oxo-1H-isoquinolin-2-ylmethyl]-benzoic acid

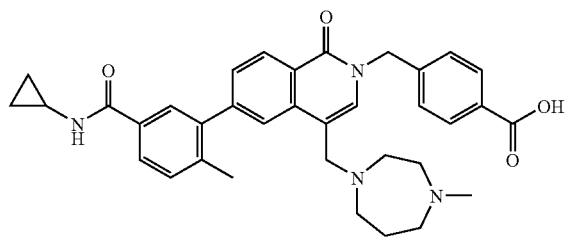

i) 4-((6-Bromo-1-oxoisoquinolin-2(1H)-yl)methyl)benzoic acid, methyl ester

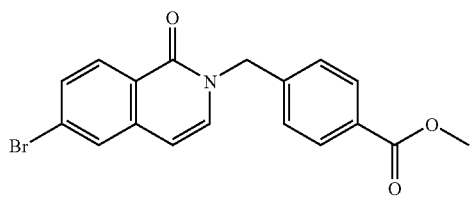

The sub-title compound was prepared by the method of intermediate 4, using intermediate 1 and 4-(bromomethyl)benzoic acid, methyl ester.

MS: APCI (+ve) 370/372 (M+H)$^+$ ii) 4-((6-Bromo-4-formyl-1-oxoisoquinolin-2(1H)-yl)methyl)benzoic acid, methyl ester

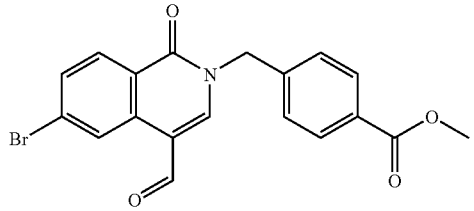

The sub-title compound was prepared by the method of Example 59 step ii) using the product of step i).

MS: APCI (+ve) 400/402 (M+H)$^+$ iii) 4-((6-Bromo-4-(4-methyl-1,4-diazepan-1-yl)methyl)-1-oxoisoquinolin-2(1H)-yl)methyl)benzoic acid, methyl ester

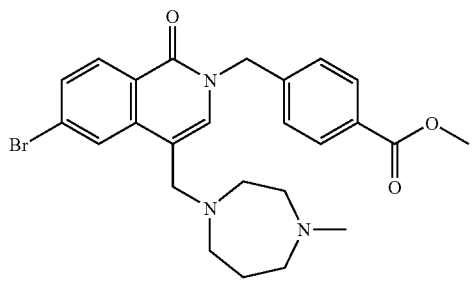

The sub-title compound was prepared by the method of Example 59 step iv) using the product of step ii) and 1-methyl-1,4-diazepane.
MS: APCI (+ve) 498/500 (M+H)+ iv) 4-((6-(5-(Cyclopropylcarbamoyl)-2-methylphenyl)-4-((4-methyl-1,4-diazepan-1-yl)methyl)-1-oxoisoquinolin-2(1H)-yl)methyl)benzoic acid, methyl ester

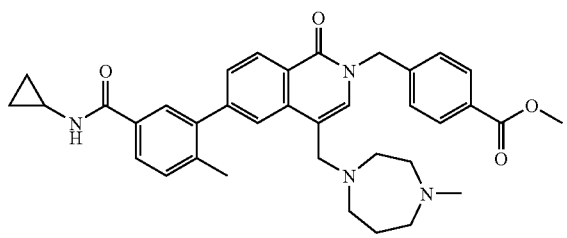

The sub-title compound was prepared by the method of Example 75 step i) using the product of step iv) and N-cyclopropyl-4-methyl-3-(4,4,5,5-tetramethyl-1,3,2-dioxaborolan-2-yl)benzamide.
MS: APCI (+ve) 593 (M+H)+ v) 4-((6-(5-(Cyclopropylcarbamoyl)-2-methylphenyl)-((4-methyl-1,4-diazepan-1-yl)methyl)-1-oxoisoquinolin-2(1H)-yl)methyl)benzoic acid

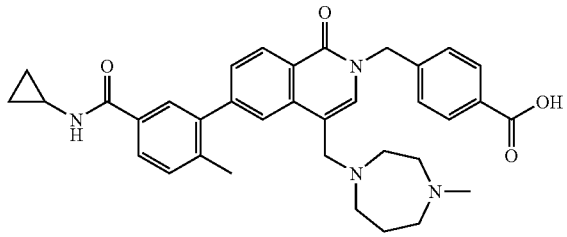

The title compound was prepared as a solid by the method of Example 60 step i) using the product of step iv).
MS: APCI (+ve) 579 (M+H)+
$^1$H NMR DMSO-d$_6$ 8.43 (d, J=4.0 Hz, 1H), 8.33 (d, J=8.3 Hz, 1H), 7.98 (s, 1H), 7.89 (d, J=8.1 Hz, 2H), 7.78 (d, J=8.7 Hz, 1H), 7.76 (s, 1H), 7.57-7.52 (m, 2H), 7.43 (d, J=7.9 Hz, 1H), 7.35 (d, J=8.3 Hz, 2H), 5.26 (s, 2H), 3.63 (s, 2H), 2.90-2.80 (m, 1H), 2.68-2.60 (m, 4H), 2.57-2.45 (m, 4H), 2.33 (s, 3H), 2.23 (s, 3H), 1.69 (t, J=5.7 Hz, 2H), 0.72-0.64 (m, 2H), 0.59-0.52 (m, 2H)

EXAMPLE 105

N-Cyclopropyl-3-(2-(4-(dimethylcarbamoyl)benzyl)-4-((4-methyl-1,4-diazepan-1-yl)methyl)-1-oxo-1,2-dihydroisoquinolin-6-yl)-4-methylbenzamide

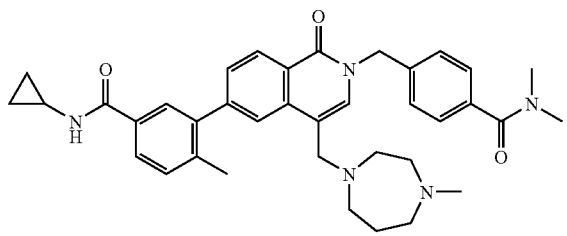

The title compound was prepared as a solid by the method of Example 47 step iv) using the product of Example 104 and dimethylamine.
MS: APCI (+ve) 606 (M+H)+
$^1$H NMR CDCL$_3$ 8.53 (s, 1H), 7.91 (d, J=10.8 Hz, 1H), 7.69 (d, J=19.2 Hz, 2H), 7.50-7.33 (m, 4H), 7.28 (d, J=10.3 Hz, 1H), 7.07 (d, J=9.7 Hz, 1H), 6.36 (s, 1H), 5.32-5.22 (m, 2H), 3.66-3.58 (m, 2H), 3.54-3.44 (m, 4H), 3.11 (s, 3H), 2.97 (s, 3H), 2.70 (s, 3H), 2.61 (s, 2H), 2.55-2.49 (m, 1H), 2.34 (s, 3H), 1.88-1.65 (m, 4H), 0.93-0.82 (m, 2H), 0.67-0.57 (m, 2H)

EXAMPLE 106

(R)—N-Cyclopropyl-3-(2-(cyclopropylmethyl)-4-((3-(methylamino)pyrrolidin-1-yl)methyl)-1-oxo-1,2-dihydroisoquinolin-6-yl)-5-fluoro-4-methylbenzamide

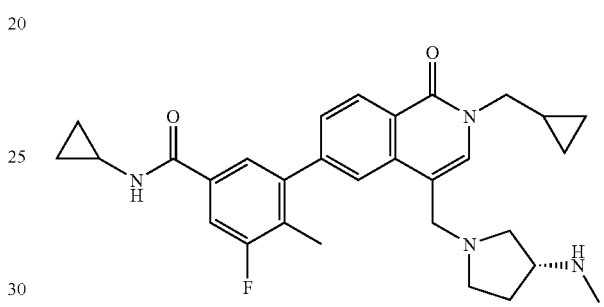

The title compound was prepared as a solid by the method of Example 75 step ii) using the product of Example 75 step i) and (R)—N-methylpyrrolidin-3-amine.
MS: APCI (+ve) 503 (M+H)+
$^1$H NMR DMSO-d$_6$ 8.53 (d, J=4.4 Hz, 1H), 8.34 (d, J=8.2 Hz, 1H), 7.91 (d, J=1.5 Hz, 1H), 7.66 (s, 1H), 7.66 (d, J=9.6 Hz, 1H), 7.54 (dd, J=8.2, 1.5 Hz, 1H), 7.51 (s, 1H), 3.86 (d, J=7.2 Hz, 2H), 3.67-3.59 (m, 2H), 3.06-2.98 (m, 1H), 2.90-2.82 (m, 1H), 2.72 (dd, J=9.1, 6.8 Hz, 1H), 2.53-2.47 (m, 2H), 2.24-2.18 (m, 1H), 2.21 (d, J=3.1 Hz, 3H), 2.17 (s, 3H), 1.95-1.84 (m, 1H), 1.48-1.38 (m, 1H), 1.31-1.21 (m, 1H), 0.73-0.66 (m, 2H), 0.60-0.54 (m, 2H), 0.52-0.45 (m, 2H), 0.45-0.39 (m, 2H)

EXAMPLE 107

(R)—N-Cyclopropyl-3-(2-(cyclopropylmethyl)-4-((3-methylpiperazin-1-yl)methyl)-1-oxo-1,2-dihydroisoquinolin-6-yl)-5-fluoro-4-methylbenzamide

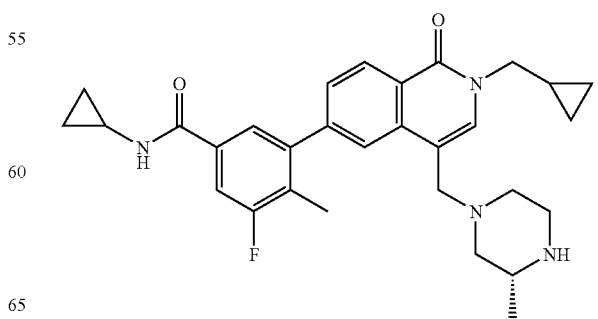

The title compound was prepared as a solid according to the method of Example 81 using the product of Example 75 step i) and (R)-2-methyl-piperazine-1-carboxylic acid tert, butyl ester and the product purified by SiO₂ chromatography (eluting with 93:5:2 dichloromethane:methanol:ammonia).

MS: APCI (+ve) 503 (M+H)⁺

1H NMR DMSO-d$_6$ 8.53 (d, J=4.1 Hz, 1H), 8.34 (d, J=8.2 Hz, 1H), 7.96 (d, J=1.3 Hz, 1H), 7.68-7.64 (m, 2H), 7.54 (dd, J=8.3, 1.7 Hz, 1H), 7.53 (s, 1H), 3.90-3.81 (m, 2H), 3.52-3.44 (m, 2H), 2.89-2.82 (m, 1H), 2.81-2.68 (m, 3H), 2.63-2.55 (m, 2H), 2.24 (d, J=2.3 Hz, 3H), 1.93-1.86 (m, 1H), 1.60-1.53 (m, 1H), 1.29-1.22 (m, 1H), 0.89 (d, J=6.4 Hz, 3H), 0.72-0.67 (m, 2H), 0.59-0.54 (m, 2H), 0.51-0.46 (m, 2H), 0.43-0.39 (m, 2H).

EXAMPLE 108

(S)—N-Cyclopropyl-3-(2-(cyclopropylmethyl)-4-((2-(hydroxymethyl)piperazin-1-yl)methyl)-1-oxo-1,2-dihydroisoquinolin-6-yl)-5-fluoro-4-methylbenzamide

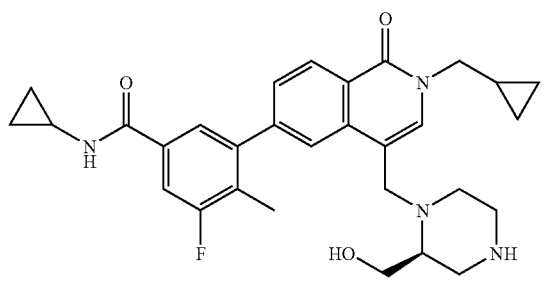

The product of Example 75 step i) (0.4 g), (S)-3-hydroxymethyl-piperazine-1-carboxylic acid, tert-butyl ester (0.83 g) and sodium triacetoxyborohydride (0.81 g) were stirred in dichloromethane (20 mL) at room temperature for 12 hours. A few drops of acetic acid were added and stirring continued for 12 hours. Methanol (10 ml) and sodium cyanoborohydride (0.70 g) were added and stirring continued for a further 12 hours. Methanol (10 ml) and 4M HCl in 1,4-dioxane (10 ml) were added and stirred for 12 hours. The volatiles were removed under vacuum, dilute aqueous ammonia was added and the mixture extracted into dichloromethane. The organics were combined and evaporated under reduced pressure. The residue was purified by HPLC to give the title compound (0.035 g) as a solid.

MS: APCI (+ve) 519 (M+H)⁺

1H NMR DMSO-d$_6$ 8.52 (d, J=4.4 Hz, 1H), 8.34 (d, J=8.2 Hz, 1H), 8.12 (d, J=1.3 Hz, 1H), 7.68-7.63 (m, 2H), 7.54 (dd, J=8.3, 1.7 Hz, 1H), 7.50 (s, 1H), 4.25 (d, J=13.3 Hz, 1H), 3.91-3.79 (m, 2H), 3.71-3.66 (m, 1H), 3.62-3.56 (m, 1H), 3.20 (d, J=13.1 Hz, 1H), 2.89-2.78 (m, 2H), 2.68-2.45 (m, 6H), 2.27 (d, J=2.3 Hz, 3H), 2.27-2.24 (m, 1H), 2.08-2.01 (m, 1H), 1.30-1.22 (m, 1H), 0.73-0.67 (m, 2H), 0.59-0.56 (m, 2H), 0.51-0.47 (m, 2H), 0.44-0.39 (m, 2H)

EXAMPLE 109

(R)-3-(4-((3-Aminopyrrolidin-1-yl)methyl)-2-(cyclopropylmethyl)-1-oxo-1,2-dihydroisoquinolin-6-yl)-N-cyclopropyl-5-fluoro-4-methylbenzamide

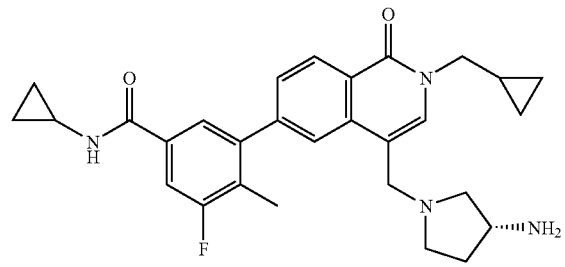

The title compound was prepared as a solid according to the method of Example 75 step ii) using the product of Example 75 step i) and (R)-pyrrolidin-3-ylamine.

MS: APCI (+ve) 489 (M+H)⁺

¹H NMR DMSO-d$_6$ 8.53 (d, J=4.4 Hz, 1H), 8.34 (d, J=8.2 Hz, 1H), 7.91 (d, J=1.5 Hz, 1H), 7.67 (s, 1H), 7.66 (d, J=8.7 Hz, 1H), 7.54 (dd, J=8.2, 1.5 Hz, 1H), 7.51 (s, 1H), 3.86 (d, J=7.2 Hz, 2H), 3.68-3.57 (m, 2H), 3.37-3.26 (m, 1H), 2.90-2.82 (m, 1H), 2.72-2.65 (m, 1H), 2.62-2.54 (m, 1H), 2.50-2.43 (m, 1H), 2.21 (d, J=2.3 Hz, 3H), 2.16 (dd, J=9.1, 4.7 Hz, 1H), 2.04-1.94 (m, 1H), 1.41-1.30 (m, 1H), 1.30-1.20 (m, 1H), 0.73-0.65 (m, 2H), 0.60-0.54 (m, 2H), 0.52-0.45 (m, 2H), 0.45-0.39 (m, 2H)

EXAMPLE 110

(R)—N-Cyclopropyl-3-(2-(cyclopropylmethyl)-1-oxo-4-((pyrrolidin-3-ylamino)methyl)-1,2-dihydroisoquinolin-6-yl)-5-fluoro-4-methylbenzamide

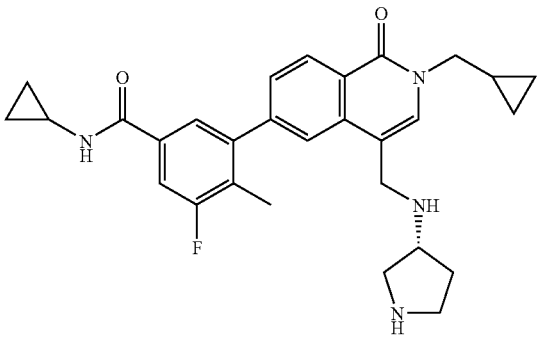

The title compound was isolated as a by-product from Example 109 as a solid.

MS: APCI (+ve) 489 (M+H)⁺

¹H NMR DMSO-d$_6$ 8.54 (d, J=4.1 Hz, 1H), 8.35 (d, J=8.2 Hz, 1H), 7.88 (d, J=1.5 Hz, 1H), 7.68 (s, 1H), 7.67 (d, J=9.2 Hz, 1H), 7.53 (d, J=8.6 Hz, 1H), 7.53 (s, 1H), 3.85 (d, J=7.7 Hz, 2H), 3.79 (d, J=3.7 Hz, 2H), 3.27-3.20 (m, 1H), 2.96-2.75 (m, 4H), 2.70-2.65 (m, 1H), 2.21 (d, J=2.1 Hz, 3H), 1.89-1.80 (m, 1H), 1.61-1.52 (m, 1H), 1.31-1.21 (m, 1H), 0.73-0.65 (m, 2H), 0.60-0.54 (m, 2H), 0.52-0.45 (m, 2H), 0.45-0.40 (m, 2H)

EXAMPLE 111

3-(4-((1S,4S)-2,5-Diazabicyclo[2.2.1]heptan-2-ylmethyl)-2-(cyclopropylmethyl)-1-oxo-1,2-dihydroisoquinolin-6-yl)-N-cyclopropyl-5-fluoro-4-methylbenzamide

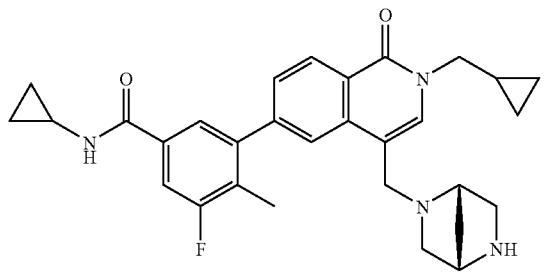

The title compound was prepared as a solid according to the method of Example 81 using the product of Example 75 step i) and (1S,4S)-2,5-diaza-bicyclo[2.2.1]heptane-2-carboxylic acid, tert-butyl ester.

MS: APCI (+ve) 501 (M+H)$^+$ $^1$H NMR DMSO-d$_6$ 8.54 (d, J=4.4 Hz, 1H), 8.34 (d, J=8.2 Hz, 1H), 7.95 (d, J=1.5 Hz, 1H), 7.67 (s, 1H), 7.66 (d, J=9.7 Hz, 1H), 7.53 (dd, J=8.2, 1.8 Hz, 1H), 7.48 (s, 1H), 3.93-3.79 (m, 2H), 3.80-3.65 (m, 2H), 3.40 (s, 1H), 3.35 (s, 1H), 3.00 (d, J=9.7 Hz, 1H), 2.90-2.82 (m, 1H), 2.75 (dd, J=9.2, 2.3 Hz, 1H), 2.68-2.64 (m, 1H), 2.37 (d, J=9.2 Hz, 1H), 2.22 (d, J=2.3 Hz, 3H), 1.65 (d, J=9.2 Hz, 1H), 1.39 (d, J=9.2 Hz, 1H), 1.30-1.20 (m, 1H), 0.73-0.66 (m, 2H), 0.60-0.53 (m, 2H), 0.52-0.45 (m, 2H), 0.45-0.38 (m, 2H)

EXAMPLE 112

N-Cyclopropyl-3-fluoro-4-methyl-5-(4-((4-methylpiperazin-1-yl)methyl)-2-(4-(methylsulfonyl)benzyl)-1-oxo-1,2-dihydroisoquinolin-6-yl)benzamide

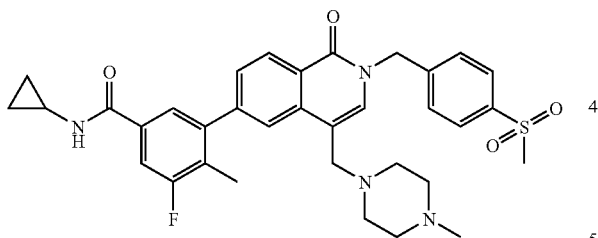

i) N-Cyclopropyl-3-fluoro-5-(4-formyl-2-(4-(methylsulfonyl)benzyl)-1-oxo-1,2-dihydroisoquinolin-6-yl)-4-methylbenzamide

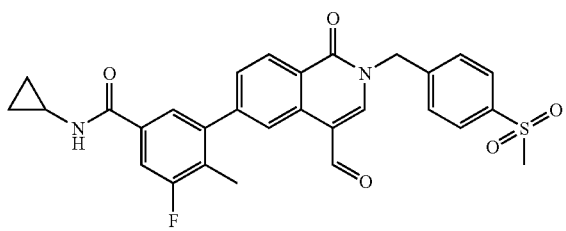

The sub-title compound was prepared by the method of Example 60 step iii) using product of Example 103 step ii) and N-cyclopropyl-3-fluoro-4-methyl-5-(4,4,5,5-tetramethyl-1,3,2-dioxaborolan-2-yl)benzamide.

MS: APCI (+ve) 533 (M+H)$^+$ ii) N-Cyclopropyl-3-fluoro-4-methyl-5-(4-((4-methylpiperazin-1-yl)methyl)-2-(4-(methylsulfonyl)benzyl)-1-oxo-1,2-dihydroisoquinolin-6-yl)benzamide

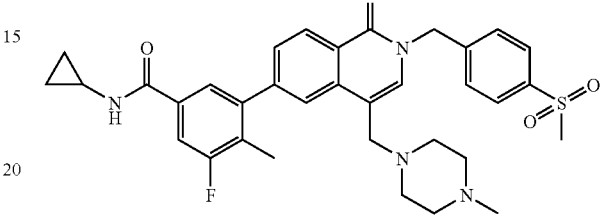

The title compound was prepared by the method of Example 59 step iv) using product of example 112 step i) and 1-methyl-piperazine.

MS: APCI (+ve) 617 (M+H)$^+$

1H NMR DMSO-d$_6$ 8.53 (d, J=4.1 Hz, 1H), 8.34 (d, J=8.2 Hz, 1H), 8.00 (d, J=1.5 Hz, 1H), 7.91 (d, J=8.5 Hz, 2H), 7.68-7.64 (m, 2H), 7.63 (s, 1H), 7.59-7.53 (m, 3H), 5.31 (s, 2H), 3.52 (s, 2H), 3.19 (s, 3H), 2.88-2.82 (m, 1H), 2.47-2.27 (m, 8H), 2.25 (d, J=2.3 Hz, 3H), 2.13 (s, 3H), 0.73-0.67 (m, 2H), 0.60-0.55 (m, 2H)

EXAMPLE 113

(R)—N-Cyclopropyl-3-fluoro-5-(4-((3-(hydroxymethyl)piperazin-1-yl)methyl)-2-(4-(methylsulfonyl)benzyl)-1-oxo-1,2-dihydroisoquinolin-6-yl)-4-methylbenzamide

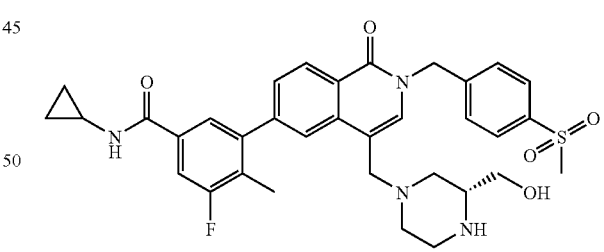

The title compound was prepared as a solid according to the method of Example 81 using the product of Example 112 step i) and (R)-2-(hydroxymethyl)-piperazine-1-carboxylic acid, tert-butyl ester.

MS: APCI (+ve) 633 (M+H)$^+$

1H NMR DMSO-d$_6$ 8.54 (d, J=4.1 Hz, 1H), 8.34 (d, J=8.2 Hz, 1H), 8.00 (d, J=1.3 Hz, 1H), 7.91 (d, J=8.5 Hz, 2H), 7.69-7.61 (m, 3H), 7.59-7.53 (m, 3H), 5.31 (s, 2H), 4.50 (t, J=5.0 Hz, 1H), 3.56-3.43 (m, 2H), 3.28-3.16 (m, 6H), 2.89-2.79 (m, 3H), 2.76-2.70 (m, 1H), 2.63-2.54 (m, 2H), 2.25 (d, J=2.1 Hz, 3H), 1.97-1.90 (m, 1H), 1.66-1.59 (m, 1H), 0.73-0.67 (m, 2H), 0.59-0.55 (m, 2H)

EXAMPLE 114

N-Cyclopropyl-4-methyl-3-(4-((4-methyl-1,4-diazepan-1-yl)methyl)-2-(4-(methylsulfonylcarbamoyl)benzyl)-1-oxo-1,2-dihydroisoquinolin-6-yl)benzamide

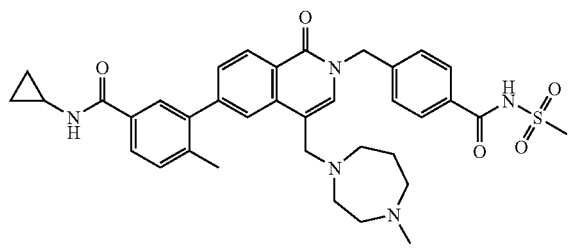

The title compound was prepared as a solid by the method of Example 47 step iv) using the product of Example 104 and methanesulphonamide.

MS: APCI (+ve) 656 (M+H)+

¹H NMR DMSO-$d_6$ 8.45 (d, J=3.8 Hz, 1H), 8.35 (d, J=8.2 Hz, 1H), 7.93-7.88 (m, 3H), 7.82-7.79 (m, 2H), 7.58 (d, J=8.5 Hz, 1H), 7.54 (s, 1H), 7.43 (d, J=8.5 Hz, 1H), 7.27 (d, J=7.9 Hz, 2H), 5.24 (s, 2H), 3.70 (s, 2H), 3.22 (s, 2H), 3.09 (s, 2H), 2.89-2.79 (m, 1H), 2.87 (s, 3H), 2.82 (s, 2H), 2.75 (s, 3H), 2.71 (s, 2H), 2.34 (s, 3H), 1.90 (s, 2H), 0.73-0.65 (m, 2H), 0.59-0.54 (m, 2H)

EXAMPLE 115

(R)—N-Cyclopropyl-3-fluoro-5-(4-((3-(hydroxymethyl)-4-methylpiperazin-1-yl)methyl)-2-(4-(methylsulfonyl)benzyl)-1-oxo-1,2-dihydroisoquinolin-6-yl)-4-methylbenzamide

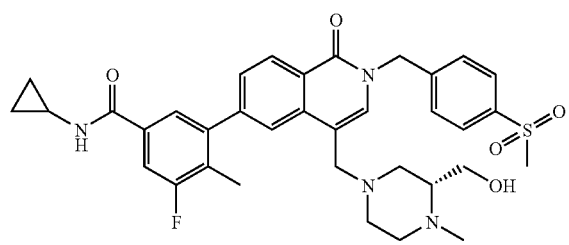

The title compound was prepared as a solid by the method of Example 87 using product of Example 113.

MS: APCI (+ve) 647 (M+H)+

1H NMR DMSO-$d_6$ 8.53 (d, J=4.0 Hz, 1H), 8.33 (d, J=8.3 Hz, 1H), 8.00 (d, J=1.2 Hz, 1H), 7.90 (d, J=8.5 Hz, 2H), 7.69-7.63 (m, 3H), 7.60-7.51 (m, 3H), 5.32 (s, 2H), 4.39 (t, J=5.3 Hz, 1H), 3.59-3.45 (m, 3H), 3.25-3.19 (m, 1H), 3.18 (s, 3H), 2.95-2.80 (m, 2H), 2.75-2.62 (m, 2H), 2.25 (d, J=2.1 Hz, 3H), 2.17 (s, 3H), 2.11-2.04 (m, 2H), 1.96-1.88 (m, 1H), 1.86-1.78 (m, 1H), 0.74-0.67 (m, 2H), 0.61-0.54 (m, 2H)

EXAMPLE 116

(S)—N-Cyclopropyl-3-(2-(cyclopropylmethyl)-4-((3-ethylpiperazin-1-yl)methyl)-1-oxo-1,2-dihydroisoquinolin-6-yl)-5-fluoro-4-methylbenzamide

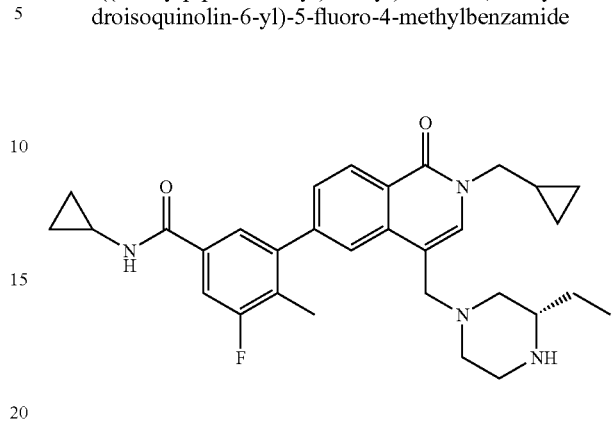

The title compound was prepared as a solid according to the method of Example 81 using the product of Example 75 step i) and (S)-2-ethyl-piperazine-1-carboxylic acid, tert-butyl ester.

MS: APCI (+ve) 517 (M+H)+

1H NMR DMSO-$d_6$ 8.53 (d, J=4.1 Hz, 1H), 8.34 (d, J=8.5 Hz, 1H), 7.95 (d, J=1.5 Hz, 1H), 7.68-7.64 (m, 2H), 7.57-7.52 (m, 1H), 7.48 (s, 1H), 3.92-3.79 (m, 2H), 3.48 (s, 2H), 2.89-2.83 (m, 1H), 2.81-2.75 (m, 2H), 2.71-2.66 (m, 1H), 2.60-2.53 (m, 1H), 2.41-2.34 (m, 1H), 2.24 (d, J=2.3 Hz, 3H), 1.95-1.88 (m, 1H), 1.63-1.57 (m, 1H), 1.28-1.21 (m, 3H), 0.80 (t, J=7.4 Hz, 3H), 0.72-0.67 (m, 2H), 0.58-0.54 (m, 2H), 0.50-0.45 (m, 2H), 0.43-0.39 (m, 2H)

EXAMPLE 117

(S)—N-Cyclopropyl-3-(2-(cyclopropylmethyl)-4-((3-(2-hydroxyethyl)piperazin-1-yl)methyl)-1-oxo-1,2-dihydroisoquinolin-6-yl)-5-fluoro-4-methylbenzamide

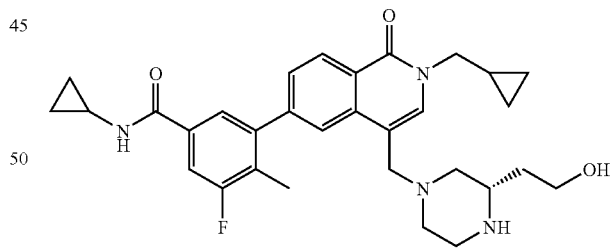

The title compound was prepared as a solid according to the method of Example 81 using the product of Example 75 step i) and (S)-2-(hydroxy-ethyl)-piperazine-1-carboxylic acid, tert-butyl ester.

MS: APCI (+ve) 533 (M+H)+

1H NMR DMSO-$d_6$ 8.53 (d, J=4.4 Hz, 1H), 8.34 (d, J=8.5 Hz, 1H), 7.94 (d, J=1.5 Hz, 1H), 7.68-7.64 (m, 2H), 7.54 (dd, J=8.2, 1.8 Hz, 1H), 7.49 (s, 1H), 4.41-4.36 (m, 1H), 3.92-3.79 (m, 2H), 3.51-3.40 (m, 4H), 2.90-2.83 (m, 1H), 2.80-2.56 (m, 4H), 2.24 (d, J=2.1 Hz, 3H), 1.95-1.87 (m, 2H), 1.68-1.61 (m, 1H), 1.43-1.34 (m, 2H), 1.29-1.22 (m, 1H), 0.73-0.66 (m, 2H), 0.59-0.55 (m, 2H), 0.51-0.47 (m, 2H), 0.44-0.40 (m, 2H)

EXAMPLE 118

(S)—N-Cyclopropyl-3-(2-(cyclopropylmethyl)-4-((2-methylpiperazin-1-yl)methyl)-1-oxo-1,2-dihydroisoquinolin-6-yl)-5-fluoro-4-methylbenzamide

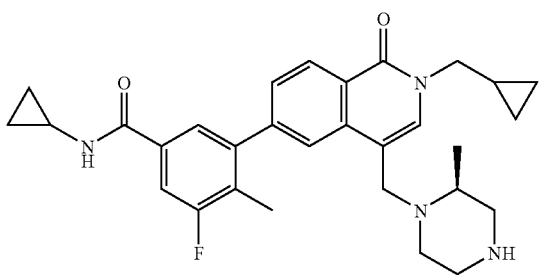

The product of Example 75 step i) (200 mg), (S)-3-methyl-piperazine-1-carboxylic acid, tert-butyl ester (287 mg) and titanium(IV) isopropoxide (3 mL) were stirred at room temperature for 15 hours. Methanol (10 mL) was then added followed by sodium cyanoborohydride (90 mg) and the mixture stirred for 15 hours. Methanol (10 mL) was then added followed by 4M HCl in 1,4-dioxane (10 mL) and the mixture stirred overnight at room temperature. The mixture was then poured into aqueous dilute ammonia and ethyl acetate added. The organics were decanted and evaporated to dryness. The residue was purified by HPLC to give the title compound as a solid (40 mg).

MS: APCI (+ve) 503 (M+H)$^+$

1H NMR DMSO-d$_6$ 8.53 (d, J=4.1 Hz, 1H), 8.34 (d, J=8.2 Hz, 1H), 8.03 (s, 1H), 7.71-7.64 (m, 2H), 7.55 (dd, J=8.2, 1.3 Hz, 1H), 7.51 (s, 1H), 4.16 (d, J=12.8 Hz, 1H), 3.91-3.80 (m, 2H), 3.05 (d, J=12.8 Hz, 1H), 2.89-2.83 (m, 1H), 2.82-2.76 (m, 1H), 2.73-2.66 (m, 1H), 2.59-2.52 (m, 2H), 2.43-2.33 (m, 2H), 2.26 (d, J=2.1 Hz, 3H), 2.04-1.98 (m, 1H), 1.29-1.22 (m, 1H), 1.09 (d, J=5.9 Hz, 3H), 0.73-0.67 (m, 2H), 0.59-0.54 (m, 2H), 0.51-0.47 (m, 2H), 0.44-0.40 (m, 2H)

EXAMPLE 119

3-(4-(((2R,4S)-4-Amino-2-(hydroxymethyl)pyrrolidin-1-yl)methyl)-2-(cyclopropylmethyl)-1-oxo-1,2-dihydroisoquinolin-6-yl)-N-cyclopropyl-5-fluoro-4-methylbenzamide

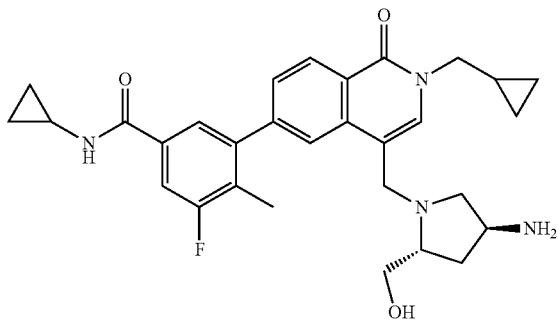

The title compound was prepared as a solid according to the method of Example 81 using the product of Example 75 step i) and ((3S,5R)-5-hydroxymethyl-pyrrolidin-3-yl)-carbamic acid, tert-butyl ester.

MS: APCI (+ve) 519 (M+H)$^+$ $^1$H NMR DMSO-d$_6$ 8.52 (d, J=4.4 Hz, 1H), 8.34 (d, J=8.5 Hz, 1H), 8.07 (d, J=1.5 Hz, 1H), 7.69-7.63 (m, 2H), 7.53 (dd, J=8.2, 1.5 Hz, 1H), 7.51 (s, 1H), 4.47-4.42 (m, 1H), 4.22 (d, J=12.8 Hz, 1H), 3.91-3.80 (m, 2H), 3.40-3.21 (m, 3H), 3.21-3.12 (m, 1H), 2.90-2.82 (m, 2H), 2.79-2.72 (m, 1H), 2.22 (d, J=2.1 Hz, 3H), 1.99-1.93 (m, 1H), 1.81-1.72 (m, 1H), 1.58-1.49 (m, 1H), 1.31-1.22 (m, 1H), 0.73-0.67 (m, 2H), 0.60-0.55 (m, 2H), 0.52-0.46 (m, 2H), 0.46-0.39 (m, 2H)

EXAMPLE 120

(R)-3-(4-((2-(Aminomethyl)pyrrolidin-1-yl)methyl)-2-(cyclopropylmethyl)-1-oxo-1,2-dihydroisoquinolin-6-yl)-N-cyclopropyl-5-fluoro-4-methylbenzamide

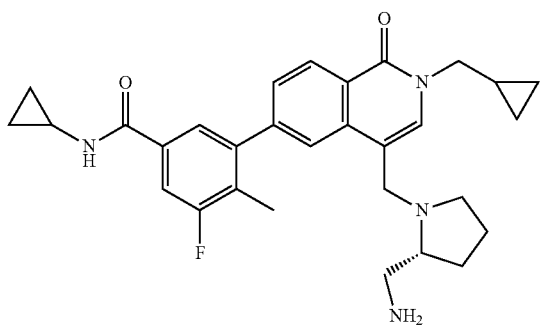

The title compound was prepared as a solid according to the method of Example 81 using the product of Example 75 step i) and (R)-1-pyrrolidine-2-ylmethyl-carbamic acid tert-butyl ester hydrochloride. The product was purified using SCX ion-exchange chromatography (eluting with methanol followed by 3N ammonia in methanol), followed by HPLC.

MS: APCI (+ve) 503 (M+H)$^+$ $^1$H NMR DMSO-d$_6$ 8.62 (d, J=4.1 Hz, 1H), 8.34 (d, J=8.2 Hz, 1H), 7.98 (d, J=1.5 Hz, 1H), 7.69-7.63 (m, 2H), 7.55 (dd, J=8.3, 1.7 Hz, 1H), 7.53 (s, 1H), 4.13 (d, J=13.1 Hz, 1H), 3.91-3.80 (m, 2H), 3.29 (d, J=13.8 Hz, 1H), 2.89-2.82 (m, 1H), 2.82-2.76 (m, 1H), 2.64-2.58 (m, 1H), 2.54-2.44 (m, 2H), 2.23-2.21 (m, 1H), 2.21 (d, J=2.8 Hz, 3H), 1.91-1.80 (m, 1H), 1.67-1.48 (m, 3H), 1.31-1.19 (m, 1H), 0.73-0.66 (m, 2H), 0.60-0.54 (m, 2H), 0.52-0.45 (m, 2H), 0.45-0.38 (m, 2H)

EXAMPLE 121

N-Cyclopropyl-4-methyl-3-(1-oxo-2-(1-phenylethyl)-1,2-dihydroisoquinolin-6-yl)benzamide

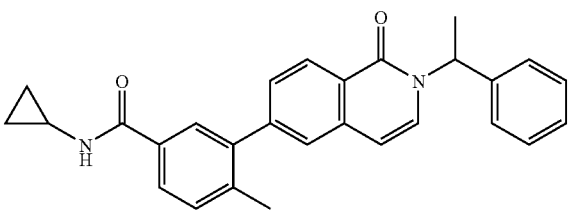

A mixture of the product of Example 11 (200 mg), potassium carbonate (260 mg) and (1-bromoethyl)benzene (0.100 mL) in DMF (2 mL) was stirred at 80° C. for 17 hours. Further (1-bromoethyl)benzene (0.100 mL) and potassium carbonate (260 mg) was added and stirred at 80° C. for a further 24 hours. Additional (1-bromoethyl)benzene (0.5 mL) and potassium carbonate (500 mg) were added and the reaction stirred at 80° C. for a further 48 hours. The reaction mixture was filtered and purified by HPLC to yield the title compound (14 mg) as a solid.

MS: APCI (+ve) 423 (M+H)$^+$ $^1$H NMR DMSO-d$_6$ 8.43 (d, J=3.8 Hz, 1H), 8.32 (d, J=8.2 Hz, 1H), 7.79 (dd, J=7.8, 1.7 Hz, 1H), 7.74 (s, 1H), 7.65 (d, J=1.3 Hz, 1H), 7.52 (dd, J=8.2, 1.5 Hz, 1H), 7.45-7.39 (m, 2H), 7.39-7.35 (m, 4H), 7.33-7.27 (m, 1H), 6.72-6.68 (m, 1H), 6.34 (q, J=7.1 Hz, 1H), 2.88-2.81 (m, 1H), 2.28 (s, 3H), 1.76 (d, J=7.2 Hz, 3H), 0.71-0.64 (m, 2H), 0.58-0.53 (m, 2H)

EXAMPLE 122

N-Cyclopropyl-3-(2-cyclopropylmethyl-1-oxo-1,2-dihydro-isoquinolin-6-yl)-4-methylbenzamide

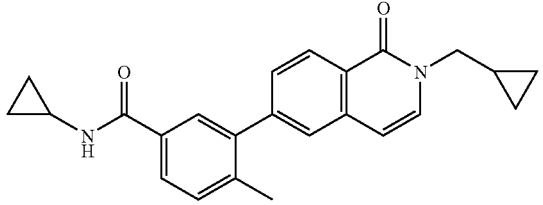

A mixture of the product of Example 11 (100 mg), potassium carbonate (174 mg) and (bromomethyl)cyclopropane (63 mg) in DMF (2 mL) was stirred at room temperature for 16 hours and at 70° C. for 24 hours. Further (bromomethyl)cyclopropane (300 mg) was added and the mixture heated at 70° C. for a further 24 hours. The reaction mixture was filtered and purified by HPLC to give the title compound (70 mg) as a solid.

MS: APCI (+ve) 373 (M+H)$^+$

1H NMR DMSO-d$_6$ 8.44 (d, J=4.1 Hz, 1H), 8.29 (d, J=8.1 Hz, 1H), 7.79 (dd, J=7.9, 1.8 Hz, 1H), 7.75 (d, J=1.5 Hz, 1H), 7.66 (d, J=1.3 Hz, 1H), 7.57 (d, J=7.4 Hz, 4H), 7.50 (dd, J=8.3, 1.4 Hz, 5H), 7.42 (d, J=7.9 Hz, 3H), 6.68 (d, J=7.2 Hz, 3H), 3.86 (d, J=7.2 Hz, 2H), 2.87-2.80 (m, 1H), 2.29 (s, 3H), 1.31-1.21 (m, 1H), 0.71-0.65 (m, 2H), 0.59-0.52 (m, 2H), 0.51-0.45 (m, 2H), 0.44-0.38 (m, 2H)

EXAMPLE 123

N-Cyclopropyl-3-(2-(2-ethylbutyl)-1-oxo-1,2-dihydroisoquinolin-6-yl)-4-methylbenzamide

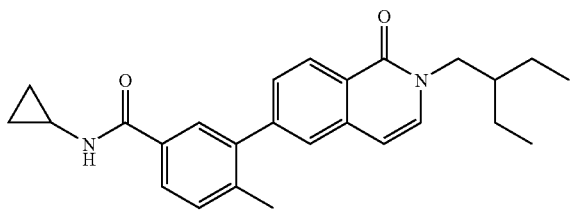

To a solution of the product of Example 11 (100 mg) in DMF (3 mL) was added potassium carbonate (217 mg) followed by 3-(bromomethyl)pentane (0.44 mL) and the mixture stirred at 80° C. for 17 hrs. The reaction mixture was filtered and purified by HPLC to give the title compound (55.0 mg) as a solid.

MS: APCI (+ve) 403 (M+H)$^+$ $^1$H NMR DMSO-d$_6$ 8.40 (s, 1H), 8.24 (d, J=7.9 Hz, 1H), 7.76 (d, J=7.7 Hz, 1H), 7.72 (s, 1H), 7.62 (s, 1H), 7.50-7.41 (m, 2H), 7.38 (d, J=7.7 Hz, 1H), 6.63 (d, J=7.2 Hz, 1H), 3.86 (d, J=6.9 Hz, 2H), 2.87-2.77 (m, 1H), 2.26 (s, 3H), 1.83-1.74 (m, 1H), 1.26 (t, J=6.8 Hz, 4H), 0.84 (t, J=7.2 Hz, 6H), 0.69-0.59 (m, 2H), 0.59-0.48 (m, 2H)

EXAMPLE 124

3-(2-(Cyclobutylmethyl)-1-oxo-1,2-dihydroisoquinolin-6-yl)-N-cyclopropyl-4-methylbenzamide

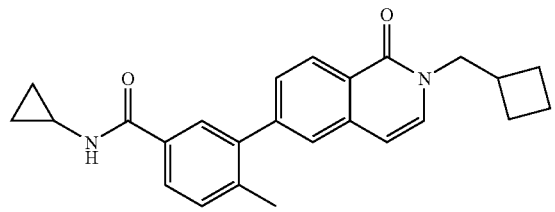

The title compound was prepared as a solid according to the method of Example 123 using the product of Example 11 and (bromomethyl)cyclobutane.

MS: APCI (+ve) 387 (M+H)$^+$ $^1$H NMR DMSO-d$_6$ 8.43 (d, J=3.3 Hz, 1H), 8.28 (d, J=8.2 Hz, 1H), 7.79 (d, J=7.9 Hz, 1H), 7.75 (s, 1H), 7.64 (s, 1H), 7.54-7.47 (m, 2H), 7.41 (d, J=7.9 Hz, 1H), 6.65 (d, J=7.2 Hz, 1H), 4.03 (d, J=7.4 Hz, 2H), 2.90-2.81 (m, 1H), 2.81-2.71 (m, 1H), 2.29 (s, 3H), 2.00-1.90 (m, 2H), 1.90-1.76 (m, 4H), 0.72-0.62 (m, 2H), 0.62-0.52 (m, 2H)

EXAMPLE 125

N-Cyclopropyl-4-methyl-3-(1-oxo-2-piperidin-4-ylmethyl-1,2-dihydro-isoquinolin-6-yl)-benzamide

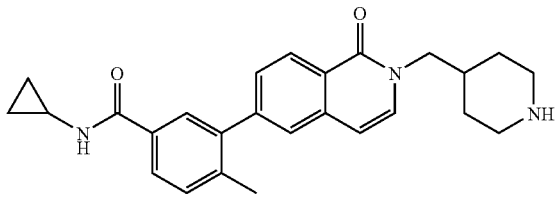

i) 4-[6-(5-Cyclopropylcarbamoyl-2-methyl-phenyl)-1-oxo-1H-isoquinolin-2-ylmethyl]-piperidine-1-carboxylic acid, tert-butyl ester

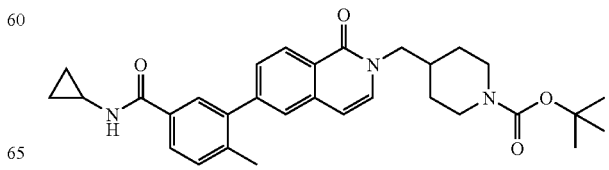

Example 11 (0.40 g), cesium carbonate (0.80 g), 4-bromomethyl-piperidine-1-carboxylic acid tert-butyl ester (0.42 g) and DMF (5 mL) were stirred and heated at 50° C. for 12 hours. The mixture was allowed to cool then added water (20 mL) and extracted with dichloromethane (100 mL). The organics were combined and evaporated under reduced pressure. The residue was purified by $SiO_2$ chromatography (eluting with 1% MeOH in dichloromethane) to give the sub-titled compound as a solid (0.20 g).

1H NMR $CDCl_3$ 8.46 (d, J=7.9 Hz, 1H), 7.67 (dd, J=7.8, 1.9 Hz, 1H), 7.63 (d, J=1.8 Hz, 1H), 7.44 (s, 1H), 7.42 (d, J=1.5 Hz, 1H), 7.35 (d, J=7.7 Hz, 1H), 7.04 (d, J=7.4 Hz, 1H), 6.49 (d, J=7.2 Hz, 1H), 6.24 (s, 1H), 4.20 ii) N-Cyclopropyl-4-methyl-3-(1-oxo-2-piperidin-4-ylmethyl-1,2-dihydro-isoquinolin-6-yl)-benzamide

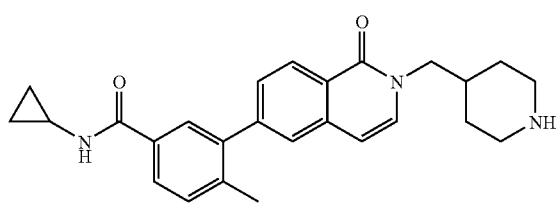

To a solution of the product of step i) (170 mg) in methanol (5 mL) was added 4M HCl in 1,4-dioxane (5 mL). The solution was stirred at room temperature for 2 hours. The volatiles were removed under vacuum and the residue was purified by HPLC to yield the title compound as a solid (25 mg).

MS: APCI (+ve) 416 (M+H)+

1H NMR DMSO-$d_6$ 8.45 (s, 1H), 8.28 (d, J=8.2 Hz, 1H), 7.80 (d, J=7.7 Hz, 1H), 7.76 (s, 1H), 7.66 (s, 1H), 7.50 (t, J=7.6 Hz, 2H), 7.42 (d, J=7.7 Hz, 1H), 6.66 (d, J=6.9 Hz, 1H), 3.87 (d, J=6.4 Hz, 2H), 3.05-2.94 (m, 2H), 2.89-2.82 (m, 1H), 2.28 (s, 3H), 2.00-1.91 (m, 1H), 1.57-1.47 (m, 2H), 1.28-1.16 (m, 2H), 0.72-0.65 (m, 2H), 0.60-0.53 (m, 2H)

EXAMPLE 126

N-Cyclopropyl-4-methyl-3-(1-oxo-2-(pyridin-2-ylmethyl)-1,2-dihydroisoquinolin-6-yl)benzamide

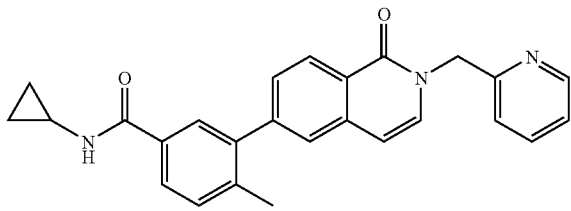

The title compound was prepared according to the method of Example 123 using the product of Example 11 and 2-(chloromethyl)pyridine hydrochloride.

MS: APCI (+ve) 410 (M+H)+

1H NMR DMSO-$d_6$ 8.52-8.49 (m, 1H), 8.45-8.41 (m, 1H), 8.26 (d, J=8.2 Hz, 1H), 7.82-7.74 (m, 3H), 7.69 (s, 1H), 7.62 (dd, J=7.3, 1.9 Hz, 1H), 7.53-7.49 (m, 1H), 7.42 (d, J=7.9 Hz, 1H), 7.32-7.24 (m, 2H), 6.72 (d, J=7.2 Hz, 1H), 5.30 (s, 2H), 2.89-2.81 (m, 1H), 2.29 (s, 3H), 0.72-0.65 (m, 2H), 0.59-0.53 (m, 2H)

EXAMPLE 127

N-Cyclopropyl-3-[2-cyclopropylmethyl-4-(5-hydroxymethyl-[1,4]diazepan-1-ylmethyl)-1-oxo-1,2-dihydro-isoquinolin-6-yl]-5-fluoro-4-methyl-benzamide

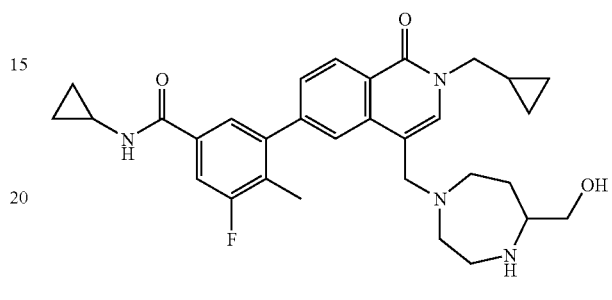

i) [1,4]Diazepan-5-yl-methanol

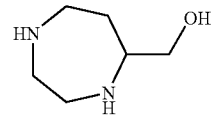

To a solution of (1,4-dibenzyl-1,4-diazepan-5-yl)methanol (500 mg) (prepared as described in *Chin. Chem. Lett.*, 2001, 12, 951) in methanol (10 mL) was added 5% wt. palladium on charcoal (171 mg) and the mixture stirred under a 5 bar hydrogen atmosphere for 16 hours. The reaction mixture was filtered through celite and the liquors concentrated to dryness to give the sub-title compound (210 mg) as a colourless oil.

1H NMR DMSO-$d_6$ 3.25 (dd, J=10.5, 5.1 Hz, 1H), 3.12 (dd, J=10.4, 7.9 Hz, 1H), 2.93-2.86 (m, 1H), 2.79-2.48 (m, 6H), 1.73-1.60 (m, 1H), 1.24-1.11 (m, 1H)

ii) N-Cyclopropyl-3-[2-cyclopropylmethyl-4-(5-hydroxymethyl-[1,4]diazepan-1-ylmethyl)-1-oxo-1,2-dihydro-isoquinolin-6-yl]-5-fluoro-4-methyl-benzamide

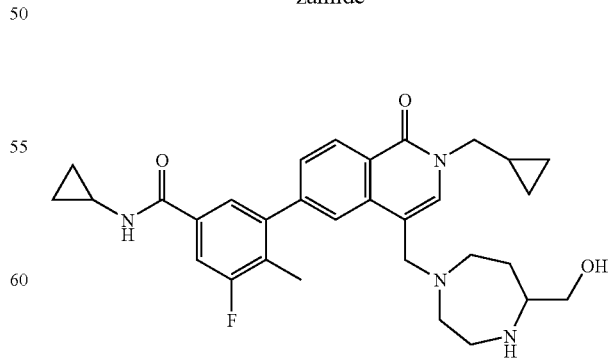

The title compound was prepared as a solid according to the method of Example 75 step ii) using the product of Example 75 step i) and the product of step i).

MS: APCI (+ve) 533 (M+H)+

1H NMR CDCl₃ 8.50 (d, J=8.3 Hz, 1H), 8.08 (d, J=1.5 Hz, 1H), 7.61 (s, 1H), 7.42 (dd, J=8.4, 1.6 Hz, 1H), 7.38 (d, J=9.8 Hz, 1H), 7.11 (s, 1H), 6.44 (s, 1H), 3.90 (d, J=7.1 Hz, 2H), 3.66 (s, 2H), 3.53 (dd, J=10.9, 3.9 Hz, 1H), 3.25 (t, J=10.2 Hz, 1H), 3.14-2.96 (m, 2H), 2.93-2.84 (m, 1H), 2.82-2.64 (m, 4H), 2.25 (d, J=2.5 Hz, 3H), 1.78-1.67 (m, 1H), 1.49-1.37 (m, 1H), 1.34-1.27 (m, 1H), 0.92-0.84 (m, 2H), 0.67-0.58 (m, 4H), 0.48-0.40 (m, 2H)

EXAMPLE 128

(S)-3-(4-((2-(Aminomethyl)pyrrolidin-1-yl)methyl)-2-(cyclopropylmethyl)-1-oxo-1,2-dihydroisoquinolin-6-yl)-N-cyclopropyl-5-fluoro-4-methylbenzamide

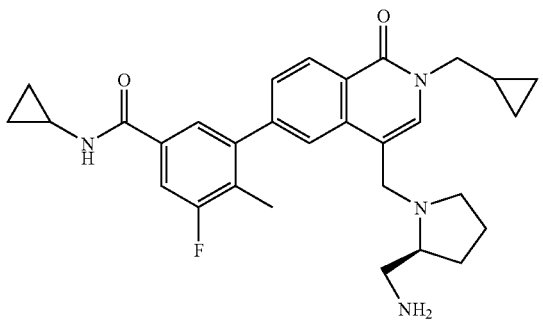

The title compound was prepared according to the method of Example 81 using the product of Example 75 step i) and (S)-1-pyrrolidine-2-ylmethyl-carbamic acid tert-butyl ester hydrochloride. The product was purified using SCX ion-exchange chromatography (eluting with methanol followed by 3N ammonia in methanol), followed by HPLC.

MS: APCI (+ve) 503 (M+H)+

¹H NMR DMSO-d₆ 8.62 (d, J=4.1 Hz, 1H), 8.34 (d, J=8.2 Hz, 1H), 7.98 (d, J=1.5 Hz, 1H), 7.69-7.63 (m, 2H), 7.55 (dd, J=8.3, 1.7 Hz, 1H), 7.53 (s, 1H), 4.13 (d, J=13.1 Hz, 1H), 3.91-3.80 (m, 2H), 3.29 (d, J=13.8 Hz, 1H), 2.89-2.82 (m, 1H), 2.82-2.76 (m, 1H), 2.64-2.58 (m, 1H), 2.54-2.44 (m, 2H), 2.23-2.21 (m, 1H), 2.21 (d, J=2.8 Hz, 3H), 1.91-1.80 (m, 1H), 1.67-1.48 (m, 3H), 1.31-1.19 (m, 1H), 0.73-0.66 (m, 2H), 0.60-0.54 (m, 2H), 0.52-0.45 (m, 2H), 0.45-0.38 (m, 2H)

Physical Form Data

DESCRIPTION OF FIGURES

FIG. 1: X-ray powder diffraction pattern of polymorph A Example 47

FIG. 2: X-ray powder diffraction pattern of polymorph A Example 60

FIG. 3: X-ray powder diffraction pattern of polymorph A Example 78

FIG. 4: X-ray powder diffraction pattern of polymorph A Example 88

Instrument Details:

XRPD

Data was collected with a PANalytical CubiX PRO machine in θ-2θ configuration over the scan range 2° to 40° 2θ with 100-second exposure per 0.02° increment. The X-rays were generated by a copper long-fine focus tube operated at 45 kV and 40 mA. The wavelength of the copper X-rays was 1.5418 Å. The Data was collected on zero back- ground holders on which ~2 mg of the compound was placed. The holder was made from a single crystal of silicon, which had been cut along a non-diffracting plane and then polished on an optically flat finish. The X-rays incident upon this surface were negated by Bragg extinction.

DSC

DSC thermograms were measured using a TA Q1000 Differential Scanning Calorimeter, with aluminium pans and pierced lids. The sample weights varied between 0.5 to 5 mg. The procedure was carried out under a flow of nitrogen gas (50 ml/min) and the temperature studied from 25 to 300° C. at a constant rate of temperature increase of 10° C. per minute.

GVS

GVS profiles were measured using a Dynamic Vapour Sorption DVS-1 instrument. The solid sample ca. 1-5 mg was placed into a glass vessel and the weight of the sample was recorded during a dual cycle step method (40 to 90 to 0 to 90 to 0% relative humidity (RH), in steps of 10% RH).

Analysis of Example 47

2-Benzyl-6-(5-(cyclopropylcarbamoyl)-2-methylphenyl)-N-(2-(dimethylamino)ethyl)-1-oxo-1,2-dihydroisoquinoline-4-carboxamide Polymorph A A sample of crystalline Example 47 polymorph A obtained as described above was analysed by XRPD, DSC and GVS.

The melting temperature of Example 47 polymorph A as determined by DSC gave a single endothermic event, occurring at 201° C. (±2° C.).

GVS determination gave 0.9% weight increase (% w/w) at 80% RH (±0.2%).

An XRPD diffraction pattern of Example 47 polymorph A is presented in FIG. 1

Analysis of Example 60

2-Benzyl-6-(5-(cyclopropylcarbamoyl)-3-fluoro-2-methylphenyl)-N-(2-(dimethylamino)ethyl)-1-oxo-1,2-dihydroisoquinoline-4-carboxamide, Polymorph A A sample of crystalline Example 60 polymorph A obtained by the procedure described above was analysed by XRPD.

An XRPD diffraction pattern of Example 60 polymorph A is presented in FIG. 2

Analysis of Example 78

N-Cyclopropyl-3-(2-(cyclopropylmethyl)-4-((4-(2-hydroxyethyl)-1,4-diazepan-1-yl)methyl)-1-oxo-1,2-dihydroisoquinolin-6-yl)-5-fluoro-4-methylbenzamide. Polymorph A A sample of crystalline Example 78 polymorph A obtained by the procedure described above was analysed by XRPD.

An XRPD diffraction pattern of Example 78 polymorph A is presented in FIG. 3.

Analysis of Example 88

N-Cyclopropyl-3-(2-(cyclopropylmethyl)-1-oxo-4-(piperazin-1-ylmethyl)-1,2-dihydroisoquinolin-6-yl)-5-fluoro-4-methylbenzamide, dihydrochloride, Polymorph A A sample of crystalline Example 88 polymorph A obtained by the procedure described above was analysed by XRPD.

An XRPD diffraction pattern of Example 88 polymorph A is presented in FIG. 4.

Experimental Methods

The ability of the compounds of formula (I) to inhibit p38 kinase may be determined using the following biological assay:

p38 Alpha Enzyme Assay

Enzyme assays were performed in polypropylene 96 well plates. The following solutions were added to each well; 10 µL of compound dilutions in assay buffer (20 mM HEPES pH 7.4, containing 20 mM magnesium acetate, 0.005% (w/v) Tween-20, 10 mM DTT) containing 1% (v/v) DMSO or assay buffer containing 1% (v/v) DMSO alone, 70 µL of assay buffer containing 36 nM substrate (biotinylated-ATF2) and 10 µL of an appropriate dilution of human active recombinant p38α-6His tagged. Depending on batch of p38, an appropriate dilution was typically a 5 nM solution to give a final enzyme concentration of 0.5 nM. At this stage, background control wells also received 50 µL of AlphaScreen quench buffer (10 mM HEPES pH 7.4 containing 100 mM EDTA, 0.2% (w/v) bovine serum albumin). The plate was covered, pre-incubated for 4 hours at 37° C. and the enzyme reaction initiated by addition of 10 µL 1 mM ATP. After incubation for a further 45 minutes at 37° C., the reaction was stopped by addition of 50 µL quench reagent and 50 µL of the quenched reaction mixture transferred to an opaque, white 96-well plate. Detection reagent, 25 µL of 10 mM HEPES pH 7.4 containing 100 mM EDTA, 0.2% (w/v) bovine serum albumin, 0.3 nM anti phosphoATF2 antibody and 25 µg/mL of 'AlphaScreen protein A acceptor and donor beads' (PerkinElmer Inc.), was added to all wells in a darkened room, the plate sealed and left in the dark for at least 5 hours before AlphaScreen readings were taken using a Perkin Elmer EnVision reader. Total, uninhibited activity was determined from assays performed in each assay plate. The mean control in the absence of p38 activity was subtracted from each well. Data were expressed as percent inhibition of total activity using equation 1.

$$\text{Percent Inhibition} = 100*(1-\text{Test}/\text{Control}) \quad \text{Eq.1}$$

Where . . . .
Test=p38 kinase activity in the presence of compound
Control=p38 kinase activity in the absence of compound.

$pIC_{50}$ is defined as the logarithm of the reciprocal of the concentration of compound required for 50% reduction in total p38 kinase activity.

Using this assay, the compounds of the present invention all exhibit a potency, expressed as a $pIC_{50}$, of greater than 6.0. The potency values are given in Table 1.

TABLE 1

| Example Number | p38 $pIC_{50}$ | Example Number | p38 $pIC_{50}$ | Example Number | p38 $pIC_{50}$ | Example Number | p38 $pIC_{50}$ |
|---|---|---|---|---|---|---|---|
| 1 | 9.1 | 2 | 8.1 | 3 | 8.6 | 4 | 8.9 |
| 5 | 8.5 | 6 | 8.2 | 7 | 9.4 | 8 | 9.3 |
| 9 | 9.7 | 10 | 8.7 | 11 | 7.6 | 12 | 8.1 |
| 13 | 6.5 | 14 | 8.6 | 15 | 8.5 | 16 | 7.3 |
| 17 | 9.0 | 18 | 8.7 | 19 | 9.0 | 20 | 8.9 |
| 21 | 8.5 | 22 | 9.1 | 23 | 8.7 | 24 | 9.2 |
| 25 | 8.5 | 26 | 8.5 | 27 | 9.0 | 28 | 9.0 |
| 29 | 8.8 | 30 | 9.0 | 31 | 9.2 | 32 | 9.3 |
| 33 | 8.7 | 34 | 8.6 | 35 | 8.7 | 36 | 9.4 |
| 37 | 8.4 | 38 | 8.4 | 39 | 8.3 | 40 | 8.4 |
| 41 | 8.8 | 42 | 8.9 | 43 | 8.3 | 44 | 7.6 |
| 45 | 8.6 | 46 | 7.6 | 47 | 8.9 | 48 | 8.6 |
| 49 | 8.5 | 50 | 8.7 | 51 | 8.7 | 52 | 8.0 |
| 53 | 8.7 | 54 | 7.6 | 55 | 7.5 | 56 | 8.1 |
| 57 | 8.8 | 58 | 8.7 | 59 | 9.5 | 60 | 9.4 |
| 61 | 8.0 | 62 | 8.3 | 63 | 9.0 | 64 | 8.5 |
| 65 | 8.1 | 66 | 9.8 | 67 | 8.3 | 68 | 8.4 |
| 69 | 9.7 | 70 | 9.8 | 71 | 8.0 | 72 | 9.4 |
| 73 | 8.9 | 74 | 9.2 | 75 | 10.3 | 76 | 10.0 |
| 77 | 8.8 | 78 | 9.8 | 79 | 9.2 | 80 | 9.5 |
| 81 | 10.0 | 82 | 10.0 | 83 | 10.1 | 84 | 9.7 |
| 85 | 10.4 | 86 | 10.1 | 87 | 10.2 | 88 | 10.2 |
| 89 | 9.1 | 90 | 9.8 | 91 | 8.1 | 92 | 10.0 |
| 93 | 8.7 | 94 | 8.5 | 95 | 8.6 | 96 | 8.0 |
| 97 | 9.6 | 98 | 8.6 | 99 | 9.4 | 100 | 9.0 |
| 101 | 8.5 | 102 | 10.3 | 103 | 9.9 | 104 | 9.7 |
| 105 | 9.8 | 106 | 9.5 | 107 | 9.1 | 108 | 10.2 |
| 109 | 8.8 | 110 | 9.0 | 111 | 10.0 | 112 | 9.9 |
| 113 | 10.1 | 114 | 9.6 | 115 | 10.0 | 116 | 9.3 |
| 117 | 9.8 | 118 | 9.6 | 119 | 9.4 | 120 | 9.1 |
| 121 | 8.4 | 122 | 8.8 | 123 | 8.5 | 124 | 8.4 |
| 125 | 7.2 | 126 | 8.0 | 127 | 9.8 | 128 | 9.5 |

The invention claimed is:

1. A compound of formula (I):

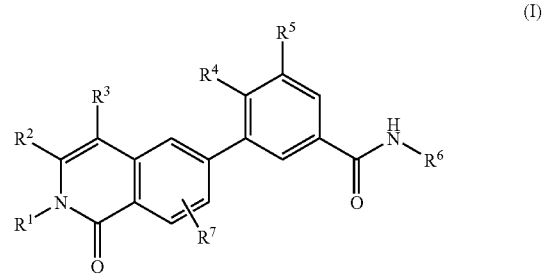

wherein:

$R^1$ is selected from H, $(C_1$-$C_6)$alkyl, $(C_2$-$C_6)$alkenyl, $(C_3$-$C_6)$alkynyl, $(CH_2)_a$—X—Ar and $(CR^{101}R^{102})_a$—X—Ar wherein said $(C_1$-$C_6)$alkyl is optionally substituted with 1, 2 or 3 groups independently selected from —($C_1$-$C_6$)alkoxy, -halo, —OH, -heterocycloalkyl, ($C_3$-$C_7$)cycloalkyl, and —$NR^8R^9$;

$R^2$ and $R^3$ are independently selected from H, halo, ($C_1$-$C_6$)alkyl, ($C_1$-$C_6$)alkoxy and $(CH_2)_d$—Y; wherein said ($C_1$-$C_6$)alkyl is optionally substituted with 1, 2 or 3 groups independently selected from —($C_1$-$C_6$)alkoxy, -halo and —OH; and wherein said ($C_1$-$C_6$)alkoxy is optionally substituted with 1, 2 or 3 groups independently selected from -halo and —OH; and provided that when $R^2$ is $(CH_2)_d$—Y, $R^3$ is selected from H, halo, ($C_1$-$C_6$)alkyl and ($C_1$-$C_6$)alkoxy; and provided that when $R^3$ is $(CH_2)_d$—Y, $R^2$ is selected from H, halo, ($C_1$-$C_6$)alkyl and ($C_1$-$C_6$) alkoxy;

$R^4$ and $R^5$ are independently selected from H, ($C_1$-$C_6$) alkyl, ($C_1$-$C_6$)alkoxy, halo, $CF_3$, and CN;

$R^6$ is selected from ($C_1$-$C_6$)alkyl, ($C_1$-$C_6$)alkoxy, ($C_3$-$C_7$) cycloalkyl, aryl, heteroaryl and OH, wherein said ($C_1$-$C_6$)alkyl, ($C_1$-$C_6$)alkoxy, ($C_3$-$C_7$)cycloalkyl, aryl or heteroaryl group may be substituted by 1 or more halo atoms;

$R^7$ is selected from H, ($C_1$-$C_6$)alkyl, ($C_1$-$C_6$)alkoxy and halo;

Ar is an aryl or heteroaryl ring optionally substituted with 1, 2 or 3 groups independently selected from —($C_1$-$C_6$) alkyl, —($C_2$-$C_6$)alkenyl, —($C_3$-$C_6$)alkynyl, —$(CH_2)_e$—O—($C_1$-$C_6$)alkyl, —$(CH_2)_e$—S(O)$_f$—($C_1$-$C_6$)alkyl, —$(CH_2)_e$—N($R^{10}$)—($C_1$-$C_6$)alkyl, —$(CH_2)_e$-Z-($C_1$-$C_6$)alkyl, —O-heterocycloalkyl, —S—(O)$_b$-heterocycloalkyl, —N($R^{11}$)-heterocycloalkyl, —CN, —OH, -halo, -phenyl, -heterocycloalkyl, —($C_3$-$C_7$)cycloalkyl, —C(O)$NR^8R^9$, —$NR^8R^9$, —C(O)OH and C(O)$NR^{10}SO_2$—($C_1$-$C_6$) alkyl, wherein each occurrence of ($C_1$-$C_6$)alkyl is, independently, optionally substituted with 1, 2 or 3 groups independently selected from -halo, —OH, —($C_1$-$C_6$) alkoxy, —$NR^{12}R^{13}$ and heterocycloalkyl;

X is selected from a single bond, O, $NR^{14}$ and S(O)$_g$;

Y is selected from heterocycloalkyl, O-heterocycloalkyl, O—$(CH_2)_h$—$NR^{16}R^{17}$, $NR^{18}$—$(CH_2)_h$—$NR^{16}R^{17}$, S—(O)$_j$-heterocycloalkyl, S—(O)$_j$—$(CH_2)_h$—$NR^{16}R^{17}$, $NR^{16}R^{17}$, $NR^{15}C(O)R^{16}$, $NR^{15}SO_2R^{16}$, C(O)$NR^{16}R^{17}$, OC(O)$NR^{16}R^{17}$, OC(O)$R^{16}$, C(O)O$R^{16}$ and $NR^{15}C(O)OR^{16}$;

Z is selected from C(O)N($R^{18}$), N($R^{18}$)C(O), C(O)O, OC(O), SO$_2$N($R^{18}$), N($R^{18}$)SO$_2$, OC(O)N($R^{18}$), N($R^{18}$)C(O)O, and OC(O)O;

$R^8$ and $R^9$ are independently selected from H and ($C_1$-$C_6$) alkyl, wherein said ($C_1$-$C_6$)alkyl is optionally substituted with 1, 2 or 3 groups independently selected from —($C_1$-$C_6$)alkoxy, -halo, —OH and $NR^{19}R^{20}$; or $R^8$ and $R^9$ together with the nitrogen atom to which they are attached form a 3 to 7 membered ring, optionally containing a further heteroatom selected from $NR^{21}$, S and O; and optionally containing, where possible, 1 or 2 double bonds; wherein said ring is optionally substituted on carbon by 1 or 2 substituents independently selected from —($C_1$-$C_6$)alkyl, ($C_1$-$C_6$)alkoxy, ($C_2$-$C_6$)alkenyl, —OH, —CN, halo and —$NR^{19}R^{20}$;

$R^{12}$ and $R^{13}$ are independently selected from H and ($C_1$-$C_6$)alkyl wherein said ($C_1$-$C_6$)alkyl is optionally substituted with —($C_1$-$C_6$)alkoxy, —OH, -halo, —($C_3$-$C_7$) cycloalkyl and —$NR^{22}R^{23}$; or $R^{12}$ and $R^{13}$ together with the nitrogen atom to which they are attached form a 3 to 7 membered ring, optionally containing a further heteroatom selected from $NR^{24}$, S and O; and optionally containing, where possible, 1 or 2 double bonds; wherein said ring is optionally substituted on carbon by 1 or 2 substituents independently selected from —($C_1$-$C_6$)alkyl, ($C_1$-$C_6$) alkoxy, ($C_2$-$C_6$)alkenyl, —OH, —CN, halo and —$NR^{22}R^{23}$;

$R^{16}$ is selected from H, ($C_1$-$C_6$)alkyl and heterocycloalkyl, wherein said ($C_1$-$C_6$)alkyl is optionally substituted with —($C_1$-$C_6$)alkoxy, —OH, -halo, —($C_3$-$C_7$)cycloalkyl and —$NR^{25}R^{26}$;

$R^{17}$ is selected from H and ($C_1$-$C_6$)alkyl;

or $R^{16}$ and $R^{17}$ together with the nitrogen atom to which they are attached form a 3 to 7 membered ring, optionally containing a further heteroatom selected from $NR^{27}$, S and O; and optionally containing, where possible, 1 or 2 double bonds; wherein said ring is optionally substituted on carbon by 1 or 2 substituents independently selected from —($C_1$-$C_6$)alkyl, ($C_1$-$C_6$) alkoxy, ($C_2$-$C_6$)alkenyl, —OH, —CN, halo and —$NR^{25}R^{26}$, wherein said —($C_1$-$C_6$)alkyl is optionally substituted by —OH;

$R^{25}$ and $R^{26}$ are independently selected from H and ($C_1$-$C_6$)alkyl wherein said ($C_1$-$C_6$)alkyl is optionally substituted with —($C_1$-$C_6$)alkoxy, —OH, -halo, —($C_3$-$C_7$) cycloalkyl and —$NR^{22}R^{23}$; or $R^{25}$ and $R^{26}$ together with the nitrogen atom to which they are attached form a 3 to 7 membered ring, optionally containing a further heteroatom selected from $NR^{24}$, S and O; and optionally containing, where possible, 1 or 2 double bonds; wherein said ring is optionally substituted on carbon by 1 or 2 substituents independently selected from —($C_1$-$C_6$)alkyl, ($C_1$-$C_6$) alkoxy, ($C_2$-$C_6$)alkenyl, —OH, —CN, halo and —$NR^{22}R^{23}$;

$R^{27}$ is selected from H, ($C_1$-$C_6$)alkyl and heterocycloalkyl, wherein said ($C_1$-$C_6$)alkyl is optionally substituted by a substituent selected from —OH, -halo and —$NR^{22}R^{23}$;

$R^{10}$, $R^{11}$, $R^{14}$, $R^{15}$, $R^{18}$, $R^{19}$, $R^{20}R^{21}$, $R^{22}$, $R^{23}$ and $R^{24}$ are independently selected from H and ($C_1$-$C_6$)alkyl;

a is selected from 0, 1, 2, 3, 4, 5 and 6;

d, e and h are independently selected from 0, 1, 2 and 3;

b, f, g and j are independently selected from 0, 1 and 2;

heterocycloalkyl is a C-linked 3 to 7 membered non-aromatic cyclic ring, containing from 1 to 2 $NR^{28}$ atoms, or one $NR^{28}$ atom and an S or an O atom, or one S atom, or one O atom; optionally containing, where possible, 1 or 2 double bonds; which unless otherwise stated, may be optionally substituted with 1 to 3 substituents independently selected from ($C_1$-$C_6$) alkyl, ($C_1$-$C_6$)alkoxy, ($C_2$-$C_6$)alkenyl, —OH, —CN, halo and —$NR^{29}R^{30}$, wherein said —($C_1$-$C_6$) alkyl is optionally substituted by —OH;

heteroaryl is a 5, 6, 9 or 10 membered aromatic ring, containing from 1 to 2 N atoms and, optionally, an $NR^{31}$ atom, or one $NR^{31}$ atom and an S or an O atom, or one S atom, or one O atom; which, unless otherwise stated, may be optionally substituted with 1-3 substituents independently selected from ($C_1$-$C_6$)alkyl, ($C_1$-$C_6$)alkoxy, ($C_2$-$C_6$)alkenyl, —OH, —CN, halo and —$NR^{38}R^{39}$;

cycloalkyl is a non-aromatic carbocyclic ring containing the requisite number of carbon atoms, optionally containing, where possible, up to 3 double bonds; which, unless otherwise stated, may be optionally substituted with 1 to 3 substituents independently selected from ($C_1$-$C_6$) alkyl, ($C_1$-$C_6$)alkoxy, ($C_2$-$C_6$)alkenyl, —OH, —CN, halo and —$NR^{34}R^{35}$;

aryl is an aromatic ring containing 6 or 10 carbon atoms; which unless otherwise stated, may be optionally substituted with 1 to 3 substituents independently selected from (C$_1$-C$_6$)alkyl, (C$_1$-C$_6$) alkoxy, (C$_2$-C$_6$)alkenyl, —OH, —CN, halo and —NR$^{36}$R$^{37}$;

R$^{28}$ and R$^{31}$ are each independently selected from H, (C$_1$-C$_6$)alkyl and —C(O)O—(C$_1$-C$_6$)alkyl, wherein said (C$_1$-C$_6$)alkyl may be optionally substituted with (C$_1$-C$_6$) alkoxy, —OH, halo, (C$_3$-C$_7$) cycloalkyl and —NR$^{32}$R$^{33}$;

R$^{29}$, R$^{30}$, R$^{32}$ and R$^{33}$ are each independently selected from H and (C$_1$-C$_6$)alkyl;

R$^{34}$, R$^{35}$, R$^{36}$, R$^{37}$, R$^{38}$ and R$^{39}$ are each independently selected from H, and (C$_1$-C$_6$)alkyl;

R$^{101}$ is (C$_1$-C$_6$)alkyl;

R$^{102}$ is H or (C$_1$-C$_6$)alkyl;

or a pharmaceutically acceptable salt or N-oxide thereof.

2. The compound according to claim 1 wherein R$^1$ is selected from (C$_1$-C$_6$)alkyl and (CH$_2$)$_a$—X—Ar, wherein said (C$_1$-C$_6$)alkyl is substituted with a substituent selected from (C$_3$-C$_7$)cycloalkyl and —NR$^8$R$^9$.

3. The compound according to claim 1 wherein R$^1$ is selected from:

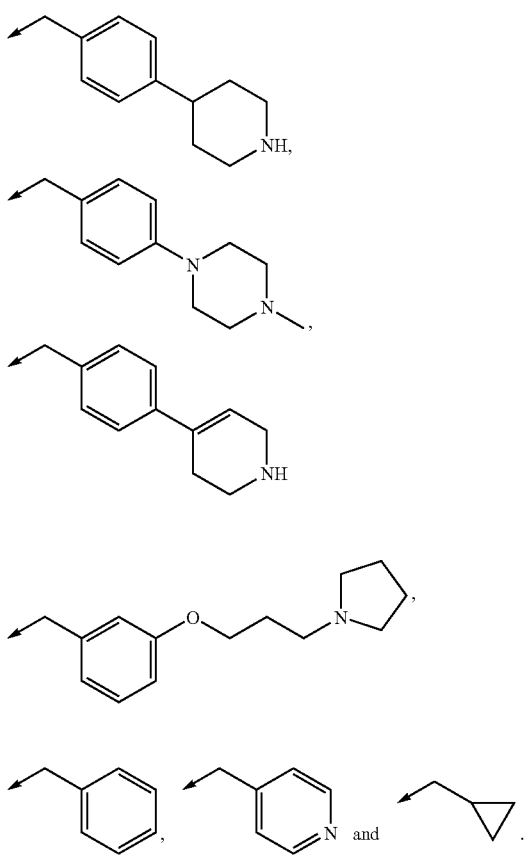

4. The compound according to claim 1, wherein R$^2$ is H and R$^3$ is (CH$_2$)$_d$—Y.

5. The compound according to claim 1, wherein R$^4$ is methyl and R$^5$ is selected from H and F.

6. The compound according to claim 1, wherein R$^6$ is selected from (C$_1$-C$_3$)alkyl, (C$_1$-C$_3$)alkoxy and (C$_3$-C$_7$)cycloalkyl.

7. The compound according to claim 1 of formula (ID),

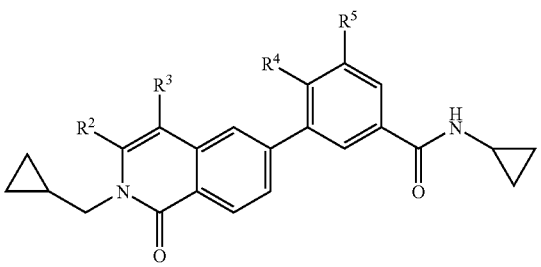

(ID)

wherein

R$^2$ is hydrogen;

R$^3$ is (CH$_2$)$_d$—Y;

R$^4$ is methyl;

R$^5$ is selected from H and F;

d is 1;

Y represents NR$^{16}$R$^{17}$;

R$^{16}$ and R$^{17}$ together with the nitrogen atom to which they are attached form a 6 to 7 membered ring, optionally containing a further heteroatom NR$^{27}$, wherein said ring is optionally substituted on carbon by 1 or 2 substituents independently selected from —(C$_1$-C$_6$)alkyl wherein said —(C$_1$-C$_6$)alkyl is optionally substituted by —OH; and wherein R$^{27}$ is selected from H and (C$_1$-C$_6$)alkyl wherein said (C$_1$-C$_6$)alkyl is optionally substituted by —OH;

or a pharmaceutically acceptable salt or N-oxide thereof.

8. The compound according to claim 1, selected from:

3-(2-Benzyl-1-oxo-1,2-dihydro-isoquinolin-6-yl)-N-cyclopropyl -4-methyl-benzamide;

3-(2-Benzyl-1-oxo-1,2-dihydro-isoquinolin-6-yl)-N-ethyl-4-methyl-benzamide;

3-[2-(4-Bromo-benzyl)-1-oxo-1,2-dihydro-isoquinolin-6-yl-N-cyclopropyl-4-methyl-benzamide;

N-Cyclopropyl-4-methyl-3-{2-[4-(4-methyl-piperazin-1-yl)-benzyl]-1-oxo-1,2-dihydro-isoquinolin-6-yl}-benzamide;

N-Cyclopropyl-3-[2-(4-methanesulfonyl-benzyl)-1-oxo-1,2-dihydro-isoquinolin-6-yl]-4-methyl-benzamide;

4-{4-[6-(5-Cyclopropylcarbamoyl-2-methyl-phenyl)-1-oxo-1H-isoquinolin-2-ylmethyl]-phenyl}-3,6-dihydro-2H-pyridine-1-carboxylic acid, tert-butyl ester;

N-Cyclopropyl-4-methyl-3-[1-oxo-2-{4-(1,2,3,6-tetrahydro-pyridin-4-yl)-benzyl}-1,2-dihydro-isoquinolin-6-yl]-benzamide;

N-Cyclopropyl-4-methyl-3-[1-oxo-2-(4-piperidin-4-yl -benzyl)-1,2-dihydro-isoquinolin-6-yl]-benzamide;

N-Methoxy-4-methyl-3-{1-oxo-2-[4-(1,2,3,6-tetrahydropyridin-4-yl)-benzyl]-1,2-dihydro-isoquinolin-6-yl}-benzamide;

N-Cyclopropyl-3-{2-[3-(3-dimethylamino-propoxy)-benzyl]-1-oxo-1,2-dihydro-isoquinolin-6-yl}-4-methyl-benzamide;

N-Cyclopropyl-4-methyl-3-(1-oxo-1,2-dihydro-isoquinolin-6-yl) -benzamide;

3-(2-Allyl-1-oxo-1,2-dihydro-isoquinolin-6-yl)-N-cyclopropyl-4-methyl-benzamide;

N-Cyclopropyl-4-methyl-3-[1-oxo-2-(3-pyrrolidin-1-yl-propyl)-1,2-dihydro-isoquinolin-6-yl]-benzamide;

N-Cyclopropyl-3-[2-(4-dimethylaminomethyl-benzyl)-1-oxo-1,2-dihydro-isoquinolin-6-yl]-4-methyl-benzamide;

N-Cyclopropyl-3-[2-(3-dimethylaminomethyl-benzyl)-1-oxo-1,2-dihydro-isoquinolin-6-yl]-4-methyl-benzamide;

N-Cyclopropyl-3-[2-(2-dimethylaminomethyl-benzyl)-1-oxo-1,2-dihydro-isoquinolin-6-yl]-4-methyl-benzamide;

N-Cyclopropyl-3-[2-(4-methoxy-benzyl)-1-oxo-1,2-dihydro-isoquinolin-6-yl]-4-methyl-benzamide, N-Cyclopropyl-3-(2-(4-((2-(dimethylamino)ethyl)(methyl)carbamoyl)benzyl)-1-oxo-1,2-dihydroisoquinolin-6-yl)-4-methylbenzamide, N-Cyclopropyl-3-(2-(4-(2-(dimethylamino)ethylcarbamoyl)benzyl)-1-oxo-1,2-dihydroisoquinolin-6-yl)-4-methylbenzamide, N-Cyclopropyl-4-methyl-3-(2-(4-(4-methylpiperazine-1-carbonyl)benzyl)-1-oxo-1,2-dihydroisoquinolin-6-yl)benzamide, N-Cyclopropyl-3-(2-(4-((3-(dimethylamino)propyl)(methyl)carbamoyl)benzyl)-1-oxo-1,2-dihydroisoquinolin-6-yl)-4-methylbenzamide, N-Cyclopropyl-4-methyl-3-(1-oxo-2-(4-(2-(pyrrolidin-1-yl)ethylcarbamoyl)benzyl)-1,2-dihydroisoquinolin-6-yl)benzamide, N-Cyclopropyl-4-methyl-3-(2-(4-(methyl(2-(methylamino)ethyl)carbamoyl)benzyl)-1-oxo-1,2-dihydroisoquinolin-6-yl)benzamide, N-Cyclopropyl-4-methyl-3-(1-oxo-2-(4-(3-(pyrrolidin-1-yl)propylcarbamoyl)benzyl)-1,2-dihydroisoquinolin-6-yl)benzamide, N-Cyclopropyl-4-methyl-3-(1-oxo-2-(4-(pyrrolidin-1-ylmethyl)benzyl)-1,2-dihydroisoquinolin-6-yl)benzamide, N-Cyclopropyl-4-methyl-3-(2-(4-((4-methylpiperazin-1-yl)methyl)benzyl)-1-oxo-1,2-dihydroisoquinolin-6-yl)benzamide, 3-(2-(4-((Tert-butyl(methyl)amino)methyl)benzyl)-1-oxo-1,2-dihydroisoquinolin-6-yl)-N-cyclopropyl-4-methylbenzamide, 3-(2-(4-((Tert-butylamino)methyl)benzyl)-1-oxo-1,2-dihydroisoquinolin-6-yl)-N-cyclopropyl-4-methylbenzamide, N-Cyclopropyl-3-(2-((6-(3-(dimethylamino)propoxy)pyridin-3-yl)methyl)-1-oxo-1,2-dihydroisoquinolin-6-yl)-4-methylbenzamide, N-Cyclopropyl-3-(2-((6-(2-(dimethylamino)ethoxy)pyridin-3-yl)methyl)-1-oxo-1,2-dihydroisoquinolin-6-yl)-4-methylbenzamide, N-Cyclopropyl-4-methyl-3-(1-oxo-2-((6-(2-(pyrrolidin-1-yl)ethoxy)pyridin-3-yl)methyl)-1,2-dihydroisoquinolin-6-yl)benzamide, N-Cyclopropyl-3-(2-(4-(2-(dimethylamino)ethoxy)benzyl)-1-oxo-1,2-dihydroisoquinolin-6-yl)-4-methylbenzamide, N-cyclopropyl-4-methyl-3-{1-oxo-2-[3-(2-pyrrolidin-1-ylethoxy)benzyl]-1,2-dihydroisoquinolin-6-yl}benzamide, N-Cyclopropyl-4-methyl-3-(2-{3-[2-(methylamino)ethoxy]benzyl}-1-oxo-1,2-dihydroisoquinolin-6-yl)benzamide, N-Cyclopropyl-3-[2-(3-{2-[(2-hydroxyethyl)amino]ethoxy}benzyl)-1-oxo-1,2-dihydroisoquinolin-6-yl]-4-methylbenzamide, N-Cyclopropyl-4-methyl-3-(2-(4-(2-(methylamino)ethoxy)benzyl)-1-oxo-1,2-dihydroisoquinolin-6-yl)benzamide, 6-(5-(Cyclopropylcarbamoyl)-2-methylphenyl)-2-(cyclopropylmethyl)-1-oxo-N-(piperidin-4-yl)-1,2-dihydroisoquinoline-4-carboxamide, 3-(4-(4-Aminopiperidine-1-carbonyl)-2-(cyclopropylmethyl)-1-oxo-1,2-dihydroisoquinolin-6-yl)-N-cyclopropyl-4-methylbenzamide, N-Cyclopropyl-3-(2-(cyclopropylmethyl)-4-(4-(dimethylamino)piperidine-1-carbonyl)-1-oxo-1,2-dihydroisoquinolin-6-yl)-4-methylbenzamide, 2-Benzyl-6-(5-(cyclopropylcarbamoyl)-2-methylphenyl)-N-(2-(dimethylamino)ethyl)-1-oxo-1,2-dihydroisoquinoline-4-carboxamide, 2-Benzyl-6-(5-(cyclopropylcarbamoyl)-2-methylphenyl)-1-oxo-N-(2-(piperidin-1-yl)ethyl)-1,2-dihydroisoquinoline-4-carboxamide, 2-Benzyl-6-{5-[(cyclopropylamino)carbonyl]-2-methylphenyl}-1-oxo-N-(2-pyrrolidin-1-ylethyl)-1,2-dihydroisoquinoline-4-carboxamide, 2-Benzyl-6-{5-[(cyclopropylamino)carbonyl]-2-methylphenyl}-N-(1-methylpiperidin-4-yl)-1-oxo-1,2-dihydroisoquinoline-4-carboxamide, 2-Benzyl-6-{5-[(cyclopropylamino)carbonyl]-2-methylphenyl}-N-[3-(dimethylamino)propyl]-1-oxo-1,2-dihydroisoquinoline-4-carboxamide, (R)-3-(4-(3-Aminopyrrolidine-1-carbonyl)-2-benzyl-1-oxo-1,2-dihydroisoquinolin-6-yl)-N-cyclopropyl-4-methylbenzamide, 6-(5-(Cyclopropylcarbamoyl)-2-methylphenyl)-1-oxo-N-(piperidin-4-yl)-2-(pyridin-4-ylmethyl)-1,2-dihydroisoquinoline-4-carboxamide, 3-(4-(4-Aminopiperidine-1-carbonyl)-1-oxo-2-(pyridin-4-ylmethyl)-1,2-dihydroisoquinolin-6-yl)-N-cyclopropyl-4-methylbenzamide, N-Cyclopropyl-3-[2-cyclopropylmethyl-4-(4-methyl-[1,4]diazepan-1-ylmethyl)-1-oxo-1,2-dihydro-isoquinolin-6-yl]-4-methyl-benzamide, 2-Benzyl-6-(5-(cyclopropylcarbamoyl)-3-fluoro-2-methylphenyl)-N-(2-(dimethylamino)ethyl)-1-oxo-1,2-dihydroisoquinoline-4-carboxamide, (S)—N-Cyclopropyl-3-(2-(cyclopropylmethyl)-4-((3-methylpiperazin-1-yl)methyl)-1-oxo-1,2-dihydroisoquinolin-6-yl)-4-methylbenzamide N-Cyclopropyl-3-(2-cyclopropylmethyl-4-[1,4]diazepan-1-ylmethyl-1-oxo-1,2-dihydro-isoquinolin-6-yl)-4-methyl-benzamide N-Cyclopropyl-3-(2-(cyclopropylmethyl)-4-((4-(2-hydroxyethyl)-1,4-diazepan-1-yl)methyl)-1-oxo-1,2-dihydroisoquinolin-6-yl)-4-methylbenzamide N-Cyclopropyl-3-(2-(cyclopropylmethyl)-4-((4-methylpiperazin-1-yl)methyl)-1-oxo-1,2-dihydroisoquinolin-6-yl)-4-methylbenzamide N-Cyclopropyl-3-(2-(cyclopropylmethyl)-4-((4-methyl-1,4-diazepan-1-yl)methyl)-1-oxo-1,2-dihydroisoquinolin-6-yl)-5-fluoro-4-methylbenzamide N-Cyclopropyl-3-(2-(cyclopropylmethyl)-4-((4-(2-hydroxyethyl)-1,4-diazepan-1-yl)methyl)-1-oxo-1,2-dihydroisoquinolin-6-yl)-5-fluoro-4-methylbenzamide N-Cyclopropyl-3-(2-(cyclopropylmethyl)-4-(((3S,5R)-3,5-dimethylpiperazin-1-yl)methyl)-1-oxo-1,2-dihydroisoquinolin-6-yl)-5-fluoro-4-methylbenzamide (S)—N-Cyclopropyl-3-(2-(cyclopropylmethyl)-4-((3-methylpiperazin-1-yl)methyl)-1-oxo-1,2-dihydroisoquinolin-6-yl)-5-fluoro-4-methylbenzamide (R)—N-Cyclopropyl-3-(2-(cyclopropylmethyl)-4-((3-(hydroxymethyl)piperazin-1-yl)methyl)-1-oxo-1,2-dihydroisoquinolin-6-yl)-5-fluoro-4-methylbenzamide (R)—N-Cyclopropyl-3-(2-(cyclopropylmethyl)-4-((2-methylpiperazin-1-yl)methyl)-1-oxo-1,2-dihydroisoquinolin-6-yl)-5-fluoro-4-methylbenzamide (R)—N-Cyclopropyl-3-(2-(cyclopropylmethyl)-4-((3-(hydroxymethyl)-4-methylpiperazin-1-yl)methyl)-1-oxo-1,2-dihydroisoquinolin-6-yl)-5-fluoro-4-methylbenzamide N-Cyclopropyl-3-(2-(cyclopropylmethyl)-1-oxo-4-(piperazin-1-ylmethyl)-1,2-dihydroisoquinolin-6-yl)-5-fluoro-4-methylbenzamide N-Cyclopropyl-3-(2-(cyclopropylmethyl)-4-((4-(2-hydroxyethyl)piperazin-1-yl)methyl)-1-oxo-1,2-dihydroisoquinolin-6-yl)-5-fluoro-4-methylbenzamide 3-(4-((1,4-Diazepan-1-yl)methyl)-2-(cyclopropylmethyl)-1-oxo-1,2-dihydroisoquinolin-6-yl)-N-cyclopropyl-5-fluoro-4-methylbenzamide (S)—N-Cyclopropyl-3-(2-(cyclopropylmethyl)-4-((3-(hydroxymethyl)piperazin-1-yl)methyl)-1-oxo-1,2-dihydroisoquinolin-6-yl)-5-fluoro-4-methylbenzamide (R)—N-Cyclopropyl-3-(2-(cyclopropylmethyl)-4-((3-methylpiperazin-1-yl)methyl)-1-oxo-1,2-dihydroisoquinolin-6-yl)-5-fluoro-4-methylbenzamide (S)—N-Cyclopropyl-3-(2-(cyclopropylmethyl)-4-((2-(hydroxymethyl)piperazin-1-yl)methyl)-1-oxo-1,2-dihydroisoquinolin-6-yl)-5-fluoro-4-methylbenzamide (S)—N-Cyclopropyl-3-(2-(cyclopropylmethyl)-4-((3-ethylpiperazin-1-yl)methyl)-1-oxo-1,2-dihydroisoquinolin-6-yl)-5-fluoro-4-methylbenzamide (S)—N-Cyclopropyl-3-(2-(cyclopropylmethyl)-4-((3-(2-hydroxyethyl)piperazin-1-yl)methyl)-1-oxo-1,2-dihydroisoquinolin-6-yl)-5-fluoro-4-methylbenzamide (S)—N-Cyclopropyl-3-(2-(cyclopropylmethyl)-4-((2-methylpiperazin-1-yl)methyl)-1-oxo-1,2-dihydroisoquinolin-6-yl)-5-fluoro-4-methylbenzamide 3-(4-(((2R,4S)-4-Amino-2-(hydroxymethyl)pyrrolidin-1-yl)methyl)-2-(cyclopropylmethyl)-1-oxo-1,2-dihydroisoquinolin-6-yl)-N-cyclopropyl-5-fluoro-4-methylbenzamide and pharmaceutically acceptable salts or N-oxides thereof.

9. A pharmaceutical composition that comprises a compound of formula (I) or (ID) or a pharmaceutically acceptable salt or N-oxide thereof, as defined in any one of claims 1 to 8, and a pharmaceutically acceptable adjuvant, diluent or carrier.

10. A pharmaceutical product comprising, in combination, a first active ingredient which is a compound of formula (I) or (ID), or a pharmaceutically acceptable salt thereof or N-oxide thereof, as defined in claim 1 or claim 7, and at least one further active ingredient selected from:—
a phosphodiesterase inhibitor;
a β2 adrenoceptor agonist;
a modulator of chemokine receptor function;
a protease inhibitor;
a steroidal glucocorticoid receptor agonist;
an anticholinergic agent; and
a non-steroidal glucocorticoid receptor agonist.

11. A process for the preparation of a compound of formula (I) as defined in claim 1, or a pharmaceutically-acceptable salt or N-oxide thereof, by
(a) reacting a compound of formula (II):

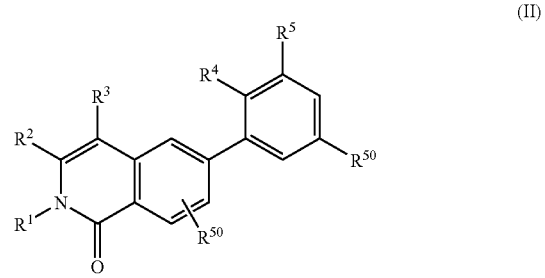

wherein $R^1$, $R^2$, $R^3$, $R^4$, $R^5$ and $R^7$ are as defined in claim 1 and $R^{50}$ is a carboxylic acid or a derivative thereof with an amine of formula (III)

wherein $R^6$ is as defined formula (I), in an inert solvent or
(b) when $R^3$ is $CH_2NR^{16}R^{17}$, reacting a compound of formula (XXXI) wherein $R^1$, $R^2$, $R^4$, $R^5$, $R^6$ and $R^7$ are as defined in formula (I)

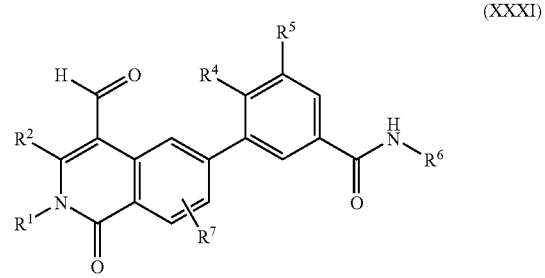

with an amine of formula $HNR^{16}R^{17}$, wherein $R^{16}$ and $R^{17}$ are as defined in formula (I), in the presence of a suitable reducing agent in an inert solvent;
and optionally after (a) or (b) converting the compound obtained to a pharmaceutically acceptable salt or N-oxide of the compound.

12. A method of treating chronic obstructive pulmonary disease (COPD) in a warm-blooded animal, which comprises administering to a mammal in need of such treatment an effective amount of a compound of formula (I) or (ID) or a pharmaceutically acceptable salt or N-oxide thereof, as defined in claim 1 or claim 7.

13. A method of treating asthma in a warm-blooded animal, which comprises administering to a mammal in need of such treatment an effective amount of a compound of formula (I) or (ID) or a pharmaceutically acceptable salt or N-oxide thereof, as defined in claim 1 or claim 7.

* * * * *